(12) United States Patent
Kuntz et al.

(10) Patent No.: US 9,175,331 B2
(45) Date of Patent: *Nov. 3, 2015

(54) INHIBITORS OF HUMAN EZH2, AND METHODS OF USE THEREOF

(75) Inventors: Kevin Wayne Kuntz, Woburn, MA (US); Sarah Kathleen Knutson, Cambridge, MA (US); Timothy James Nelson Wigle, Waltham, MA (US)

(73) Assignee: Epizyme, Inc., Cambridge, MA (US)

( * ) Notice: Subject to any disclaimer, the term of this patent is extended or adjusted under 35 U.S.C. 154(b) by 178 days.

This patent is subject to a terminal disclaimer.

(21) Appl. No.: 13/418,242

(22) Filed: Mar. 12, 2012

(65) Prior Publication Data
US 2013/0040906 A1 Feb. 14, 2013

Related U.S. Application Data

(63) Continuation-in-part of application No. 13/230,703, filed on Sep. 12, 2011, now Pat. No. 8,895,245.

(60) Provisional application No. 61/381,684, filed on Sep. 10, 2010.

(51) Int. Cl.
| A61P 35/00 | (2006.01) |
| C12Q 1/68 | (2006.01) |
| C07D 473/34 | (2006.01) |
| C12Q 1/48 | (2006.01) |
| G01N 33/50 | (2006.01) |
| G01N 33/574 | (2006.01) |
| A61K 31/711 | (2006.01) |
| A61K 38/17 | (2006.01) |
| C07D 405/12 | (2006.01) |
| A61P 35/02 | (2006.01) |

(52) U.S. Cl.
CPC .............. *C12Q 1/68* (2013.01); *A61K 31/711* (2013.01); *A61K 38/17* (2013.01); *C07D 405/12* (2013.01); *C07D 473/34* (2013.01); *C12Q 1/48* (2013.01); *G01N 33/5011* (2013.01); *G01N 33/57426* (2013.01); *G01N 2333/91011* (2013.01); *G01N 2800/52* (2013.01); *Y10T 436/143333* (2015.01)

(58) Field of Classification Search
None
See application file for complete search history.

(56) References Cited

U.S. PATENT DOCUMENTS

| 5,716,993 | A | 2/1998 | Ozaki et al. |
| 5,948,803 | A | 9/1999 | Maeda et al. |
| 6,689,583 | B1 | 2/2004 | Jenuwein et al. |
| 7,122,547 | B1 | 10/2006 | Huth et al. |
| 7,252,968 | B2 | 8/2007 | Jenuwein et al. |
| 7,442,685 | B2 | 10/2008 | Zhang et al. |
| 7,563,589 | B2 | 7/2009 | Zhang et al. |
| 7,923,219 | B2 | 4/2011 | Wang et al. |
| 8,691,507 | B2 | 4/2014 | Copeland et al. |
| 8,765,732 | B2 | 7/2014 | Kuntz et al. |
| 8,895,245 | B2 | 11/2014 | Copeland et al. |
| 2002/0183324 | A1 | 12/2002 | Jacobson et al. |
| 2004/0082619 | A1 | 4/2004 | Tada et al. |
| 2005/0059682 | A1 | 3/2005 | Rubinfeld |
| 2005/0266473 | A1 | 12/2005 | Zhang et al. |
| 2008/0182844 | A1 | 7/2008 | Bjergarde et al. |
| 2008/0222741 | A1 | 9/2008 | Chinnaiyan |
| 2008/0269289 | A1 | 10/2008 | Frank et al. |
| 2008/0312292 | A1 | 12/2008 | Yasui et al. |
| 2009/0012031 | A1 | 1/2009 | Chinnaiyan et al. |
| 2009/0061443 | A1 | 3/2009 | Zhang et al. |
| 2009/0203057 | A1 | 8/2009 | Zhang et al. |
| 2010/0035912 | A1 | 2/2010 | Debnath et al. |
| 2010/0113415 | A1 | 5/2010 | Rajapakse et al. |
| 2011/0021362 | A1 | 1/2011 | Trojer et al. |

FOREIGN PATENT DOCUMENTS

| CN | 1683526 A | 10/2005 |
| EP | 1357111 A1 | 10/2003 |
| JP | 7033729 A | 2/1995 |
| WO | WO-9640100 A1 | 12/1996 |
| WO | WO-0018725 A1 | 4/2000 |
| WO | WO-03079788 A2 | 10/2003 |
| WO | WO 2005018578 A2 | 3/2005 |
| WO | WO-2006116713 A1 | 11/2006 |
| WO | WO-2007045462 A2 | 4/2007 |
| WO | WO-2007050347 A1 | 5/2007 |

(Continued)

OTHER PUBLICATIONS

Fiskus et al., "Combined epigenetic therapy with the histone methyltransferase EZH2 inhibitor 3-deazaneplanocin A and the histone deacetylase inhibitor panobinostat against human AML cells" 114(13) Blood 2733-2743 (2009).*
Siegel et al., "Cancer Statistics, 2013" 63(1) CA: A Cancer Journal for Clinicians 11-30 (2013).*
Richon, Victoria M. et al.: "Lymphoma-Associated Mutations of EZH2 Result in a Change-of-function", Blood, American Society of Hematology, vol. 116, No. 21, Nov. 1, 2010, p. 312, XP009176070, ISSN: 0006-4971.
Garapaty-Rao, Shivani et al.: "Identification of EZH2 and EZH1 Small Molecule Inhibitors with Selective Impact on Diffuse Large B Cell Lymphoma Cell Growth", Chemistry & Biology, vol. 20, No. 11, Nov. 1, 2013, pp. 1329-1339, XP055101733, ISSN: 1074-5521, DOI: 10.1016/j.chembiol.2013.09.013.

(Continued)

*Primary Examiner* — Nancy J Leith
(74) *Attorney, Agent, or Firm* — Cooley LLP; Ivor R. Elrifi; Heidi A. Erlacher

(57) ABSTRACT

The invention relates to inhibition of wild-type and certain mutant forms of human histone methyltransferase EZH2, the catalytic subunit of the PRC2 complex which catalyzes the mono- through tri-methylation of lysine 27 on histone H3 (H3-K27). In one embodiment the inhibition is selective for the mutant form of the EZH2, such that trimethylation of H3-K27, which is associated with certain cancers, is inhibited. The methods can be used to treat cancers including follicular lymphoma and diffuse large B-cell lymphoma (DL-BCL). Also provided are methods for identifying small molecule selective inhibitors of the mutant forms of EZH2 and also methods for determining responsiveness to an EZH2 inhibitor in a subject.

8 Claims, 16 Drawing Sheets

(56) References Cited

FOREIGN PATENT DOCUMENTS

| | | |
|---|---|---|
| WO | WO-2007070818 A1 | 6/2007 |
| WO | WO 2007072225 A2 | 6/2007 |
| WO | WO-2007136592 A2 | 11/2007 |
| WO | WO-2008073138 A2 | 6/2008 |
| WO | WO-2008103277 A2 | 8/2008 |
| WO | WO-2008104077 A1 | 9/2008 |
| WO | WO-2008108825 A2 | 9/2008 |
| WO | WO-2008113006 A1 | 9/2008 |
| WO | WO-2009058298 A1 | 5/2009 |
| WO | WO-2009077766 A1 | 6/2009 |
| WO | WO-2009124137 A2 | 10/2009 |
| WO | WO-2010018328 A1 | 2/2010 |
| WO | WO-2010111653 A2 | 9/2010 |
| WO | WO-2011082044 A1 | 7/2011 |
| WO | WO-2011140324 A1 | 11/2011 |
| WO | WO-2011140325 A1 | 11/2011 |
| WO | WO-2011160206 A1 | 12/2011 |
| WO | WO-2012005805 A1 | 1/2012 |
| WO | WO-2012034132 A2 | 3/2012 |
| WO | WO-2012068589 A2 | 5/2012 |
| WO | WO-2012075080 A1 | 6/2012 |
| WO | WO-2012075500 A2 | 6/2012 |
| WO | WO-2012118812 A2 | 9/2012 |
| WO | WO-2012142513 A1 | 10/2012 |
| WO | WO-2013049770 A2 | 4/2013 |

OTHER PUBLICATIONS

Wei, Qi et al.: "Selective inhibition of Ezh2 by a small molecule inhibitor blocks tumor cells proliferation", Proceedings of the National Academy of Sciences of the United States of America, Dec. 26, 2012, vol. 109, No. 52, pp. 21360-21365, XP002720302, ISSN: 1091-6490.
Gura et al. "Systems for Identifying New Drugs are Often Faulty." *Science*. 278.5340(1997):1041-1042.
Johnson et al. "Relationships Between Drug Activity in NCI Preclinical in vitro and in vivo Models and Early Clinical Trials." *Brit. J. Cancer*. 84.10(2001):1424-1431.
Knutson et al. "A Selective Inhibitor of EZH2 Blocks H3K27 Methylation and Kills Mutant Lymphoma Cells." *Nat. Chem. Biol.* 8(2012):890-896.
Pearce et al. "Failure Modes in Anticancer Drug Discovery and Development." *Cancer Drug Design and Discovery*. Neidle, ed. Boston: Elsevier. (2008):424-435.
Simone. "Oncology: Introduction." *Cecil Textbook of Medicine*. Bennett et al., eds. Philadelphia: W. B. Saunders Co. 20th ed. 1(1996):1004-1104.
Wilson et al. "Epigenetic Antagonism Between Polycomb and SWI/SNF Complexes During Oncogenic Transformation." *Cancer Cell*. 18(2010):316-328.
Barski et al. "High-Resolution Profiling of Histone Methylations in the Human Genome." *Cell*. 129.4(2007):823-837.
Beisel et al. "Histone Methylation by the *Drosophila* Epigenetic Transcriptional Regulator Ash 1." *Nature*. 419(2002):857-862.
Bernstein et al. "A Bivalent Chromatin Structure Marks Key Developmental Genes in Embryonic Stem Cells." *Cell*. 125.2(2006):315-326.
Bracken et al. "*EZH2* is Downstream of the pRB-E2F Pathway, Essential for Proliferation and Amplified in Cancer." *EMBO J*. 22.20(2003):5323-5335.
Braña et al. "Reaction of *N*-(2-Pyridylmethyl)-3,5-dimethylbenzamide and *N*-(3-Pyridylmethyl)-3,5-dimethylbenzamide *N*-Oxides With Acetic Anhydride." *Journal of Heterocyclic Chemistry*. 19.6(1982):1297-1300.
Cao et al. "Role of Histone H3 Lysine 27 Methylation in Polycomb-Group Silencing." *Science*. 298(2002):1039-1043.
Cao et al. "Role of hPHF1 in H3K27 Methylation and Hox Gene Silencing." *Mol. Cell. Biol.* 28.5(2008):1862-1872.
Cao et al. "SUZ12 is Required for Both the Histone Methyltransferase Activity and the Silencing Function of the EED-EZH2 Complex." *Mol. Cell*. 15.1(2004):57-67.

Chen et al. "Cloning of a Human Homolog of the *Drosophila* Enhancer of Zeste Gene(*EZH2*) That Maps to Chromosome 21q22. 2." *Genomics*. 38.1(1996):30-37.
Copeland et al. "Protein Methyltransferases as a Target Class for Drug Discovery." *Nat. Rev. Drug Disc*. 8(2009):724-732.
Copeland et al. "Targeting Epigenetic Enzymes for Drug Discovery." *Curr. Opin. Chem. Biol*. 14.4(2010):505-510.
Cui et al. "Chromatin Signatures in Multipotent Human Hematopoietic Stem Cells Indicate the Fate of Bivalent Genes During Differentiation." *Cell Stem Cell*. 4.1(2009):80-93.
Czermin et al. "*Drosphila* Enhancer of Zeste/ESC Complexes Have a Histone H3 Methyltransferase Activity That Marks Chromosomal Polycomb Sites." *Cell*. 111.2(2002):185-196.
Erhardt et al. "Consequence of the Depletion of Zygotic and Embryonic Enhancer of Zests 2 During Preimplantation Mouse Development." *Development*. 130(2003):4235-4248.
Francis et al. "Mechanisms of Transcriptional Memory." *Nat. Rev. Mol. Cell Biol.* 2(2001):409-421.
GenBank Accession No. CAB02546, Apr. 18, 2005.
GenBank Accession No. NM_001203249.1, Jun. 26, 2012.
GenBank Accession No. NM_003797, Jun. 27, 2012.
GenBank Accession No. NM_004447, Jun. 26, 2012.
GenBank Accession No. NM_004456, Jun. 26, 2012.
GenBank Accession No. NM_005610, Jun. 27, 2012.
GenBank Accession No. NM_015355, Jun. 28, 2012.
GenBank Accession No. NM_152998, Jun. 26, 2012.
GenBank Accession No. NM_153207, Jun. 30, 2012.
GenBank Accession No. NP_001190178.1, Jun. 26, 2012.
GenBank Accession No. NP_694543, Jun. 26, 2012.
International Application No. PCT/US2012/026953 filed Feb. 28, 2012.
International Application No. PCT/US2012/033662 filed Apr. 13, 2012.
Kirmizis et al. "Identification of the Polycomb Group Protein SU(Z)12 as a Potential Molecular Target for Human Cancer Therapy." *Mol. Cancer Ther*. 2(2003):113-121.
Kirmizis et al. "Silencing of Human Polycomb Target Genes is Associated With Methylation of Histone H3 Lys 27." *Genes Dev*. 18(2004):1592-1605.
Kleer et al. "EZH2 is a Marker of Aggressive Breast Cancer and Promotes Neoplastic Transformation of Breast Epithelial Cells." *PNAS*. 100.20(2003):11606-11611.
Kuzmichev et al. "Histone Methyltransferase Activity Associated With a Human Multiprotein Complex Containing the Enhancer of Zeste Protein." *Genes Dev*. 16(2002):2893-2905.
Müller et al. "Histone Methyltransferase Activity of a *Drosophila* Polycomb Group Repressor Complex." *Cell*. 111.2(2002):197-208.
Martinez-Garcia et al. "Deregulation of H3K27 Methylation in Cancer." *Nat. Genet*. 42(2010):100-101.
McCabe et al. "EZH2 Inhibition as a Therapeutic Strategy for Lymphoma With EZH2-Activating Mutations." *Nature*. Epub: Oct. 10, 2012.
Milne et al. "MLL Targets SET Domain Methyltransferase Activity to *Hox* Gene Promoters." *Mol. Cell*. 10.5(2002):1107-1117.
Nakamura et al. "ALL-1 is a Histone Methyltransferase That Assembles a Supercomplex of Proteins Involved in Transcriptional Regulation." *Mol. Cell*. 10.5(2002):1119-1128.
Otte et al. "Gene Repression by Polycomb Group Protein Complexes: A Distinct Complex for Every Occasion?" *Curr. Opin. Genet. Dev.* 13.5(2003):448-454.
Plath et al. "Role of Histone H3 Lysince 27 Methylation in X Inactivation." *Science*. 300(2003):131-135.
Pollock et al. "Epigenetic Approaches to Cancer Therapy." *Drug Disc. Today*. 6.2(2009):71-79.
Sarma et al. "EZH2 Requires PHF1 to Efficiently Catalyze H3 Lysine 27 Trimethylation in Vivo." *Mol. Cell. Biol*. 28.8(2008):2718-2731.
Sculley et al. "Some Amide Derivatives of Certain Aminomethylpyridines." *J. Am. Chem. Soc.* 75.14(1953):3400-3403.
Shen et al. "EZH1 Mediates Methylation on Histone H3 Lysine 27 and Complements EZH2 in Maintaining Stem Cell Identity and Executing Pluripotency." *Mol. Cell*. 32.4(2008):491-502.

(56) References Cited

OTHER PUBLICATIONS

Silva et al. "Establishment of Histone H3 Methylation on the Inactive X Chromosome Requires Transient Recruitment of Eed-Enx1 Polycomb Group Complexes." *Dev. Cell.* 4.4(2003):481-495.

Simon et al. "Roles of the EZH2 Histone Methyltransferase in Cancer Epigenetics." *Mutat. Res.* 647.1-2(2008):21-29.

Swiss-Prot Accession No. Q15910, Mar. 21, 2012.

Townsend et al. "New S-Adenosyl-L-Methionine Analogues: Synthesis and Reactivity Studies." *Org. Lett.* 11.14(2009):2976-2979.

van Haaften et al. "Somatic Mutations of the Histone H3K27 Demethylase Gene *UTX* in Human Cancer." *Nat. Genet.* 41(2009):521-523.

Varambally et al. "The Polycomb Group Protein EZH2 is Involved in Progression of Prostate Cancer." *Nature.* 419(2002):624-629.

Wang et al. "A Novel Human Homologue of *Drosophila* Polycomb-like Gene is Up-Regulated in Multiple Cancers." *Gene.* 343.1(2004):69-78.

Kubicek et al. "Reversal of H3K9me2 by a Small Molecule Inhibitor for the G9a Histone Methytransferase." *Mol. Cell.* 25(2007):473-481.

Majer et al. "A687V EZH2 is a Gain-of-Function Mutation Found in Lymphoma Patients." *FEBS Lett.* 586.19(2012):3448-3451.

Ryan et al. "EZH2 Codon 641 Mutations are Common in BCL2-Rearranged Germinal Center B Cell Lymphomas." *PLoS One.* 6.12(2011):E28585.

Lohr et al. "Discovery and Prioritization of Somatic Mutations in Diffuse Large B-Cell Lymphoma (DLBCL) by Whole-Exome Sequencing." *PNAS.* 109.10(2012):3879-3884. Epub Feb. 17, 2012.

Martinez-Garcia et al. "The MMSET Histone Methyl Transferase Switches Global Histone Methylation and Alters Gene Expression in t(4;14) Multiple Myeloma Cells." *Blood.* 117(2011):211-220.

McCabe et al. "Mutation of A677 in Histone Methyltransferase EZH2 in Human B-Cell Lymphoma Promotes Hypertrimethylation of Histone H3 on Lysine 27 (H3K27)." *PNAS.* 109.8(2012):2989-2994.

Miranda et al. "DZNep is a Global Histone Methylation Inhibitor That Reactivates Developmental Genes not Silenced by DNA Methylation." *Mol. Cancer Ther.* 8.6(2009):1579-1588.

Morin et al. "Somatic Mutations Altering EZh2 (Tyr641) in Follicular and Diffuse Large B-Cell Lymphomas of Germinal-Center Origin." *Nat. Genet.* 42.2(2010):181-185.

Sneeringer et al. "Coordinated Activities of Wild-Type Plus Mutant EZH2 Drive Tumor-Associated Hypertrimethylation of Lysine 27 on Histone H3 (H3K27) in Human B-Cell Lymphomas." *PNAS.* 107.49(2010):20980-20985.

Wigle et al. "The Y641C Mutation of EZH Alters Substrate Specificity for Histone H3 Lysine 27 Methylation States." *FEBS Lett.* 585.19(2011):3011-3014.

Yap et al. "Somatic Mutations at EZH2 Y641 Act Dominantly Through a Mechanism of Selectively Altered PRC2 Catalytic Activity, to Increase H3K27 Trimethylation." *Blood.* 117.8(2010):2451-2459.

* cited by examiner

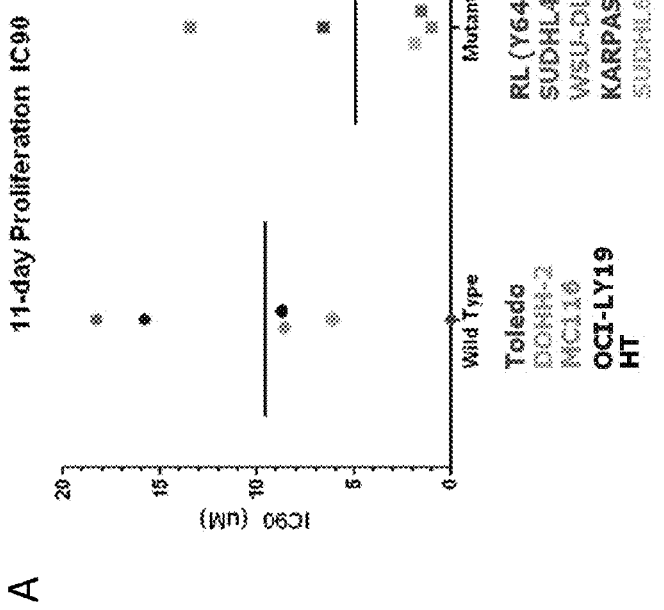
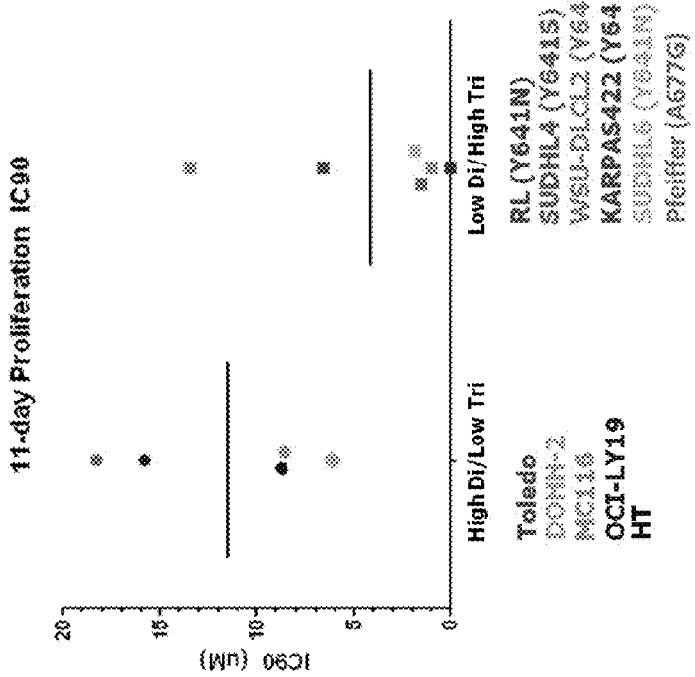
FIG. 14

SEQUENCE LISTING

<160> NUMBER OF SEQ ID NOS: 22

<210> SEQ ID NO 1
<211> LENGTH: 746
<212> TYPE: PRT
<213> ORGANISM: Homo sapiens

<400> SEQUENCE: 1

```
Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Gly Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
    210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Pro Phe His Ala Thr Pro Asn
    290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
                325                 330                 335

Ala Leu Thr Ala Glu Arg Ile Lys Thr Pro Pro Lys Arg Pro Gly Gly
            340                 345                 350

Arg Arg Arg Gly Arg Leu Pro Asn Asn Ser Ser Arg Pro Ser Thr Pro
        355                 360                 365
```

Thr Ile Asn Val Leu Glu Ser Lys Asp Thr Asp Ser Asp Arg Glu Ala
370                 375                 380

Gly Thr Glu Thr Gly Gly Glu Asn Asn Asp Lys Glu Glu Glu Glu Lys
385                 390                 395                 400

Lys Asp Glu Thr Ser Ser Ser Glu Ala Asn Ser Arg Cys Gln Thr
                405                 410                 415

Pro Ile Lys Met Lys Pro Asn Ile Glu Pro Glu Asn Val Glu Trp
            420                 425                 430

Ser Gly Ala Glu Ala Ser Met Phe Arg Val Leu Ile Gly Thr Tyr Tyr
                435                 440                 445

Asp Asn Phe Cys Ala Ile Ala Arg Leu Ile Gly Thr Lys Thr Cys Arg
450                 455                 460

Gln Val Tyr Glu Phe Arg Val Lys Glu Ser Ser Ile Ala Pro Ala
465                 470                 475                 480

Pro Ala Glu Asp Val Asp Thr Pro Arg Lys Lys Arg Lys His
                485                 490                 495

Arg Leu Trp Ala Ala His Cys Arg Lys Ile Gln Leu Lys Lys Asp Gly
                500                 505                 510

Ser Ser Asn His Val Tyr Asn Tyr Gln Pro Cys Asp His Pro Arg Gln
                515                 520                 525

Pro Cys Asp Ser Ser Cys Pro Cys Val Ile Ala Gln Asn Phe Cys Glu
530                 535                 540

Lys Phe Cys Gln Cys Ser Ser Glu Cys Gln Asn Arg Phe Pro Gly Cys
545                 550                 555                 560

Arg Cys Lys Ala Gln Cys Asn Thr Lys Gln Cys Pro Cys Tyr Leu Ala
                565                 570                 575

Val Arg Glu Cys Asp Pro Asp Leu Cys Leu Thr Cys Gly Ala Ala Asp
                580                 585                 590

His Trp Asp Ser Lys Asn Val Ser Cys Lys Asn Cys Ser Ile Gln Arg
                595                 600                 605

Gly Ser Lys Lys His Leu Leu Leu Ala Pro Ser Asp Val Ala Gly Trp
610                 615                 620

Gly Ile Phe Ile Lys Asp Pro Val Gln Lys Asn Glu Phe Ile Ser Glu
625                 630                 635                 640

Tyr Cys Gly Glu Ile Ile Ser Gln Asp Glu Ala Asp Arg Arg Gly Lys
                645                 650                 655

Val Tyr Asp Lys Tyr Met Cys Ser Phe Leu Phe Asn Leu Asn Asn Asp
                660                 665                 670

Phe Val Val Asp Ala Thr Arg Lys Gly Asn Lys Ile Arg Phe Ala Asn
                675                 680                 685

His Ser Val Asn Pro Asn Cys Tyr Ala Lys Val Met Met Val Asn Gly
690                 695                 700

Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr
                725                 730                 735

Val Gly Ile Glu Arg Glu Met Glu Ile Pro
                740                 745

<210> SEQ ID NO 2
<211> LENGTH: 2723
<212> TYPE: DNA
<213> ORGANISM: Homo sapiens

<400> SEQUENCE: 2

-continued

```
ggcggcgctt gattgggctg gggggggccaa ataaaagcga tggcgattgg gctgccgcgt    60
ttggcgctcg gtccggtcgc gtccgacacc cggtgggact cagaaggcag tggagccccg   120
gcggcggcgg cggcggcgcg cggggggcgac gcgcgggaac aacgcgagtc ggcgcgcggg   180
acgaagaata atcatgggcc agactgggaa gaaatctgag aagggaccag tttgttggcg   240
gaagcgtgta aaatcagagt acatgcgact gagacagctc aagaggttca gacgagctga   300
tgaagtaaag agtatgttta gttccaatcg tcagaaaatt ttggaaagaa cggaaatctt   360
aaaccaagaa tggaaacagc gaaggataca gcctgtgcac atcctgactt ctgtgagctc   420
attgcgcggg actagggagt gttcggtgac cagtgacttg gattttccaa cacaagtcat   480
cccattaaag actctgaatg cagttgcttc agtacccata atgtattctt ggtctcccct   540
acagcagaat tttatggtgg aagatgaaac tgttttacat aacattcctt atatgggaga   600
tgaagttttta gatcaggatg gtactttcat tgaagaacta ataaaaaatt atgatgggaa   660
agtacacggg gatagagaat gtgggtttat aaatgatgaa attttttgtgg agttggtgaa   720
tgcccttggt caatataatg atgatgacga tgatgatgat ggagacgatc ctgaagaaag   780
agaagaaaag cagaaagatc tggaggatca ccgagatgat aaagaaagcc gcccacctcg   840
gaaatttcct tctgataaaa ttttttgaagc catttcctca atgtttccag ataagggcac   900
agcagaagaa ctaaaggaaa aatataaaga actcaccgaa cagcagctcc caggcgcact   960
tcctcctgaa tgtaccccca acatagatgg accaaatgct aaatctgttc agagagagca  1020
aagcttacac tcctttcata cgcttttctg taggcgatgt tttaaatatg actgcttcct  1080
acatcgtaag tgcaattatt cttttcatgc aacacccaac acttataagc ggaagaacac  1140
agaaacagct ctagacaaca aaccttgtgg accacagtgt taccagcatt tggagggagc  1200
aaaggagttt gctgctgctc tcaccgctga gcggataaag accccaccaa aacgtccagg  1260
aggccgcaga agaggacggc ttcccaataa cagtagcagg cccagcaccc ccaccattaa  1320
tgtgctggaa tcaaaggata cagacagtga tagggaagca gggactgaaa cggggggaga  1380
gaacaatgat aaagaagaag aagagaagaa agatgaaact tcgagctcct ctgaagcaaa  1440
ttctcggtgt caaacaccaa taaagatgaa gccaaatatt gaacctcctg agaatgtgga  1500
gtggagtggt gctgaagcct caatgtttag agtcctcatt ggcacttact atgacaattt  1560
ctgtgccatt gctaggttaa ttgggaccaa aacatgtaga caggtgtatg agtttagagt  1620
caaagaatct agcatcatag ctccagctcc cgctgaggat gtggatactc ctccaaggaa  1680
aaagaagagg aaacaccggt tgtgggctgc acactgcaga aagatacagc tgaaaaagga  1740
cggctcctct aaccatgttt acaactatca accctgtgat catccacggc agccttgtga  1800
cagttcgtgc ccttgtgtga tagcacaaaa ttttttgtgaa aagttttgtc aatgtagttc  1860
agagtgtcaa aaccgctttc cgggatgccg ctgcaaagca cagtgcaaca ccaagcagtg  1920
cccgtgctac ctggctgtcc gagagtgtga ccctgacctc tgtcttactt gtggagccgc  1980
tgaccattgg gacagtaaaa atgtgtcctg caagaactgc agtattcagc ggggctccaa  2040
aaagcatcta ttgctggcac catctgacgt ggcaggctgg gggattttta tcaaagatcc  2100
tgtgcagaaa aatgaattca tctcagaata ctgtggagag attatttctc aagatgaagc  2160
tgacagaaga gggaaagtgt atgataaata catgtgcagc tttctgttca acttgaacaa  2220
tgattttgtg gtggatgcaa cccgcaaggg taacaaaatt cgtttttgcaa atcattcggt  2280
aaatccaaac tgctatgcaa aagttatgat ggttaacggt gatcacagga taggtatttt  2340
```

```
tgccaagaga gccatccaga ctggcgaaga gctgttttt gattacagat acagccaggc    2400
tgatgccctg aagtatgtcg gcatcgaaag agaaatggaa atcccttgac atctgctacc    2460 tcctccccc tcctctgaaa cagctgcctt agcttcagga acctcgagta ctgtgggcaa    2520
tttagaaaaa gaacatgcag tttgaaattc tgaatttgca agtactgta agaataattt    2580 atagtaatga gtttaaaaat caactttta ttgccttctc accagctgca aagtgttttg    2640
taccagtgaa tttttgcaat aatgcagtat ggtacatttt tcaactttga ataaagaata    2700
cttgaacttg tccttgttga atc                                            2723
```

<210> SEQ ID NO 3
<211> LENGTH: 751
<212> TYPE: PRT
<213> ORGANISM: Homo sapiens

<400> SEQUENCE: 3

```
Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
                20                  25                  30

Arg Arg Ala Asp Glu Val Lys Ser Met Phe Ser Ser Asn Arg Gln Lys
            35                  40                  45

Ile Leu Glu Arg Thr Glu Ile Leu Asn Gln Glu Trp Lys Gln Arg Arg
        50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Gly Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
    210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Arg Lys Cys Asn Tyr Ser Phe
    290                 295                 300
```

```
His Ala Thr Pro Asn Thr Tyr Lys Arg Lys Asn Thr Glu Thr Ala Leu
305                 310                 315                 320

Asp Asn Lys Pro Cys Gly Pro Gln Cys Tyr Gln His Leu Glu Gly Ala
            325                 330                 335

Lys Glu Phe Ala Ala Ala Leu Thr Ala Glu Arg Ile Lys Thr Pro Pro
        340                 345                 350

Lys Arg Pro Gly Gly Arg Arg Gly Arg Leu Pro Asn Asn Ser Ser
        355                 360                 365

Arg Pro Ser Thr Pro Thr Ile Asn Val Leu Glu Ser Lys Asp Thr Asp
        370                 375                 380

Ser Asp Arg Glu Ala Gly Thr Glu Thr Gly Gly Glu Asn Asn Asp Lys
385                 390                 395                 400

Glu Glu Glu Glu Lys Lys Asp Glu Thr Ser Ser Ser Glu Ala Asn
            405                 410                 415

Ser Arg Cys Gln Thr Pro Ile Lys Met Lys Pro Asn Ile Glu Pro Pro
            420                 425                 430

Glu Asn Val Glu Trp Ser Gly Ala Glu Ala Ser Met Phe Arg Val Leu
            435                 440                 445

Ile Gly Thr Tyr Tyr Asp Asn Phe Cys Ala Ile Ala Arg Leu Ile Gly
    450                 455                 460

Thr Lys Thr Cys Arg Gln Val Tyr Glu Phe Arg Val Lys Glu Ser Ser
465                 470                 475                 480

Ile Ile Ala Pro Ala Pro Ala Glu Asp Val Asp Thr Pro Pro Arg Lys
            485                 490                 495

Lys Lys Arg Lys His Arg Leu Trp Ala Ala His Cys Arg Lys Ile Gln
            500                 505                 510

Leu Lys Lys Asp Gly Ser Ser Asn His Val Tyr Asn Tyr Gln Pro Cys
        515                 520                 525

Asp His Pro Arg Gln Pro Cys Asp Ser Ser Cys Pro Cys Val Ile Ala
        530                 535                 540

Gln Asn Phe Cys Glu Lys Phe Cys Gln Cys Ser Ser Glu Cys Gln Asn
545                 550                 555                 560

Arg Phe Pro Gly Cys Arg Cys Lys Ala Gln Cys Asn Thr Lys Gln Cys
            565                 570                 575

Pro Cys Tyr Leu Ala Val Arg Glu Cys Asp Pro Asp Leu Cys Leu Thr
        580                 585                 590

Cys Gly Ala Ala Asp His Trp Asp Ser Lys Asn Val Ser Cys Lys Asn
        595                 600                 605

Cys Ser Ile Gln Arg Gly Ser Lys Lys His Leu Leu Leu Ala Pro Ser
    610                 615                 620

Asp Val Ala Gly Trp Gly Ile Phe Ile Lys Asp Pro Val Gln Lys Asn
625                 630                 635                 640

Glu Phe Ile Ser Glu Tyr Cys Gly Glu Ile Ile Ser Gln Asp Glu Ala
            645                 650                 655

Asp Arg Arg Gly Lys Val Tyr Asp Lys Tyr Met Cys Ser Phe Leu Phe
            660                 665                 670

Asn Leu Asn Asn Asp Phe Val Val Asp Ala Thr Arg Lys Gly Asn Lys
        675                 680                 685

Ile Arg Phe Ala Asn His Ser Val Asn Pro Asn Cys Tyr Ala Lys Val
        690                 695                 700

Met Met Val Asn Gly Asp His Arg Ile Gly Ile Phe Ala Lys Arg Ala
705                 710                 715                 720

Ile Gln Thr Gly Glu Glu Leu Phe Phe Asp Tyr Arg Tyr Ser Gln Ala
```

```
                      725                 730                 735
Asp Ala Leu Lys Tyr Val Gly Ile Glu Arg Glu Met Glu Ile Pro
        740                 745                 750

<210> SEQ ID NO 4
<211> LENGTH: 2591
<212> TYPE: DNA
<213> ORGANISM: Homo sapiens

<400> SEQUENCE: 4
ggcggcgctt gattgggctg gggggggccaa ataaaagcga tggcgattgg gctgccgcgt    60
ttggcgctcg gtccggtcgc gtccgacacc cggtgggact cagaaggcag tggagccccg   120
gcggcggcgg cggcggcgcg cggggggcgac gcgcgggaac aacgcgagtc ggcgcgcggg   180
acgaagaata atcatgggcc agactgggaa gaaatctgag aagggaccag tttgttggcg   240
gaagcgtgta aaatcagagt acatgcgact gagacagctc aagaggttca gacgagctga   300
tgaagtaaag agtatgtttta gttccaatcg tcagaaaatt ttggaaagaa cggaaatctt   360
aaaccaagaa tggaaacagc gaaggataca gcctgtgcac atcctgactt ctgtgagctc   420
attgcgcggg actagggagg tggaagatga aactgtttta cataacattc cttatatggg   480
agatgaagtt ttagatcagg atggtacttt cattgaagaa ctaataaaaa attatgatgg   540
gaaagtacac ggggatagag aatgtgggtt tataaatgat gaaatttttg tggagttggt   600
gaatgccctt ggtcaatata tgatgatga cgatgatgat gatggagacg atcctgaaga   660
aagagaagaa aagcagaaag atctggagga tcaccgagat gataaagaaa gccgcccacc   720
tcggaaattt ccttctgata aaattttttga agccatttcc tcaatgtttc cagataaggg   780
cacagcagaa gaactaaagg aaaaatataa agaactcacc gaacagcagc tcccaggcgc   840
acttcctcct gaatgtaccc ccaacataga tggaccaaat gctaaatctg ttcagagaga   900
gcaaagctta cactcctttc atacgctttt ctgtaggcga tgtttttaaat atgactgctt   960 cctacatcct tttcatgcaa cacccaacac ttataagcgg aagaacacag aaacagctct  1020
agacaacaaa ccttgtggac cacagtgtta ccagcatttg gagggagcaa aggagtttgc  1080
tgctgctctc accgctgagc ggataaagac cccaccaaaa cgtccaggag ccgcagaag   1140 aggacggctt cccaataaca gtagcaggcc cagcaccccc accattaatg tgctggaatc  1200
aaaggataca gacagtgata gggaagcagg gactgaaacg gggggagaga caatgataaa  1260
agaagaagaa gagaagaaag atgaaacttc gagctcctct gaagcaaatt ctcggtgtca  1320
aacaccaata aagatgaagc caaatattga acctcctgag aatgtggagt ggagtggtgc  1380
tgaagcctca atgttgagag tcctcattgg cacttactat gacaatttct gtgccattgc  1440
taggttaatt gggaccaaaa catgtagaca ggtgtatgaa tttagagtca agaatctag   1500 catcatagct ccagctcccg ctgaggatgt ggatactcct ccaaggaaaa agaagaggaa  1560
acaccggttg tgggctgcac actgcagaaa gatacagctg aaaaaggacg ctcctctaa   1620 ccatgtttac aactatcaac cctgtgatca tccacggcag ccttgtgaca gttcgtgccc  1680
ttgtgtgata gcacaaaatt tttgtgaaaa gttttgtcaa tgtagttcag agtgtcaaaa  1740
ccgctttccg ggatgccgct gcaaagcaca gtgcaacacc aagcagtgcc cgtgctacct  1800
ggctgtccga gagtgtgacc ctgacctctg tcttacttgt ggagccgctg accattggga  1860
cagtaaaaat gtgtcctgca agaactgcag tattcagcgg ggctccaaaa agcatctatt  1920
gctggcacca tctgacgtgg caggctgggg gattttttatc aaagatcctg tgcagaaaaa  1980
```

```
tgaattcatc tcagaatact gtggagagat tatttctcaa gatgaagctg acagaagagg    2040
gaaagtgtat gataaataca tgtgcagctt tctgttcaac ttgaacaatg attttgtggt    2100
ggatgcaacc cgcaagggta acaaaattcg ttttgcaaat cattcggtaa atccaaactg    2160
ctatgcaaaa gttatgatgg ttaacggtga tcacaggata ggtattttg  ccaagagagc    2220 catccagact ggcgaagagc tgttttttga ttacagatac agccaggctg atgccctgaa    2280
gtatgtcggc atcgaaagag aaatggaaat cccttgacat ctgctacctc ctcccccctc    2340
ctctgaaaca gctgccttag cttcaggaac ctcgagtact gtgggcaatt tagaaaaaga    2400
acatgcagtt tgaaattctg aatttgcaaa gtactgtaag aataatttat agtaatgagt    2460
ttaaaaatca acttttatt gccttctcac cagctgcaaa gtgttttgta ccagtgaatt     2520
tttgcaataa tgcagtatgg tacatttttc aactttgaat aaagaatact tgaacttgtc    2580
cttgttgaat c                                                         2591
```

<210> SEQ ID NO 5
<211> LENGTH: 707
<212> TYPE: PRT
<213> ORGANISM: Homo sapiens

<400> SEQUENCE: 5

```
Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Ser Leu Arg Gly Thr
65                  70                  75                  80

Arg Glu Val Glu Asp Thr Val Leu His Asn Ile Pro Tyr Met Gly
                85                  90                  95

Asp Glu Val Leu Asp Gln Asp Gly Thr Phe Ile Glu Glu Leu Ile Lys
            100                 105                 110

Asn Tyr Asp Gly Lys Val His Gly Asp Arg Glu Cys Gly Phe Ile Asn
        115                 120                 125

Asp Glu Ile Phe Val Glu Leu Val Asn Ala Leu Gly Gln Tyr Asn Asp
    130                 135                 140

Asp Asp Asp Asp Asp Gly Asp Asp Pro Glu Glu Arg Glu Glu Lys
145                 150                 155                 160

Gln Lys Asp Leu Glu Asp His Arg Asp Asp Lys Glu Ser Arg Pro Pro
                165                 170                 175

Arg Lys Phe Pro Ser Asp Lys Ile Phe Glu Ala Ile Ser Ser Met Phe
            180                 185                 190

Pro Asp Lys Gly Thr Ala Glu Glu Leu Lys Glu Lys Tyr Lys Glu Leu
        195                 200                 205

Thr Glu Gln Gln Leu Pro Gly Ala Leu Pro Pro Glu Cys Thr Pro Asn
    210                 215                 220

Ile Asp Gly Pro Asn Ala Lys Ser Val Gln Arg Glu Gln Ser Leu His
225                 230                 235                 240

Ser Phe His Thr Leu Phe Cys Arg Arg Cys Phe Lys Tyr Asp Cys Phe
                245                 250                 255

Leu His Pro Phe His Ala Thr Pro Asn Thr Tyr Lys Arg Lys Asn Thr
```

-continued

```
              260                 265                 270
Glu Thr Ala Leu Asp Asn Lys Pro Cys Gly Pro Gln Cys Tyr Gln His
            275                 280                 285
Leu Glu Gly Ala Lys Glu Phe Ala Ala Leu Thr Ala Glu Arg Ile
        290                 295                 300
Lys Thr Pro Pro Lys Arg Pro Gly Gly Arg Arg Gly Arg Leu Pro
305                 310                 315                 320
Asn Asn Ser Ser Arg Pro Ser Thr Pro Thr Ile Asn Val Leu Glu Ser
                325                 330                 335
Lys Asp Thr Asp Ser Asp Arg Glu Ala Gly Thr Glu Thr Gly Gly Glu
            340                 345                 350
Asn Asn Asp Lys Glu Glu Glu Lys Lys Asp Glu Thr Ser Ser Ser
        355                 360                 365
Ser Glu Ala Asn Ser Arg Cys Gln Thr Pro Ile Lys Met Lys Pro Asn
    370                 375                 380
Ile Glu Pro Pro Glu Asn Val Glu Trp Ser Gly Ala Glu Ala Ser Met
385                 390                 395                 400
Phe Arg Val Leu Ile Gly Thr Tyr Tyr Asp Asn Phe Cys Ala Ile Ala
                405                 410                 415
Arg Leu Ile Gly Thr Lys Thr Cys Arg Gln Val Tyr Glu Phe Arg Val
            420                 425                 430
Lys Glu Ser Ser Ile Ile Ala Pro Ala Pro Ala Glu Asp Val Asp Thr
        435                 440                 445
Pro Pro Arg Lys Lys Lys Arg Lys His Arg Leu Trp Ala Ala His Cys
    450                 455                 460
Arg Lys Ile Gln Leu Lys Lys Asp Gly Ser Ser Asn His Val Tyr Asn
465                 470                 475                 480
Tyr Gln Pro Cys Asp His Pro Arg Gln Pro Cys Asp Ser Ser Cys Pro
                485                 490                 495
Cys Val Ile Ala Gln Asn Phe Cys Glu Lys Phe Cys Gln Cys Ser Ser
            500                 505                 510
Glu Cys Gln Asn Arg Phe Pro Gly Cys Arg Cys Lys Ala Gln Cys Asn
        515                 520                 525
Thr Lys Gln Cys Pro Cys Tyr Leu Ala Val Arg Glu Cys Asp Pro Asp
    530                 535                 540
Leu Cys Leu Thr Cys Gly Ala Ala Asp His Trp Asp Ser Lys Asn Val
545                 550                 555                 560
Ser Cys Lys Asn Cys Ser Ile Gln Arg Gly Ser Lys Lys His Leu Leu
                565                 570                 575
Leu Ala Pro Ser Asp Val Ala Gly Trp Gly Ile Phe Ile Lys Asp Pro
            580                 585                 590
Val Gln Lys Asn Glu Phe Ile Ser Glu Tyr Cys Gly Glu Ile Ile Ser
        595                 600                 605
Gln Asp Glu Ala Asp Arg Arg Gly Lys Val Tyr Asp Lys Tyr Met Cys
    610                 615                 620
Ser Phe Leu Phe Asn Leu Asn Asn Asp Phe Val Val Asp Ala Thr Arg
625                 630                 635                 640
Lys Gly Asn Lys Ile Arg Phe Ala Asn His Ser Val Asn Pro Asn Cys
                645                 650                 655
Tyr Ala Lys Val Met Met Val Asn Gly Asp His Arg Ile Gly Ile Phe
            660                 665                 670
Ala Lys Arg Ala Ile Gln Thr Gly Glu Glu Leu Phe Phe Asp Tyr Arg
        675                 680                 685
```

```
Tyr Ser Gln Ala Asp Ala Leu Lys Tyr Val Gly Ile Glu Arg Glu Met
    690                 695                 700

Glu Ile Pro
705

<210> SEQ ID NO 6
<211> LENGTH: 200
<212> TYPE: PRT
<213> ORGANISM: Homo sapiens

<400> SEQUENCE: 6

Ser Cys Pro Cys Val Ile Ala Gln Asn Phe Cys Glu Lys Phe Cys Gln
  1               5                  10                  15

Cys Ser Ser Glu Cys Gln Asn Arg Phe Pro Gly Cys Arg Cys Lys Ala
             20                  25                  30

Gln Cys Asn Thr Lys Gln Cys Pro Cys Tyr Leu Ala Val Arg Glu Cys
         35                  40                  45

Asp Pro Asp Leu Cys Leu Thr Cys Gly Ala Ala Asp His Trp Asp Ser
     50                  55                  60

Lys Asn Val Ser Cys Lys Asn Cys Ser Ile Gln Arg Gly Ser Lys Lys
 65                  70                  75                  80

His Leu Leu Leu Ala Pro Ser Asp Val Ala Gly Trp Gly Ile Phe Ile
                 85                  90                  95

Lys Asp Pro Val Gln Lys Asn Glu Phe Ile Ser Glu Tyr Cys Gly Glu
            100                 105                 110

Ile Ile Ser Gln Asp Glu Ala Asp Arg Arg Gly Lys Val Tyr Asp Lys
        115                 120                 125

Tyr Met Cys Ser Phe Leu Phe Asn Leu Asn Asn Asp Phe Val Val Asp
    130                 135                 140

Ala Thr Arg Lys Gly Asn Lys Ile Arg Phe Ala Asn His Ser Val Asn
145                 150                 155                 160

Pro Asn Cys Tyr Ala Lys Val Met Met Val Asn Gly Asp His Arg Ile
                165                 170                 175

Gly Ile Phe Ala Lys Arg Ala Ile Gln Thr Gly Glu Glu Leu Phe Phe
            180                 185                 190

Asp Tyr Arg Tyr Ser Gln Ala Asp
        195                 200

<210> SEQ ID NO 7
<211> LENGTH: 114
<212> TYPE: PRT
<213> ORGANISM: Homo sapiens

<400> SEQUENCE: 7

His Leu Leu Leu Ala Pro Ser Asp Val Ala Gly Trp Gly Ile Phe Ile
  1               5                  10                  15

Lys Asp Pro Val Gln Lys Asn Glu Phe Ile Ser Glu Tyr Cys Gly Glu
             20                  25                  30

Ile Ile Ser Gln Asp Glu Ala Asp Arg Arg Gly Lys Val Tyr Asp Lys
         35                  40                  45

Tyr Met Cys Ser Phe Leu Phe Asn Leu Asn Asn Asp Phe Val Val Asp
     50                  55                  60

Ala Thr Arg Lys Gly Asn Lys Ile Arg Phe Ala Asn His Ser Val Asn
 65                  70                  75                  80

Pro Asn Cys Tyr Ala Lys Val Met Met Val Asn Gly Asp His Arg Ile
                 85                  90                  95
```

```
Gly Ile Phe Ala Lys Arg Ala Ile Gln Thr Gly Glu Glu Leu Phe Phe
                100                 105                 110
Asp Tyr

<210> SEQ ID NO 8
<211> LENGTH: 342
<212> TYPE: DNA
<213> ORGANISM: Homo sapiens

<400> SEQUENCE: 8
catctattgc tggcaccatc tgacgtggca ggctggggga tttttatcaa agatcctgtg     60
cagaaaaatg aattcatctc agaatactgt ggagagatta tttctcaaga tgaagctgac    120
agaagaggga aagtgtatga taaatacatg tgcagctttc tgttcaactt gaacaatgat    180
tttgtggtgg atgcaacccg caagggtaac aaaattcgtt ttgcaaatca ttcggtaaat    240
ccaaactgct atgcaaaagt tatgatggtt aacggtgatc acaggatagg tatttttgcc    300
aagagagcca tccagactgg cgaagagctg tttttttgatt ac                      342

<210> SEQ ID NO 9
<211> LENGTH: 746
<212> TYPE: PRT
<213> ORGANISM: Artificial Sequence
<220> FEATURE:
<223> OTHER INFORMATION: Y641 mutant of Homo sapiens EZH2, wherein x can
      be any amino acid residue other than tyrosine (Y)
<220> FEATURE:
<221> NAME/KEY: MISC_FEATURE
<222> LOCATION: (641)..(641)
<223> OTHER INFORMATION: Xaa can be any naturally occurring amino acid
      other than tyrosine (Y)

<400> SEQUENCE: 9

Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
                20                  25                  30

Arg Arg Ala Asp Glu Val Lys Ser Met Phe Ser Ser Asn Arg Gln Lys
            35                  40                  45

Ile Leu Glu Arg Thr Glu Ile Leu Asn Gln Glu Trp Lys Gln Arg Arg
        50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
                100                 105                 110

Trp Ser Pro Leu Gln Gln Asn Phe Met Val Glu Asp Glu Thr Val Leu
            115                 120                 125

His Asn Ile Pro Tyr Met Gly Asp Glu Val Leu Asp Gln Asp Gly Thr
        130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Asp Gly Asp Asp
                180                 185                 190

Pro Glu Glu Arg Glu Glu Lys Gln Lys Asp Leu Glu Asp His Arg Asp
```

```
                195                 200                 205
Asp Lys Glu Ser Arg Pro Pro Arg Lys Phe Pro Ser Asp Lys Ile Phe
210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Pro Phe His Ala Thr Pro Asn
290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
                325                 330                 335

Ala Leu Thr Ala Glu Arg Ile Lys Thr Pro Pro Lys Arg Pro Gly Gly
            340                 345                 350

Arg Arg Arg Gly Arg Leu Pro Asn Asn Ser Ser Arg Pro Ser Thr Pro
        355                 360                 365

Thr Ile Asn Val Leu Glu Ser Lys Asp Thr Asp Ser Asp Arg Glu Ala
370                 375                 380

Gly Thr Glu Thr Gly Gly Glu Asn Asn Asp Lys Glu Glu Glu Glu Lys
385                 390                 395                 400

Lys Asp Glu Thr Ser Ser Ser Glu Ala Asn Ser Arg Cys Gln Thr
                405                 410                 415

Pro Ile Lys Met Lys Pro Asn Ile Glu Pro Pro Glu Asn Val Glu Trp
            420                 425                 430

Ser Gly Ala Glu Ala Ser Met Phe Arg Val Leu Ile Gly Thr Tyr Tyr
        435                 440                 445

Asp Asn Phe Cys Ala Ile Ala Arg Leu Ile Gly Thr Lys Thr Cys Arg
450                 455                 460

Gln Val Tyr Glu Phe Arg Val Lys Glu Ser Ser Ile Ile Ala Pro Ala
465                 470                 475                 480

Pro Ala Glu Asp Val Asp Thr Pro Pro Arg Lys Lys Lys Arg Lys His
                485                 490                 495

Arg Leu Trp Ala Ala His Cys Arg Lys Ile Gln Leu Lys Lys Asp Gly
            500                 505                 510

Ser Ser Asn His Val Tyr Asn Tyr Gln Pro Cys Asp His Pro Arg Gln
        515                 520                 525

Pro Cys Asp Ser Ser Cys Pro Cys Val Ile Ala Gln Asn Phe Cys Glu
530                 535                 540

Lys Phe Cys Gln Cys Ser Ser Glu Cys Gln Asn Arg Phe Pro Gly Cys
545                 550                 555                 560

Arg Cys Lys Ala Gln Cys Asn Thr Lys Gln Cys Pro Cys Tyr Leu Ala
                565                 570                 575

Val Arg Glu Cys Asp Pro Asp Leu Cys Leu Thr Cys Gly Ala Ala Asp
            580                 585                 590

His Trp Asp Ser Lys Asn Val Ser Cys Lys Asn Cys Ser Ile Gln Arg
        595                 600                 605

Gly Ser Lys Lys His Leu Leu Leu Ala Pro Ser Asp Val Ala Gly Trp
610                 615                 620
```

```
Gly Ile Phe Ile Lys Asp Pro Val Gln Lys Asn Glu Phe Ile Ser Glu
625                 630                 635                 640

Xaa Cys Gly Glu Ile Ile Ser Gln Asp Glu Ala Asp Arg Arg Gly Lys
                645                 650                 655

Val Tyr Asp Lys Tyr Met Cys Ser Phe Leu Phe Asn Leu Asn Asn Asp
            660                 665                 670

Phe Val Val Asp Ala Thr Arg Lys Gly Asn Lys Ile Arg Phe Ala Asn
        675                 680                 685

His Ser Val Asn Pro Asn Cys Tyr Ala Lys Val Met Met Val Asn Gly
    690                 695                 700

Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr
                725                 730                 735

Val Gly Ile Glu Arg Glu Met Glu Ile Pro
            740                 745

<210> SEQ ID NO 10
<211> LENGTH: 746
<212> TYPE: PRT
<213> ORGANISM: Artificial Sequence
<220> FEATURE:
<223> OTHER INFORMATION: Y641F mutant of Homo sapiens EZH2

<400> SEQUENCE: 10

Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Asp Gly Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
    210                 215                 220

Glu Ala Ile Ser Ser Met Phe Pro Asp Lys Gly Thr Ala Glu Glu Leu
225                 230                 235                 240
```

-continued

Lys Glu Lys Tyr Lys Glu Leu Thr Glu Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Pro Phe His Ala Thr Pro Asn
    290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
                325                 330                 335

Ala Leu Thr Ala Glu Arg Ile Lys Thr Pro Lys Arg Pro Gly Gly
            340                 345                 350

Arg Arg Arg Gly Arg Leu Pro Asn Asn Ser Ser Arg Pro Ser Thr Pro
        355                 360                 365

Thr Ile Asn Val Leu Glu Ser Lys Asp Thr Asp Ser Asp Arg Glu Ala
    370                 375                 380

Gly Thr Glu Thr Gly Gly Glu Asn Asn Asp Lys Glu Glu Glu Glu Lys
385                 390                 395                 400

Lys Asp Glu Thr Ser Ser Ser Glu Ala Asn Ser Arg Cys Gln Thr
            405                 410                 415

Pro Ile Lys Met Lys Pro Asn Ile Glu Pro Pro Glu Asn Val Glu Trp
                420                 425                 430

Ser Gly Ala Glu Ala Ser Met Phe Arg Val Leu Ile Gly Thr Tyr Tyr
        435                 440                 445

Asp Asn Phe Cys Ala Ile Ala Arg Leu Ile Gly Thr Lys Thr Cys Arg
    450                 455                 460

Gln Val Tyr Glu Phe Arg Val Lys Glu Ser Ser Ile Ile Ala Pro Ala
465                 470                 475                 480

Pro Ala Glu Asp Val Asp Thr Pro Pro Arg Lys Lys Arg Lys His
            485                 490                 495

Arg Leu Trp Ala Ala His Cys Arg Lys Ile Gln Leu Lys Lys Asp Gly
        500                 505                 510

Ser Ser Asn His Val Tyr Asn Tyr Gln Pro Cys Asp His Pro Arg Gln
    515                 520                 525

Pro Cys Asp Ser Ser Cys Pro Cys Val Ile Ala Gln Asn Phe Cys Glu
530                 535                 540

Lys Phe Cys Gln Cys Ser Ser Glu Cys Gln Asn Arg Phe Pro Gly Cys
545                 550                 555                 560

Arg Cys Lys Ala Gln Cys Asn Thr Lys Gln Cys Pro Cys Tyr Leu Ala
            565                 570                 575

Val Arg Glu Cys Asp Pro Asp Leu Cys Leu Thr Cys Gly Ala Ala Asp
        580                 585                 590

His Trp Asp Ser Lys Asn Val Ser Cys Lys Asn Cys Ser Ile Gln Arg
    595                 600                 605

Gly Ser Lys Lys His Leu Leu Leu Ala Pro Ser Asp Val Ala Gly Trp
610                 615                 620

Gly Ile Phe Ile Lys Asp Pro Val Gln Lys Asn Glu Phe Ile Ser Glu
625                 630                 635                 640

Phe Cys Gly Glu Ile Ile Ser Gln Asp Glu Ala Asp Arg Arg Gly Lys
            645                 650                 655

```
Val Tyr Asp Lys Tyr Met Cys Ser Phe Leu Phe Asn Leu Asn Asn Asp
            660                 665                 670

Phe Val Val Asp Ala Thr Arg Lys Gly Asn Lys Ile Arg Phe Ala Asn
        675                 680                 685

His Ser Val Asn Pro Asn Cys Tyr Ala Lys Val Met Met Val Asn Gly
    690                 695                 700

Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr
                725                 730                 735

Val Gly Ile Glu Arg Glu Met Glu Ile Pro
            740                 745

<210> SEQ ID NO 11
<211> LENGTH: 746
<212> TYPE: PRT
<213> ORGANISM: Artificial Sequence
<220> FEATURE:
<223> OTHER INFORMATION: Y641H mutant of Homo sapiens EZH2

<400> SEQUENCE: 11

Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Asp Gly Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
    210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270
```

```
Gln Arg Glu Gln Ser Leu His Ser Phe His Thr Leu Phe Cys Arg Arg
            275                 280                 285

Cys Phe Lys Tyr Asp Cys Phe Leu His Pro Phe His Ala Thr Pro Asn
290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
                325                 330                 335

Ala Leu Thr Ala Glu Arg Ile Lys Thr Pro Pro Lys Arg Pro Gly Gly
            340                 345                 350

Arg Arg Arg Gly Arg Leu Pro Asn Asn Ser Ser Arg Pro Ser Thr Pro
        355                 360                 365

Thr Ile Asn Val Leu Glu Ser Lys Asp Thr Asp Ser Asp Arg Glu Ala
    370                 375                 380

Gly Thr Glu Thr Gly Gly Glu Asn Asn Asp Lys Glu Glu Glu Glu Lys
385                 390                 395                 400

Lys Asp Glu Thr Ser Ser Ser Glu Ala Asn Ser Arg Cys Gln Thr
                405                 410                 415

Pro Ile Lys Met Lys Pro Asn Ile Glu Pro Pro Glu Asn Val Glu Trp
                420                 425                 430

Ser Gly Ala Glu Ala Ser Met Phe Arg Val Leu Ile Gly Thr Tyr Tyr
            435                 440                 445

Asp Asn Phe Cys Ala Ile Ala Arg Leu Ile Gly Thr Lys Thr Cys Arg
        450                 455                 460

Gln Val Tyr Glu Phe Arg Val Lys Glu Ser Ser Ile Ile Ala Pro Ala
465                 470                 475                 480

Pro Ala Glu Asp Val Asp Thr Pro Pro Arg Lys Lys Arg Lys His
                485                 490                 495

Arg Leu Trp Ala Ala His Cys Arg Lys Ile Gln Leu Lys Lys Asp Gly
            500                 505                 510

Ser Ser Asn His Val Tyr Asn Tyr Gln Pro Cys Asp His Pro Arg Gln
        515                 520                 525

Pro Cys Asp Ser Ser Cys Pro Cys Val Ile Ala Gln Asn Phe Cys Glu
    530                 535                 540

Lys Phe Cys Gln Cys Ser Ser Glu Cys Gln Asn Arg Phe Pro Gly Cys
545                 550                 555                 560

Arg Cys Lys Ala Gln Cys Asn Thr Lys Gln Cys Pro Cys Tyr Leu Ala
                565                 570                 575

Val Arg Glu Cys Asp Pro Asp Leu Cys Leu Thr Cys Gly Ala Ala Asp
            580                 585                 590

His Trp Asp Ser Lys Asn Val Ser Cys Lys Asn Cys Ser Ile Gln Arg
        595                 600                 605

Gly Ser Lys Lys His Leu Leu Leu Ala Pro Ser Asp Val Ala Gly Trp
    610                 615                 620

Gly Ile Phe Ile Lys Asp Pro Val Gln Lys Asn Glu Phe Ile Ser Glu
625                 630                 635                 640

His Cys Gly Glu Ile Ile Ser Gln Asp Glu Ala Asp Arg Arg Gly Lys
                645                 650                 655

Val Tyr Asp Lys Tyr Met Cys Ser Phe Leu Phe Asn Leu Asn Asn Asp
            660                 665                 670

Phe Val Val Asp Ala Thr Arg Lys Gly Asn Lys Ile Arg Phe Ala Asn
        675                 680                 685

His Ser Val Asn Pro Asn Cys Tyr Ala Lys Val Met Met Val Asn Gly
```

```
                690             695             700
Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr
                725                 730                 735

Val Gly Ile Glu Arg Glu Met Glu Ile Pro
            740                 745

<210> SEQ ID NO 12
<211> LENGTH: 746
<212> TYPE: PRT
<213> ORGANISM: Artificial Sequence
<220> FEATURE:
<223> OTHER INFORMATION: Y641N mutant of Homo sapiens EZH2

<400> SEQUENCE: 12

Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Gly Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
    210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Pro Phe His Ala Thr Pro Asn
    290                 295                 300

Thr Tyr Lys Arg Lys Asn Thr Glu Thr Ala Leu Asp Asn Lys Pro Cys
```

-continued

```
                305                 310                 315                 320
        Gly Pro Gln Cys Tyr Gln His Leu Glu Gly Ala Lys Glu Phe Ala Ala
                        325                 330                 335
        Ala Leu Thr Ala Glu Arg Ile Lys Thr Pro Lys Arg Pro Gly Gly
                        340                 345                 350
        Arg Arg Arg Gly Arg Leu Pro Asn Ser Ser Arg Pro Ser Thr Pro
                        355                 360                 365
        Thr Ile Asn Val Leu Glu Ser Lys Asp Thr Asp Ser Asp Arg Glu Ala
        370                 375                 380
        Gly Thr Glu Thr Gly Gly Glu Asn Asn Asp Lys Glu Glu Glu Lys
        385                 390                 395                 400
        Lys Asp Glu Thr Ser Ser Ser Glu Ala Asn Ser Arg Cys Gln Thr
                        405                 410                 415
        Pro Ile Lys Met Lys Pro Asn Ile Glu Pro Pro Glu Asn Val Glu Trp
                        420                 425                 430
        Ser Gly Ala Glu Ala Ser Met Phe Arg Val Leu Ile Gly Thr Tyr Tyr
                        435                 440                 445
        Asp Asn Phe Cys Ala Ile Ala Arg Leu Ile Gly Thr Lys Thr Cys Arg
                        450                 455                 460
        Gln Val Tyr Glu Phe Arg Val Lys Glu Ser Ser Ile Ile Ala Pro Ala
        465                 470                 475                 480
        Pro Ala Glu Asp Val Asp Thr Pro Pro Arg Lys Lys Arg Lys His
                        485                 490                 495
        Arg Leu Trp Ala Ala His Cys Arg Lys Ile Gln Leu Lys Lys Asp Gly
                        500                 505                 510
        Ser Ser Asn His Val Tyr Asn Tyr Gln Pro Cys Asp His Pro Arg Gln
                        515                 520                 525
        Pro Cys Asp Ser Ser Cys Pro Cys Val Ile Ala Gln Asn Phe Cys Glu
                        530                 535                 540
        Lys Phe Cys Gln Cys Ser Ser Glu Cys Gln Asn Arg Phe Pro Gly Cys
        545                 550                 555                 560
        Arg Cys Lys Ala Gln Cys Asn Thr Lys Gln Cys Pro Cys Tyr Leu Ala
                        565                 570                 575
        Val Arg Glu Cys Asp Pro Asp Leu Cys Leu Thr Cys Gly Ala Ala Asp
                        580                 585                 590
        His Trp Asp Ser Lys Asn Val Ser Cys Lys Asn Cys Ser Ile Gln Arg
                        595                 600                 605
        Gly Ser Lys Lys His Leu Leu Leu Ala Pro Ser Asp Val Ala Gly Trp
                        610                 615                 620
        Gly Ile Phe Ile Lys Asp Pro Val Gln Lys Asn Glu Phe Ile Ser Glu
        625                 630                 635                 640
        Asn Cys Gly Glu Ile Ile Ser Gln Asp Glu Ala Asp Arg Arg Gly Lys
                        645                 650                 655
        Val Tyr Asp Lys Tyr Met Cys Ser Phe Leu Phe Asn Leu Asn Asn Asp
                        660                 665                 670
        Phe Val Val Asp Ala Thr Arg Lys Gly Asn Lys Ile Arg Phe Ala Asn
                        675                 680                 685
        His Ser Val Asn Pro Asn Cys Tyr Ala Lys Val Met Met Val Asn Gly
                        690                 695                 700
        Asp His Arg Ile Gly Ile Phe Ala Lys Arg Ala Ile Gln Thr Gly Glu
        705                 710                 715                 720
        Glu Leu Phe Phe Asp Tyr Arg Tyr Ser Gln Ala Asp Ala Leu Lys Tyr
                        725                 730                 735
```

```
Val Gly Ile Glu Arg Glu Met Glu Ile Pro
            740                 745

<210> SEQ ID NO 13
<211> LENGTH: 746
<212> TYPE: PRT
<213> ORGANISM: Artificial Sequence
<220> FEATURE:
<223> OTHER INFORMATION: Y641S mutant of Homo sapiens EZH2

<400> SEQUENCE: 13

Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Asp Gly Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
    210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Pro Phe His Ala Thr Pro Asn
    290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
                325                 330                 335

Ala Leu Thr Ala Glu Arg Ile Lys Thr Pro Pro Lys Arg Pro Gly Gly
            340                 345                 350
```

```
Arg Arg Arg Gly Arg Leu Pro Asn Asn Ser Ser Arg Pro Ser Thr Pro
            355                 360                 365

Thr Ile Asn Val Leu Glu Ser Lys Asp Thr Asp Ser Asp Arg Glu Ala
    370                 375                 380

Gly Thr Glu Thr Gly Gly Glu Asn Asn Asp Lys Glu Glu Glu Lys
385                 390                 395                 400

Lys Asp Glu Thr Ser Ser Ser Glu Ala Asn Ser Arg Cys Gln Thr
                405                 410                 415

Pro Ile Lys Met Lys Pro Asn Ile Glu Pro Pro Glu Asn Val Glu Trp
                420                 425                 430

Ser Gly Ala Glu Ala Ser Met Phe Arg Val Leu Ile Gly Thr Tyr Tyr
            435                 440                 445

Asp Asn Phe Cys Ala Ile Ala Arg Leu Ile Gly Thr Lys Thr Cys Arg
        450                 455                 460

Gln Val Tyr Glu Phe Arg Val Lys Glu Ser Ser Ile Ile Ala Pro Ala
465                 470                 475                 480

Pro Ala Glu Asp Val Asp Thr Pro Pro Arg Lys Lys Arg Lys His
                485                 490                 495

Arg Leu Trp Ala Ala His Cys Arg Lys Ile Gln Leu Lys Lys Asp Gly
            500                 505                 510

Ser Ser Asn His Val Tyr Asn Tyr Gln Pro Cys Asp His Pro Arg Gln
            515                 520                 525

Pro Cys Asp Ser Ser Cys Pro Cys Val Ile Ala Gln Asn Phe Cys Glu
        530                 535                 540

Lys Phe Cys Gln Cys Ser Ser Glu Cys Gln Asn Arg Phe Pro Gly Cys
545                 550                 555                 560

Arg Cys Lys Ala Gln Cys Asn Thr Lys Gln Cys Pro Cys Tyr Leu Ala
                565                 570                 575

Val Arg Glu Cys Asp Pro Asp Leu Cys Leu Thr Cys Gly Ala Ala Asp
            580                 585                 590

His Trp Asp Ser Lys Asn Val Ser Cys Lys Asn Cys Ser Ile Gln Arg
        595                 600                 605

Gly Ser Lys Lys His Leu Leu Leu Ala Pro Ser Asp Val Ala Gly Trp
        610                 615                 620

Gly Ile Phe Ile Lys Asp Pro Val Gln Lys Asn Glu Phe Ile Ser Glu
625                 630                 635                 640

Ser Cys Gly Glu Ile Ile Ser Gln Asp Glu Ala Asp Arg Arg Gly Lys
                645                 650                 655

Val Tyr Asp Lys Tyr Met Cys Ser Phe Leu Phe Asn Leu Asn Asn Asp
                660                 665                 670

Phe Val Val Asp Ala Thr Arg Lys Gly Asn Lys Ile Arg Phe Ala Asn
            675                 680                 685

His Ser Val Asn Pro Asn Cys Tyr Ala Lys Val Met Met Val Asn Gly
        690                 695                 700

Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr
                725                 730                 735

Val Gly Ile Glu Arg Glu Met Glu Ile Pro
            740                 745

<210> SEQ ID NO 14
<211> LENGTH: 746
```

```
<212> TYPE: PRT
<213> ORGANISM: Artificial Sequence
<220> FEATURE:
<223> OTHER INFORMATION: Y641C mutant of Homo sapiens EZH2

<400> SEQUENCE: 14

Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
                20                  25                  30

Arg Arg Ala Asp Glu Val Lys Ser Met Phe Ser Ser Asn Arg Gln Lys
            35                  40                  45

Ile Leu Glu Arg Thr Glu Ile Leu Asn Gln Glu Trp Lys Gln Arg Arg
50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
                100                 105                 110

Trp Ser Pro Leu Gln Gln Asn Phe Met Val Glu Asp Glu Thr Val Leu
            115                 120                 125

His Asn Ile Pro Tyr Met Gly Asp Glu Val Leu Asp Gln Asp Gly Thr
130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Asp Gly Asp Asp
            180                 185                 190

Pro Glu Glu Arg Glu Glu Lys Gln Lys Asp Leu Glu Asp His Arg Asp
            195                 200                 205

Asp Lys Glu Ser Arg Pro Pro Arg Lys Phe Pro Ser Asp Lys Ile Phe
210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
            275                 280                 285

Cys Phe Lys Tyr Asp Cys Phe Leu His Pro His Ala Thr Pro Asn
290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
                325                 330                 335

Ala Leu Thr Ala Glu Arg Ile Lys Thr Pro Pro Lys Arg Pro Gly Gly
            340                 345                 350

Arg Arg Arg Gly Arg Leu Pro Asn Asn Ser Ser Arg Pro Ser Thr Pro
            355                 360                 365

Thr Ile Asn Val Leu Glu Ser Lys Asp Thr Asp Ser Asp Arg Glu Ala
    370                 375                 380
```

-continued

```
Gly Thr Glu Thr Gly Gly Glu Asn Asn Asp Lys Glu Glu Glu Lys
385                 390                 395                 400
Lys Asp Glu Thr Ser Ser Ser Glu Ala Asn Ser Arg Cys Gln Thr
            405                 410                 415
Pro Ile Lys Met Lys Pro Asn Ile Glu Pro Pro Glu Asn Val Glu Trp
        420                 425                 430
Ser Gly Ala Glu Ala Ser Met Phe Arg Val Leu Ile Gly Thr Tyr Tyr
        435                 440                 445
Asp Asn Phe Cys Ala Ile Ala Arg Leu Ile Gly Thr Lys Thr Cys Arg
    450                 455                 460
Gln Val Tyr Glu Phe Arg Val Lys Glu Ser Ser Ile Ile Ala Pro Ala
465                 470                 475                 480
Pro Ala Glu Asp Val Asp Thr Pro Pro Arg Lys Lys Arg Lys His
                485                 490                 495
Arg Leu Trp Ala Ala His Cys Arg Lys Ile Gln Leu Lys Lys Asp Gly
            500                 505                 510
Ser Ser Asn His Val Tyr Asn Tyr Gln Pro Cys Asp His Pro Arg Gln
        515                 520                 525
Pro Cys Asp Ser Ser Cys Pro Cys Val Ile Ala Gln Asn Phe Cys Glu
    530                 535                 540
Lys Phe Cys Gln Cys Ser Ser Glu Cys Gln Asn Arg Phe Pro Gly Cys
545                 550                 555                 560
Arg Cys Lys Ala Gln Cys Asn Thr Lys Gln Cys Pro Cys Tyr Leu Ala
            565                 570                 575
Val Arg Glu Cys Asp Pro Asp Leu Cys Leu Thr Cys Gly Ala Ala Asp
        580                 585                 590
His Trp Asp Ser Lys Asn Val Ser Cys Lys Asn Cys Ser Ile Gln Arg
    595                 600                 605
Gly Ser Lys Lys His Leu Leu Leu Ala Pro Ser Asp Val Ala Gly Trp
610                 615                 620
Gly Ile Phe Ile Lys Asp Pro Val Gln Lys Asn Glu Phe Ile Ser Glu
625                 630                 635                 640
Cys Cys Gly Glu Ile Ile Ser Gln Asp Glu Ala Asp Arg Arg Gly Lys
            645                 650                 655
Val Tyr Asp Lys Tyr Met Cys Ser Phe Leu Phe Asn Leu Asn Asn Asp
        660                 665                 670
Phe Val Val Asp Ala Thr Arg Lys Gly Asn Lys Ile Arg Phe Ala Asn
    675                 680                 685
His Ser Val Asn Pro Asn Cys Tyr Ala Lys Val Met Met Val Asn Gly
690                 695                 700
Asp His Arg Ile Gly Ile Phe Ala Lys Arg Ala Ile Gln Thr Gly Glu
705                 710                 715                 720
Glu Leu Phe Phe Asp Tyr Arg Tyr Ser Gln Ala Asp Ala Leu Lys Tyr
            725                 730                 735
Val Gly Ile Glu Arg Glu Met Glu Ile Pro
        740                 745
```

<210> SEQ ID NO 15
<211> LENGTH: 746
<212> TYPE: PRT
<213> ORGANISM: Artificial Sequence
<220> FEATURE:
<223> OTHER INFORMATION: A677 mutant of Homo sapiens EZH2, wherein X is
      preferably a glycine (G)
<220> FEATURE:
<221> NAME/KEY: MISC_FEATURE
<222> LOCATION: (677)..(677)
<223> OTHER INFORMATION: Xaa can be any naturally occurring amino acid,
      preferably a glycine (G)

<400> SEQUENCE: 15

```
Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Asp Asp Gly Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Pro Phe His Ala Thr Pro Asn
290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
                325                 330                 335

Ala Leu Thr Ala Glu Arg Ile Lys Thr Pro Pro Lys Arg Pro Gly Gly
            340                 345                 350

Arg Arg Arg Gly Arg Leu Pro Asn Asn Ser Ser Arg Pro Ser Thr Pro
        355                 360                 365

Thr Ile Asn Val Leu Glu Ser Lys Asp Thr Asp Ser Asp Arg Glu Ala
370                 375                 380

Gly Thr Glu Thr Gly Gly Glu Asn Asn Asp Lys Glu Glu Glu Glu Lys
```

385                 390                 395                 400
Lys Asp Glu Thr Ser Ser Ser Glu Ala Asn Ser Arg Cys Gln Thr
                    405                 410                 415

Pro Ile Lys Met Lys Pro Asn Ile Glu Pro Glu Asn Val Glu Trp
                420                 425                 430

Ser Gly Ala Glu Ala Ser Met Phe Arg Val Leu Ile Gly Thr Tyr Tyr
                435                 440                 445

Asp Asn Phe Cys Ala Ile Ala Arg Leu Ile Gly Thr Lys Thr Cys Arg
450                 455                 460

Gln Val Tyr Glu Phe Arg Val Lys Glu Ser Ser Ile Ile Ala Pro Ala
465                 470                 475                 480

Pro Ala Glu Asp Val Asp Thr Pro Pro Arg Lys Lys Arg Lys His
                    485                 490                 495

Arg Leu Trp Ala Ala His Cys Arg Lys Ile Gln Leu Lys Lys Asp Gly
                500                 505                 510

Ser Ser Asn His Val Tyr Asn Tyr Gln Pro Cys Asp His Pro Arg Gln
                515                 520                 525

Pro Cys Asp Ser Ser Cys Pro Cys Val Ile Ala Gln Asn Phe Cys Glu
530                 535                 540

Lys Phe Cys Gln Cys Ser Ser Glu Cys Gln Asn Arg Phe Pro Gly Cys
545                 550                 555                 560

Arg Cys Lys Ala Gln Cys Asn Thr Lys Gln Cys Pro Cys Tyr Leu Ala
                565                 570                 575

Val Arg Glu Cys Asp Pro Asp Leu Cys Leu Thr Cys Gly Ala Ala Asp
                580                 585                 590

His Trp Asp Ser Lys Asn Val Ser Cys Lys Asn Cys Ser Ile Gln Arg
                595                 600                 605

Gly Ser Lys Lys His Leu Leu Leu Ala Pro Ser Asp Val Ala Gly Trp
                610                 615                 620

Gly Ile Phe Ile Lys Asp Pro Val Gln Lys Asn Glu Phe Ile Ser Glu
625                 630                 635                 640

Tyr Cys Gly Glu Ile Ile Ser Gln Asp Glu Ala Asp Arg Arg Gly Lys
                645                 650                 655

Val Tyr Asp Lys Tyr Met Cys Ser Phe Leu Phe Asn Leu Asn Asn Asp
                660                 665                 670

Phe Val Val Asp Xaa Thr Arg Lys Gly Asn Lys Ile Arg Phe Ala Asn
                675                 680                 685

His Ser Val Asn Pro Asn Cys Tyr Ala Lys Val Met Met Val Asn Gly
                690                 695                 700

Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr
                    725                 730                 735

Val Gly Ile Glu Arg Glu Met Glu Ile Pro
                740                 745

<210> SEQ ID NO 16
<211> LENGTH: 746
<212> TYPE: PRT
<213> ORGANISM: Artificial Sequence
<220> FEATURE:
<223> OTHER INFORMATION: A687 mutant of Homo sapiens EZH2, wherein X is
      preferably a valine (V)
<220> FEATURE:
<221> NAME/KEY: MISC_FEATURE
<222> LOCATION: (687)..(687)

<223> OTHER INFORMATION: Xaa can be any naturally occurring amino acid,
      preferably a valine (V)

<400> SEQUENCE: 16

```
Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Asp Gly Asp Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Pro Phe His Ala Thr Pro Asn
290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
                325                 330                 335

Ala Leu Thr Ala Glu Arg Ile Lys Thr Pro Pro Lys Arg Pro Gly Gly
            340                 345                 350

Arg Arg Arg Gly Arg Leu Pro Asn Asn Ser Ser Arg Pro Ser Thr Pro
        355                 360                 365

Thr Ile Asn Val Leu Glu Ser Lys Asp Thr Asp Ser Asp Arg Glu Ala
370                 375                 380

Gly Thr Glu Thr Gly Gly Glu Asn Asn Asp Lys Glu Glu Glu Glu Lys
385                 390                 395                 400
```

-continued

```
Lys Asp Glu Thr Ser Ser Ser Glu Ala Asn Ser Arg Cys Gln Thr
            405                 410                 415
Pro Ile Lys Met Lys Pro Asn Ile Glu Pro Pro Glu Asn Val Glu Trp
        420                 425                 430
Ser Gly Ala Glu Ala Ser Met Phe Arg Val Leu Ile Gly Thr Tyr Tyr
    435                 440                 445
Asp Asn Phe Cys Ala Ile Ala Arg Leu Ile Gly Thr Lys Thr Cys Arg
450                 455                 460
Gln Val Tyr Glu Phe Arg Val Lys Glu Ser Ser Ile Ile Ala Pro Ala
465                 470                 475                 480
Pro Ala Glu Asp Val Asp Thr Pro Pro Arg Lys Lys Lys Arg Lys His
                485                 490                 495
Arg Leu Trp Ala Ala His Cys Arg Lys Ile Gln Leu Lys Lys Asp Gly
                500                 505                 510
Ser Ser Asn His Val Tyr Asn Tyr Gln Pro Cys Asp His Pro Arg Gln
            515                 520                 525
Pro Cys Asp Ser Ser Cys Pro Cys Val Ile Ala Gln Asn Phe Cys Glu
        530                 535                 540
Lys Phe Cys Gln Cys Ser Ser Glu Cys Gln Asn Arg Phe Pro Gly Cys
545                 550                 555                 560
Arg Cys Lys Ala Gln Cys Asn Thr Lys Gln Cys Pro Cys Tyr Leu Ala
                565                 570                 575
Val Arg Glu Cys Asp Pro Asp Leu Cys Leu Thr Cys Gly Ala Ala Asp
                580                 585                 590
His Trp Asp Ser Lys Asn Val Ser Cys Lys Asn Cys Ser Ile Gln Arg
            595                 600                 605
Gly Ser Lys Lys His Leu Leu Leu Ala Pro Ser Asp Val Ala Gly Trp
        610                 615                 620
Gly Ile Phe Ile Lys Asp Pro Val Gln Lys Asn Glu Phe Ile Ser Glu
625                 630                 635                 640
Tyr Cys Gly Glu Ile Ile Ser Gln Asp Glu Ala Asp Arg Arg Gly Lys
                645                 650                 655
Val Tyr Asp Lys Tyr Met Cys Ser Phe Leu Phe Asn Leu Asn Asn Asp
                660                 665                 670
Phe Val Val Asp Ala Thr Arg Lys Gly Asn Lys Ile Arg Phe Xaa Asn
            675                 680                 685
His Ser Val Asn Pro Asn Cys Tyr Ala Lys Val Met Met Val Asn Gly
        690                 695                 700
Asp His Arg Ile Gly Ile Phe Ala Lys Arg Ala Ile Gln Thr Gly Glu
705                 710                 715                 720
Glu Leu Phe Phe Asp Tyr Arg Tyr Ser Gln Ala Asp Ala Leu Lys Tyr
                725                 730                 735
Val Gly Ile Glu Arg Glu Met Glu Ile Pro
            740                 745
```

<210> SEQ ID NO 17
<211> LENGTH: 746
<212> TYPE: PRT
<213> ORGANISM: Artificial Sequence
<220> FEATURE:
<223> OTHER INFORMATION: Homo sapiens EZH2 with a mutation at residue
      685, wherein X is preferably a cysteine (C) or a histidine (H)
<220> FEATURE:
<221> NAME/KEY: MISC_FEATURE
<222> LOCATION: (685)..(685)
<223> OTHER INFORMATION: Xaa can be any naturally occurring amino acid, preferably a cysteine (C) or a histidine (H)

<400> SEQUENCE: 17

```
Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Gly Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Pro Phe His Ala Thr Pro Asn
290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
                325                 330                 335

Ala Leu Thr Ala Glu Arg Ile Lys Thr Pro Pro Lys Arg Pro Gly Gly
            340                 345                 350

Arg Arg Arg Gly Arg Leu Pro Asn Asn Ser Ser Arg Pro Ser Thr Pro
        355                 360                 365

Thr Ile Asn Val Leu Glu Ser Lys Asp Thr Asp Ser Asp Arg Glu Ala
370                 375                 380

Gly Thr Glu Thr Gly Gly Glu Asn Asn Asp Lys Glu Glu Glu Glu Lys
385                 390                 395                 400
```

```
Lys Asp Glu Thr Ser Ser Ser Glu Ala Asn Ser Arg Cys Gln Thr
                405                 410                 415

Pro Ile Lys Met Lys Pro Asn Ile Glu Pro Pro Glu Asn Val Glu Trp
            420                 425                 430

Ser Gly Ala Glu Ala Ser Met Phe Arg Val Leu Ile Gly Thr Tyr Tyr
            435                 440                 445

Asp Asn Phe Cys Ala Ile Ala Arg Leu Ile Gly Thr Lys Thr Cys Arg
        450                 455                 460

Gln Val Tyr Glu Phe Arg Val Lys Glu Ser Ser Ile Ile Ala Pro Ala
465                 470                 475                 480

Pro Ala Glu Asp Val Asp Thr Pro Pro Arg Lys Lys Arg Lys His
                485                 490                 495

Arg Leu Trp Ala Ala His Cys Arg Lys Ile Gln Leu Lys Lys Asp Gly
            500                 505                 510

Ser Ser Asn His Val Tyr Asn Tyr Gln Pro Cys Asp His Pro Arg Gln
            515                 520                 525

Pro Cys Asp Ser Ser Cys Pro Cys Val Ile Ala Gln Asn Phe Cys Glu
        530                 535                 540

Lys Phe Cys Gln Cys Ser Ser Glu Cys Gln Asn Arg Phe Pro Gly Cys
545                 550                 555                 560

Arg Cys Lys Ala Gln Cys Asn Thr Lys Gln Cys Pro Cys Tyr Leu Ala
                565                 570                 575

Val Arg Glu Cys Asp Pro Asp Leu Cys Leu Thr Cys Gly Ala Ala Asp
            580                 585                 590

His Trp Asp Ser Lys Asn Val Ser Cys Lys Asn Cys Ser Ile Gln Arg
            595                 600                 605

Gly Ser Lys Lys His Leu Leu Leu Ala Pro Ser Asp Val Ala Gly Trp
        610                 615                 620

Gly Ile Phe Ile Lys Asp Pro Val Gln Lys Asn Glu Phe Ile Ser Glu
625                 630                 635                 640

Tyr Cys Gly Glu Ile Ile Ser Gln Asp Glu Ala Asp Arg Arg Gly Lys
                645                 650                 655

Val Tyr Asp Lys Tyr Met Cys Ser Phe Leu Phe Asn Leu Asn Asn Asp
            660                 665                 670

Phe Val Val Asp Ala Thr Arg Lys Gly Asn Lys Ile Xaa Phe Ala Asn
            675                 680                 685

His Ser Val Asn Pro Asn Cys Tyr Ala Lys Val Met Met Val Asn Gly
        690                 695                 700

Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr
                725                 730                 735

Val Gly Ile Glu Arg Glu Met Glu Ile Pro
            740                 745
```

<210> SEQ ID NO 18
<211> LENGTH: 745
<212> TYPE: PRT
<213> ORGANISM: Artificial Sequence
<220> FEATURE:
<223> OTHER INFORMATION: Mutant Homo sapiens EZH2 comprising one or more
      mutations in the substrate pocket domain, wherein X can be any
      amino acid except the corresponding wild type residue
<220> FEATURE:
<221> NAME/KEY: MISC_FEATURE
<222> LOCATION: (641)..(641)
<223> OTHER INFORMATION: Xaa can be any naturally occurring amino acid,

```
         except the corresponding wild type residue
<220> FEATURE:
<221> NAME/KEY: MISC_FEATURE
<222> LOCATION: (663)..(665)
<223> OTHER INFORMATION: Xaa can be any naturally occurring amino acid,
      except the corresponding wild type residue
<220> FEATURE:
<221> NAME/KEY: MISC_FEATURE
<222> LOCATION: (667)..(667)
<223> OTHER INFORMATION: Xaa can be any naturally occurring amino acid,
      except the corresponding wild type residue
<220> FEATURE:
<221> NAME/KEY: MISC_FEATURE
<222> LOCATION: (674)..(675)
<223> OTHER INFORMATION: Xaa can be any naturally occurring amino acid,
      except the corresponding wild type residue
<220> FEATURE:
<221> NAME/KEY: MISC_FEATURE
<222> LOCATION: (677)..(677)
<223> OTHER INFORMATION: Xaa can be any naturally occurring amino acid,
      except the corresponding wild type residue
<220> FEATURE:
<221> NAME/KEY: MISC_FEATURE
<222> LOCATION: (684)..(687)
<223> OTHER INFORMATION: Xaa can be any naturally occurring amino acid,
      except the corresponding wild type residue
<220> FEATURE:
<221> NAME/KEY: MISC_FEATURE
<222> LOCATION: (707)..(707)
<223> OTHER INFORMATION: Xaa can be any naturally occurring amino acid,
      except the corresponding wild type residue
<220> FEATURE:
<221> NAME/KEY: MISC_FEATURE
<222> LOCATION: (723)..(723)
<223> OTHER INFORMATION: Xaa can be any naturally occurring amino acid,
      except the corresponding wild type residue
<220> FEATURE:
<221> NAME/KEY: MISC_FEATURE
<222> LOCATION: (725)..(725)
<223> OTHER INFORMATION: Xaa can be any naturally occurring amino acid,
      except the corresponding wild type residue
<220> FEATURE:
<221> NAME/KEY: MISC_FEATURE
<222> LOCATION: (729)..(729)
<223> OTHER INFORMATION: Xaa can be any naturally occurring amino acid,
      except the corresponding wild type residue

<400> SEQUENCE: 18

Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145                 150                 155                 160
```

-continued

```
Arg Glu Cys Gly Phe Ile Asn Asp Glu Ile Phe Val Glu Leu Val Asn
                165                 170                 175
Ala Leu Gly Gln Tyr Asn Asp Asp Asp Asp Asp Gly Asp Asp
        180                 185                 190
Pro Glu Glu Arg Glu Glu Lys Gln Lys Asp Leu Glu Asp His Arg Asp
            195                 200                 205
Asp Lys Glu Ser Arg Pro Pro Arg Lys Phe Pro Ser Asp Lys Ile Phe
210                 215                 220
Glu Ala Ile Ser Ser Met Phe Pro Asp Lys Gly Thr Ala Glu Glu Leu
225                 230                 235                 240
Lys Glu Lys Tyr Lys Glu Leu Thr Glu Gln Gln Leu Pro Gly Ala Leu
                245                 250                 255
Pro Pro Glu Cys Thr Pro Asn Ile Asp Gly Pro Asn Ala Lys Ser Val
            260                 265                 270
Gln Arg Glu Gln Ser Leu His Ser Phe His Thr Leu Phe Cys Arg Arg
        275                 280                 285
Cys Phe Lys Tyr Asp Cys Phe Leu His Pro Phe His Ala Thr Pro Asn
    290                 295                 300
Thr Tyr Lys Arg Lys Asn Thr Glu Thr Ala Leu Asp Asn Lys Pro Cys
305                 310                 315                 320
Gly Pro Gln Cys Tyr Gln His Leu Glu Gly Ala Lys Glu Phe Ala Ala
                325                 330                 335
Ala Leu Thr Ala Glu Arg Ile Lys Thr Pro Pro Lys Arg Pro Gly Gly
            340                 345                 350
Arg Arg Arg Gly Arg Leu Pro Asn Asn Ser Ser Arg Pro Ser Thr Pro
        355                 360                 365
Thr Ile Asn Val Leu Glu Ser Lys Asp Thr Asp Ser Asp Arg Glu Ala
    370                 375                 380
Gly Thr Glu Thr Gly Gly Glu Asn Asn Asp Lys Glu Glu Glu Glu Lys
385                 390                 395                 400
Lys Asp Glu Thr Ser Ser Ser Ser Glu Ala Asn Ser Arg Cys Gln Thr
                405                 410                 415
Pro Ile Lys Met Lys Pro Asn Ile Glu Pro Pro Glu Asn Val Glu Trp
            420                 425                 430
Ser Gly Ala Glu Ala Ser Met Phe Arg Val Leu Ile Gly Thr Tyr Tyr
        435                 440                 445
Asp Asn Phe Cys Ala Ile Ala Arg Leu Ile Gly Thr Lys Thr Cys Arg
    450                 455                 460
Gln Val Tyr Glu Phe Arg Val Lys Glu Ser Ser Ile Ile Ala Pro Ala
465                 470                 475                 480
Pro Ala Glu Asp Val Asp Thr Pro Pro Arg Lys Lys Arg Lys His
                485                 490                 495
Arg Leu Trp Ala Ala His Cys Arg Lys Ile Gln Leu Lys Lys Asp Gly
            500                 505                 510
Ser Ser Asn His Val Tyr Asn Tyr Gln Pro Cys Asp His Pro Arg Gln
        515                 520                 525
Pro Cys Asp Ser Ser Cys Pro Cys Val Ile Ala Gln Asn Phe Cys Glu
    530                 535                 540
Lys Phe Cys Gln Cys Ser Ser Glu Cys Gln Asn Arg Phe Pro Gly Cys
545                 550                 555                 560
Arg Cys Lys Ala Gln Cys Asn Thr Lys Gln Cys Pro Cys Tyr Leu Ala
                565                 570                 575
Val Arg Glu Cys Asp Pro Asp Leu Cys Leu Thr Cys Gly Ala Ala Asp
```

```
                580                 585                 590
His Trp Asp Ser Lys Asn Val Ser Cys Lys Asn Cys Ser Ile Gln Arg
            595                 600                 605

Gly Ser Lys Lys His Leu Leu Leu Ala Pro Ser Asp Val Ala Gly Trp
        610                 615                 620

Gly Ile Phe Ile Lys Asp Pro Val Gln Lys Asn Glu Phe Ile Ser Glu
625                 630                 635                 640

Xaa Cys Gly Glu Ile Ile Ser Gln Asp Glu Ala Asp Arg Arg Gly Lys
                645                 650                 655

Val Tyr Asp Lys Tyr Met Xaa Xaa Xaa Leu Xaa Asn Leu Asn Asn Asp
            660                 665                 670

Phe Xaa Xaa Asp Xaa Thr Arg Lys Gly Asn Lys Xaa Xaa Xaa Xaa His
        675                 680                 685

Ser Val Asn Pro Asn Cys Tyr Ala Lys Val Met Met Val Asn Gly Asp
        690                 695                 700

His Arg Xaa Gly Ile Phe Ala Lys Arg Ala Ile Gln Thr Gly Glu Glu
705                 710                 715                 720

Leu Phe Xaa Asp Xaa Arg Tyr Ser Xaa Ala Asp Ala Leu Lys Tyr Val
            725                 730                 735

Gly Ile Glu Arg Glu Met Glu Ile Pro
            740                 745

<210> SEQ ID NO 19
<211> LENGTH: 24
<212> TYPE: PRT
<213> ORGANISM: Artificial Sequence
<220> FEATURE:
<223> OTHER INFORMATION: Peptide fragment from Homo sapiens histone H3

<400> SEQUENCE: 19

Leu Ala Thr Lys Ala Ala Arg Lys Ser Ala Pro Ala Thr Gly Gly Val
1               5                   10                  15

Lys Lys Pro His Arg Tyr Arg Pro
            20

<210> SEQ ID NO 20
<211> LENGTH: 26
<212> TYPE: PRT
<213> ORGANISM: Artificial Sequence
<220> FEATURE:
<223> OTHER INFORMATION: modified peptide
<220> FEATURE:
<221> NAME/KEY: MISC_FEATURE
<222> LOCATION: (26)..(26)
<223> OTHER INFORMATION: Biotin is attached through an aminohexyl linker
      (AHX)

<400> SEQUENCE: 20

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25

<210> SEQ ID NO 21
<211> LENGTH: 695
<212> TYPE: PRT
<213> ORGANISM: Homo sapiens

<400> SEQUENCE: 21

Met Gly Gln Thr Gly Lys Lys Ser Glu Lys Gly Pro Val Cys Trp Arg
1               5                   10                  15
```

```
Lys Arg Val Lys Ser Glu Tyr Met Arg Leu Arg Gln Leu Lys Arg Phe
             20                  25                  30

Arg Arg Ala Asp Glu Val Lys Ser Met Phe Ser Ser Asn Arg Gln Lys
         35                  40                  45

Ile Leu Glu Arg Thr Glu Ile Leu Asn Gln Glu Trp Lys Gln Arg Arg
 50                  55                  60

Ile Gln Pro Val His Ile Leu Thr Ser Cys Ser Val Thr Ser Asp Leu
 65                  70                  75                  80

Asp Phe Pro Thr Gln Val Ile Pro Leu Lys Thr Leu Asn Ala Val Ala
                 85                  90                  95

Ser Val Pro Ile Met Tyr Ser Trp Ser Pro Leu Gln Gln Asn Phe Met
                100                 105                 110

Val Glu Asp Glu Thr Val Leu His Asn Ile Pro Tyr Met Gly Asp Glu
             115                 120                 125

Val Leu Asp Gln Asp Gly Thr Phe Ile Glu Glu Leu Ile Lys Asn Tyr
 130                 135                 140

Asp Gly Lys Val His Gly Asp Arg Glu Cys Gly Phe Ile Asn Asp Glu
145                 150                 155                 160

Ile Phe Val Glu Leu Val Asn Ala Leu Gly Gln Tyr Asn Asp Asp Asp
                 165                 170                 175

Asp Asp Asp Asp Gly Asp Asp Pro Glu Glu Arg Glu Glu Lys Gln Lys
             180                 185                 190

Asp Leu Glu Asp His Arg Asp Asp Lys Glu Ser Arg Pro Pro Arg Lys
             195                 200                 205

Phe Pro Ser Asp Lys Ile Phe Glu Ala Ile Ser Ser Met Phe Pro Asp
             210                 215                 220

Lys Gly Thr Ala Glu Glu Leu Lys Glu Lys Tyr Lys Glu Leu Thr Glu
225                 230                 235                 240

Gln Gln Leu Pro Gly Ala Leu Pro Pro Glu Cys Thr Pro Asn Ile Asp
                 245                 250                 255

Gly Pro Asn Ala Lys Ser Val Gln Arg Glu Gln Ser Leu His Ser Phe
             260                 265                 270

His Thr Leu Phe Cys Arg Arg Cys Phe Lys Tyr Asp Cys Phe Leu His
             275                 280                 285

Pro Phe His Ala Thr Pro Asn Thr Tyr Lys Arg Lys Asn Thr Glu Thr
             290                 295                 300

Ala Leu Asp Asn Lys Pro Cys Gly Pro Gln Cys Tyr Gln His Leu Glu
305                 310                 315                 320

Gly Ala Lys Glu Phe Ala Ala Ala Leu Thr Ala Glu Arg Ile Lys Thr
                 325                 330                 335

Pro Pro Lys Arg Pro Gly Gly Arg Arg Gly Arg Leu Pro Asn Asn
             340                 345                 350

Ser Ser Arg Pro Ser Thr Pro Thr Ile Asn Val Leu Glu Ser Lys Asp
             355                 360                 365

Thr Asp Ser Asp Arg Glu Ala Gly Thr Glu Thr Gly Gly Glu Asn Asn
             370                 375                 380

Asp Lys Glu Glu Glu Lys Lys Asp Glu Thr Ser Ser Ser Ser Glu
385                 390                 395                 400

Ala Asn Ser Arg Cys Gln Thr Pro Ile Lys Met Lys Pro Asn Ile Glu
                 405                 410                 415

Pro Pro Glu Asn Val Glu Trp Ser Gly Ala Glu Ala Ser Met Phe Arg
             420                 425                 430
```

```
Val Leu Ile Gly Thr Tyr Tyr Asp Asn Phe Cys Ala Ile Ala Arg Leu
            435                 440                 445

Ile Gly Thr Lys Thr Cys Arg Gln Val Tyr Glu Phe Arg Val Lys Glu
        450                 455                 460

Ser Ser Ile Ile Ala Pro Ala Pro Ala Glu Asp Val Asp Thr Pro Pro
465                 470                 475                 480

Arg Lys Lys Lys Arg Lys His Arg Leu Trp Ala Ala His Cys Arg Lys
                485                 490                 495

Ile Gln Leu Lys Lys Gly Gln Asn Arg Phe Pro Gly Cys Arg Cys Lys
            500                 505                 510

Ala Gln Cys Asn Thr Lys Gln Cys Pro Cys Tyr Leu Ala Val Arg Glu
        515                 520                 525

Cys Asp Pro Asp Leu Cys Leu Thr Cys Gly Ala Ala Asp His Trp Asp
    530                 535                 540

Ser Lys Asn Val Ser Cys Lys Asn Cys Ser Ile Gln Arg Gly Ser Lys
545                 550                 555                 560

Lys His Leu Leu Leu Ala Pro Ser Asp Val Ala Gly Trp Gly Ile Phe
                565                 570                 575

Ile Lys Asp Pro Val Gln Lys Asn Glu Phe Ile Ser Glu Tyr Cys Gly
            580                 585                 590

Glu Ile Ile Ser Gln Asp Glu Ala Asp Arg Arg Gly Lys Val Tyr Asp
        595                 600                 605

Lys Tyr Met Cys Ser Phe Leu Phe Asn Leu Asn Asn Asp Phe Val Val
    610                 615                 620

Asp Ala Thr Arg Lys Gly Asn Lys Ile Arg Phe Ala Asn His Ser Val
625                 630                 635                 640

Asn Pro Asn Cys Tyr Ala Lys Val Met Met Val Asn Gly Asp His Arg
                645                 650                 655

Ile Gly Ile Phe Ala Lys Arg Ala Ile Gln Thr Gly Glu Glu Leu Phe
            660                 665                 670

Phe Asp Tyr Arg Tyr Ser Gln Ala Asp Ala Leu Lys Tyr Val Gly Ile
        675                 680                 685

Glu Arg Glu Met Glu Ile Pro
    690                 695

<210> SEQ ID NO 22
<211> LENGTH: 2682
<212> TYPE: DNA
<213> ORGANISM: Homo sapiens

<400> SEQUENCE: 22
gacgacgttc gcggcgggga actcggagta gcttcgcctc tgacgtttcc ccacgacgca     60
ccccgaaatc ccctgagct ccggcggtcg cgggctgccc tcgccgcctg gtctggcttt    120
atgctaagtt tgagggaaga gtcgagctgc tctgctctct attgattgtg tttctggagg    180
gcgtcctgtt gaattcccac ttcattgtgt acatcccctt ccgttccccc caaaaatctg    240
tgccacaggg ttacttttg aaagcgggag gaatcgagaa gcacgatctt ttggaaaact    300
tggtgaacgc ctaaataatc atgggccaga ctgggaagaa atctgagaag ggaccagttt    360
gttggcggaa gcgtgtaaaa tcagagtaca tgcgactgag acagctcaag aggttcagac    420
gagctgatga agtaaagagt atgtttagtt ccaatcgtca gaaattttg gaagaacgg    480 aaatcttaaa ccaagaatgg aaacagcgaa ggatacagcc tgtgcacatc ctgacttctt    540
gttcggtgac cagtgacttg gatttccaa cacaagtcat cccattaaag actctgaatg    600
```

```
cagttgcttc agtacccata atgtattctt ggtctcccct acagcagaat tttatggtgg      660
aagatgaaac tgttttacat aacattcctt atatgggaga tgaagtttta gatcaggatg      720
gtactttcat tgaagaacta ataaaaaatt atgatgggaa agtacacggg gatagagaat      780
gtgggtttat aaatgatgaa attttgtgg agttggtgaa tgcccttggt caatataatg       840
atgatgacga tgatgatgat ggagacgatc ctgaagaaag agaagaaaag cagaaagatc      900
tggaggatca ccgagatgat aaagaaagcc gcccacctcg gaatttcct tctgataaaa       960 tttttgaagc catttcctca atgtttccag ataagggcac agcagaagaa ctaaaggaaa     1020
aatataaaga actcaccgaa cagcagctcc caggcgcact tcctcctgaa tgtaccccca     1080
acatagatgg accaaatgct aaatctgttc agagagagca aagcttacac tcctttcata     1140
cgcttttctg taggcgatgt tttaaatatg actgcttcct acatccttt catgcaacac      1200 ccaacactta taagcggaag aacacagaaa cagctctaga caacaaacct tgtggaccac     1260
agtgttacca gcatttggag ggagcaaagg agtttgctgc tgctctcacc gctgagcgga     1320
taaagacccc accaaaacgt ccaggaggcc gcagaagagg acggcttccc aataacagta     1380
gcaggcccag caccccccacc attaatgtgc tggaatcaaa ggatacagac agtgataggg    1440
aagcagggac tgaaacgggg ggagagaaca atgataaaga agaagaagag aagaaagatg    1500
aaacttcgag ctcctctgaa gcaaattctc ggtgtcaaac accaataaag atgaagccaa      1560
atattgaacc tcctgagaat gtggagtgga gtggtgctga agcctcaatg tttagagtcc      1620
tcattggcac ttactatgac aatttctgtg ccattgctag gttaattggg accaaaacat      1680
gtagacaggt gtatgagttt agagtcaaag aatctagcat catagctcca gctcccgctg      1740
aggatgtgga tactcctcca aggaaaaaga agaggaaaca ccggttgtgg gctgcacact     1800
gcagaaagat acagctgaaa aagggtcaaa accgctttcc gggatgccgc tgcaaagcac     1860
agtgcaacac caagcagtgc ccgtgctacc tggctgtccg agagtgtgac cctgacctct      1920
gtcttacttg tggagccgct gaccattggg acagtaaaaa tgtgtcctgc aagaactgca     1980
gtattcagcg gggctccaaa aagcatctat tgctggcacc atctgacgtg gcaggctggg     2040
ggatttttat caaagatcct gtgcagaaaa atgaattcat ctcagaatac tgtggagaga    2100
ttatttctca agatgaagct gacagaagag ggaaagtgta tgataaatac atgtgcagct     2160
ttctgttcaa cttgaacaat gattttgtgg tggatgcaac ccgcaagggt aacaaaattc    2220 gtttttgcaaa tcattcggta aatccaaact gctatgcaaa agttatgatg gttaacggtg   2280
atcacaggat aggtattttt gccaagagag ccatccagac tggcgaagag ctgttttttg   2340
attacagata cagccaggct gatgccctga agtatgtcgg catcgaaaga gaaatggaaa    2400
tcccttgaca tctgctacct cctcccccct cctctgaaac agctgcctta gcttcaggaa      2460
cctcgagtac tgtgggcaat ttagaaaaag aacatgcagt ttgaaattct gaatttgcaa     2520
agtactgtaa gaataattta tagtaatgag tttaaaaatc aacttttat tgccttctca      2580 ccagctgcaa agtgttttgt accagtgaat ttttgcaata atgcagtatg gtacattttt    2640
caactttgaa taaagaatac ttgaacttgt ccttgttgaa tc                       2682
```

US 9,175,331 B2

INHIBITORS OF HUMAN EZH2, AND METHODS OF USE THEREOF

RELATED REFERENCE

This application is a continuation-in-part of the U.S. patent application Ser. No. 13/230,703, filed Sep. 12, 2011, which claims priority to, and the benefit of, U.S. Ser. No. 61/381,684, filed Sep. 10, 2010, each of which is incorporated herein by reference in its entirety.

INCORPORATION-BY-REFERENCE OF SEQUENCE LISTING

The contents of the text file named "41478_506002US_ST25.txt", which was created on Oct. 18, 2012 and is 105 KB in size, are hereby incorporated by reference in their entirety.

FIELD OF THE INVENTION

This invention relates to inhibition of wild-type and certain mutant forms of human histone methyltransferase EZH2, the catalytic subunit of the PRC2 complex which catalyzes the mono- through tri-methylation of lysine 27 on histone H3 (H3-K27), methods for treating cancers including follicular lymphoma and diffuse large B-cell lymphoma (DLBCL) and methods for determining responsiveness to an EZH2 inhibitor in a subject.

BACKGROUND

In eukaryotic cells DNA is packaged with histones to form chromatin. Approximately 150 base pairs of DNA are wrapped twice around an octamer of histones (two each of histones 2A, 2B, 3 and 4) to form a nucleosome, the basic unit of chromatin. Changes in the ordered structure of chromatin can lead to alterations in transcription of associated genes. This process is highly controlled because changes in gene expression patterns can profoundly affect fundamental cellular processes, such as differentiation, proliferation and apoptosis. Control of changes in chromatin structure (and hence of transcription) is mediated by covalent modifications to histones, most notably of their N-terminal tails. These modifications are often referred to as epigenetic because they can lead to heritable changes in gene expression, but they do not affect the sequence of the DNA itself. Covalent modifications (for example, methylation, acetylation, phosphorylation and ubiquitination) of the side chains of amino acids are enzymatically mediated.

The selective addition of methyl groups to specific amino acid sites on histones is controlled by the action of a unique family of enzymes known as histone methyltransferases (HMTs). The level of expression of a particular gene is influenced by the presence or absence of one or more methyl groups at a relevant histone site. The specific effect of a methyl group at a particular histone site persists until the methyl group is removed by a histone demethylase, or until the modified histone is replaced through nucleosome turnover. In a like manner, other enzyme classes can decorate DNA and histones with other chemical species, and still other enzymes can remove these species to provide control of gene expression.

The orchestrated collection of biochemical systems behind transcriptional regulation must be tightly controlled in order for cell growth and differentiation to proceed optimally. Disease states result when these controls are disrupted by aberrant expression and/or activity of the enzymes responsible for DNA and histone modification. In human cancers, for example, there is a growing body of evidence to suggest that dysregulated epigenetic enzyme activity contributes to the uncontrolled cell proliferation associated with cancer as well as other cancer-relevant phenotypes such as enhanced cell migration and invasion. Beyond cancer, there is growing evidence for a role of epigenetic enzymes in a number of other human diseases, including metabolic diseases (such as diabetes), inflammatory diseases (such as Crohn's disease), neurodegenerative diseases (such as Alzheimer's disease), and cardiovascular diseases. Therefore, selectively modulating the aberrant action of epigenetic enzymes holds great promise for the treatment of a range of diseases.

Histone Methyltransferase EZH2

Polycomb group (PcG) and trithorax group (trxG) proteins are known to be part of the cellular memory system. Francis et al. (2001) Nat Rev Mol Cell Biol 2:409-21; Simon et al. (2002) Curr Opin Genet Dev 12:210-8. Both groups of proteins are involved in maintaining the spatial patterns of homeotic box (Hox) gene expression, which are established early in embryonic development by transiently expressed segmentation genes. In general, PcG proteins are transcriptional repressors that maintain the "off state," and trxG proteins are transcriptional activators that maintain the "on state." Because members of PcG and trxG proteins contain intrinsic histone methyltransferase (HMTase) activity, PcG and trxG proteins may participate in cellular memory through methylation of core histones. Beisel et al. (2002) Nature 419:857-62; Cao et al. (2002) Science 298:1039-43; Czermin et al. (2002) Cell 111:185-96; Kuzmichev et al. (2002) Genes Dev 16:2893-905; Milne et al. (2002) Mol Cell 10:1107-17; Muller et al. (2002) Cell 111:197-208; Nakamura et al. (2002) Mol Cell 10:1119-28.

Biochemical and genetic studies have provided evidence that Drosophila PcG proteins function in at least two distinct protein complexes, the Polycomb repressive complex 1 (PRC1) and the ESC-E(Z) complex (also known as Polycomb repressive complex 2 (PRC2)), although the compositions of the complexes may be dynamic. Otte et al. (2003) Curr Opin Genet Dev 13:448-54. Studies in Drosophila (Czermin et al. (supra); Muller et al. (supra)) and mammalian cells (Cao et al. (supra); Kuzmichev et al. (supra)) have demonstrated that the ESC-E(Z)/EED-EZH2 (i.e., PRC2) complexes have intrinsic histone methyltransferase activity. Although the compositions of the complexes isolated by different groups are slightly different, they generally contain EED, EZH2, SUZ12, and RbAp48 or Drosophila homologs thereof. However, a reconstituted complex comprising only EED, EZH2, and SUZ12 retains histone methyltransferase activity for lysine 27 of histone H3. U.S. Pat. No. 7,563,589 (incorporated by reference).

Of the various proteins making up PRC2 complexes, EZH2 (Enhancer of Zeste Homolog 2) is the catalytic subunit. The catalytic site of EZH2 in turn is present within a SET domain, a highly conserved sequence motif (named after Su(var)3-9, Enhancer of Zeste, Trithorax) that is found in several chromatin-associated proteins, including members of both the Trithorax group and Polycomb group. SET domain is characteristic of all known histone lysine methyltransferases except the H3-K79 methyltransferase DOT1.

In addition to Hox gene silencing, PRC2-mediated histone H3-K27 methylation has been shown to participate in X-inactivation. Plath et al. (2003) Science 300:131-5; Silva et al. (2003) Dev Cell 4:481-95. Recruitment of the PRC2 complex to Xi and subsequent trimethylation on histone H3-K27 occurs during the initiation stage of X-inactivation and is dependent on Xist RNA. Furthermore, EZH2 and its associated histone H3-K27 methyltransferase activity was found to mark differentially the pluripotent epiblast cells and the differentiated trophectoderm. Erhardt et al. (2003) *Development* 130:4235-48).

Consistent with a role of EZH2 in maintaining the epigenetic modification patterns of pluripotent epiblast cells, Cre-mediated deletion of EZH2 results in loss of histone H3-K27 methylation in the cells. Erhardt et al. (supra). Further, studies in prostate and breast cancer cell lines and tissues have revealed a strong correlation between the levels of EZH2 and SUZ12 and the invasiveness of these cancers (Bracken et al. (2003) *EMBO J* 22:5323-35; Kirmizis et al. (2003) *Mol Cancer Ther* 2:113-21; Kleer et al. (2003) *Proc Natl Acad Sci USA* 100:11606-11; Varambally et al. (2002) *Nature* 419:624-9), indicating that dysfunction of the PRC2 complex may contribute to cancer.

Recently, somatic mutations of EZH2 were reported to be associated with follicular lymphoma (FL) and the germinal center B cell-like (GCB) subtype of diffuse large B-cell lymphoma (DLBCL). Morin et al. (2010) *Nat Genet* 42:181-5. In all cases, occurrence of the mutant EZH2 gene was found to be heterozygous, and expression of both wild-type and mutant alleles was detected in the mutant samples profiled by transcriptome sequencing. Currently, the standard of care for the treatment of most cases of DLBCL is the R—CHOP regimen. However, the outcome of this regimen is far from satisfactory. Therefore, there is a great medical need to identify novel and effective therapies, optionally based on the genetic profiles of the subject.

SUMMARY OF THE INVENTION

The invention is based upon the discovery that cells expressing certain EZH2 mutants are more responsive to EZH2 inhibitors than cells expressing wild type EZH2.

The invention features a method for treating or alleviating a symptom of cancer or precancerous condition in a subject administering to a subject expressing a mutant EZH2 comprising a mutation in the substrate pocket domain as defined in SEQ ID NO: 6 a therapeutically effective amount of an EZH2 inhibitor.

The invention also features a method of determining a responsiveness of a subject having a cancer or a precancerous condition to an EZH2 inhibitor by providing a sample from the subject; and detecting a mutation in the EZH2 substrate pocket domain as defined in SEQ ID NO: 6; and the presence of said mutation indicates the subject is responsive to the EZH2 inhibitor.

The mutant EZH2 of the present invention is a mutant EZH2 polypeptide or a nucleic acid sequence encoding a mutant EZH2 polypeptide. Preferably, the mutant EZH2 comprises a mutation at amino acid position 677, 687, 674, 685, or 641 of SEQ ID NO: 1. More preferably, mutation is selected from the group consisting of a substitution of glycine (G) for the wild type residue alanine (A) at amino acid position 677 of SEQ ID NO: 1 (A677G); a substitution of valine (V) for the wild type residue alanine (A) at amino acid position 687 of SEQ ID NO: 1 (A687V); a substitution of methionine (M) for the wild type residue valine (V) at amino acid position 674 of SEQ ID NO: 1 (V674M); a substitution of histidine (H) for the wild type residue arginine (R) at amino acid position 685 of SEQ ID NO: 1 (R685H); a substitution of cysteine (C) for the wild type residue arginine (R) at amino acid position 685 of SEQ ID NO: 1 (R685C); a substitution of phenylalanine (F) for the wild type residue tyrosine (Y) at amino acid position 641 of SEQ ID NO: 1 (Y641F); a substitution of histidine (H) for the wild type residue tyrosine (Y) at amino acid position 641 of SEQ ID NO: 1 (Y641H); a substitution of asparagine (N) for the wild type residue tyrosine (Y) at amino acid position 641 of SEQ ID NO: 1 (Y641N); a substitution of serine (S) for the wild type residue tyrosine (Y) at amino acid position 641 of SEQ ID NO: 1 (Y641S); and a substitution of cysteine (C) for the wild type residue tyrosine (Y) at amino acid position 641 of SEQ ID NO: 1 (Y641C).

The subject of the present invention includes any human subject who has been diagnosed with, has symptoms of, or is at risk of developing a cancer or a precancerous condition. For example, the cancer is lymphoma, leukemia or melanoma. Preferably, the lymphoma is non-Hodgkin lymphoma, follicular lymphoma or diffuse large B-cell lymphoma. Alternatively, the leukemia is chronic myelogenous leukemia (CML). The precancerous condition is myelodysplastic syndromes (MDS, formerly known as preleukemia).

Preferred EZH2 inhibitor for the methods of the present invention is selected from compounds listed in Table 1.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTION OF THE FIGURES

FIG. 14 is a graph showing the presence of an EZH2 (Y641) mutation and/or high H3-K27me3 and low H3-K27me2 levels predict sensitivity to EZH2 inhibitors. Cell lines were maintained in the presence of increasing concentrations of one EZH2 inhibitor up to 25 μM. Viable cells counts were used to derive $IC_{90}$ values after 11 days of treatment. Results are plotted with cell lines segregated according to EZH2 mutational status (A), or segregated according to H3-K27me2 and H3-K27me3 levels (B). In both plots, the line shows the average IC90 values from the indicated cell line group.

DETAILED DESCRIPTION

Figure 1:
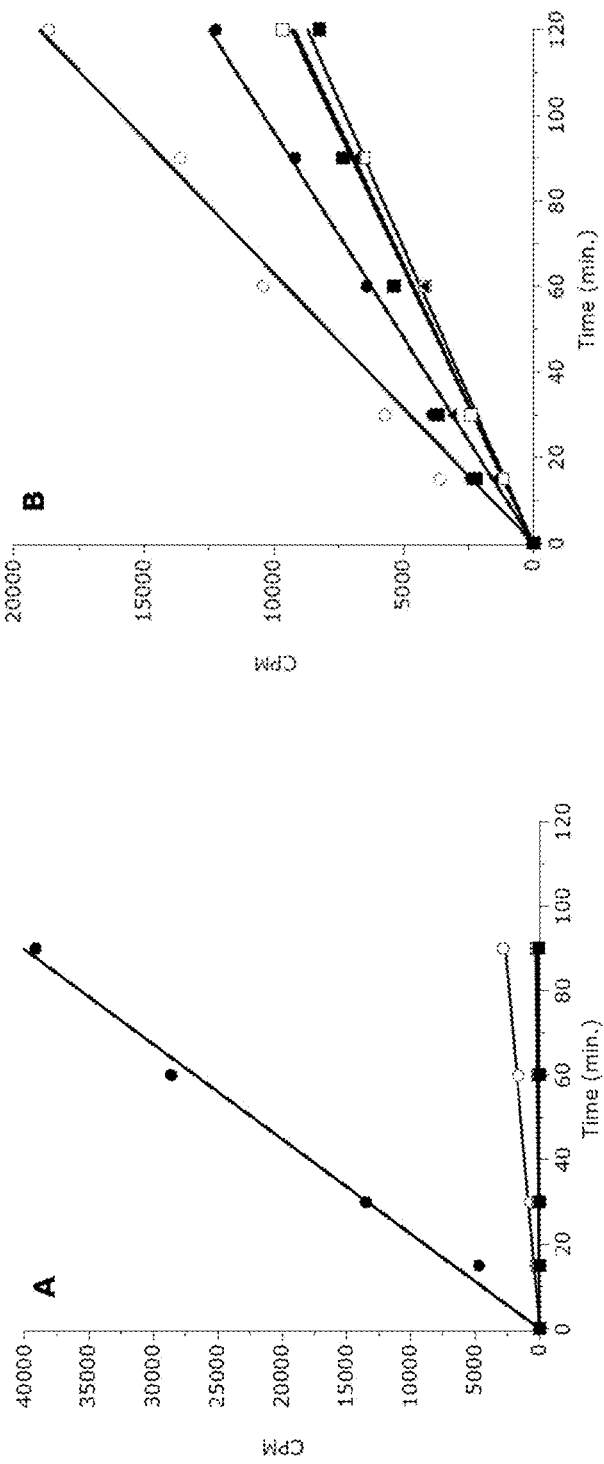
FIG. 1 is two graphs establishing that B-cell lymphoma-associated mutants of EZH2 are active histone methyltransferases. In vitro methyltransferase activity of PRC2 complexes containing wild-type and various Y641 mutants of EZH2 was measured as (A) methyl transfer reactions using a peptide (H3 21-44) as substrate, and (B) methyl transfer reactions using avian nucleosomes as substrate. Symbols: wild-type (●), Y641F (○), Y641H (□), Y641N (■), and Y641S (▲). CPM is counts per minute, referring to scintillation counting as a result of $^3$H radiation.

Chromatin structure is important in gene regulation and epigenetic inheritance. Post-translational modifications of histones, such as methylation are involved in the establishment and maintenance of higher-order chromatin structure.

EZH2 Mutants

EZH2 is a histone methyltransferase that is the catalytic subunit of the PRC2 complex which catalyzes the mono- through tri-methylation of lysine 27 on histone H3 (H3-K27).

Point mutations of the EZH2 gene at a single amino acid residue (e.g., Tyr641, herein referred to as Y641) of EZH2 have been reported to be linked to subsets of human B-cell lymphoma. Morin et al. (2010) *Nat Genet* 42(2):181-5. In particular, Morin et al. reported that somatic mutations of tyrosine 641 (Y641F, Y641H, Y641N, and Y641S) of EZH2 were associated with follicular lymphoma (FL) and the germinal center B cell-like (GCB) subtype of diffuse large B-cell lymphoma (DLBCL). The mutant allele is always found associated with a wild-type allele (heterozygous) in disease cells, and the mutations were reported to ablate the enzymatic activity of the PRC2 complex for methylating an unmodified peptide substrate.

The present invention is based in part upon the surprising discovery that cells expressing an EZH2 mutant are more sensitive to EZH2 inhibitors of the instant invention than cells expressing wild type EZH2. Accordingly, an aspect of the present invention relates to methods for treating or alleviating a symptom of cancer or precancerous condition in a subject by administering to a subject expressing a mutant EZH2 a therapeutically effective amount of an EZH2 inhibitor. The mutant EZH2 of the present invention refers to a mutant EZH2 polypeptide or a nucleic acid sequence encoding a mutant EZH2 polypeptide. Preferably the mutant EZH2 comprises one or more mutations in its substrate pocket domain as defined in SEQ ID NO: 6. For example, the mutation may be a substitution, a point mutation, a nonsense mutation, a miss sense mutation, a deletion, or an insertion. Exemplary substitution amino acid mutation includes a substitution at amino acid position 677, 687, 674, 685, or 641 of SEQ ID NO: 1, such as, but is not limited to a substitution of glycine (G) for the wild type residue alanine (A) at amino acid position 677 of SEQ ID NO: 1 (A677G); a substitution of valine (V) for the wild type residue alanine (A) at amino acid position 687 of SEQ ID NO: 1 (A687V); a substitution of methionine (M) for the wild type residue valine (V) at amino acid position 674 of SEQ ID NO: 1 (V674M); a substitution of histidine (H) for the wild type residue arginine (R) at amino acid position 685 of SEQ ID NO: 1 (R685H); a substitution of cysteine (C) for the wild type residue arginine (R) at amino acid position 685 of SEQ ID NO: 1 (R685C); a substitution of phenylalanine (F) for the wild type residue tyrosine (Y) at amino acid position 641 of SEQ ID NO: 1 (Y641F); a substitution of histidine (H) for the wild type residue tyrosine (Y) at amino acid position 641 of SEQ ID NO: 1 (Y641H); a substitution of asparagine (N) for the wild type residue tyrosine (Y) at amino acid position 641 of SEQ ID NO: 1 (Y641N); a substitution of serine (S) for the wild type residue tyrosine (Y) at amino acid position 641 of SEQ ID NO: 1 (Y641S); or a substitution of cysteine (C) for the wild type residue tyrosine (Y) at amino acid position 641 of SEQ ID NO: 1 (Y641C).

The mutation of the present invention may also include a substitution of serine (S) for the wild type residue asparagine (N) at amino acid position 322 of SEQ ID NO: 3 (N322S), a substitution of glutamine (Q) for the wild type residue arginine (R) at amino acid position 288 of SEQ ID NO: 3 (R288Q), a substitution of isoleucine (I) for the wild type residue threonine (T) at amino acid position 573 of SEQ ID NO: 3 (T573I), a substitution of glutamic acid (E) for the wild type residue aspartic acid (D) at amino acid position 664 of SEQ ID NO: 3 (D664E), a substitution of glutamine (Q) for the wild type residue arginine (R) at amino acid position 458 of SEQ ID NO: 5 (R458Q), a substitution of lysine (K) for the wild type residue glutamic acid (E) at amino acid position 249 of SEQ ID NO: 3 (E249K), a substitution of cysteine (C) for the wild type residue arginine (R) at amino acid position 684 of SEQ ID NO: 3 (R684C), a substitution of histidine (H) for the wild type residue arginine (R) at amino acid position 628 of SEQ ID NO: 21 (R628H), a substitution of histidine (H) for the wild type residue glutamine (Q) at amino acid position 501 of SEQ ID NO: 5 (Q501H), a substitution of asparagine (N) for the wild type residue aspartic acid (D) at amino acid position 192 of SEQ ID NO: 3 (D192N), a substitution of valine (V) for the wild type residue aspartic acid (D) at amino acid position 664 of SEQ ID NO: 3 (D664V), a substitution of leucine (L) for the wild type residue valine (V) at amino acid position 704 of SEQ ID NO: 3 (V704L), a substitution of serine (S) for the wild type residue proline (P) at amino acid position 132 of SEQ ID NO: 3 (P132S), a substitution of lysine (K) for the wild type residue glutamic acid (E) at amino acid position 669 of SEQ ID NO: 21 (E669K), a substitution of threonine (T) for the wild type residue alanine (A) at amino acid position 255 of SEQ ID NO: 3 (A255T), a substitution of valine (V) for the wild type residue glutamic acid (E) at amino acid position 726 of SEQ ID NO: 3 (E726V), a substitution of tyrosine (Y) for the wild type residue cysteine (C) at amino acid position 571 of SEQ ID NO: 3 (C571Y), a substitution of cysteine (C) for the wild type residue phenylalanine (F) at amino acid position 145 of SEQ ID NO: 3 (F145C), a substitution of threonine (T) for the wild type residue asparagine (N) at amino acid position 693 of SEQ ID NO: 3 (N693T), a substitution of serine (S) for the wild type residue phenylalanine (F) at amino acid position 145 of SEQ ID NO: 3 (F145S), a substitution of histidine (H) for the wild type residue glutamine (Q) at amino acid position 109 of SEQ ID NO: 21 (Q109H), a substitution of cysteine (C) for the wild type residue phenylalanine (F) at amino acid position 622 of SEQ ID NO: 21 (F622C), a substitution of arginine (R) for the wild type residue glycine (G) at amino acid position 135 of SEQ ID NO: 3 (G135R), a substitution of glutamine (Q) for the wild type residue arginine (R) at amino acid position 168 of SEQ ID NO: 5 (R168Q), a substitution of arginine (R) for the wild type residue glycine (G) at amino acid position 159 of SEQ ID NO: 3 (G159R), a substitution of cysteine (C) for the wild type residue arginine (R) at amino acid position 310 of SEQ ID NO: 5 (R310C), a substitution of histidine (H) for the wild type residue arginine (R) at amino acid position 561 of SEQ ID NO: 3 (R561H), a substitution of histidine (H) for the wild type residue arginine (R) at amino acid position 634 of SEQ ID NO: 21 (R634H), a substitution of arginine (R) for the wild type residue glycine (G) at amino acid position 660 of SEQ ID NO: 3 (G660R), a substitution of cysteine (C) for the wild type residue tyrosine (Y) at amino acid position 181 of SEQ ID NO: 3 (Y181C), a substitution of arginine (R) for the wild type residue histidine (H) at amino acid position 297 of SEQ ID NO: 3 (H297R), a substitution of serine (S) for the wild type residue cysteine (C) at amino acid position 612 of SEQ ID NO: 21 (C612S), a substitution of tyrosine (Y) for the wild type residue histidine (H) at amino acid position 694 of SEQ ID NO: 3 (H694Y), a substitution of alanine (A) for the wild type residue aspartic acid (D) at amino acid position 664 of SEQ ID NO: 3 (D664A), a substitution of threonine (T) for the wild type residue isoleucine (I) at amino acid position 150 of SEQ ID NO: 3 (I150T), a substitution of arginine (R) for the wild type residue isoleucine (I) at amino acid position 264 of SEQ ID NO: 3 (I264R), a substitution of leucine (L) for the wild type residue proline (P) at amino acid position 636 of SEQ ID NO: 3 (P636L), a substitution of threonine (T) for the wild type residue isoleucine (I) at amino acid position 713 of SEQ ID NO: 3 (I713T), a substitution of proline (P) for the wild type residue glutamine (Q) at amino acid position 501 of SEQ ID NO: 5 (Q501P), a substitution of glutamine (Q) for the wild type residue lysine (K) at amino acid position 243 of SEQ ID NO: 3 (K243Q), a substitution of aspartic acid (D) for the wild type residue glutamic acid (E) at amino acid position 130 of SEQ ID NO: 5 (E130D), a substitution of glycine (G) for the wild type residue arginine (R) at amino acid position 509 of SEQ ID NO: 3 (R509G), a substitution of histidine (H) for the wild type residue arginine (R) at amino acid position 566 of SEQ ID NO: 3 (R566H), a substitution of histidine (H) for the wild type residue aspartic acid (D) at amino acid position 677 of SEQ ID NO: 3 (D677H), a substitution of asparagine (N) for the wild type residue lysine (K) at amino acid position 466 of SEQ ID NO: 5 (K466N), a substitution of histidine (H) for the wild type residue arginine (R) at amino acid position 78 of SEQ ID NO: 3 (R78H), a substitution of methionine (M) for the wild type residue lysine (K) at amino acid position 1 of SEQ ID NO: 6 (K6M), a substitution of leucine (L) for the wild type residue serine (S) at amino acid position 538 of SEQ ID NO: 3 (S538L), a substitution of glutamine (Q) for the wild type residue leucine (L) at amino acid position 149 of SEQ ID NO: 3 (L149Q), a substitution of valine (V) for the wild type residue leucine (L) at amino acid position 252 of SEQ ID NO: 3 (L252V), a substitution of valine (V) for the wild type residue leucine (L) at amino acid position 674 of SEQ ID NO: 3 (L674V), a substitution of valine (V) for the wild type residue alanine (A) at amino acid position 656 of SEQ ID NO: 3 (A656V), a substitution of aspartic acid (D) for the wild type residue alanine (A) at amino acid position 731 of SEQ ID NO: 3 (Y731D), a substitution of threonine (T) for the wild type residue alanine (A) at amino acid position 345 of SEQ ID NO: 3 (A345T), a substitution of aspartic acid (D) for the wild type residue alanine (A) at amino acid position 244 of SEQ ID NO: 3 (Y244D), a substitution of tryptophan (W) for the wild type residue cysteine (C) at amino acid position 576 of SEQ ID NO: 3 (C576W), a substitution of lysine (K) for the wild type residue asparagine (N) at amino acid position 640 of SEQ ID NO: 3 (N640K), a substitution of lysine (K) for the wild type residue asparagine (N) at amino acid position 675 of SEQ ID NO: 3 (N675K), a substitution of tyrosine (Y) for the wild type residue aspartic acid (D) at amino acid position 579 of SEQ ID NO: 21 (D579Y), a substitution of isoleucine (I) for the wild type residue asparagine (N) at amino acid position 693 of SEQ ID NO: 3 (N693I), and a substitution of lysine (K) for the wild type residue asparagine (N) at amino acid position 693 of SEQ ID NO: 3 (N693K).

The mutation of the present invention may be a frameshift at amino acid position 730, 391, 461, 441, 235, 254, 564, 662, 715, 405, 685, 64, 73, 656, 718, 374, 592, 505, 730, or 363 of SEQ ID NO: 3, 5 or 21 or the corresponding nucleotide position of the nucleic acid sequence encoding SEQ ID NO: 3, 5, or 21. The mutation of the EZH2 may also be an insertion of a glutamic acid (E) between amino acid positions 148 and 149 of SEQ ID NO: 3, 5 or 21. Another example of EZH2 mutation is a deletion of glutamic acid (E) and leucine (L) at amino acid positions 148 and 149 of SEQ ID NO: 3, 5 or 21. The mutant EZH2 may further comprise a nonsense mutation at amino acid position 733, 25, 317, 62, 553, 328, 58, 207, 123, 63, 137, or 60 of SEQ ID NO: 3, 5 or 21.

It has also been unexpectedly discovered that the wild-type (WT) EZH2 enzyme displays greatest catalytic efficiency (kcat/K) for the zero- to mono-methylation reaction of H3-K27 and lesser efficiency for subsequent (mono- to di- and di- to tri-methylation) reactions; whereas, in stark contrast, the disease-associated Y641 mutations display very limited ability to perform the first methylation reaction but have enhanced catalytic efficiency for the subsequent reactions relative to wild-type enzyme. These results imply that the malignant phenotype of disease exploits the combined activities of a H3-K27 mono-methylating enzyme (PRC2 containing WT EZH2 or EZH1) together with PRC2 containing mutant EZH2 for augmented conversion of H3-K27 to the tri-methylated form (H3-K27me3). Therefore, an aspect of the present invention relates to inhibiting the activity of EZH2, including certain mutant forms of EZH2. In one embodiment the present invention relates to inhibiting selectively the activity of certain mutant forms of EZH2.

While not intending to be bound by any one theory, it is hypothesized that the mutation of EZH2 in its substrate pocket domain may facilitate multiple rounds of H3-K27 methylation by impacting the H-bonding pattern and/or steric crowding in the active site of the enzyme-bisubstrate ternary complex, affecting the formation of a proper water channel for deprotonation of the reacting lysine.

Human EZH2 nucleic acids and polypeptides have previously been described. See, e.g., Chen et al. (1996) *Genomics* 38:30-7 [746 amino acids]; Swiss-Prot Accession No. Q15910 [746 amino acids]; GenBank Accession Nos. NM_004456 and NP_004447 (isoform a [751 amino acids]); and GenBank Accession Nos. NM_152998 and NP_694543 (isoform b [707 amino acids]), each of which is incorporated herein by reference in its entirety.

```
Amino acid sequence of human EZH2 (Swiss-Prot Accession No. Q15910)
                                                              (SEQ ID NO: 1)
MGQTGKKSEKGPVCWRKRVKSEYMRLRQLKRFRRADEVKSMFSSNRQKILERTEILNQEW

KQRRIQPVHILTSVSSLRGTRECSVTSDLDFPTQVIPLKTLNAVASVPIMYSWSPLQQNF

MVEDETVLHNIPYMGDEVLDQDGTFIEELIKNYDGKVHGDRECGFINDEIFVELVNALGQ

YNDDDDDDGDDPEEREEKQKDLEDHRDDKESRPPRKFPSDKIFEAISSMFPDKGTAEEL

KEKYKELTEQQLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRPGGRRRGRLPN

NSSRPSTPTINVLESKDTDSDREAGTETGGENNDKEEEEKKDETSSSSEANSRCQTPIKM

KPNIEPPENVEWSGAEASMFRVLIGTYYDNFCAIARLIGTKTCRQVYEFRVKESSIIAPA

PAEDVDTPPRKKKRKHRLWAAHCRKIQLKKDGSSNHVYNYQPCDHPRQPCDSSCPCVIAQ

NFCEKFCQCSSECQNRFPGCRCKAQCNTKQCPCYLAVRECDPDLCLTCGAADHWDSKNVS
```

CKNCSIQRGSKKHLLLAPSDVAGWGIFIKDPVQKNEFISEYCGEIISQDEADRRGKVYDK

YMCSFLFNLNNDFVVDATRKGNKIRFANHSVNPNCYAKVMMVNGDHRIGIFAKRAIQTGE

ELFFDYRYSQADALKYVGIEREMEIP mRNA sequence of human EZH2, transcript variant 1 (GenBank Accession No. NM_004456)

(SEQ ID NO: 2)

ggcggcgcttgattgggctggggggggccaaataaaagcgatggcgattgggctgccgcgt ttggcgctcggtccggtcgcgtccgacaccggtgggactcagaaggcagtggagccccg gcggcggcggcggcggcgcgcgggggcgacgcgcgggaacaacgcgagtcggcgcgcggg acgaagaataatcatgggccagactgggaagaaatctgagaagggaccagtttgttggcg gaagcgtgtaaaatcagagtacatgcgactgagacagctcaagaggttcagacgagctga tgaagtaaagagtatgtttagttccaatcgtcagaaaattttggaaagaacggaaatctt aaaccaagaatggaaacagcgaaggatacagcctgtgcacatcctgacttctgtgagctc attgcgcgggactagggagtgttcggtgaccagtgacttggattttccaacacaagtcat cccattaaagactctgaatgcagttgcttcagtacccataatgtattcttggtctcccct acagcagaatttatggtggaagatgaaactgttttacataacattccttatatgggaga tgaagttttagatcaggatggtactttcattgaagaactaataaaaaattatgatgggaa agtacacggggatagagaatgtgggtttataaatgatgaattttttgtggagttggtgaa tgcccttggtcaatataatgatgatgacgatgatgatgatggagacgatcctgaagaaag agaagaaaagcagaaagatctggaggatcaccgagatgataaagaaagccgcccacctcg gaaatttccttctgataaaatttttgaagccatttcctcaatgtttccagataagggcac agcagaagaactaaaggaaaaatataaagaactcaccgaacagcagctcccaggcgcact tcctcctgaatgtaccccaacatagatggaccaaatgctaaatctgttcagagagagca aagcttacactcctttcatacgcttttctgtaggcgatgttttaaatatgactgcttcct acatcgtaagtgcaattattcttttcatgcaacacccaacacttataagcggaagaacac agaaacagctctagacaacaaaccttgtgaccacagtgttaccagcatttggagggagc aaaggagtttgctgctgctctcaccgctgagcggataaagaccccaccaaaacgtccagg aggccgcagaagaggacggcttcccaataacagtagcaggcccagcaccccaccattaa tgtgctggaatcaaaggatacagacagtgatagggaagcagggactgaaacgggggga gaacaatgataaagaagaagaagagaagaaagatgaaacttcgagctcctctgaagcaaa ttctcggtgtcaaacaccaataaagatgaagccaaatattgaacctcctgagaatgtgga gtggagtggtgctgaagcctcaatgtttagagtcctcattggcacttactatgacaattt ctgtgccattgctaggttaattgggaccaaaacatgtagacaggtgtatgagtttagagt caaagaatctagcatcatagctccagctcccgctgaggatgtggatactcctccaaggaa aaagaagaggaaacaccggttgtgggctgcacactgcagaaagatacagctgaaaagga cggctcctctaaccatgttacaactatcaaccctgtgatcatccacggcagccttgtga cagttcgtgcccttgtgtgatagcacaaaattttgtgaaaagtttttgtcaatgtagttc agagtgtcaaaaccgctttccgggatgccgctgcaaagcacagtgcaacaccaagcagtg cccgtgctacctggctgtccgagagtgtgaccctgacctctgtcttacttgtggagccgc tgaccattgggacagtaaaaatgtgtcctgcaagaactgcagtattcagcggggctccaa aaagcatctattgctggcaccatctgacgtggcaggctggggatttttatcaaagatcc tgtgcagaaaaatgaattcatctcagaatactgtggagagattatttctcaagatgaagc

```
tgacagaagagggaaagtgtatgataaatacatgtgcagctttctgttcaacttgaacaa tgattttgtggtggatgcaacccgcaagggtaacaaaattcgttttgcaaatcattcggt aaatccaaactgctatgcaaaagttatgatggttaacggtgatcacaggataggtatttt tgccaagagagccatccagactggcgaagagctgtttttgattacagatacagccaggc tgatgccctgaagtatgtcggcatcgaaagagaaatggaaatcccttgacatctgctacc tcctcccccctcctctgaaacagctgccttagcttcaggaacctcgagtactgtgggcaa tttagaaaaagaacatgcagtttgaaattctgaatttgcaaagtactgtaagaataattt atagtaatgagtttaaaaatcaacttttttattgccttctcaccagctgcaaagtgttttg taccagtgaattttttgcaataatgcagtatggtacattttttcaactttgaataaagaata cttgaacttgtccttgttgaatc
```

Full amino acid of EZH2, isoform a (GenBank Accession No. NP_004447)

(SEQ ID NO: 3)

```
MGQTGKKSEKGPVCWRKRVKSEYMRLRQLKRFRRADEVKSMFSSNRQKILERTEILNQEW

KQRRIQPVHILTSVSSLRGTRECSVTSDLDFPTQVIPLKTLNAVASVPIMYSWSPLQQNF

MVEDETVLHNIPYMGDEVLDQDGTFIEELIKNYDGKVHGDRECGFINDEIFVELVNALGQ

YNDDDDDDGDDPEEREEKQKDLEDHRDDKESRPPRKFPSDKIFEAISSMFPDKGTAEEL

KEKYKELTEQQLPGALPPECTPNIDGPNAKSVQREQSLHSFHTLFCRRCFKYDCFLHRKC

NYSFHATPNTYKRKNTETALDNKPCGPQCYQHLEGAKEFAAALTAERIKTPPKRPGGRRR

GRLPNNSSRPSTPTINVLESKDTDSDREAGTETGGENNDKEEEEKKDETSSSSEANSRCQ

TPIKMKPNIEPPENVEWSGAEASMFRVLIGTYYDNFCAIARLIGTKTCRQVYEFRVKESS

IIAPAPAEDVDTPPRKKKRKHRLWAAHCRKIQLKKDGSSNHVYNYQPCDHPRQPCDSSCP

CVIAQNFCEKFCQCSSECQNRFPGCRCKAQCNTKQCPCYLAVRECDPDLCLTCGAADHWD

SKNVSCKNCSIQRGSKKHLLLAPSDVAGWGIFIKDPVQKNEFISEYCGEIISQDEADRRG

KVYDKYMCSFLFNLNNDFVVDATRKGNKIRFANHSVNPNCYAKVMMVNGDHRIGIFAKRA

IQTGEELFFDYRYSQADALKYVGIEREMEIP
``` mRNA sequence of human EZH2, transcript variant 2 (GenBank Accession No. NM_152998)

(SEQ ID NO: 4)

```
ggcggcgcttgattgggctggggggggccaaataaaagcgatggcgattgggctgccgcgt ttggcgctcggtccggtcgcgtccgacacccggtgggactcagaaggcagtggagccccg gcggcggcggcggcgcgcggggcgacgcgcgggaacaacgcgagtcggcgcgcggg acgaagaataatcatgggccagactgggaagaaatctgagaagggaccagtttgttggcg gaagcgtgtaaaatcagagtacatgcgactgagacagctcaagaggttcagacgagctga tgaagtaaagagtatgtttagttccaatcgtcagaaaattttggaaagaacggaaatctt aaaccaagaatggaaacagcgaaggatacagcctgtgcacatcctgacttctgtgagctc attgcgcgggactagggaggtggaagatgaaactgttttacataacattccttatatggg agatgaagttttagatcaggatggtacttcattgaagaactaataaaaaaattatgatgg gaaagtacacggggatagagaatgtgggtttataaatgatgaattttttgtggagttggt gaatgcccttggtcaatataatgatgatgacgatgatgatgatgagacgatcctgaaga aagagaagaaaagcagaaagatctggaggatcaccgagatgataaagaaagccgcccacc tcggaaattccttctgataaaattttttgaagccatttcctcaatgtttccagataaggg cacagcagaagaactaaaggaaaaatataaagaactcaccgaacagcagctcccaggcgc
```

-continued

```
acttcctcctgaatgtaccccaacatagatggaccaaatgctaaatctgttcagagaga
gcaaagcttacactcctttcatacgcttttctgtaggcgatgttttaaatatgactgctt
cctacatccttttcatgcaacacccaacacttataagcggaagaacacagaaacagctct
agacaacaaaccttgtggaccacagtgttaccagcatttggagggagcaaaggagtttgc
tgctgctctcaccgctgagcggataaagaccccaccaaaacgtccaggaggccgcagaag
aggacggcttcccaataacagtagcaggcccagcaccccaccattaatgtgctggaatc
aaaggatacagacagtgatagggaagcagggactgaaacgggggagagaacaatgataa
agaagaagaagagaagaaagatgaaacttcgagctcctctgaagcaaattctcggtgtca
aacaccaataaagatgaagccaaatattgaacctcctgagaatgtggagtggagtggtgc
tgaagcctcaatgtttagagtcctcattggcacttactatgacaatttctgtgccattgc
taggttaattgggaccaaaacatgtagacaggtgtatgagtttagagtcaaagaatctag
catcatagctccagctcccgctgaggatgtggatactcctccaaggaaaagaagaggaa
acaccggttgtgggctgcacactgcagaaagatacagctgaaaaaggacggctcctctaa
ccatgtttacaactatcaaccctgtgatcatccacggcagccttgtgacagttcgtgccc
ttgtgtgatagcacaaaattttttgtgaaaagttttgtcaatgtagttcagagtgtcaaaa
ccgctttccgggatgccgctgcaaagcacagtgcaacaccaagcagtgcccgtgctacct
ggctgtccgagagtgtgaccctgacctctgtcttacttgtggagccgctgaccattggga
cagtaaaaatgtgtcctgcaagaactgcagtattcagcggggctccaaaaagcatctatt
gctggcaccatctgacgtggcaggctgggggattttatcaaagatcctgtgcagaaaaa
tgaattcatctcagaatactgtggagagattatttctcaagatgaagctgacagaagagg
gaaagtgtatgataaatacatgtgcagctttctgttcaacttgaacaatgattttgtggt
ggatgcaacccgcaagggtaacaaaattcgttttgcaaatcattcggtaaatccaaactg
ctatgcaaaagttatgatggttaacggtgatcacaggataggtattttttgccaagagagc
catccagactggcgaagagctgttttttgattacagatacagccaggctgatgccctgaa
gtatgtcggcatcgaaagagaaatggaaatcccttgacatctgctacctcctcccccctc
ctctgaaacagctgccttagcttcaggaacctcgagtactgtgggcaatttagaaaaaga
acatgcagtttgaaattctgaatttgcaaagtactgtaagaataatttatagtaatgagt
ttaaaaatcaacttttattgccttctcaccagctgcaaagtgttttgtaccagtgaatt
tttgcaataatgcagtatggtacattttcaactttgaataaagaatacttgaacttgtc
cttgttgaatc
```

Full amino acid of EZH2, isoform b (GenBank Accession No. NP_694543)

(SEQ ID NO: 5)

```
MGQTGKKSEKGPVCWRKRVKSEYMRLRQLKRFRRADEVKSMFSSNRQKIL
ERTEILNQEWKQRRIQPVHILTSVSSLRGTREVEDETVLHNIPYMGDEVL
DQDGTFIEELIKNYDGKVHGDRECGFINDEIFVELVNALGQYNDDDDDDD
GDDPEEREEKQKDLEDHRDDKESRPPRKFPSDKIFEAISSMFPDKGTAEE
LKEKYKELTEQQLPGALPPECTPNIDGPNAKSVQREQSLHSFHTLFCRRC
FKYDCFLHPFHATPNTYKRKNTETALDNKPCGPQCYQHLEGAKEFAAALT
AERIKTPPKRPGGRRRGRLPNNSSRPSTPTINVLESKDTDSDREAGTETG
GENNDKEEEEKKDETSSSSEANSRCQTPIKMKPNIEPPENVEWSGAEASM
FRVLIGTYYDNFCAIARLIGTKTCRQVYEFRVKESSIIAPAPAEDVDTPP
```

-continued

RKKKRKHRLWAAHCRKIQLKKDGSSNHVYNYQPCDHPRQPCDSSCPCVIA

QNFCEKFCQCSSECQNRFPGCRCKAQCNTKQCPCYLAVRECDPDLCLTCG

AADHWDSKNVSCKNCSIQRGSKKHLLLAPSDVAGWGIFIKDPVQKNEFIS

EYCGEIISQDEADRRGKVYDKYMCSFLFNLNNDFVVDATRKGNKIRFANH

SVNPNCYAKVMMVNGDHRIGIFAKRAIQTGEELFFDYRYSQADALKYVGI

EREMEIP

Full amino acid of EZH2, isoform e (GenBank Accession No. NP_001190178.1)

(SEQ ID NO: 21)

MGQTGKKSEKGPVCWRKRVKSEYMRLRQLKRFRRADEVKSMFSSNRQKILERTEILNQEWKQRRIQPVHI

LTSCSVTSDLDFPTQVIPLKTLNAVASVPIMYSWSPLQQNFMVEDETVLHNIPYMGDEVLDQDGTFIEEL

IKNYDGKVHGDRECGFINDEIFVELVNALGQYNDDDDDDGDDPEEREEKQKDLEDHRDDKESRPPRKFP

SDKIFEAISSMFPDKGTAEELKEKYKELTEQQLPGALPPECTPNIDGPNAKSVQREQSLHSFHTLFCRRC

FKYDCFLHPFHATPNTYKRKNTETALDNKPCGPQCYQHLEGAKEFAAALTAERIKTPPKRPGGRRRGRLP

NNSSRPSTPTINVLESKDTDSDREAGTETGGENNDKEEEEKKDETSSSSEANSRCQTPIKMKPNIEPPEN

VEWSGAEASMFRVLIGTYYDNFCAIARLIGTKTCRQVYEFRVKESSIIAPAPAEDVDTPPRKKKRKHRLW

AAHCRKIQLKKGQNRFPGCRCKAQCNTKQCPCYLAVRECDPDLCLTCGAADHWDSKNVSCKNCSIQRGSK

KHLLLAPSDVAGWGIFIKDPVQKNEFISEYCGEIISQDEADRRGKVYDKYMCSFLFNLNNDFVVDATRKG

NKIRFANHSVNPNCYAKVMMVNGDHRIGIFAKRAIQTGEELFFDYRYSQADALKYVGIEREMEIP

*Homo sapiens* enhancer of zeste homolog 2 (*Drosophila*) (EZH2), transcript variant 5, mRNA (GenBank Accession No. NM_001203249.1)

(SEQ ID NO: 22)

GACGACGTTCGCGGCGGGGAACTCGGAGTAGCTTCGCCTCTGACGTTTCCCCACGACGCACCCCGAAATC

CCCCTGAGCTCCGGCGGTCGCGGGCTGCCCTCGCCGCCTGGTCTGGCTTTATGCTAAGTTTGAGGGAAGA

GTCGAGCTGCTCTGCTCTCTATTGATTGTGTTTCTGGAGGGCGTCCTGTTGAATTCCCACTTCATTGTGT

ACATCCCCTTCCGTTCCCCCCAAAAATCTGTGCCACAGGGTTACTTTTTGAAAGCGGGAGGAATCGAGAA

GCACGATCTTTTGGAAAACTTGGTGAACGCCTAAATAATCATGGGCCAGACTGGGAAGAAATCTGAGAAG

GGACCAGTTTGTTGGCGGAAGCGTGTAAAATCAGAGTACATGCGACTGAGACAGCTCAAGAGGTTCAGAC

GAGCTGATGAAGTAAAGAGTATGTTTAGTTCCAATCGTCAGAAAATTTTGGAAAGAACGGAAATCTTAAA

CCAAGAATGGAAACAGCGAAGGATACAGCCTGTGCACATCCTGACTTCTTGTTCGGTGACCAGTGACTTG

GATTTTCCAACACAAGTCATCCCATTAAAGACTCTGAATGCAGTTGCTTCAGTACCCATAATGTATTCTT

GGTCTCCCCTACAGCAGAATTTTATGGTGGAAGATGAAACTGTTTTACATAACATTCCTTATATGGGAGA

TGAAGTTTTAGATCAGGATGGTACTTTCATTGAAGAACTAATAAAAAATTATGATGGGAAAGTACACGGG

GATAGAGAATGTGGGTTTATAAATGATGAAATTTTTGTGGAGTTGGTGAATGCCCTTGGTCAATATAATG

ATGATGACGATGATGATGATGGAGACGATCCTGAAGAAAGAGAAGAAAAGCAGAAAGATCTGGAGGATCA

CCGAGATGATAAAGAAAGCCGCCCACCTCGGAAATTTCCTTCTGATAAAATTTTTGAAGCCATTTCCTCA

ATGTTTCCAGATAAGGGCACAGCAGAAGAACTAAAGGAAAAATATAAAGAACTCACCGAACAGCAGCTCC

CAGGCGCACTTCCTCCTGAATGTACCCCCAACATAGATGGACCAAATGCTAAATCTGTTCAGAGAGAGCA

AAGCTTACACTCCTTTCATACGCTTTTCTGTAGGCGATGTTTTAAATATGACTGCTTCCTACATCCTTTT

CATGCAACACCCAACACTTATAAGCGGAAGAACACAGAAACAGCTCTAGACAACAAACCTTGTGGACCAC

```
-continued
AGTGTTACCAGCATTTGGAGGGAGCAAAGGAGTTTGCTGCTGCTCTCACCGCTGAGCGGATAAAGACCCC

ACCAAAACGTCCAGGAGGCCGCAGAAGAGGACGGCTTCCCAATAACAGTAGCAGGCCCAGCACCCCCACC

ATTAATGTGCTGGAATCAAAGGATACAGACAGTGATAGGGAAGCAGGGACTGAAACGGGGGGAGAGAACA

ATGATAAAGAAGAAGAAGAGAAGAAAGATGAAACTTCGAGCTCCTCTGAAGCAAATTCTCGGTGTCAAAC

ACCAATAAAGATGAAGCCAAATATTGAACCTCCTGAGAATGTGGAGTGGAGTGGTGCTGAAGCCTCAATG

TTTAGAGTCCTCATTGGCACTTACTATGACAATTTCTGTGCCATTGCTAGGTTAATTGGGACCAAAACAT

GTAGACAGGTGTATGAGTTTAGAGTCAAAGAATCTAGCATCATAGCTCCAGCTCCCGCTGAGGATGTGGA

TACTCCTCCAAGGAAAAAGAAGAGGAAACACCGGTTGTGGGCTGCACACTGCAGAAAGATACAGCTGAAA

AAGGGTCAAAACCGCTTTCCGGGATGCCGCTGCAAAGCACAGTGCAACACCAAGCAGTGCCCGTGCTACC

TGGCTGTCCGAGAGTGTGACCCTGACCTCTGTCTTACTTGTGGAGCCGCTGACCATTGGGACAGTAAAAA

TGTGTCCTGCAAGAACTGCAGTATTCAGCGGGGCTCCAAAAAGCATCTATTGCTGGCACCATCTGACGTG

GCAGGCTGGGGGATTTTTATCAAAGATCCTGTGCAGAAAAATGAATTCATCTCAGAATACTGTGGAGAGA

TTATTTCTCAAGATGAAGCTGACAGAAGAGGGAAAGTGTATGATAAATACATGTGCAGCTTTCTGTTCAA

CTTGAACAATGATTTTGTGGTGGATGCAACCCGCAAGGGTAACAAAATTCGTTTTGCAAATCATTCGGTA

AATCCAAACTGCTATGCAAAAGTTATGATGGTTAACGGTGATCACAGGATAGGTATTTTTGCCAAGAGAG

CCATCCAGACTGGCGAAGAGCTGTTTTTTGATTACAGATACAGCCAGGCTGATGCCCTGAAGTATGTCGG

CATCGAAAGAGAAATGGAAATCCCTTGACATCTGCTACCTCCTCCCCCCTCCTCTGAAACAGCTGCCTTA

GCTTCAGGAACCTCGAGTACTGTGGGCAATTTAGAAAAAGAACATGCAGTTTGAAATTCTGAATTTGCAA

AGTACTGTAAGAATAATTTATAGTAATGAGTTTAAAAATCAACTTTTTATTGCCTTCTCACCAGCTGCAA

AGTGTTTTGTACCAGTGAATTTTTGCAATAATGCAGTATGGTACATTTTTCAACTTTGAATAAAGAATAC

TTGAACTTGTCCTTGTTGAATC
```

Figure 16:
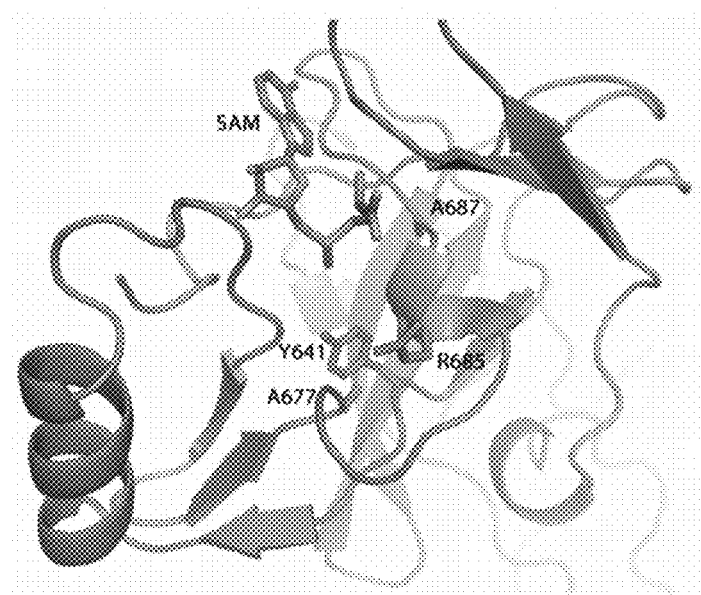
FIG. 16 is a structure model of partial EZH2 protein based on the A chain of nuclear receptor binding SET domain protein 1 (NSD1). This model corresponds to amino acid residues 533-732 of EZH2 sequence of SEQ ID NO: 1.

A structure model of partial EZH2 protein based on the A chain of nuclear receptor binding SET domain protein 1 (NSD1) is provided at FIG. 16. This model corresponds to amino acid residues 533-732 of EZH2 sequence of SEQ ID NO: 1.

The corresponding amino acid sequence of this structure model is provided below. The residues in the substrate pocket domain are underlined. The residues in the SET domain are shown italic.

```
                                                    (SEQ ID NO: 6)
SCPCVIAQNFCEKFCQCSSECQNRFPGCRCKAQCNTKQCPCYLAVRECDPDLCLTCGAA

DHWDSKNVSCKNCSIQRGSKKHLLLAPSDVAGWGIFIKDPVQKNEFISEY⁶⁴¹CGEIISQDEA

DRRGKVYDKYMCSFLFNLNNDFV⁶⁷⁴VDA⁶⁷⁷TRKGNKIR⁶⁸⁵FA⁶⁸⁷NHSVNPNCYAKVMMVNGD

HRIGIFAKRAIQTGEELFFDYRYSQAD
```

The catalytic site of EZH2 is believed to reside in a conserved domain of the protein known as the SET domain. The amino acid sequence of the SET domain of EZH2 is provided by the following partial sequence spanning amino acid residues 613-726 of Swiss-Prot Accession No. Q15910 (SEQ ID NO: 1):

The tyrosine (Y) residue shown underlined in SEQ ID NO: 7 is Tyr641 (Y641) in Swiss-Prot Accession No. Q15910 (SEQ ID NO: 1).

The SET domain of GenBank Accession No. NP_004447 (SEQ ID NO: 3) spans amino acid residues 618-731 and is identical to SEQ ID NO:6. The tyrosine residue corresponding to Y641 in Swiss-Prot Accession No. Q15910 shown underlined in SEQ ID NO: 7 is Tyr646 (Y646) in GenBank Accession No. NP_004447 (SEQ ID NO: 3).

The SET domain of GenBank Accession No. NP_694543 (SEQ ID NO: 5) spans amino acid residues 574-687 and is identical to SEQ ID NO: 7. The tyrosine residue corresponding to Y641 in Swiss-Prot Accession No. Q15910 shown underlined in SEQ ID NO: 7 is Tyr602 (Y602) in GenBank Accession No. NP_694543 (SEQ ID NO: 5).

```
                                                    (SEQ ID NO: 7)
HLLLAPSDVAGWGIFIKDPVQKNEFISEYCGEIISQDEADRRGKVYDKYMCSFLFNLNNDFVVD

ATRKGNKIRFANHSVNPNCYAKVMMVNGDHRIGIFAKRAIQTGEELFFDY.
```

The nucleotide sequence encoding the SET domain of GenBank Accession No. NP_004447 is (SEQ ID NO: 8)
catctattgctggcaccatctgacgtggcaggctgggggattttatcaaagatcctgtgcaga aaaatgaattcatctcagaatactgtggagagattatttctcaagatgaagctgacagaagagg gaaagtgtatgataaatacatgtgcagctttctgttcaacttgaacaatgattttgtggtggat gcaacccgcaagggtaacaaaattcgttttgcaaatcattcggtaaatccaaactgctatgcaa aagttatgatggttaacggtgatcacaggataggtattttttgccaagagagccatccagactgg cgaagagctgttttttgattac, where the codon encoding Y641 is shown underlined.

For purposes of this application, amino acid residue Y641 of human EZH2 is to be understood to refer to the tyrosine residue that is or corresponds to Y641 in Swiss-Prot Accession No. Q15910.

Full amino acid sequence of Y641 mutant EZH2
(SEQ ID NO: 9)
MGQTGKKSEKGPVCWRKRVKSEYMRLRQLKRFRRADEVKSMFSSNRQKILERTEILNQEW

KQRRIQPVHILTSVSSLRGTRECSVTSDLDFPTQVIPLKTLNAVASVPIMYSWSPLQQNF

MVEDETVLHNIPYMGDEVLDQDGTFIEELIKNYDGKVHGDRECGFINDEIFVELVNALGQ

YNDDDDDDGDDPEEREEKQKDLEDHRDDKESRPPRKFPSDKIFEAISSMFPDKGTAEEL

KEKYKELTEQQLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRPGGRRRGRLPN

NSSRPSTPTINVLESKDTDSDREAGTETGGENNDKEEEEKKDETSSSSEANSRCQTPIKM

KPNIEPPENVEWSGAEASMFRVLIGTYYDNFCAIARLIGTKTCRQVYEFRVKESSIIAPA

PAEDVDTPPRKKKRKHRLWAAHCRKIQLKKDGSSNHVYNYQPCDHPRQPCDSSCPCVIAQ

NFCEKFCQCSSECQNRFPGCRCKAQCNTKQCPCYLAVRECDPDLCLTCGAADHWDSKNVS

CKNCSIQRGSKKHLLLAPSDVAGWGIFIKDPVQKNEFISEXCGEIISQDEADRRGKVYDK

YMCSFLFNLNNDFVVDATRKGNKIRFANHSVNPNCYAKVMMVNGDHRIGIFAKRAIQTGE

ELFFDYRYSQADALKYVGIEREMEIP
Wherein x can be any amino acid residue other than tyrosine (Y)

Also for purposes of this application, a Y641 mutant of human EZH2, and, equivalently, a Y641 mutant of EZH2, is to be understood to refer to a human EZH2 in which the amino acid residue corresponding to Y641 of wild-type human EZH2 is substituted by an amino acid residue other than tyrosine.

In one embodiment the amino acid sequence of a Y641 mutant of EZH2 differs from the amino acid sequence of wild-type human EZH2 only by substitution of a single amino acid residue corresponding to Y641 of wild-type human EZH2 by an amino acid residue other than tyrosine.

In one embodiment the amino acid sequence of a Y641 mutant of EZH2 differs from the amino acid sequence of wild-type human EZH2 only by substitution of phenylalanine (F) for the single amino acid residue corresponding to Y641 of wild-type human EZH2. The Y641 mutant of EZH2 according to this embodiment is referred to herein as a Y641F mutant or, equivalently, Y641F.

Y641F
(SEQ ID NO: 10)
MGQTGKKSEKGPVCWRKRVKSEYMRLRQLKRFRRADEVKSMFSSNRQKILERTEILNQEW

KQRRIQPVHILTSVSSLRGTRECSVTSDLDFPTQVIPLKTLNAVASVPIMYSWSPLQQNF

MVEDETVLHNIPYMGDEVLDQDGTFIEELIKNYDGKVHGDRECGFINDEIFVELVNALGQ

YNDDDDDDGDDPEEREEKQKDLEDHRDDKESRPPRKFPSDKIFEAISSMFPDKGTAEEL

KEKYKELTEQQLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRPGGRRRGRLPN

-continued

NSSRPSTPTINVLESKDTDSDREAGTETGGENNDKEEEEKKDETSSSSEANSRCQTPIKM

KPNIEPPENVEWSGAEASMFRVLIGTYYDNFCAIARLIGTKTCRQVYEFRVKESSIIAPA

PAEDVDTPPRKKKRKHRLWAAHCRKIQLKKDGSSNHVYNYQPCDHPRQPCDSSCPCVIAQ

NFCEKFCQCSSECQNRFPGCRCKAQCNTKQCPCYLAVRECDPDLCLTCGAADHWDSKNVS

CKNCSIQRGSKKHLLLAPSDVAGWGIFIKDPVQKNEFISEFCGEIISQDEADRRGKVYDK

YMCSFLFNLNNDFVVDATRKGNKIRFANHSVNPNCYAKVMMVNGDHRIGIFAKRAIQTGE

ELFFDYRYSQADALKYVGIEREMEIP

In one embodiment the amino acid sequence of a Y641 mutant of EZH2 differs from the amino acid sequence of wild-type human EZH2 only by substitution of histidine (H) for the single amino acid residue corresponding to Y641 of wild-type human EZH2. The Y641 mutant of EZH2 according to this embodiment is referred to herein as a Y641H mutant or, equivalently, Y641H.

Y641H
(SEQ ID NO: 11)
MGQTGKKSEKGPVCWRKRVKSEYMRLRQLKRFRRADEVKSMFSSNRQKILERTEILNQEW

KQRRIQPVHILTSVSSLRGTRECSVTSDLDFPTQVIPLKTLNAVASVPIMYSWSPLQQNF

MVEDETVLHNIPYMGDEVLDQDGTFIEELIKNYDGKVHGDRECGFINDEIFVELVNALGQ

YNDDDDDDGDDPEEREEKQKDLEDHRDDKESRPPRKFPSDKIFEAISSMFPDKGTAEEL

KEKYKELTEQQLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRPGGRRRGRLPN

NSSRPSTPTINVLESKDTDSDREAGTETGGENNDKEEEEKKDETSSSSEANSRCQTPIKM

KPNIEPPENVEWSGAEASMFRVLIGTYYDNFCAIARLIGTKTCRQVYEFRVKESSIIAPA

PAEDVDTPPRKKKRKHRLWAAHCRKIQLKKDGSSNHVYNYQPCDHPRQPCDSSCPCVIAQ

NFCEKFCQCSSECQNRFPGCRCKAQCNTKQCPCYLAVRECDPDLCLTCGAADHWDSKNVS

CKNCSIQRGSKKHLLLAPSDVAGWGIFIKDPVQKNEFISEHCGEIISQDEADRRGKVYDK

YMCSFLFNLNNDFVVDATRKGNKIRFANHSVNPNCYAKVMMVNGDHRIGIFAKRAIQTGE

ELFFDYRYSQADALKYVGIEREMEIP

In one embodiment the amino acid sequence of a Y641 mutant of EZH2 differs from the amino acid sequence of wild-type human EZH2 only by substitution of asparagine (N) for the single amino acid residue corresponding to Y641 of wild-type human EZH2. The Y641 mutant of EZH2 according to this embodiment is referred to herein as a Y641N mutant or, equivalently, Y641N.

Y641N
(SEQ ID NO: 12)
MGQTGKKSEKGPVCWRKRVKSEYMRLRQLKRFRRADEVKSMFSSNRQKILERTEILNQEW

KQRRIQPVHILTSVSSLRGTRECSVTSDLDFPTQVIPLKTLNAVASVPIMYSWSPLQQNF

MVEDETVLHNIPYMGDEVLDQDGTFIEELIKNYDGKVHGDRECGFINDEIFVELVNALGQ

YNDDDDDDGDDPEEREEKQKDLEDHRDDKESRPPRKFPSDKIFEAISSMFPDKGTAEEL

KEKYKELTEQQLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRPGGRRRGRLPN

NSSRPSTPTINVLESKDTDSDREAGTETGGENNDKEEEEKKDETSSSSEANSRCQTPIKM

```
KPNIEPPENVEWSGAEASMFRVLIGTYYDNFCAIARLIGTKTCRQVYEFRVKESSIIAPA

PAEDVDTPPRKKKRKHRLWAAHCRKIQLKKDGSSNHVYNYQPCDHPRQPCDSSCPCVIAQ

NFCEKFCQCSSECQNRFPGCRCKAQCNTKQCPCYLAVRECDPDLCLTCGAADHWDSKNVS

CKNCSIQRGSKKHLLLAPSDVAGWGIFIKDPVQKNEFISENCGEIISQDEADRRGKVYDK

YMCSFLFNLNNDFVVDATRKGNKIRFANHSVNPNCYAKVMMVNGDHRIGIFAKRAIQTGE

ELFFDYRYSQADALKYVGIEREMEIP
```

In one embodiment the amino acid sequence of a Y641 mutant of EZH2 differs from the amino acid sequence of wild-type human EZH2 only by substitution of serine (S) for the single amino acid residue corresponding to Y641 of wild-type human EZH2. The Y641 mutant of EZH2 according to this embodiment is referred to herein as a Y641S mutant or, equivalently, Y641S.

```
Y641S
                                                 (SEQ ID NO: 13)
MGQTGKKSEKGPVCWRKRVKSEYMRLRQLKRFRRADEVKSMFSSNRQKILERTEILNQEW

KQRRIQPVHILTSVSSLRGTRECSVTSDLDFPTQVIPLKTLNAVASVPIMYSWSPLQQNF

MVEDETVLHNIPYMGDEVLDQDGTFIEELIKNYDGKVHGDRECGFINDEIFVELVNALGQ

YNDDDDDDGDDPEEREEKQKDLEDHRDDKESRPPRKFPSDKIFEAISSMFPDKGTAEEL

KEKYKELTEQQLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRPGGRRRGRLPN

NSSRPSTPTINVLESKDTDSDREAGTETGGENNDKEEEEKKDETSSSSEANSRCQTPIKM

KPNIEPPENVEWSGAEASMFRVLIGTYYDNFCAIARLIGTKTCRQVYEFRVKESSIIAPA

PAEDVDTPPRKKKRKHRLWAAHCRKIQLKKDGSSNHVYNYQPCDHPRQPCDSSCPCVIAQ

NFCEKFCQCSSECQNRFPGCRCKAQCNTKQCPCYLAVRECDPDLCLTCGAADHWDSKNVS

CKNCSIQRGSKKHLLLAPSDVAGWGIFIKDPVQKNEFISESCGEIISQDEADRRGKVYDK

YMCSFLFNLNNDFVVDATRKGNKIRFANHSVNPNCYAKVMMVNGDHRIGIFAKRAIQTGE

ELFFDYRYSQADALKYVGIEREMEIP
```

In one embodiment the amino acid sequence of a Y641 mutant of EZH2 differs from the amino acid sequence of wild-type human EZH2 only by substitution of cysteine (C) for the single amino acid residue corresponding to Y641 of wild-type human EZH2. The Y641 mutant of EZH2 according to this embodiment is referred to herein as a Y641C mutant or, equivalently, Y641C.

```
Y641C
                                                 (SEQ ID NO: 14)
MGQTGKKSEKGPVCWRKRVKSEYMRLRQLKRFRRADEVKSMFSSNRQKILERTEILNQEW

KQRRIQPVHILTSVSSLRGTRECSVTSDLDFPTQVIPLKTLNAVASVPIMYSWSPLQQNF

MVEDETVLHNIPYMGDEVLDQDGTFIEELIKNYDGKVHGDRECGFINDEIFVELVNALGQ

YNDDDDDDGDDPEEREEKQKDLEDHRDDKESRPPRKFPSDKIFEAISSMFPDKGTAEEL

KEKYKELTEQQLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRPGGRRRGRLPN

NSSRPSTPTINVLESKDTDSDREAGTETGGENNDKEEEEKKDETSSSSEANSRCQTPIKM

KPNIEPPENVEWSGAEASMFRVLIGTYYDNFCAIARLIGTKTCRQVYEFRVKESSIIAPA
```

-continued

```
PAEDVDTPPRKKKRKHRLWAAHCRKIQLKKDGSSNHVYNYQPCDHPRQPCDSSCPCVIAQ

NFCEKFCQCSSECQNRFPGCRCKAQCNTKQCPCYLAVRECDPDLCLTCGAADHWDSKNVS

CKNCSIQRGSKKHLLLAPSDVAGWGIFIKDPVQKNEFISECCGEIISQDEADRRGKVYDK

YMCSFLFNLNNDFVVDATRKGNKIRFANHSVNPNCYAKVMMVNGDHRIGIFAKRAIQTGE

ELFFDYRYSQADALKYVGIEREMEIP
```

In one embodiment the amino acid sequence of a A677 mutant of EZH2 differs from the amino acid sequence of wild-type human EZH2 only by substitution of a non-alanine amino acid, preferably glycine (G) for the single amino acid residue corresponding to A677 of wild-type human EZH2. The A677 mutant of EZH2 according to this embodiment is referred to herein as an A677 mutant, and preferably an A677G mutant or, equivalently, A677G.

```
A677
                                            (SEQ ID NO: 15)
MGQTGKKSEKGPVCWRKRVKSEYMRLRQLKRFRRADEVKSMFSSNRQKILERTEILNQEW

KQRRIQPVHILTSVSSLRGTRECSVTSDLDFPTQVIPLKTLNAVASVPIMYSWSPLQQNF

MVEDETVLHNIPYMGDEVLDQDGTFIEELIKNYDGKVHGDRECGFINDEIFVELVNALGQ

YNDDDDDDGDDPEEREEKQKDLEDHRDDKESRPPRKFPSDKIFEAISSMFPDKGTAEEL

KEKYKELTEQQLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRPGGRRRGRLPN

NSSRPSTPTINVLESKDTDSDREAGTETGGENNDKEEEEKKDETSSSSEANSRCQTPIKM

KPNIEPPENVEWSGAEASMFRVLIGTYYDNFCAIARLIGTKTCRQVYEFRVKESSIIAPA

PAEDVDTPPRKKKRKHRLWAAHCRKIQLKKDGSSNHVYNYQPCDHPRQPCDSSCPCVIAQ

NFCEKFCQCSSECQNRFPGCRCKAQCNTKQCPCYLAVRECDPDLCLTCGAADHWDSKNVS

CKNCSIQRGSKKHLLLAPSDVAGWGIFIKDPVQKNEFISEYCGEIISQDEADRRGKVYDK

YMCSFLFNLNNDFVVDXTRKGNKIRFANHSVNPNCYAKVMMVNGDHRIGIFAKRAIQTGE

ELFFDYRYSQADALKYVGIEREMEIP
Wherein X is preferably a glycine (G).
```

In one embodiment the amino acid sequence of a A687 mutant of EZH2 differs from the amino acid sequence of wild-type human EZH2 only by substitution of a non-alanine amino acid, preferably valine (V) for the single amino acid residue corresponding to A687 of wild-type human EZH2. The A687 mutant of EZH2 according to this embodiment is referred to herein as an A687 mutant and preferably an A687V mutant or, equivalently, A687V.

```
A687
                                            (SEQ ID NO: 16)
MGQTGKKSEKGPVCWRKRVKSEYMRLRQLKRFRRADEVKSMFSSNRQKILERTEILNQEW

KQRRIQPVHILTSVSSLRGTRECSVTSDLDFPTQVIPLKTLNAVASVPIMYSWSPLQQNF

MVEDETVLHNIPYMGDEVLDQDGTFIEELIKNYDGKVHGDRECGFINDEIFVELVNALGQ

YNDDDDDDGDDPEEREEKQKDLEDHRDDKESRPPRKFPSDKIFEAISSMFPDKGTAEEL

KEKYKELTEQQLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRPGGRRRGRLPN

NSSRPSTPTINVLESKDTDSDREAGTETGGENNDKEEEEKKDETSSSSEANSRCQTPIKM

KPNIEPPENVEWSGAEASMFRVLIGTYYDNFCAIARLIGTKTCRQVYEFRVKESSIIAPA

PAEDVDTPPRKKKRKHRLWAAHCRKIQLKKDGSSNHVYNYQPCDHPRQPCDSSCPCVIAQ
```

```
-continued
NFCEKFCQCSSECQNRFPGCRCKAQCNTKQCPCYLAVRECDPDLCLTCGAADHWDSKNVS

CKNCSIQRGSKKHLLLAPSDVAGWGIFIKDPVQKNEFISEYCGEIISQDEADRRGKVYDK

YMCSFLFNLNNDFVVDATRKGNKIRFXNHSVNPNCYAKVMMVNGDHRIGIFAKRAIQTGE

ELFFDYRYSQADALKYVGIEREMEIP
Wherein X is preferably a valine (V).
```

In one embodiment the amino acid sequence of a R685 mutant of EZH2 differs from the amino acid sequence of wild-type human EZH2 only by substitution of a non-arginine amino acid, preferably histidine (H) or cysteine (C) for the single amino acid residue corresponding to R685 of wild-type human EZH2. The R685 mutant of EZH2 according to this embodiment is referred to herein as an R685 mutant and preferably an R685C mutant or an R685H mutant or, equivalently, R685H or R685C.

```
R685
                                                  (SEQ ID NO: 17)
MGQTGKKSEKGPVCWRKRVKSEYMRLRQLKRFRRADEVKSMFSSNRQKILERTEILNQEW

KQRRIQPVHILTSVSSLRGTRECSVTSDLDFPTQVIPLKTLNAVASVPIMYSWSPLQQNF

MVEDETVLHNIPYMGDEVLDQDGTFIEELIKNYDGKVHGDRECGFINDEIFVELVNALGQ

YNDDDDDDDGDDPEEREEKQKDLEDHRDDKESRPPRKFPSDKIFEAISSMFPDKGTAEEL

KEKYKELTEQQLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRPGGRRRGRLPN

NSSRPSTPTINVLESKDTDSDREAGTETGGENNDKEEEEKKDETSSSSEANSRCQTPIKM

KPNIEPPENVEWSGAEASMFRVLIGTYYDNFCAIARLIGTKTCRQVYEFRVKESSIIAPA

PAEDVDTPPRKKKRKHRLWAAHCRKIQLKKDGSSNHVYNYQPCDHPRQPCDSSCPCVIAQ

NFCEKFCQCSSECQNRFPGCRCKAQCNTKQCPCYLAVRECDPDLCLTCGAADHWDSKNVS

CKNCSIQRGSKKHLLLAPSDVAGWGIFIKDPVQKNEFISEYCGEIISQDEADRRGKVYDK

YMCSFLFNLNNDFVVDATRKGNKIXFANHSVNPNCYAKVMMVNGDHRIGIFAKRAIQTGE

ELFFDYRYSQADALKYVGIEREMEIP
Wherein X is preferably a cysteine (C) or a histidine (H).
```

In one embodiment the amino acid sequence of a mutant of EZH2 differs from the amino acid sequence of wild-type human EZH2 in one or more amino acid residues in its substrate pocket domain as defined in SEQ ID NO: 6. The mutant of EZH2 according to this embodiment is referred to herein as an EZH2 mutant.

```
Mutant EZH2 comprising one or more mutations in the substrate
pocket domain
                                                  (SEQ ID NO: 18)
MGQTGKKSEKGPVCWRKRVKSEYMRLRQLKRFRRADEVKSMFSSNRQKILERTEILNQEW

KQRRIQPVHILTSVSSLRGTRECSVTSDLDFPTQVIPLKTLNAVASVPIMYSWSPLQQNF

MVEDETVLHNIPYMGDEVLDQDGTFIEELIKNYDGKVHGDRECGFINDEIFVELVNALGQ

YNDDDDDDDGDDPEEREEKQKDLEDHRDDKESRPPRKFPSDKIFEAISSMFPDKGTAEEL

KEKYKELTEQQLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRPGGRRRGRLPN

NSSRPSTPTINVLESKDTDSDREAGTETGGENNDKEEEEKKDETSSSSEANSRCQTPIKM

KPNIEPPENVEWSGAEASMFRVLIGTYYDNFCAIARLIGTKTCRQVYEFRVKESSIIAPA

PAEDVDTPPRKKKRKHRLWAAHCRKIQLKKDGSSNHVYNYQPCDHPRQPCDSSCPCVIAQ

NFCEKFCQCSSECQNRFPGCRCKAQCNTKQCPCYLAVRECDPDLCLTCGAADHWDSKNVS
```

```
-continued
CKNCSIQRGSKKHLLLAPSDVAGWGIFIKDPVQKNEFISEXCGEIISQDEADRRGKVYDK

YMXXXLXNLNNDFXXDXTRKGNKXXXXHSVNPNCYAKVMMVNGDHRXGIFAKRAIQTGE

ELFXDXRYSXADALKYVGIEREMEIP
Wherein X can be any amino acid except the corresponding wild
type residue.
```

The implications of the present results for human disease are made clear by the data summarized in Table 2 (see Example 5). Cells heterozygous for EZH2 would be expected to display a malignant phenotype due to the efficient formation of H3-K27me1 by the WT enzyme and the efficient, subsequent transition of this progenitor species to H3-K27me2, and, especially, H3-K27me3, by the mutant enzyme form(s).

Figure 4:
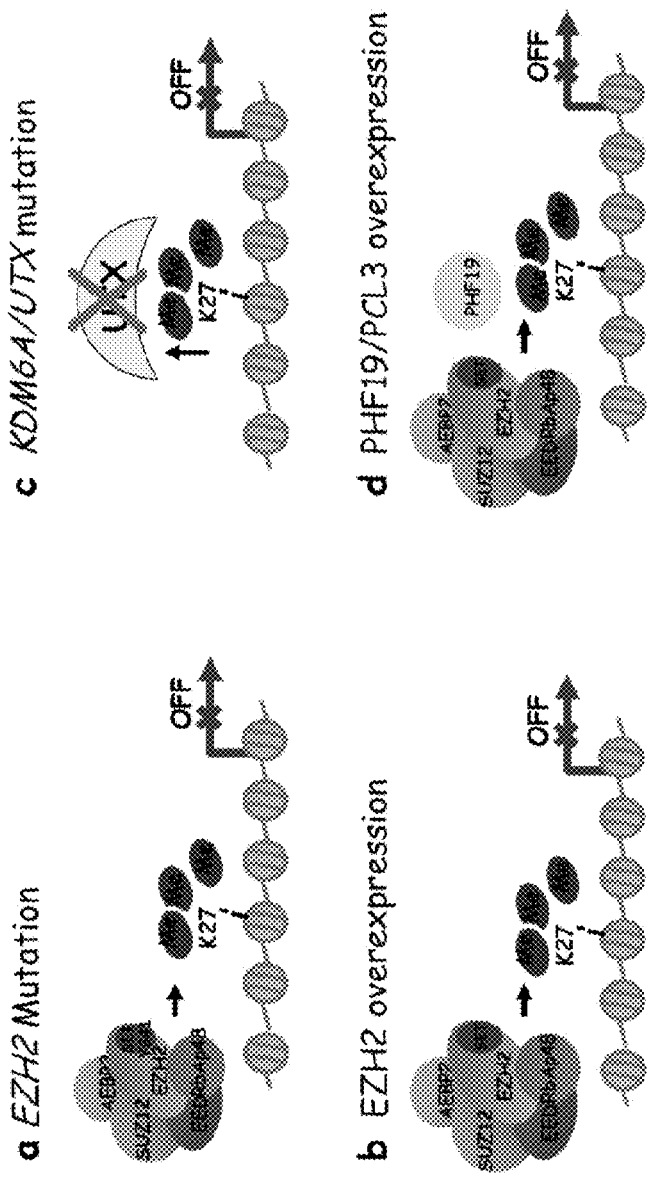
FIG. 4 depicts selected proposed mechanisms leading to aberrantly high levels of trimethylation on histone H3-K27 in cancer. These include: a) mutation of Y641 in EZH2 resulting in a change in substrate preference from the nonmethylated to the mono- and di-methylated histone H3-K27; b) overexpression of EZH2; c) mutations in UTX that inactivate enzyme function, causing a decrease in demethylation of H3-K27me3; and d) overexpression of the PRC2 complex subunit PHF19/PCL3 that leads to increases in recruitment of the PRC2 complex to specific genes and an increase in histone H3-K27 trimethylation. In all four models the alteration leads to aberrant histone H3-K27 trimethylation in the proximal promoter regions of genes resulting in transcriptional repression of key genes in cancer.
Figure 5:
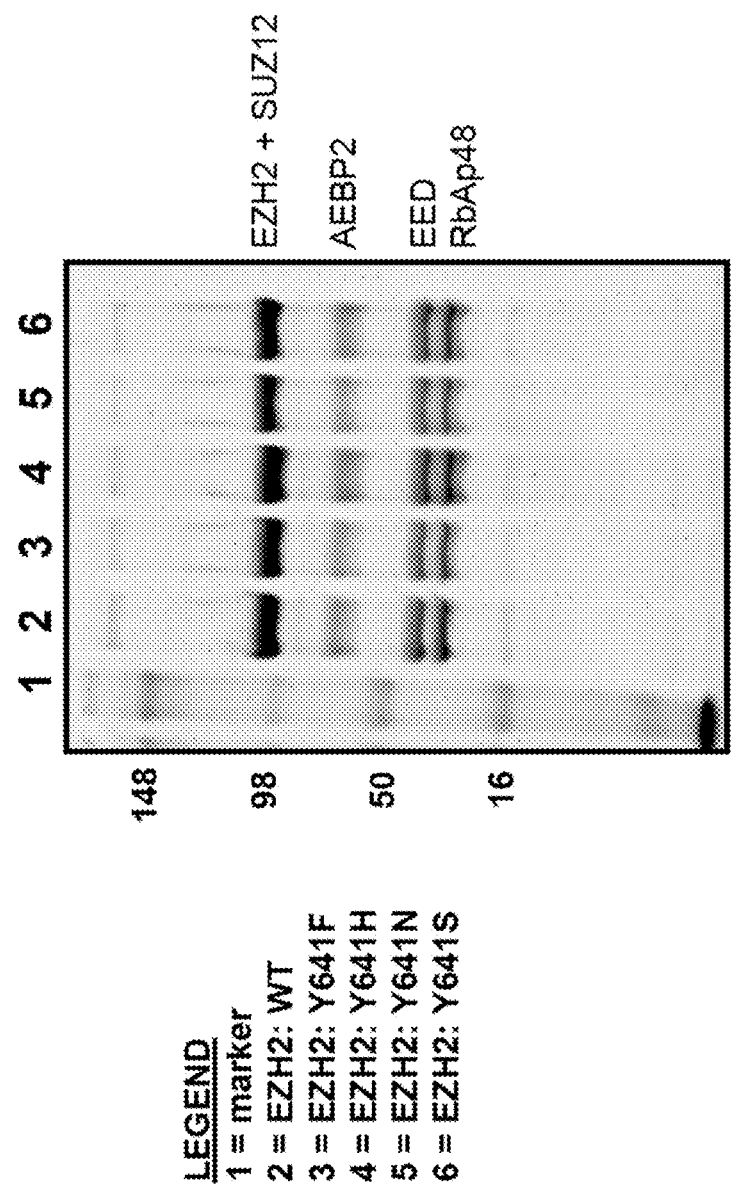
FIG. 5 depicts a SDS-PAGE gel showing that the expression levels of each of the five-component PRC2 complexes are similar with mutant and wild-type EZH2.
Figure 6:
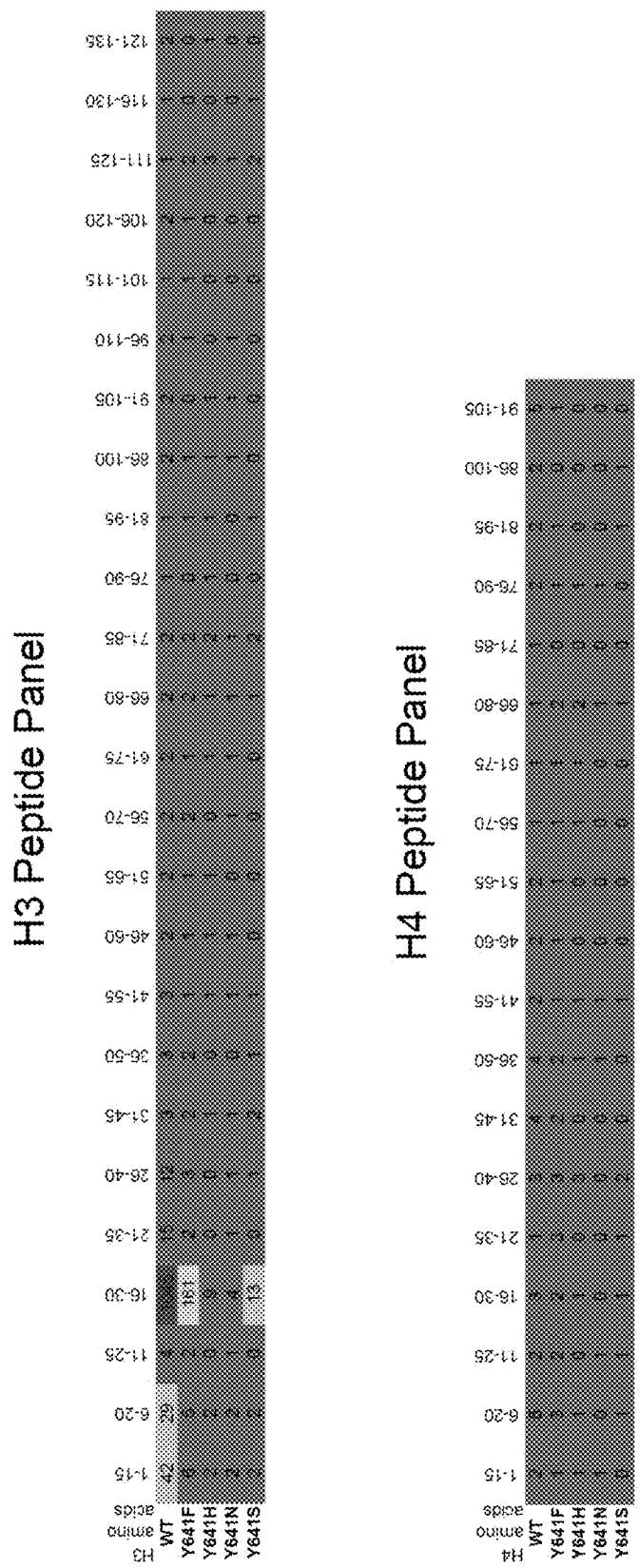
FIG. 6 is a pair of tables showing that mutant and wild-type (WT) PRC2 complexes display strong substrate preference for H3-K27-containing peptides. Each enzyme was tested against a panel of overlapping 15-mer peptides covering all of H3 and H4. Activity was measured as velocity (CPM per minute), and the reported value represents the mean of two independent determinations for each reaction. For all the complexes the most favored peptide was H3:16-30. WT complex had greater than 6-fold more activity against this peptide than any of the mutant complexes.

It has been reported that H3-K27me1 formation is not exclusively dependent on WT-EZH2 catalysis. Knockout studies of EZH2 and of another PRC2 subunit, EED, have demonstrated H3-K27me1 formation can be catalyzed by PRC2 complexes containing either EZH2 or the related protein EZH1 as the catalytic subunit. Shen, X. et al. (2008) *Mol Cell* 32:491-502. Hence, catalytic coupling between the mutant EZH2 species and PRC2 complexes containing either WT-EZH2 or WT-EZH1 would suffice to augment H3-K27me2/3 formation, and thus produce the attendant malignant phenotype. The data therefore suggest that the malignant phenotype of follicular lymphoma (FL) and diffuse large B-cell lymphoma (DLBCL) of the germinal center B cell (GCB) subtype, associated with expression of mutant forms of EZH2, is the result of an overall gain of function with respect to formation of the trimethylated form of H3-K27. This interpretation of the data also helps to reconcile the existence of cancer-associated overexpression of EZH2 or PRC2 associated proteins (e.g., PHF19/PCL3) and also loss-of-function genotypes for the histone H3-K27 demethylase UTX. Loss of UTX activity would be enzymatically equivalent to a gain of function for EZH2, in either situation resulting in greater steady state levels of tri-methylated H3-K27 in cancer cells (FIG. 4).

The mono-, di-, and tri-methylation states of histone H3-K27 are associated with different functions in transcriptional control. Histone H3-K27 monomethylation is associated with active transcription of genes that are poised for transcription. Cui et al. (2009) *Cell Stem Cell* 4:80-93; Barski (2007) *Cell* 129:823-37. In contrast, trimethylation of histone H3-K27 is associated with either transcriptionally repressed genes or genes that are poised for transcription when histone H3-K4 trimethylation is in cis. Cui et al. (supra); Kirmizis et al. (2007) *Genes Dev* 18:1592-1605; Bernstein et al. (2006) *Cell* 125:315-26. Taken together, alterations in the PRC2 complex activity reported in cancer, including the Y641 mutation of EZH2, are predicted to result in an increase in the trimethylated state of histone H3-K27 and thus to result in transcriptional repression.

Figure 13:
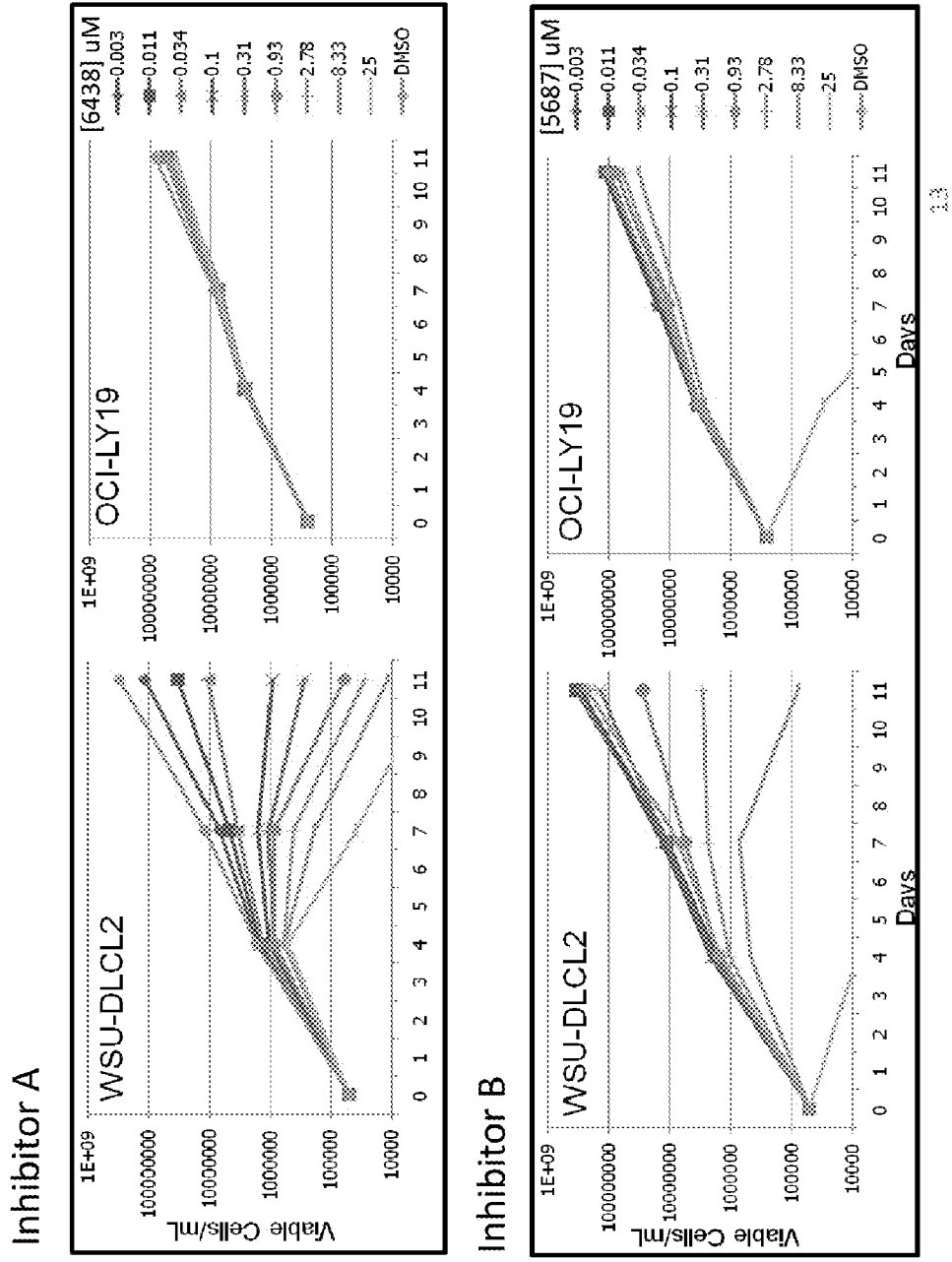
FIG. 13 is a graph showing that the EZH2 inhibitors can block proliferation of a Y641 mutant WSU-DLCL2 cells, but has little effect on non Y641 mutant OCI-LY19 cells. Cells were incubated in the presence of increasing concentrations of EZH2 inhibitor A or B for eleven days. Vehicle treated (DMSO) cells were included as controls. Cell number and viability was determined using the Guava VIACOUNT™ assay in a Guava EASYCITE™ Plus instrument. Cells were split and media and compound was replenished every 3-4 days.

Another discovery of the present invention is that cells expressing a mutant EZH2 comprising a mutation in the substrate pocket domain as defined in SEQ ID NO: 6 are, in general, more sensitive to small molecule EZH2 inhibitors than cells expressing wild type (WT) EZH2. Specifically, cells expressing Y641 mutant EZH2 show reduced growing, dividing or proliferation, or even undergo apoptosis or necrosis after the treatment of EZH2 inhibitors. In contrast, cells expressing WT EZH2 are not responsive to the anti-proliferative effect of the EZH2 inhibitors (FIGS. 13 and 14). Particularly, cells expressing a substitution mutation at amino acid position 677 of SEQ ID NO: 1 show greater sensitivity to EZH2 inhibitors than cells expressing other EZH2 mutants (Example 19).

EZH2 and other protein methyltransferases have been suggested to be attractive targets for drug discovery. Copeland et al. (2009) *Nat Rev Drug Discov* 8:724-32; Copeland et al. (2010) *Curr Opin Chem Biol* 14(4):505-10; Pollock et al. (2010) *Drug Discovery Today: Therapeutic Strategies* 6(1): 71-9. The present data also suggest an experimental strategy for development of FL and GCB lymphoma-specific drugs. As the differences in substrate recognition between the WT and disease-associated mutants derive from transition state interactions, small molecule inhibitors that selectively mimic the transition state of the mutant EZH2 over that of the WT enzyme should prove to be effective in blocking H3-K27 methylation in mutation-bearing cells. Inhibitors of this type would be expected to display a large therapeutic index, as target-mediated toxicity would be minimal for any cells bearing only the WT enzyme. Transition state mimicry has proved to be an effective strategy for drug design in many disease areas. See, for example, Copeland, R. A. *Enzymes: A Practical Introduction to Structure, Mechanism and Data Analysis.* 2nd ed, (Wiley, 2000).

The present results point to a previously unrecognized, surprising dependency on enzymatic coupling between enzymes that perform H3-K27 mono-methylation and certain mutant forms of EZH2 for pathogenesis in follicular lymphoma and diffuse large B-cell lymphoma. While not intending to be bound by any one theory, it is believed the data constitute the first example of a human disease that is dependent on such coupling of catalytic activity between normal (WT) and disease-associated mutant (such as Y641) enzymes.

An aspect of the present invention is a method for treating or alleviating a symptom of cancer or precancerous condition in a subject by administering to a subject expressing a mutant EZH2 comprising a mutation in the substrate pocket domain as defined in SEQ ID NO: 6 a therapeutically effective amount of an EZH2 inhibitor.

Another aspect of the invention is a method for inhibiting in a subject conversion of H3-K27 to trimethylated H3-K27. The inhibition can involve inhibiting in a subject conversion of unmethylated H3-K27 to monomethylated H3-K27, conversion of monomethylated H3-K27 to dimethylated H3-K27, conversion of dimethylated H3-K27 to trimethylated H3-K27, or any combination thereof, including, for example, conversion of monomethylated H3-K27 to dimethylated H3-K27 and conversion of dimethylated H3-K27 to trimethylated H3-K27. As used herein, unmethylated H3-K27 refers to histone H3 with no methyl group covalently linked to the amino group of lysine 27. As used herein, monomethylated H3-K27 refers to histone H3 with a single methyl group covalently linked to the amino group of lysine 27. Monomethylated H3-K27 is also referred to herein as H3-K27me1. As used herein, dimethylated H3-K27 refers to histone H3 with two methyl groups covalently linked to the amino group of lysine 27. Dimethylated H3-K27 is also referred to herein as H3-K27me2. As used herein, trimethylated H3-K27 refers to histone H3 with three methyl groups covalently linked to the amino group of lysine 27. Trimethylated H3-K27 is also referred to herein as H3-K27me3.

Histone H3 is a 136 amino acid long protein, the sequence of which is known. See, for example, GenBank Accession No. CAB02546, the content of which is incorporated herein by reference. As disclosed further herein, in addition to full-length histone H3, peptide fragments of histone H3 comprising the lysine residue corresponding to K27 of full-length histone H3 can be used as substrate for EZH2 (and likewise for mutant forms of EZH2) to assess conversion of H3-K27 m1 to H3-K27m2 and conversion of H3-K27m2 to H3-K27m3. In one embodiment, such peptide fragment corresponds to amino acid residues 21-44 of histone H3. Such peptide fragment has the amino acid sequence LATKAARKSAPATGGVKKPHRYRP (SEQ ID NO: 19).

The method of the present invention involves administering to a subject expressing a mutant EZH2 a therapeutically effective amount of an inhibitor of EZH2, wherein the inhibitor inhibits histone methyltransferase activity of EZH2, thereby inhibiting conversion of H3-K27 to trimethylated H3-K27 in the subject and thus treating or allieviating a symptom of cancer or disorders associated with abnormal histon methylation levels in the subject.

A subject expressing a mutant EZH2 of the present invention refers to a subject having a detectable amount of a mutant EZH2 polypeptide. Preferably the mutant EZH2 polypeptide comprises one or more mutations in its substrate pocket domain as defined in SEQ ID NO: 6. Exemplary mutation includes a substitution at amino acid position 677, 687, 674, 685, or 641 of SEQ ID NO: 1, such as, but is not limited to a substitution of glycine (G) for the wild type residue alanine (A) at amino acid position 677 of SEQ ID NO: 1 (A677G); a substitution of valine (V) for the wild type residue alanine (A) at amino acid position 687 of SEQ ID NO: 1 (A687V); a substitution of methionine (M) for the wild type residue valine (V) at amino acid position 674 of SEQ ID NO: 1 (V674M); a substitution of histidine (H) for the wild type residue arginine (R) at amino acid position 685 of SEQ ID NO: 1 (R685H); a substitution of cysteine (C) for the wild type residue arginine (R) at amino acid position 685 of SEQ ID NO: 1 (R685C); a substitution of phenylalanine (F) for the wild type residue tyrosine (Y) at amino acid position 641 of SEQ ID NO: 1 (Y641F); a substitution of histidine (H) for the wild type residue tyrosine (Y) at amino acid position 641 of SEQ ID NO: 1 (Y641H); a substitution of asparagine (N) for the wild type residue tyrosine (Y) at amino acid position 641 of SEQ ID NO: 1 (Y641N); a substitution of serine (S) for the wild type residue tyrosine (Y) at amino acid position 641 of SEQ ID NO: 1 (Y641S); or a substitution of cysteine (C) for the wild type residue tyrosine (Y) at amino acid position 641 of SEQ ID NO: 1 (Y641C). More preferablly, the subject has a detectable amount of a mutant EZH2 polypeptide comprising a substitution of glycine (G) for the wild type residue alanine (A) at amino acid position 677 of SEQ ID NO: 1 (A677G); a substitution of valine (V) for the wild type residue alanine (A) at amino acid position 687 of SEQ ID NO: 1 (A687V); a substitution of histidine (H) for the wild type residue arginine (R) at amino acid position 685 of SEQ ID NO: 1 (R685H); or a substitution of cysteine (C) for the wild type residue arginine (R) at amino acid position 685 of SEQ ID NO: 1 (R685C).

Alternatively a subject expressing a mutant EZH2 of the present invention refers to a subject having a detectable amount of a nucleic acid sequence encoding a mutant EZH2 polypeptide. Preferably a nucleic acid sequence encoding a mutant EZH2 polypeptide comprises one or more mutations in its substrate pocket domain as defined in SEQ ID NO: 6. Exemplary mutation includes a substitution at amino acid position 677, 687, 674, 685, or 641 of SEQ ID NO: 1, such as, but is not limited to a substitution of glycine (G) for the wild type residue alanine (A) at amino acid position 677 of SEQ ID NO: 1 (A677G); a substitution of valine (V) for the wild type residue alanine (A) at amino acid position 687 of SEQ ID NO: 1 (A687V); a substitution of methionine (M) for the wild type residue valine (V) at amino acid position 674 of SEQ ID NO: 1 (V674M); a substitution of histidine (H) for the wild type residue arginine (R) at amino acid position 685 of SEQ ID NO: 1 (R685H); a substitution of cysteine (C) for the wild type residue arginine (R) at amino acid position 685 of SEQ ID NO: 1 (R685C); a substitution of phenylalanine (F) for the wild type residue tyrosine (Y) at amino acid position 641 of SEQ ID NO: 1 (Y641F); a substitution of histidine (H) for the wild type residue tyrosine (Y) at amino acid position 641 of SEQ ID NO: 1 (Y641H); a substitution of asparagine (N) for the wild type residue tyrosine (Y) at amino acid position 641 of SEQ ID NO: 1 (Y641N); a substitution of serine (S) for the wild type residue tyrosine (Y) at amino acid position 641 of SEQ ID NO: 1 (Y641S); or a substitution of cysteine (C) for the wild type residue tyrosine (Y) at amino acid position 641 of SEQ ID NO: 1 (Y641C). More preferably, the subject has a detectable amount of nucleic acid sequence encoding a mutant EZH2 polypeptide comprising a substitution of glycine (G) for the wild type residue alanine (A) at amino acid position 677 of SEQ ID NO: 1 (A677G); a substitution of valine (V) for the wild type residue alanine (A) at amino acid position 687 of SEQ ID NO: 1 (A687V); a substitution of histidine (H) for the wild type residue arginine (R) at amino acid position 685 of SEQ ID NO: 1 (R685H); or a substitution of cysteine (C) for the wild type residue arginine (R) at amino acid position 685 of SEQ ID NO: 1 (R685C).

Detection of EZH2 Mutants

A mutant EZH2 polypeptide can be detected using any suitable method. For example, a mutant EZH2 polypeptide can be detected using an antibody that binds specifically to the mutant EZH2 polypeptide or to a peptide fragment that is characteristic of the mutant EZH2 polypeptide. A peptide fragment that is characteristic of the mutant EZH2 polypeptide may include, for example, a SET domain as provided in SEQ ID NO: 7, except for substitution of one or more residues in the substrate pocket domain as defined in SEQ ID NO: 6 by an amino acid residue other than the wild type residue. In another embodiment, a peptide fragment that is characteristic of the mutant EZH2 polypeptide may include, for example, a 10-113 amino acid fragment of the SET domain as provided in SEQ ID NO: 7, except for substitution of one or more residues in the substrate pocket domain as defined in SEQ ID NO: 6 by an amino acid residue other than the wild type residue, provided that the fragment includes the amino acid residue corresponding to a mutation of EZH2. An antibody is considered to bind specifically to the mutant EZH2 polypeptide or to a peptide fragment that is characteristic of the mutant EZH2 polypeptide if it binds to that mutant EZH2 polypeptide or peptide fragment thereof but not to the corresponding wild-type EZH2 polypeptide or peptide fragment thereof. In one embodiment, such antibody is considered to bind specifically to the mutant EZH2 polypeptide or to a peptide fragment that is characteristic of the mutant EZH2 polypeptide if it binds to that mutant EZH2 polypeptide or peptide fragment thereof with an affinity that is at least ca. 1000-fold greater than for the corresponding wild-type EZH2 polypeptide or peptide fragment thereof. In one embodiment, such antibody is considered to bind specifically to the mutant EZH2 polypeptide or to a peptide fragment that is characteristic of the mutant EZH2 polypeptide if it binds to that mutant EZH2 polypeptide or peptide fragment thereof with an affinity that is at least ca. 1000-fold greater than for the corresponding wild-type EZH2 polypeptide or peptide fragment thereof. The antibody can be used, for example, in an enzyme-linked immunosorbent assay (ELISA) or Western blot assay. The antibody may be monoclonal, polyclonal, chimeric, or an antibody fragment. The step of detecting the reaction product may be carried out with any suitable immunoassay.

In one embodiment the antibody is a monoclonal antibody. A monoclonal antibody can be prepared according to conventional methods well known in the art. See, for example, Köhler and Milstein (1975) *Nature* 256 (5517):495-7.

As another example, a mutant EZH2 polypeptide can be detected using mass spectrometry (MS), e.g., electrospray ionization coupled with time-of-flight (ESI-TOF) or matrix-assisted laser desorption/ionization coupled with time-of-flight (MALDI-TOF). Such methods are well known in the art. The analysis will involve identification of one or more peptide fragments comprising the mutation of interest, for example, a peptide 12 to 24 amino acids long comprising a sequence spanning the amino acid corresponding to a mutation in wild-type EZH2.

A nucleic acid sequence encoding a mutant EZH2 polypeptide or a peptide fragment that is characteristic of the mutant EZH2 polypeptide can be detected using any suitable method. For example, a nucleic acid sequence encoding a mutant EZH2 polypeptide can be detected using whole-genome resequencing or target region resequencing (the latter also known as targeted resequencing) using suitably selected sources of DNA and polymerase chain reaction (PCR) primers in accordance with methods well known in the art. See, for example, Bentley (2006) *Curr Opin Genet Dev.* 16:545-52, and Li et al. (2009) *Genome Res* 19:1124-32. The method typically and generally entails the steps of genomic DNA purification, PCR amplification to amplify the region of interest, cycle sequencing, sequencing reaction cleanup, capillary electrophoresis, and data analysis. High quality PCR primers to cover region of interest are designed using in silico primer design tools. Cycle sequencing is a simple method in which successive rounds of denaturation, annealing, and extension in a thermal cycler result in linear amplification of extension products. The products are typically terminated with a fluorescent tag that identifies the terminal nucleotide base as G, A, T, or C. Unincorporated dye terminators and salts that may compete for capillary eletrophoretic injection are removed by washing. During capillary electrophoresis, the products of the cycle sequencing reaction migrate through capillaries filled with polymer. The negatively charged DNA fragments are separated by size as they move through the'capillaries toward the positive electrode. After electrophoresis, data collection software creates a sample file of the raw data. Using downstream software applications, further data analysis is performed to translate the collected color data images into the corresponding nucleotide bases. Alternatively or in addition, the method may include the use of microarray-based targeted region genomic DNA capture and/or sequencing. Kits, reagents, and methods for selecting appropriate PCR primers and performing resequencing are commercially available, for example, from Applied Biosystems, Agilent, and NimbleGen (Roche Diagnostics GmbH). Methods such as these have been used to detect JAK2 and myeloproliferative leukemia gene (MPL) mutations and to diagnose polycythemia vera, essential thrombocythemia, and idiopathic myelofibrosis. For use in the instant invention, PCR primers may be selected so as to amplify, for example, at least a relevant portion of SEQ ID NO: 8 (above).

Alternatively or in addition, a nucleic acid sequence encoding a mutant EZH2 polypeptide may be detected using a Southern blot in accordance with methods well known in the art. In one embodiment a DNA sequence encoding a mutant EZH2 polypeptide is detected using nucleic acid hybridization performed under highly stringent conditions. A nucleic acid probe is selected such that its sequence is complementary to a target nucleic acid sequence that includes a codon for the mutant amino acid corresponding to a mutation of wild-type EZH2. Such mutation includes any mutation of EZH2, preferably one or more mutations in the substrate pocket domain as defined in SEQ ID NO: 6 of EZH2, such as, but are not limited to a substitution of glycine (G) for the wild type residue alanine (A) at amino acid position 677 of SEQ ID NO: 1 (A677G); a substitution of valine (V) for the wild type residue alanine (A) at amino acid position 687 of SEQ ID NO: 1 (A687V); a substitution of methionine (M) for the wild type residue valine (V) at amino acid position 674 of SEQ ID NO: 1 (V674M); a substitution of histidine (H) for the wild type residue arginine (R) at amino acid position 685 of SEQ ID NO: 1 (R685H); a substitution of cysteine (C) for the wild type residue arginine (R) at amino acid position 685 of SEQ ID NO: 1 (R685C); a substitution of phenylalanine (F) for the wild type residue tyrosine (Y) at amino acid position 641 of SEQ ID NO: 1 (Y641F); a substitution of histidine (H) for the wild type residue tyrosine (Y) at amino acid position 641 of SEQ ID NO: 1 (Y641H); a substitution of asparagine (N) for the wild type residue tyrosine (Y) at amino acid position 641 of SEQ ID NO: 1 (Y641N); a substitution of serine (S) for the wild type residue tyrosine (Y) at amino acid position 641 of SEQ ID NO: 1 (Y641S); or a substitution of cysteine (C) for the wild type residue tyrosine (Y) at amino acid position 641 of SEQ ID NO: 1 (Y641C).

A sequence-specific probe is combined with a sample to be tested under highly stringent conditions. The term "highly stringent conditions" as used herein refers to parameters with which the art is familiar. Nucleic acid hybridization parameters may be found in references that compile such methods, e.g., J. Sambrook, et al., eds., *Molecular Cloning: A Laboratory Manual*, Second Edition, Cold Spring Harbor Laboratory Press, Cold Spring Harbor, N.Y., 1989, or F. M. Ausubel, et al., eds., *Current Protocols in Molecular Biology*, John Wiley & Sons, Inc., New York. More specifically, highly stringent conditions, as used herein, refers, for example, to hybridization at 65° C. in hybridization buffer (3.5×SSC, 0.02% Ficoll, 0.02% polyvinyl pyrrolidone, 0.02% bovine serum albumin (BSA), 2.5 mM $NaH_2PO_4$ (pH 7), 0.5% SDS, 2 mM EDTA). SSC is 0.15 M sodium chloride/0.015 M sodium citrate, pH 7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5×SSC/0.1×SDS at temperatures up to 68° C.

There are other conditions, reagents, and so forth that can be used, which result in a similar degree of stringency. The skilled artisan will be familiar with such conditions, and thus they are not given here. It will be understood, however, that the skilled artisan will be able to manipulate the conditions in a manner to permit the clear identification of EZH2-associated nucleic acids of the invention, including, in particular, nucleic acids encoding mutants of EZH2 (e.g., by using lower stringency conditions). The skilled artisan also is familiar with the methodology for screening cells and libraries for expression of such molecules, which then are routinely isolated, followed by isolation of the pertinent nucleic acid molecule and sequencing.

The subject is administered a therapeutically effective amount of an inhibitor of EZH2. As used herein, an inhibitor of EZH2 refers, generally, to a small molecule, i.e., a molecule of molecular weight less than about 1.5 kilodaltons (kDa), which is capable of interfering with the histone methyltransferase enzymatic activity of EZH2.

In one embodiment the inhibitor of EZH2 inhibits histone methyltransferase activity of wild-type EZH2. In one embodiment the inhibitor of EZH2 inhibits histone methyltransferase activity of the mutant EZH2. In one embodiment the inhibitor of EZH2 inhibits histone methyltransferase activity of wild-type EZH2 and histone methyltransferase activity of the mutant EZH2. In one embodiment the inhibitor of EZH2 selectively inhibits histone methyltransferase activity of the mutant EZH2.

As disclosed herein, certain mutants of EZH2 (such as Y641) are relatively poor catalysts for conversion of unmethylated H3-K27 to H3-K27me1 and yet unexpectedly effective catalysts for conversion of H3-K27me2 to H3-K27me3. Certain mutants of EZH2 (such as A687) prefer monomethyl H3-K27 substrate. In contrast, certain mutants of EZH2 (such as A677) show equal preference among unmethylated, monomethylated and dimethylated H3-K27. Conversely, wild-type EZH2 is a relatively effective catalyst for conversion of unmethylated H3-K27 to H3-K27me1 and yet unexpectedly ineffective catalyst for conversion of H3-K27me2 to H3-K27me3. This is important because mono-, di- and tri-methylated states of H3-K27 exhibit different functions in transcriptional control. For example, H3-K27me1 is associated with active transcription of genes that are poised for transcription, while H3-K27me3 is associated with transcriptionally repressed genes or genes that are poised for transcription when H3-K4 trimethylation is in cis. Thus, selective inhibition of histone methyltransferase activity of the mutant of EZH2 affects selective inhibition of production of the different methylated forms of H3-K27, thereby modifying transcription associated with H3-K27 methylation levels.

An inhibitor of EZH2 "selectively inhibits" histone methyltransferase activity of the mutant EZH2 when it inhibits histone methyltransferase activity of the mutant EZH2 more effectively than it inhibits histone methyltransferase activity of wild-type EZH2. For example, in one embodiment the selective inhibitor has an IC50 for the mutant EZH2 that is at least 40 percent lower than the IC50 for wild-type EZH2. In one embodiment the selective inhibitor has an IC50 for the mutant EZH2 that is at least 50 percent lower than the IC50 for wild-type EZH2. In one embodiment the selective inhibitor has an IC50 for the mutant EZH2 that is at least 60 percent lower than the IC50 for wild-type EZH2. In one embodiment the selective inhibitor has an IC50 for the mutant EZH2 that is at least 70 percent lower than the IC50 for wild-type EZH2. In one embodiment the selective inhibitor has an IC50 for the mutant EZH2 that is at least 80 percent lower than the IC50 for wild-type EZH2. In one embodiment the selective inhibitor has an IC50 for the mutant EZH2 that is at least 90 percent lower than the IC50 for wild-type EZH2.

In one embodiment, the selective inhibitor of a mutant EZH2 exerts essentially no inhibitory effect on wild-type EZH2.

The inhibitor inhibits conversion of H3-K27me2 to H3-K27me3. In one embodiment the inhibitor is said to inhibit trimethylation of H3-K27. Since conversion of H3-K27me1 to H3-K27me2 precedes conversion of H3-K27me2 to H3-K27me3, an inhibitor of conversion of H3-K27me1 to H3-K27me2 naturally also inhibits conversion of H3-K27me2 to H3-K27me3, i.e., it inhibits trimethylation of H3-K27. It is also possible to inhibit conversion of H3-K27me2 to H3-K27me3 without inhibition of conversion of H3-K27me1 to H3-K27me2. Inhibition of this type would also result in inhibition of trimethylation of H3-K27, albeit without inhibition of dimethylation of H3-K27.

In one embodiment the inhibitor inhibits conversion of H3-K27me1 to H3-K27me2 and the conversion of H3-K27me2 to H3-K27me3. Such inhibitor may directly inhibit the conversion of H3-K27me1 to H3-K27me2 alone. Alternatively, such inhibitor may directly inhibit both the conversion of H3-K27me1 to H3-K27me2 and the conversion of H3-K27me2 to H3-K27me3.

The inhibitor inhibits histone methylase activity. Inhibition of histone methylase activity can be detected using any suitable method. The inhibition can be measured, for example, either in terms of rate of histone methylase activity or as product of histone methylase activity. Methods suitable for either of these readouts are included in the Examples below.

The inhibition is a measurable inhibition compared to a suitable negative control. In one embodiment, inhibition is at least 10 percent inhibition compared to a suitable negative control. That is, the rate of enzymatic activity or the amount of product with the inhibitor is less than or equal to 90 percent of the corresponding rate or amount made without the inhibitor. In various other embodiments, inhibition is at least 20, 25, 30, 40, 50, 60, 70, 75, 80, 90, or 95 percent inhibition compared to a suitable negative control. In one embodiment, inhibition is at least 99 percent inhibition compared to a suitable negative control. That is, the rate of enzymatic activity or the amount of product with the inhibitor is less than or equal to 1 percent of the corresponding rate or amount made without the inhibitor.

In one embodiment, the inhibitor is S-adenosyl-L-homocysteine (SAH). SAH has the structural formula

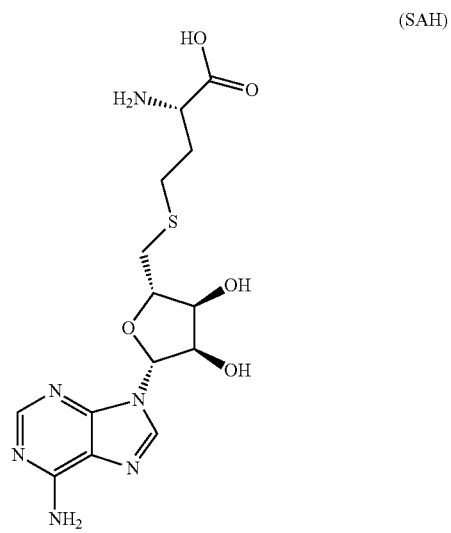 [SMILES: Nc1ncnc2c1ncn2[C@@H]1O[C@H](CSCC[C@H](N)C(=O)O)[C@@H](O)[C@H]1O]

(SAH)

and is commercially available from a number of suppliers, including, for example, Sigma-Aldrich, St. Louis, Mo. SAH has been described as an inhibitor of transmethylation by S-adenosylmethionine-dependent methyltransferases.

In one embodiment, the inhibitor is Compound 75

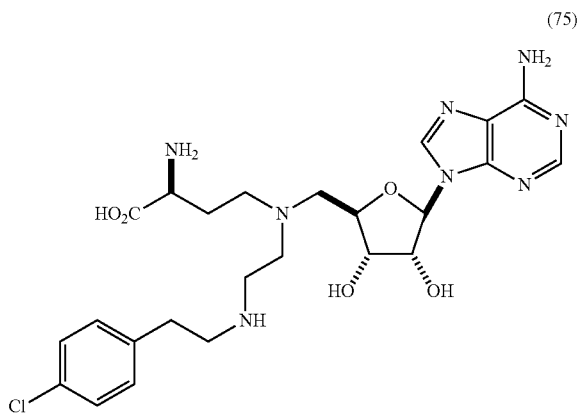

(75)

or a pharmaceutically acceptable salt thereof.

In certain embodiments the invention comprises the step of performing an assay to detect a mutant of EZH2 in a sample from a subject. Assays of this type are described above. As used herein, a "sample from a subject" refers to any suitable sample containing cells or components of cells obtained or derived from a subject. In one embodiment the sample includes cells suspected to express mutant EZH2, e.g., cancer cells. In one embodiment the sample is a blood sample. In one embodiment the sample is a biopsy sample obtained from, for example, a lymphatic tissue (e.g., lymph node) or bone marrow. In one embodiment the sample is a biopsy sample obtained from a tissue other than or in addition to a lymphatic tissue (e.g., lymph node) or bone marrow. For example, in one embodiment the sample is a biopsy from a cancer, e.g., a tumor composed of cancer cells. Cells in the sample can be isolated from other components of the sample. For example, peripheral blood mononuclear cells (PBMCs) can be isolated as a buffy coat from a blood sample that has been centrifuged in accordance with methods familiar to those of skill in the art.

When the result of the assay on a sample from a subject indicates that a mutant EZH2 is present in the sample, the subject is said to express mutant EZH2. Indeed, in one embodiment, when the result of the assay on a sample from a subject indicates that a mutant EZH2 is present in the sample, the subject is identified as a candidate for treatment with an inhibitor of EZH2, wherein the inhibitor selectively inhibits histone methyltransferase activity of the mutant EZH2.

When the result of the assay on a sample from a cancer indicates that a mutant EZH2 is present in the cancer, the cancer is said to express the mutant EZH2.

Similarly, when the result of the assay on a sample comprising cancer cells from a subject having a cancer indicates that a mutant EZH2 is present in the sample, the subject is said to express the mutant EZH2.

Detection of dimethylated H3-K27 or trimethlated H3-K27 can be accomplished using any suitable method in the art. In one embodiment, the methylation level is detected using antibodies specific for dimethylated H3-K27 or tri-methlated H3-K27. For example, the isolated tissue is formalin fixed and embedded in paraffin blocks for long term preservation. The blocks can be used to prepare slides for immunohistochemical staining or fluorescent staining with antibodies against methylated H3-K27. Alternatively, whole cell lysates or histone extracts can be prepared from the isolated tissue sample and subsequently used for immunohistochemical staining, western blot analysis or fluorescent staining. In another embodiment the methylation level is detected using a polypeptide or an aptamer specific for dimethylated H3-K27 or trimethlated H3-K27. In another embodiment, the methylation level is detected using mass spectrometry (MS).

A control dimethylated H3-K27 or a control trimethlated H3-K27 can be established from a control sample, e.g., an adjacent non-tumor tissue isolated from the subject or a healthy tissue from a healthy subject. Alternatively, the control methylation level of H3-K27me2 or H3-K27me3 can be established by a pathologist with known methods in the art.

Screening Methods

An aspect of the invention is a method for identifying a test compound as an inhibitor of a mutant EZH2. In one embodiment the method includes combining an isolated mutant EZH2 with a histone substrate, a methyl group donor (such as S-adenosyl methionine (SAM)), and a test compound, wherein the histone substrate comprises a form of H3-K27 selected from the group consisting of unmethylated H3-K27, monomethylated H3-K27, dimethylated H3-K27, and any combination thereof; and performing an assay to detect methylation of H3-K27 in the histone substrate, thereby identifying the test compound as an inhibitor of the mutant EZH2 when methylation of H3-K27 in the presence of the test compound is less than methylation of H3-K27 in the absence of the test compound. The assay to detect methylation of H3-K27 can be selected to measure the rate of methylation, the extent of methylation, or both the rate and extent of methylation.

The mutant EZH2 is isolated as a PRC2 complex or functional equivalent thereof. As used herein, the term "isolated" means substantially separated from other components with which the complex may be found as it occurs in nature. A compound can be isolated without necessarily being purified. In one embodiment the mutant of EZH2 is isolated as a complex of a mutant EZH2 together with EED and SUZ12. In another embodiment the mutant of EZH2 is isolated as a complex of a mutant EZH2 together with EED, SUZ12, and RbAp48. Under appropriate conditions, a PRC2 complex or functional equivalent thereof exhibits histone methyltransferase activity for H3-K27. In one embodiment the complex is composed of recombinantly expressed component polypeptides, e.g., EZH2, EED, SUZ12, with or without RbAp48.

The isolated mutant EZH2 is combined with a histone substrate. A histone substrate includes any suitable source of histone polypeptides or fragments thereof that can serve as substrate for EZH2. In one embodiment the histone substrate includes histones isolated from a subject. The histones can be isolated from cells of a subject using any suitable method; such methods are well known to persons skilled in the art and need not be further specified here. See, for example, Fang et al. (2004) *Methods Enzymol* 377:213-26. In accordance with the Examples below, in one embodiment the histone substrate is provided as nucleosomes. In accordance with the Examples below, in one embodiment the histone substrate is provided as avian (chicken) erythrocyte nucleosomes.

Histone substrate so provided may include an admixture of states of histone modification, including various states of H3-K27 methylation as judged by Western blotting with H3-K27 methylation state-specific antibodies. In one embodiment the histone substrate may be provided as purified full-length histone H3. Such purified full-length histone H3 may be provided as a homogeneous preparation in respect of states of H3-K27 methylation, or as an admixture of various states of H3-K27 methylation. Homogeneous preparations of isolated histone H3 in respect of states of H3-K27 methylation may be prepared in part by passage over an immunoaffinity column loaded with suitable H3-K27 methylation state-specific antibodies or by immunoprecipitation using magnetic beads coated with suitable H3-K27 methylation state-specific antibodies. Alternatively or in addition, the methylation state of H3-K27 can be characterized as part of performing the assay. For example, the starting material histone substrate might be characterized as containing 50 percent unmethylated H3-K27, 40 percent monomethylated H3-K27, 10 percent dimethylated H3-K27, and 0 percent trimethylated H3-K27.

In one embodiment the histone substrate includes a peptide library or a suitable peptide comprising one or more amino acid sequences related to histone H3, including, in particular, a sequence that encompasses H3-K27. For example, in one embodiment, the histone substrate is a peptide fragment that corresponds to amino acid residues 21-44 of histone H3. Such peptide fragment has the amino acid sequence LATKAARKSAPA-TGGVKKPHRYRP (SEQ ID NO: 19). The peptide library or peptide can be prepared by peptide synthesis according to techniques well known in the art and optionally modified so as to incorporate any desired degree of methylation of lysine corresponding to H3-K27. As described in the Examples below, such peptides can also be modified to incorporate a label, such as biotin, useful in performing downstream assays. In one embodiment the label is appended to the amino (N)-terminus of the peptide(s). In one embodiment the label is appended to the carboxy (C)-terminus of the peptide(s).

H3-K27 methylation-specific antibodies are available from a variety of commercial sources, including, for example, Cell Signaling Technology (Danvers, Mass.) and Active Motif (Carlsbad, Calif.).

The isolated mutant EZH2 is combined with a test compound. As used herein, a "test compound" refers to a small organic molecule having a molecular weight of less than about 1.5 lcDa. In one embodiment a test compound is a known compound. In one embodiment a test compound is a novel compound. In one embodiment, a test compound can be provided as part of a library of such compounds, wherein the library includes, for example, tens, hundreds, thousands, or even more compounds. A library of compounds may advantageously be screened in a high throughput screening assay, for example, using arrays of test compounds and robotic manipulation in accordance with general techniques well known in the art.

In certain embodiments a test compound is a compound that is a derivative of SAH or a derivative of Compound 75.

Detection of methylation of H3-K27 can be accomplished using any suitable method. In one embodiment, the source of donor methyl groups includes methyl groups that are labeled with a detectable label. The detectable label in one embodiment is an isotopic label, e.g., tritium. Other types of labels may include, for example, fluorescent labels.

Detection of formation of trimethylated H3-K27 can be accomplished using any suitable method. For example, detection of formation of trimethylated H3-K27 can be accomplished using an assay to detect incorporation of labeled methyl groups, such as described above, optionally combined with a chromatographic or other method to separate labeled products by size, e.g., polyacrylamide gel electrophoresis (PAGE), capillary electrophoresis (CE), or high pressure liquid chromatography (HPLC). Alternatively or in addition, detection of formation of trimethylated H3-K27 can be accomplished using antibodies that are specific for trimethylated H3-K27.

Detection of conversion of monomethylated H3-K27 to dimethylated H3-K27 can be accomplished using any suitable method. In one embodiment the conversion is measured using antibodies specific for monomethylated H3-K27 and dimethylated H3-K27. For example, starting amounts or concentrations of monomethylated H3-K27 and dimethylated H3-K27 may be determined using appropriate antibodies specific for monomethylated H3-K27 and dimethylated H3-K27. Following the combination of enzyme, substrate, methyl group donor, and test compound, resulting amounts or concentrations of monomethylated H3-K27 and dimethylated H3-K27 may then be determined using appropriate antibodies specific for monomethylated H3-K27 and dimethylated H3-K27. The beginning and resulting amounts or concentrations of monomethylated H3-K27 and dimethylated H3-K27 can then be compared. Alternatively or in addition, beginning and resulting amounts or concentrations of monomethylated H3-K27 and dimethylated H3-K27 can then be compared to corresponding amounts of concentrations from a negative control. A negative control reaction, in which no test agent is included in the assay, can be run in parallel or as a historical control. Results of such control reaction can optionally be subtracted from corresponding results of the experimental reaction prior to or in conjunction with making the comparison mentioned above.

Because the dimethylated form of H3-K27 may be further methylated in the same assay, a reduction in the amount or concentration of monomethylated H3-K27 may not appear to correspond directly to an increase in dimethylated H3-K27. In this instance, it may be presumed, however, that a reduction in the amount or concentration of monomethylated H3-K27 is, by itself, reflective of conversion of monomethylated H3-K27 to dimethylated H3-K27.

Detection of conversion of dimethylated H3-K27 to trimethylated H3-K27 can be accomplished using any suitable method. In one embodiment the conversion is measured using antibodies specific for dimethylated H3-K27 and trimethylated H3-K27. For example, starting amounts or concentrations of dimethylated H3-K27 and trimethylated H3-K27 may be determined using appropriate antibodies specific for dimethylated H3-K27 and trimethylated H3-K27. Following the combination of enzyme, substrate, and test compound, resulting amounts or concentrations of dimethylated H3-K27 and trimethylated H3-K27 may then be determined using appropriate antibodies specific for dimethylated H3-K27 and trimethylated H3-K27. The beginning and resulting amounts or concentrations of dimethylated H3-K27 and trimethylated H3-K27 can then be compared. Alternatively or in addition, beginning and resulting amounts or concentrations of dimethylated H3-K27 and trimethylated H3-K27 can then be compared to corresponding amounts of concentrations from a negative control. A negative control reaction, in which no test agent is included in the assay, can be run in parallel or as a historical control. Results of such control reaction can optionally be subtracted from corresponding results of the experimental reaction prior to or in conjunction with making the comparison mentioned above.

A test agent is identified as an inhibitor of the mutant EZH2 when methylation of H3-K27 with the test compound is less than methylation of H3-K27 without the test compound. In one embodiment, a test agent is identified as an inhibitor of the mutant EZH2 when formation of trimethylated H3-K27 in the presence of the test compound is less than formation of trimethylated H3-K27 in the absence of the test compound.

An aspect of the invention is a method for identifying a selective inhibitor of a mutant EZH2. In one embodiment the method includes combining an isolated mutant EZH2 with a histone substrate, a methyl group donor (e.g., SAM), and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a test mixture; combining an isolated wild-type EZH2 with a histone substrate, a methyl group donor (e.g., SAM), and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a control mixture; performing an assay to detect trimethylation of the histone substrate in each of the test mixture and the control mixture; calculating the ratio of (a) trimethylation with the mutant EZH2 and the test compound (M+) to (b) trimethylation with the mutant EZH2 without the test compound (M−); calculating the ratio of (c) trimethylation with wild-type EZH2 and the test compound (WT+) to (d) trimethylation with wild-type EZH2 without the test compound (WT−); comparing the ratio (a)/(b) with the ratio (c)/(d); and identifying the test compound as a selective inhibitor of the mutant EZH2 when the ratio (a)/(b) is less than the ratio (c)/(d). In one embodiment the method further includes taking into account a negative control without test compound for either or both of the test mixture and the control mixture.

The present invention also provides a previously unrecognized, surprising correlation of a patient's responsiveness to an EZH2 inhibitor. Accordingly, an aspect of the invention is a method for determining a responsiveness to an EZH2 inhibitor in a subject having a cancer or a precancerous condition. The method generally involves in detecting a mutation in the EZH2 substrate pocket domain as defined in SEQ ID NO: 6. For example, the mutation may be a substitution, a point mutation, a nonsense mutation, a miss sense mutation, a deletion, or an insertion described above. Preferred substitution amino acid mutation includes a substitution at amino acid position 677, 687, 674, 685, or 641 of SEQ ID NO: 1, such as, but is not limited to a substitution of glycine (G) for the wild type residue alanine (A) at amino acid position 677 of SEQ ID NO: 1 (A677G); a substitution of valine (V) for the wild type residue alanine (A) at amino acid position 687 of SEQ ID NO: 1 (A687V); a substitution of methionine (M) for the wild type residue valine (V) at amino acid position 674 of SEQ ID NO: 1 (V674M); a substitution of histidine (H) for the wild type residue arginine (R) at amino acid position 685 of SEQ ID NO: 1 (R685H); a substitution of cysteine (C) for the wild type residue arginine (R) at amino acid position 685 of SEQ ID NO: 1 (R685C); a substitution of phenylalanine (F) for the wild type residue tyrosine (Y) at amino acid position 641 of SEQ ID NO: 1 (Y641F); a substitution of histidine (H) for the wild type residue tyrosine (Y) at, amino acid position 641 of SEQ ID NO: 1 (Y641H); a substitution of asparagine (N) for the wild type residue tyrosine (Y) at amino acid position 641 of SEQ ID NO: 1 (Y641N); a substitution of serine (S) for the wild type residue tyrosine (Y) at amino acid position 641 of SEQ ID NO: 1 (Y641S); or a substitution of cysteine (C) for the wild type residue tyrosine (Y) at amino acid position 641 of SEQ ID NO: 1 (Y641C).

In a preferred embodiment, the subject has cancer or a cancerous condition. For example, the cancer is lymphoma, leukemia or melanoma. Preferably, the lymphoma is non-Hodgkin lymphoma, follicular lymphoma or diffuse large B-cell lymphoma. Alternatively, the leukemia is chronic myelogenous leukemia (CML). The precancerous condition is myelodysplastic syndromes (MDS, formerly known as preleukemia).

In another preferred embodiment, the mutant EZH2 polypeptide or the nucleic acid sequence encoding the mutant EZH2 polypeptide of the present invention comprises one or more mutations in the substrate pocket domain of EZH2 as defined in SEQ ID NO: 6. More preferably, the mutant EZH2 polypeptide or the nucleic acid sequence encoding the mutant EZH2 polypeptide of the present invention comprises a substitution at amino acid position 677, 687, 674, 685, or 641 of SEQ ID NO: 1, such as, but is not limited to a substitution of glycine (G) for the wild type residue alanine (A) at amino acid position 677 of SEQ ID NO: 1 (A677G); a substitution of valine (V) for the wild type residue alanine (A) at amino acid position 687 of SEQ ID NO: 1 (A687V); a substitution of methionine (M) for the wild type residue valine (V) at amino acid position 674 of SEQ ID NO: 1 (V674M); a substitution of histidine (H) for the wild type residue arginine (R) at amino acid position 685 of SEQ ID NO: 1 (R685H); a substitution of cysteine (C) for the wild type residue arginine (R) at amino acid position 685 of SEQ ID NO: 1 (R685C); a substitution of phenylalanine (F) for the wild type residue tyrosine (Y) at amino acid position 641 of SEQ ID NO: 1 (Y641F); a substitution of histidine (H) for the wild type residue tyrosine (Y) at amino acid position 641 of SEQ ID NO: 1 (Y641H); a substitution of asparagine (N) for the wild type residue tyrosine (Y) at amino acid position 641 of SEQ ID NO: 1 (Y641N); a substitution of serine (S) for the wild type residue tyrosine (Y) at amino acid position 641 of SEQ ID NO: 1 (Y641S); or a substitution of cysteine (C) for the wild type residue tyrosine (Y) at amino acid position 641 of SEQ ID NO: 1 (Y641C).

Pharmaceutical Compositions

One or more EZH2 antagonists can be administered alone to a human patient or in pharmaceutical compositions where they are mixed with suitable carriers or excipient(s) at doses to treat or ameliorate a disease or condition as described herein. Mixtures of these EZH2 antagonists can also be administered to the patient as a simple mixture or in suitable formulated pharmaceutical compositions. For example, one aspect of the invention relates to pharmaceutical composition comprising a therapeutically effective dose of an EZH2 antagonist, or a pharmaceutically acceptable salt, hydrate, enantiomer or stereoisomer thereof; and a pharmaceutically acceptable diluent or carrier.

Techniques for formulation and administration of EZH2 antagonists may be found in references well known to one of ordinary skill in the art, such as Remington's "The Science and Practice of Pharmacy," 21st ed., Lippincott Williams & Wilkins 2005.

Suitable routes of administration may, for example, include oral, rectal, or intestinal administration; parenteral delivery, including intravenous, intramuscular, intraperitoneal, subcutaneous, or intramedullary injections, as well as intrathecal, direct intraventricular, or intraocular injections; topical delivery, including eyedrop and transdermal; and intranasal and other transmucosal delivery.

Alternatively, one may administer an EZH2 antagonist in a local rather than a systemic manner, for example, via injection of the EZH2 antagonist directly into an edematous site, often in a depot or sustained release formulation.

In one embodiment, an EZH2 antagonist is administered by direct injection into a tumor or lymph node.

Furthermore, one may administer an EZH2 antagonist in a targeted drug delivery system, for example, in a liposome coated with cancer cell-specific antibody.

The pharmaceutical compositions of the present invention may be manufactured, e.g., by conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active EZH2 antagonists into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants are used in the formulation appropriate to the barrier to be permeated. Such penetrants are generally known in the art.

For oral administration, the EZH2 antagonists can be formulated readily by combining the active EZH2 antagonists with pharmaceutically acceptable carriers well known in the art. Such carriers enable the EZH2 antagonists of the invention to be formulated as tablets, pills, dragees, capsules, liquids, gels, syrups, slurries, suspensions and the like, for oral ingestion by a patient to be treated. Pharmaceutical preparations for oral use can be obtained by combining the active EZH2 antagonist with a solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active EZH2 antagonist doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active EZH2 antagonists may be dissolved or suspended in suitable liquids, such as fatty oils, liquid paraffin, or liquid polyethylene glycols. In addition, stabilizers may be added.

For buccal administration, the compositions may take the form of tablets or lozenges formulated in conventional manner.

For administration by inhalation, the EZH2 antagonists for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g., gelatin for use in an inhaler or insufflator may be formulated containing a powder mix of the EZH2 antagonist and a suitable powder base such as lactose or starch.

The EZH2 antagonists can be formulated for parenteral administration by injection, e.g., bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active EZH2 antagonists in water-soluble form. Additionally, suspensions of the active EZH2 antagonists may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the EZH2 antagonists to allow for the preparation of highly concentrated solutions.

Alternatively, the active ingredient may be in powder form for reconstitution before use with a suitable vehicle, e.g., sterile pyrogen-free water.

The EZH2 antagonists may also be formulated in rectal compositions such as suppositories or retention enemas, e.g., containing conventional suppository bases, such as cocoa butter or other glycerides.

In addition to the formulations described previously, the EZH2 antagonists may also be formulated as a depot preparation. Such long acting formulations may be administered by implantation (for example, subcutaneously or intramuscularly or by intramuscular injection). Thus, for example, the EZH2 antagonists may be formulated with suitable polymeric or hydrophobic materials (for example as an emulsion in an acceptable oil) or ion exchange resins, or as sparingly soluble derivatives (for example, as a sparingly soluble salt).

Alternatively, other delivery systems for hydrophobic pharmaceutical EZH2 antagonists may be employed. Liposomes and emulsions are examples of delivery vehicles or carriers for hydrophobic drugs. Certain organic solvents such as dimethysulfoxide also may be employed. Additionally, the EZH2 antagonists may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the EZH2 antagonists for a few weeks up to over 100 days. Depending on the chemical nature and the biological stability of the therapeutic reagent, additional strategies for protein stabilization may be employed.

The pharmaceutical compositions may also comprise suitable solid or gel phase carriers or excipients. Examples of such carriers or excipients include but are not limited to calcium carbonate, calcium phosphate, various sugars, starches, cellulose derivatives, gelatin, and polymers, such as polyethylene glycols.

Methods of Treatment

Provided herein are methods of treating, preventing or alleviating a symptom of conditions and diseases, such as cancers and precancerous conditions, the course of which can be influenced by modulating the methylation status of histones or other proteins, wherein said methylation status is mediated at least in part by the activity of EZH2. Modulation of the methylation status of histones can in turn influence the level of expression of target genes activated by methylation, and/or target genes suppressed by methylation.

For example, one aspect of the invention relates to a method for treating or alleviating a symptom of cancer or precancerous condition. The method comprises the step of administering to a subject having a cancer or a precancerous condition and expressing a mutant EZH2 a therapeutically effective amount of an inhibitor of EZH2. Preferably, a mutant EZH2 polypeptide or a nucleic acid sequence encoding a mutant EZH2 polypeptide comprises a mutation in its substrate pocket domain as defined in SEQ ID NO: 6. More preferablly, a mutant EZH2 polypeptide or a nucleic acid sequence encoding a mutant EZH2 polypeptide comprises a substitution mutation at amino acid position 677, 687, 674, 685, or 641 of SEQ ID NO: 1, such as, but is not limited to a substitution of glycine (G) for the wild type residue alanine (A) at amino acid position 677 of SEQ ID NO: 1 (A677G); a substitution of valine (V) for the wild type residue alanine (A) at amino acid position 687 of SEQ ID NO: 1 (A687V); a substitution of methionine (M) for the wild type residue valine (V) at amino acid position 674 of SEQ ID NO: 1 (V674M); a substitution of histidine (H) for the wild type residue arginine (R) at amino acid position 685 of SEQ ID NO: 1 (R685H); a substitution of cysteine (C) for the wild type residue arginine (R) at amino acid position 685 of SEQ ID NO: 1 (R685C); a substitution of phenylalanine (F) for the wild type residue tyrosine (Y) at amino acid position 641 of SEQ ID NO: 1 (Y641F); a substitution of histidine (H) for the wild type residue tyrosine (Y) at amino acid position 641 of SEQ ID NO: 1 (Y641H); a substitution of asparagine (N) for the wild type residue tyrosine (Y) at amino acid position 641 of SEQ ID NO: 1 (Y641N); a substitution of serine (S) for the wild type residue tyrosine (Y) at amino acid position 641 of SEQ ID NO: 1 (Y641S); or a substitution of cysteine (C) for the wild type residue tyrosine (Y) at amino acid position 641 of SEQ ID NO: 1 (Y641C).

In one embodiment the inhibitor inhibits histone methyltransferase activity of the mutant EZH2. In one embodiment the inhibitor selectively inhibits histone methyltransferase activity of the mutant EZH2. Optionally, the cancer is a lymphoma. Preferably, the cancer is a non-Hodgkin lymphoma, a follicular lymphoma or a diffuse large B-cell lymphoma (DLBCL). Alternatively, the cancer is leukemia (such as CML) or melanoma. The precancerous condition includes, but is not limited to, myelodysplastic syndromes (MDS, formerly known as preleukemia).

Diseases such as cancers and neurological disease can be treated by administration of modulators of protein (e.g., histone) methylation, e.g., modulators of histone methyltransferase, or histone demethylase enzyme activity. Histone methylation has been reported to be involved in aberrant expression of certain genes in cancers, and in silencing of neuronal genes in non-neuronal cells. Modulators described herein can be used to treat such diseases, i.e., to inhibit methylation of histones in affected cells.

Based at least on the fact that abnormal histone methylation has been found to be associated with certain cancers and precancerous conditions, a method for treating cancer or a precancerous condition with a mutant EZH2 in a subject comprises administering to the subject in need thereof a therapeutically effective amount of a compound that inhibits methylation or restores methylation to roughly its level in counterpart normal cells. In one embodiment a method for treating cancer or a precancerous condition in a subject comprises administering to the subject in need thereof a therapeutically effective amount of a compound that inhibits conversion of unmethylated H3-K27 to monomethylated H3-K27 (H3-K27me1). In one embodiment a method for treating cancer or a precancerous condition in a subject comprises administering to the subject in need thereof a therapeutically effective amount of a compound that inhibits conversion of monomethylated H3-K27 (H3-K27me1) to dimethylated H3-K27 (H3-K27me2). In one embodiment a method for treating cancer or a precancerous condition in a subject comprises administering to the subject in need thereof a therapeutically effective amount of a compound that inhibits conversion of H3-K27me2 to trimethylated H3-K27 (H3-K27me3). In one embodiment a method for treating cancer or a precancerous condition in a subject comprises administering to the subject in need thereof a therapeutically effective amount of a compound that inhibits both conversion of H3-K27me1 to H3-K27me2 and conversion of H3-K27me2 to H3-K27me3. It is important to note that disease-specific increase in methylation can occur at chromatin in key genomic loci in the absence of a global increase in cellular levels of histone or protein methylation. For example, it is possible for aberrant hypermethylation at key disease-relevant genes to occur against a backdrop of global histone or protein hypomethylation.

Modulators of methylation can be used for modulating cell proliferation, generally. For example, in some cases excessive proliferation may be reduced with agents that decrease methylation, whereas insufficient proliferation may be stimulated with agents that increase methylation. Accordingly, diseases that may be treated include hyperproliferative diseases, such as benign cell growth and malignant cell growth (cancer).

Exemplary cancers that may be treated include lymphomas, including non-Hodgkin lymphoma, follicular lymphoma (FL) and diffuse large B-cell lymphoma (DLBCL); melanoma; and leukemia, including CML. Exemplary precancerous condition includes myelodisplastic syndrome (MDS; formerly known as preleukemia).

Other cancers include Acute Lymphoblastic Leukemia; Acute Myeloid Leukemia; Adrenocortical Carcinoma; AIDS-Related Cancers; AIDS-Related Lymphoma; Anal Cancer; Astrocytoma, Childhood Cerebellar; Astrocytoma, Childhood Cerebral; Basal Cell Carcinoma, see Skin Cancer (non-Melanoma); Bile Duct Cancer, Extrahepatic; Bladder Cancer; Bone Cancer, osteosarcoma/Malignant Fibrous Histiocytoma; Brain Stem Glioma; Brain Tumor; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma; Breast Cancer; Bronchial Adenomas/Carcinoids; Burkitt's Lymphoma; Carcinoid Tumor; Carcinoid Tumor, Gastrointestinal; Carcinoma of Unknown Primary; Central Nervous System Lymphoma, Primary; Cerebellar Astrocytoma; Cervical Cancer; Childhood Cancers; Chronic Lymphocytic Leukemia; Chronic Myelogenous Leukemia; Chronic Myelogenous Leukemia, Hairy Cell; Chronic Myeloproliferative Disorders; Colon Cancer; Colorectal Cancer; Cutaneous T-Cell Lymphoma, see Mycosis Fungoides and Sezary Syndrome; Endometrial Cancer; Esophageal Cancer; Ewing's Family of Tumors; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma; Hodgkin's Lymphoma During Pregnancy; Hypopharyngeal Cancer; Hypothalamic and Visual Pathway Glioma; Intraocular Melanoma; Islet Cell Carcinoma (Endocrine Pancreas); Kaposi's Sarcoma; Kidney (Renal Cell) Cancer; Kidney Cancer; Laryngeal Cancer; Leukemia; Lip and Oral Cavity Cancer; Liver Cancer, Adult (Primary); Liver Cancer, Childhood (Primary); Lung Cancer, Non-Small Cell; Lung Cancer, Small Cell; Lymphoma, Primary Central Nervous System; Macroglobulinemia, Waldenstrom's; Malignant Fibrous Histiocytoma of Bone/Osteosarcoma; Medulloblastoma; Melanoma; Merkel Cell Carcinoma; Mesothelioma; Mesothelioma, Adult Malignant; Metastatic Squamous Neck Cancer with Occult Primary; Multiple Endocrine Neoplasia Syndrome; Multiple Myeloma; Multiple Myeloma/Plasma Cell Neoplasm Mycosis Fungoides; Myelodysplastic Syndromes; Myelodysplastic/Myeloproliferative Diseases; Myeloid Leukemia, Adult Acute; Myeloid Leukemia, Childhood Acute; Myeloproliferative Disorders, Chronic; Nasal Cavity and Paranasal Sinus Cancer; Nasopharyngeal Cancer; Neuroblastoma; Non-Hodgkin's Lymphoma; Non-Hodgkin's Lymphoma During Pregnancy; Oral Cancer; Oral Cavity Cancer, Lip and; Oropharyngeal Cancer; Osteosarcoma/Malignant Fibrous Histiocytoma of Bone; Ovarian Cancer; Ovarian Epithelial Cancer; Ovarian Low Malignant Potential Tumor; Pancreatic Cancer; Pancreatic Cancer, Islet Cell; Paranasal Sinus and Nasal Cavity Cancer; Parathyroid Cancer; Penile Cancer; Pheochromocytoma; Pineoblastoma and Supratentorial Primitive Neuroectodermal Tumors; Pituitary Tumor; Plasma Cell Neoplasm/Multiple Myeloma; Pleuropulmonary Blastoma; Pregnancy and Breast Cancer; Prostate Cancer; Rectal Cancer; Retinoblastoma; Rhabdomyosarcoma; Salivary Gland Cancer; Sarcoma, Ewing's Family of Tumors; Sarcoma, Soft Tissue; Sarcoma, Uterine; Sezary Syndrome; Skin Cancer; Skin Cancer (non-Melanoma); Small Intestine Cancer; Soft Tissue Sarcoma; Squamous Cell Carcinoma, see Skin Cancer (non-Melanoma); Squamous Neck Cancer with Occult Primary, Metastatic; Stomach (Gastric) Cancer; Testicular Cancer; Thymoma; Thymoma and Thymic Carcinoma; Thyroid Cancer; Transitional Cell Cancer of the Renal Pelvis and Ureter; Trophoblastic Tumor, Gestational; Unknown Primary Site, Cancer of; Unusual Cancers of Childhood; Urethral Cancer; Uterine Cancer, Endometrial; Uterine Sarcoma; Vaginal Cancer; Visual Pathway and Hypothalamic Glioma; Vulvar Cancer; Waldenstrom's Macroglobulinemia; Wilms' Tumor; and Women's Cancers.

Any other disease in which epigenetic methylation, which is mediated by EZH2, plays a role may be treatable or preventable using compounds and methods described herein.

For example, neurologic diseases that may be treated include epilepsy, schizophrenia, bipolar disorder or other psychological and/or psychiatric disorders, neuropathies, skeletal muscle atrophy, and neurodegenerative diseases, e.g., a neurodegenerative disease. Exemplary neurodegenerative diseases include: Alzheimer's, Amyotrophic Lateral Sclerosis (ALS), and Parkinson's disease. Another class of neurodegenerative diseases includes diseases caused at least in part by aggregation of poly-glutamine. Diseases of this class include: Huntington's Diseases, Spinalbulbar Muscular Atrophy (SBMA or Kennedy's Disease), Dentatorubropallidoluysian Atrophy (DRPLA), Spinocerebellar Ataxia 1 (SCA1), Spinocerebellar Ataxia 2 (SCA2), Machado-Joseph Disease (MJD; SCA3), Spinocerebellar AtaXia 6 (SCA6), Spinocerebellar Ataxia 7 (SCAT), and Spinocerebellar Ataxia 12 (SCAl2).

Combination Therapy

In one aspect of the invention, an EZH2 antagonist, or a pharmaceutically acceptable salt thereof, can be used in combination with another therapeutic agent to treat diseases such as cancer and/or neurological disorders. For example, the additional agent can be a therapeutic agent that is art-recognized as being useful to treat the disease or condition being treated by the compound of the present invention. The additional agent also can be an agent that imparts a beneficial attribute to the therapeutic composition (e.g., an agent that affects the viscosity of the composition).

The combination therapy contemplated by the invention includes, for example, administration of a compound of the invention, or a pharmaceutically acceptable salt thereof, and additional agent(s) in a single pharmaceutical formulation as well as administration of a compound of the invention, or a pharmaceutically acceptable salt thereof, and additional agent(s) in separate pharmaceutical formulations. In other words, co-administration shall mean the administration of at least two agents to a subject so as to provide the beneficial effects of the combination of both agents. For example, the agents may be administered simultaneously or sequentially over a period of time.

The agents set forth below are for illustrative purposes and not intended to be limiting. The combinations, which are part of this invention, can be the compounds of the present invention and at least one additional agent selected from the lists below. The combination can also include more than one additional agent, e.g., two or three additional agents if the combination is such that the formed composition can perform its intended function.

For example, one aspect of the invention relates to the use of an EZH2 antagonist in combination with another agent for the treatment of cancer and/or a neurological disorder. In one embodiment, an additional agent is an anticancer agent that is a compound that affects histone modifications, such as an HDAC inhibitor. In certain embodiments, an additional anticancer agent is selected from the group consisting of chemotherapetics (such as 2CdA, 5-FU, 6-Mercaptopurine, 6-TG, ABRAXANE™ (generic: paclitaxel protein-bound), ACCUTANE® (gneric: isotretinoin), Actinomycin-D, ADRIAMYCIN® (generic: doxorubicin), ALIMTA® (generic: pemetrexed), all-trans retinoic acid, amethopterin, Ara-C, Azacitadine, BCNU, BLENOXANE® (generic: bleomycin), CAMPTOSAR® (generic: irinotecan), CEENU® (generic: CEENU), Clofarabine, CLOLAR™ (generic:clofarabine), CYTOXAN® (generic: cyclophosphamide), daunorubicin hydrochloride, DAUNOXOME® (generic: daunorubicin), DACOGEN® (generic: decitabine), DIC, DOXIL® (generic: doxorubicin), ELLENCE® (generic: epirubicin), ELOXATIN® (generic: oxaliplatin), EMCYT® (generic: estramustine), etoposide phosphate, FLUDARA® (generic: fludarabine), FUDR® (generic: floxuridine), GEMZAR®(generic: gemcitabine), GLEEVEC® (generic: imatinib), hexamethylmelamine, HYCAMTIN® (generic: topotecan), HYDREA® (generic: hydroxycarbamide), IDAMYCIN® (generic: idaarubicin), IFEX® (generic: ifosfamide), ixabepilone, IXEMPRA® (generic: ixabepilone), L-asparaginase, LEUKERAN® (generic: chlorambucil), liposomal Ara-C, L-PAM, Lysodren, MATULANE® (generic: procarbazine), mithracin, Mitomycin-C, MYLERAN® (generic: busulfan), NAVELBINE® (generic: vinorelbine), NEUTREXIN® (trimetrexate), nilotinib, NIPENT® (generic: pentostatin), Nitrogen Mustard, NOVANTRONE® (generic: mitoxantrone), ONCASPAR® (generic: pegaspargase), PANRETIN® (generic: alitretinoin), PARAPLATIN®, (generic: carboplatin), PLATINOL® (generic: cisplatin), prolifeprospan 20 with carmustine implant, SANDOSTATIN® (generic: octreotide), TARGRETIN® (generic: bexarotene), TASIGNA® (generic: nilotinib), TAXOTERE® (generic: docetaxel), TEMODAR® (generic: temozolomide), TESPA, TRISENOX® (generic: arsenic trioxide), VALSTAR® (generic: valrubicin), VELBAN® (generic: vinblastine), VIDAZA™ (azacitidine), vincristine sulfate, VM 26, XELODA® (generic: capecitabine),and ZANOSAR® (generic: streptozotocin)); biologics (such as Alpha Interferon, Bacillus Calmette-Guerin, BEXXAR® (generic: tositumomab), CAMPATH® (generic: alemtuzumab), ERGAMISOL® (generic: levamisole), Erlotinib, HERCEPTIN® (generic: trastuzumab), Interleukin-2, IRESSA® (generic: gefitinib), lenalidomide, MYLOTARG® (generic: gemtuzumab ozogamicin), ONTAK® (generic: denileukin difitox), PEGASYS® (generic: peginterferon alfa-2a), REVLIMID® (generic: lenalidomide), RITUXAN® (generic: rituxmab), TARCEVA™ (generic: erlotinib), THALOMID® (generic: thalidomide), VELCADE® (generic: bortezomib) and ZEVALIN™ (generic: ibritumomab tiuxetan)); small molecules (such as TYKERB® (generic name: lapatinib)); corticosteroids (such as dexamethasone sodium phosphate, DELTASONE® (generic: prednisone),and DELTA-CORTEF® (generic: prednisolone)); hormonal therapies (such as ARIMIDEX® (generic: anastrozole), AROMASIN® (generic: exemestane), CASODEX® (generic: bicalutamide), CYTADREN® (generic: aminoglutethimide), ELIGARD® (generic: leuprolide acetate), EULEXIN®(generic: flutamide), EVISTA® (generic: raloxifene), FASLODEX® (generic: fulvestrant), FEMARA® (generic: letrozole), HALOTESTIN® (generic: fluoxymesterone), MEGRACE® (generic: megestrol acetate), NILANDRON® (generic: nilutamide), NOLVADEX® (generic: tamoxifen), PLENAXIS™(generic: abarelix),and ZOLADEX® (generic: goserelin)); and radiopharmaceuticals (such as IODOTOPE® (generic: sodium iodide-i-131), METASTRON®(generic: strontium-80), PHOSPHOCOL® (generic: chromic phosphate),and Samarium SM-153).

Dosage

As used herein, a "therapeutically effective amount" or "therapeutically effective dose" is an amount of an EZH2 antagonist or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. In one embodiment, a therapeutically effective dose refers to that amount of the EZH2 antagonists that result in amelioration of symptoms in a patient. For a given patient, a therapeutically effective amount may be determined by methods known to those of skill in the art.

Toxicity and therapeutic efficacy of EZH2 antagonists can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. The data obtained from these cell culture assays and animal studies can be used in formulating a range of dosage for use in humans. Dosage may also be guided by monitoring the EZH2 antagonist's effect on pharmacodynamic markers of enzyme inhibition (e.g., histone methylation or target gene expression) in diseased or surrogate tissue. Cell culture or animal experiments can be used to determine the relationship between doses required for changes in pharmacodynamic markers and doses required for therapeutic efficacy can be determined in cell culture or animal experiments or early stage clinical trials. The dosage of such EZH2 antagonists lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. In the treatment of crises, the administration of an acute bolus or an infusion approaching the MTD may be required to obtain a rapid response.

Dosage amount and interval may be adjusted individually to provide plasma levels of the active moiety which are sufficient to maintain the methyltransferase modulating effects, or minimal effective concentration (MEC) for the required period of time to achieve therapeutic efficacy. The MEC will vary for each EZH2 antagonist but can be estimated from in vitro data and animal experiments. Dosages necessary to achieve the MEC will depend on individual characteristics and route of administration. However, high pressure liquid chromatography (HPLC) assays or bioassays can be used to determine plasma concentrations.

Dosage intervals can also be determined using the MEC value. In certain embodiments, EZH2 antagonists should be administered using a regimen which maintains plasma levels above the MEC for 10-90% of the time, preferably between 30-90% and most preferably between 50-90% until the desired amelioration of symptoms is achieved. In other embodiments, different MEC plasma levels will be maintained for differing amounts of time. In cases of local administration or selective uptake, the effective local concentration of the drug may not be related to plasma concentration.

One of skill in the art can select from a variety of administration regimens and the amount of EZH2 antagonist administered will, of course, be dependent on the subject being treated, on the subject's weight, the severity of the affliction, the manner of administration and the judgment of the prescribing physician.

Compounds and Pharmaceutical Compositions

Aspects of the invention concern compounds which are useful according to the methods of the invention. These compounds are referred to herein as "inhibitors of EZH2" and, equivalently, "EZH2 antagonists". The compounds can be presented as the compounds per se, pharmaceutically acceptable salts of the compounds, or as pharmaceutical compositions.

The compounds suitable for use in the method of this invention include compounds of Formula (I):

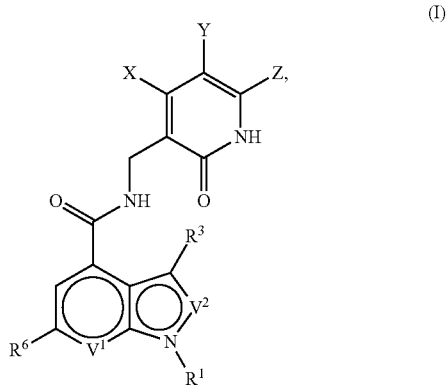

(I)

wherein, $V^1$ is N or $CR^7$, $V^2$ is N or $CR^2$, provided when. $V^1$ is N, $V^2$ is N, X and Z are selected independently from the group consisting of hydrogen, $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or —$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or —$(C_2-C_8)$alkenyl, $(C_6-C_{10})$bicycloalkyl, unsubstituted or substituted heterocycloalkyl, unsubstituted or substituted heterocycloalkyl-$(C_1-C_8)$alkyl or —$(C_2-C_8)$alkenyl, unsubstituted or substituted aryl, unsubstituted or substituted aryl-$(C_1-C_8)$alkyl or —$(C_2-C_8)$alkenyl, unsubstituted or substituted heteroaryl, unsubstituted or substituted heteroaryl-$(C_1-C_8)$alkyl or —$(C_2-C_8)$alkenyl, halo, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)ORa$, —$OR^a$, —$OC(O)R^a$, and —$OC(O)NR^aR^b$;

Y is H or halo;

$R^1$ is $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or —$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or —$(C_2-C_8)$alkenyl, unsubstituted or substituted $(C_6-C_{10})$bicycloalkyl, unsubstituted or substituted heterocycloalkyl or —$(C_2-C_8)$alkenyl, unsubstituted or substituted heterocycloalkyl-$(C_1-C_8)$alkyl, unsubstituted or substituted aryl, unsubstituted or substituted aryl-$(C_1-C_8)$alkyl or —$(C_2-C_8)$alkenyl, unsubstituted or substituted heteroaryl, unsubstituted or substituted heteroaryl-$(C_1-C_8)$alkyl or —$(C_2-C_8)$alkenyl, —$COR^a$, —$CO_2R^a$, —$CONR^aR^b$, —$CONR^aNR^aR^b$;

$R^2$ is hydrogen, $(C_1-C_8)$alkyl, trifluoromethyl, alkoxy, or halo, in which said $(C_1-C_8)$alkyl is optionally substituted with one to two groups selected from amino and $(C_1-C_3)$alkylamino;

$R^7$ is hydrogen, $(C_1-C_3)$alkyl, or alkoxy;

$R^3$ is hydrogen, $(C_1-C_8)$alkyl, cyano, trifluoromethyl, —$NR^aR^b$, or halo;

$R^6$ is selected from the group consisting of hydrogen, halo, $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl, unsubstituted or substituted $(C_5-C_8)$cycloalkenyl, unsubstituted or substituted $(C_5-C_8)$cycloalkenyl-$(C_1-C_8)$alkyl, $(C_6-C_{10})$bicycloalkyl, unsubstituted or substituted heterocycloalkyl, unsubstituted or substituted heterocycloalkyl-$(C_1-C_8)$alkyl, unsubstituted or substituted aryl, unsubstituted or substituted aryl-$(C_1-C_8)$alkyl, unsubstituted or substituted heteroaryl, unsubstituted or substituted heteroaryl-$(C_1-C_8)$alkyl, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, —$OC(O)NR^aR^b$;

wherein any $(C_1-C_8)$alkyl, $(C_2-C_8)$alkenyl, $(C_2-C_8)$alkynyl, cycloalkyl, cycloalkenyl, bicycloalkyl, heterocycloalkyl, aryl, or heteroaryl group is optionally substituted by 1, 2 or 3 groups independently selected from the group consisting of —$O(C_1-C_6)$alkyl$(R^c)_{1-2}$, —$S(C_1-C_6)$alkyl$(R^c)_{1-2}$, —$(C_1-C_6)$alkyl$(R^c)_{1-2}$, —$(C_1-C_8)$alkyl-heterocycloalkyl, $(C_3-C_8)$cycloalkyl-heterocycloalkyl, halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, $OC(O)NR^aR^b$, heterocycloalkyl, aryl, heteroaryl, aryl$(C_1-C_4)$alkyl, and heteroaryl$(C_1-C_4)$alkyl;

wherein any aryl or heteroaryl moiety of said aryl, heteroaryl, aryl$(C_1-C_4)$alkyl, or heteroaryl$(C_1-C_4)$alkyl is optionally substituted by 1, 2 or 3 groups independently selected from the group consisting of halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$;

$R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, aryl, or heteroaryl, wherein said $(C_1-C_8)$alkyl, $(C_2-C_8)$alkenyl, $(C_2-C_8)$alkynyl, cycloalkyl, cycloalkenyl, bicycloalkyl, heterocycloalkyl, aryl or heteroaryl group is optionally substituted by 1, 2 or 3 groups independently selected from halo, hydroxyl, $(C_1-C_4)$alkoxy, amino, $(C_1-C_4)$alkylamino, $((C_1-C_4)$alkyl$)((C_1-C_4)$alkyl$)$amino, —$CO_2H$, —$CO_2(C_1-C_4)$alkyl, —$CONH_2$, —$CONH(C_1-C_4)$alkyl, —$CON((C_1-C_4)$alkyl$)((C_1-C_4)$alkyl$)$, —$SO_2(C_1-C_4)$alkyl, —$SO_2NH_2$, —$SO_2NH(C_1-C_4)$alkyl, and $SO_2N((C_1-C_4)$alkyl$)((C_1-C_4)$alkyl$)$;

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from $(C_1-C_4)$alkyl, $(C_1-C_4)$haloalkyl, amino, $(C_1-C_4)$alkylamino, $((C_1-C_4)$alkyl$)((C_1-C_4)$alkyeamino, hydroxyl, oxo, $(C_1-C_4)$alkoxy, and $(C_1-C_4)$alkoxy$(C_1-C_4)$alkyl, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring;

each $R^c$ is independently $(C_1-C_4)$alkylamino, —$NR^aSO2R^b$, —$SOR^a$, —$SO_2R^a$, —$NR^aC(O)OR^a$, —$NR^aR^b$, or —$CO_2R^a$;

or a salt thereof.

Subgroups of the compounds encompassed by the general structure of Formula (I) are represented as follows:

Subgroup A of Formula (I)

X and Z are selected from the group consisting of $(C_1-C_8)$alkyl, $(C_3-C_8)$cycloalkyl, heterocycloalkyl, aryl, heteroaryl, —$NR^aR^b$, and —$OR^a$;

Y is H or F;

$R^1$ is selected from the group consisting of $(C_1-C_8)$alkyl, $(C_3-C_8)$cycloalkyl, heterocycloalkyl, aryl, and heteroaryl;

$R^2$ is hydrogen, $(C_1-C_8)$alkyl, trifluoromethyl, alkoxy, or halo, in which said $(C_1-C_8)$alkyl is optionally substituted with one to two groups selected from amino and $(C_1-C_3)$alkylamino;

$R^7$ is hydrogen, $(C_1-C_3)$alkyl, or alkoxy;

$R^3$ is selected from the group consisting of hydrogen, $(C_1-C_8)$alkyl, cyano, trifluoromethyl, —$NR^aR^b$, and halo;

$R^6$ is selected from the group consisting of hydrogen, halo, cyano, trifluoromethyl, amino, $(C_1-C_8)$alkyl, $(C_3-C_8)$cycloalkyl; aryl, heteroaryl, acylamino; $(C_2-C_8)$alkynyl, arylalkynyl, heteroarylalkynyl; —$SO_2R^a$; —$SO_2NR^aR^b$ and —$NR^aSO_2R^b$;

wherein any $(C_1-C_8)$alkyl, $(C_3-C_8)$cycloalkyl, $(C_2-C_8)$alkynyl, arylalkynyl, heteroarylalkynyl group is optionally substituted by 1, 2 or 3 groups independently selected from —$O(C_1-C_6)$alkyl$(R^c)_{1-2}$, —$S(C_1-C_6)$alkyl$(R^c)_{1-2}$, —$(C_1-C_6)$alkyl$(R^c)_{1-2}$, —$(C_1-C_8)$alkyl-heterocycloalkyl, $(C_3-C_8)$cycloalkyl-heterocycloalkyl, halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl$(C_1-C_4)$alkyl, and heteroaryl$(C_1-C_4)$alkyl;

$R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, aryl, or heteroaryl, wherein said $(C_1-C_8)$alkyl, $(C_2-C_8)$alkenyl, $(C_2-C_8)$alkynyl, cycloalkyl, cycloalkenyl, bicycloalkyl, heterocycloalkyl, aryl or heteroaryl group is optionally substituted by 1, 2 or 3 groups independently selected from halo, hydroxyl, $(C_1-C_4)$alkoxy, amino, $(C_1-C_4)$alkylamino, $((C_1-C_4)$alkyl$)((C_1-C_4)$alkyl$)$amino, —$CO_2H$, —$CO_2(C_1-C_4)$alkyl, —$CONH_2$, —$CONH(C_1-C_4)$alkyl, —$CON((C_1-C_4)$alkyl$)((C_1-C_4)$alkyl$)$, —$SO_2(C_1-C_4)$alkyl, —$SO_2NH_2$, —$SO_2NH(C_1-C_4)$alkyl, and —$SO_2N((C_1-C_4)$alkyl$)((C_1-C_4)$alkyl$)$;

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from $(C_1-C_4)$alkyl, $(C_1-C_4)$haloalkyl, amino, $(C_1-C_4)$alkylamino, $((C_1-C_4)$alkyl$)((C_1-C_4)$alkyl$)$amino, hydroxyl, oxo, $(C_1-C_4)$alkoxy, and $(C_1-C_4)$alkoxy$(C_1-C_4)$alkyl, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring. An aryl or heteroaryl group in this particular subgroup A is selected independently from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine or another aryl or heteroaryl group as follows:

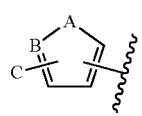
(1)

wherein in (1),
A is O, NH, or S; B is CH or N, and C is hydrogen or $C_1-C_8$ alkyl; or

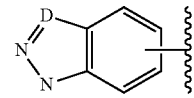
(2)

wherein in (2),
D is N or C optionally substituted by hydrogen or $C_1-C_8$ alkyl; or

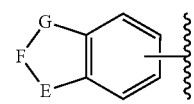
(3)

wherein in (3),
E is NH or $CH_2$; F is O or CO; and G is NH or $CH_2$; or

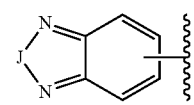
(4)

wherein in (4),
J is O, S or CO; or

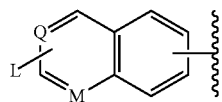
(5)

wherein in (5),
Q is CH or N;
M is CH or N; and
L/(5) is hydrogen, halo, amino, cyano, $(C_1-C_8)$alkyl, $(C_3-C_8)$cycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, or —$OR^a$, wherein any $(C_1-C_8)$alkyl or $(C_3-C_8)$cycloalkyl group is optionally substituted by 1, 2 or 3 groups independently selected from $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$; wherein $R^a$ and $R^b$ are defined as above; or

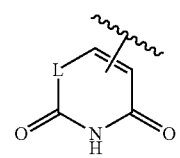
(6)

wherein in (6),
L/(6) is NH or CH$_2$; or

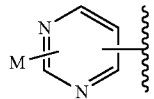
(7)

wherein in 7,
M/(7) is hydrogen, halo, amino, cyano, (C$_1$-C$_8$)alkyl, (C$_3$-C$_8$)cycloalkyl, heterocycloalkyl, —COR$^a$, —CO$_2$R$^a$, —CONR$^a$R$^b$, —CONR$^a$NR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$, —NR$^a$SO$_2$NR$^a$R$^b$, —NR$^a$NR$^a$R$^b$, —NR$^a$NR$^a$C(O)R$^b$, —NR$^a$NR$^a$C(O)NR$^a$R$^b$, or —OR$^a$,
wherein any (C$_1$-C$_8$)alkyl, (C$_3$-C$_8$)cycloalkyl, or heterocycloalkyl group is optionally substituted by 1, 2 or 3 groups independently selected from (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, and —OC(O)NR$^a$R$^b$; wherein R$^a$ and R$^b$ are defined as above; or

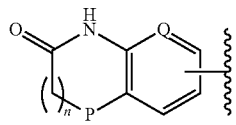
(8)

wherein in (8),
P is CH$_2$, NH, O, or S; Q/(8) is CH or N; and n is 0-2; or

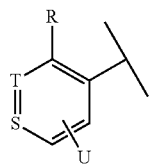
(9)

wherein in (9),
S/(9) and T/(9) is C, or S/(9) is C and T/(9) is N, or S/(9) is N and T/(9) is C;
R is hydrogen, amino, methyl, trifluoromethyl, or halo;
U is hydrogen, halo, amino, cyano, nitro, trifluoromethyl, (C$_1$-C$_8$)alkyl, (C$_3$-C$_8$)cycloalkyl, —COR$^a$, —CO$_2$R$^a$, —CONR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$,
—NR$^a$SO$_2$NR$^a$R$^b$, —NR$^a$NR$^a$R$^b$, —NR$^a$NR$^a$C(O)R$^b$, —OR$^a$, or 4-(1H-pyrazol-4-yl),
wherein any (C$_1$-C$_8$)alkyl or (C$_3$-C$_8$)cycloalkyl group is optionally substituted by 1, 2 or 3 groups independently selected from (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, and —OC(O)NR$^a$R$^b$; wherein R$^a$ and R$^b$ are defined as above.

Subgroup B of Formula (I)
X and Z are selected independently from the group consisting of (C$_1$-C$_8$)alkyl, (C$_3$-C$_8$)cycloalkyl, heterocycloalkyl, aryl, heteroaryl, —NR$^a$R$^b$, and —OR$^a$;
Y is H;
R$^1$ is (C$_1$-C$_8$)alkyl, (C$_3$-C$_8$)cycloalkyl, or heterocycloalkyl;
R$^2$ is hydrogen, (C$_1$-C$_3$)alkyl, or halo, in which said (C$_1$-C$_3$)alkyl is optionally substituted with one to two groups selected from amino and (C$_1$-C$_3$)alkylamino;
R$^7$ is hydrogen, (C$_1$-C$_3$)alkyl, or alkoxy;
R$^3$ is hydrogen, (C$_1$-C$_8$)alkyl or halo;
R$^6$ is hydrogen, halo, cyano, trifluoromethyl, amino, (C$_1$-C$_8$)alkyl, (C$_3$-C$_8$)cycloalkyl, aryl, heteroaryl, acylamino; (C$_2$-C$_8$)alkynyl, arylalkynyl, heteroarylalkynyl, —SO$_2$R$^a$, —SO$_2$NR$^a$R$^b$, or
—NR$^a$SO$_2$R$^b$;
wherein any (C$_1$-C$_8$)alkyl, (C$_3$-C$_8$)cycloalkyl, (C$_2$-C$_8$) alkynyl, arylalkynyl, or heteroarylalkynyl group is optionally substituted by 1, 2 or 3 groups independently selected from halo, (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, NR$^a$SO$_2$NR$^a$R$^b$, —OR$^a$, —OC(O)R$^a$, —OC(O)NR$^a$R$^b$, heterocycloalkyl, aryl, heteroaryl, aryl(C$_1$-C$_4$)alkyl, and heteroaryl(C$_1$-C$_4$)alkyl;

R$^a$ and R$^b$ are each independently hydrogen, (C$_1$-C$_8$)alkyl, (C$_2$-C$_8$)alkenyl, (C$_2$-C$_8$)alkynyl, (C$_3$-C$_8$)cycloalkyl, (C$_5$-C$_8$) cycloalkenyl, (C$_6$-C$_{10}$)bicycloalkyl, heterocycloalkyl, aryl, or heteroaryl, wherein said (C$_1$-C$_8$)alkyl, (C$_2$-C$_8$)alkenyl, (C$_2$-C$_8$)alkynyl, cycloalkyl, cycloalkenyl, bicycloalkyl, heterocycloalkyl, aryl or heteroaryl group is optionally substituted by 1, 2 or 3 groups independently selected from halo, hydroxyl, (C$_1$-C$_4$)alkoxy, amino, (C$_1$-C$_4$)alkylamino, ((C$_1$-C$_4$)alkyl)((C$_1$-C$_4$)alkyl)amino, —CO$_2$H, —CO$_2$(C$_1$-C$_4$) alkyl, —CONH$_2$, —CONH(C$_1$-C$_4$)alkyl,
—CON((C$_1$-C$_4$)alkyl)((C$_1$-C$_4$)alkyl), —SO$_2$(C$_1$-C$_4$)alkyl, —SO$_2$NH$_2$, —SO$_2$NH(C$_1$-C$_4$)alkyl, and —SO$_2$N((C$_1$-C$_4$) alkyl)((C$_1$-C$_4$)alkyl);

or R$^a$ and R$^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from (C$_1$-C$_4$)alkyl, (C$_1$-C$_4$)haloalkyl, amino, (C$_1$-C$_4$)alkylamino, ((C$_1$-C$_4$)alkyl)((C$_1$-C$_4$)alkyl)amino, hydroxyl, oxo, (C$_1$-C$_4$)alkoxy, and (C$_1$-C$_4$)alkoxy(C$_1$-C$_4$) alkyl, wherein said ring is optionally fused to a (C$_3$-C$_8$)cycloalkyl, heterocycloalkyl, aryl, or heteroaryl ring;

or R$^a$ and R$^b$ taken together with the nitrogen to which they are attached represent a 6- to 10-membered bridged bicyclic ring system optionally fused to a (C$_3$-C$_8$)cycloalkyl, heterocycloalkyl, aryl, or heteroaryl ring. Aryl and heteroaryl in this definition are selected from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine or a compound of another aryl or heteroaryl group as follows:

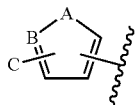
(1)

wherein in (1),
A is O, NH, or S; B is CH or N, and C is hydrogen or $C_1$-$C_8$ alkyl; or

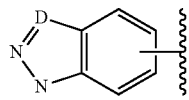
(2)

wherein in (2),
D is N or C optionally substituted by hydrogen or $C_1$-$C_8$ alkyl; or

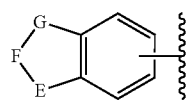
(3)

wherein in (3),
E is NH or $CH_2$; F is O or CO; and G is NH or $CH_2$; or

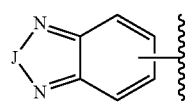
(4)

wherein in (4),
J is O, S or CO; or

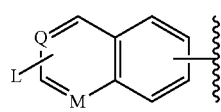
(5)

wherein in (5),
Q is CH or N;
M is CH or N; and
L/(5) is hydrogen, halo, amino, cyano, ($C_1$-$C_8$)alkyl, ($C_3$-$C_8$)cycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, or —$OR^a$,
wherein any ($C_1$-$C_8$)alkyl, ($C_3$-$C_8$)cycloalkyl, group is optionally substituted by 1, 2 or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, $NR^aSO_2R^b$, —$NR^aSO_2NR^aR^b$, —$OR^a$, —$OC(O)R^a$, and —$OC(O)NR^aR^b$, wherein $R^a$ and $R^b$ are defined as above; or

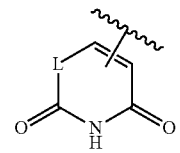
(6)

wherein in (6),
L/(6) is NH or $CH_2$; or

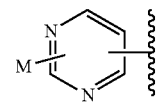
(7)

wherein in (7),
M/(7) is hydrogen, halo, amino, cyano, ($C_1$-$C_8$)alkyl, ($C_3$-$C_8$)cycloalkyl, heterocycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, or —$OR^a$,
wherein any ($C_1$-$C_8$)alkyl, ($C_3$-$C_8$)cycloalkyl, heterocycloalkyl group is optionally substituted by 1, 2 or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, $NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$; wherein $R^a$ and $R^b$ are defined as above; or

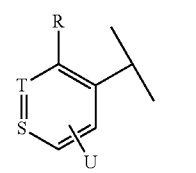
(8)

wherein in (8),
P is $CH_2$, NH, O, or S; Q/(8) is CH or N; and n is 0-2; or (9)

wherein in (9),
S/(9) and T/(9) is C, or S/(9) is C and T/(9) is N, or S/(9) is N and T/(9) is C;
R is hydrogen, amino, methyl, trifluoromethyl, halo;
U is hydrogen, halo, amino, cyano, nitro, trifluoromethyl, ($C_1$-$C_8$)alkyl, ($C_3$-$C_8$)cycloalkyl, —$COR^a$, —$CO_2R^a$, —$CONR^aR^b$, —$SO_2R^a$, —$SO_2NR^aR^b$, —$NR^aR^b$, —$NR^aC(O)R^b$, —$NR^aSO_2R^b$,
—$NR^aSO_2NR^aR^b$, —$NR^aNR^aR^b$, —$NR^aNR^aC(O)R^b$, —$OR^a$, or 4-(1H-pyrazol-4-yl), wherein any ($C_j$—$C_8$)alkyl, or ($C_3$-$C_8$)cycloalkyl group is optionally substituted by 1, 2 or 3 groups independently selected from ($C_1$-$C_6$)alkyl, ($C_3$-$C_8$)cycloalkyl, ($C_5$-$C_8$) cycloalkenyl, ($C_1$-$C_6$)haloalkyl, cyano, —COR$^a$, —CO$_2$R$^a$, —CONR$^a$R$^b$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO2NR$^a$R$^b$, —OR$^a$, —OC(O)R$^a$, and —OC(O)NR$^a$R$^b$, wherein R$^a$ and R$^b$ are defined as above.

Subgroup C of Formula (I)

X is methyl, ethyl, n-propyl, isopropyl, cyclopropyl, cyclobutyl, cyclopentyl, cyclohexyl, phenyl, trifluoromethyl, tetrahydropyran, hydroxymethyl, methoxymethyl, or benzyl;

Y is H;

Z is methyl, ethyl, n-propyl, isopropyl, trifluoromethyl, or benzyl;

R$^1$ is isopropyl, tert-butyl, cyclobutyl, cyclopentyl, cyclohexyl, (1-methylethyl)cyclopropyl, 1,1-dioxo-tetrahydrothiophene-3-yl, 1-Me-piperidin-4-yl, tetrahydrofuran-3-yl, tetrahydropyran-4-yl, N,N-dimethyl-1-propanaminyl, benzyl, or 4-pyridyl;

R$^2$ is hydrogen, ($C_1$-$C_3$)alkyl, or halo, in which said ($C_1$-$C_3$)alkyl is optionally substituted with one to two groups selected from amino and ($C_1$-$C_3$)alkylamino;

R$^7$ is hydrogen, ($C_1$-$C_3$)alkyl, or alkoxy;

R$^3$ is H, methyl, or Br; and

R$^6$ is methyl, bis(1,1-dimethylethyl), bis(1-methylethyl), cyclopropyl, propyl, dimethylamino, ethylamino, (2-hydroxyethyl)amino, 2-propen-1-ylamino, 1-piperazinyl, 1-piperidinyl, 4-morpholinyl, 4-piperidinylamino, tetrahydro-2H-pyran-4-ylamino, phenylamino, (phenylmethyl)amino, (4-pyridinylmethyl)amino, [2-(2-pyridinylamino)ethyl] amino, 2-(dimethylamino)ethyl]amino, 4-pyridinylamino, 4-(aminocarbonyl)phenyl]amino, 3-hydroxy-3-methyl-1-butyn-1-yl, 4-pyridinylethynyl, phenylethynyl, 2-furanyl, 3-thienyl; 1H-pyrazol-4-yl, 1H-pyrazol-5-yl, 1H-indazol-6-yl, 3-methyl-1H-indazol-5-yl, 1H-1,2,3-benzotriazol-5-yl, 2-oxo-2,3-dihydro-1H-benzimidazol-5-yl, 2-oxo-2,3-dihydro-1H-indol-5-yl, 2-oxo-2,3-dihydro-1H-indol-6-yl, 2,1,3-benzoxadiazol-5-yl, 2-amino-6-quinazolinyl, 2,4-dioxo-1,2,3,4-tetrahydro-5-pyrimidinyl, 2-amino-5-pyrimidinyl, 7-oxo-1,5,6,7-tetrahydro-1,8-naphthyridin-3-yl, phenyl, 2-methylphenyl, 2-nitrophenyl, 2-phenylethyl, 3-aminophenyl, 4-aminophenyl, 4-chlorophenyl, 4-fluorophenyl, 4-(methyloxy)phenyl, 3-(acetylamino)phenyl, 4-(acetylamino) phenyl, 4-(aminocarbonyl)phenyl, 4-(1H-pyrazol-4-yl) phenyl, 4-(aminosulfonyl)phenyl, 4-(methylsulfonyl)phenyl, 4-[(dimethylamino)sulfonyl]phenyl, 4-[(methylamino)carbonyl]phenyl, 4-[(methylamino)sulfonyl]phenyl, 4-[(methylsulfonyl)amino]phenyl, 3-pyridinyl, 4-pyridinyl, 2-(4-morpholinyl)-4-pyridinyl, 2-amino-4-pyridinyl, 5-(methyloxy)-3-pyridinyl, 5-(methylsulfonyl)-3-pyridinyl, 5-[(cyclopropylsulfonyl)amino]-6-(methyloxy)-3-pyridinyl, 5-[(phenylsulfonyl)amino]-3-pyridinyl, 6-(4-methyl-1-piperazinyl)-3-pyridinyl, 6-(4-morpholinyl)-3-pyridinyl, 6-(acetylamino)-3-pyridinyl, 6-(dimethylamino)-3-pyridinyl, 6-(methyloxy)-3-pyridinyl, 6-[(methylamino)carbonyl]-3-pyridinyl, 6-Rmethylamino)sulfonyl]-3-pyridinyl, 6-methyl-3-pyridinyl, or 4-pyridinyloxy. (See, e.g., WO 2011/140325; WO 2011/140324; and WO 2012/005805, each of which is incorporated by reference in its entirety.)

The compounds suitable for use in the method of this invention also include compounds of Formula (II):

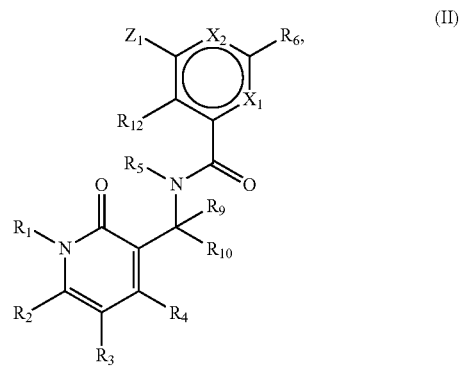

(II)

wherein $X_1$ is N or CR$_{11}$;

$X_2$ is N or CR$_{13}$;

$Z_1$ is NR$_7$R$_8$, OR$_S$, SR$_S$, or CR$_7$R$_8$R$_{14}$;

each of R$_1$, R$_5$, R$_9$, and R$_{10}$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

each of R$_2$, R$_3$, and R$_4$, independently, is -Q$_1$-T$_1$, in which Q$_1$ is a bond or $C_1$-$C_3$ alkyl linker optionally substituted with halo, cyano, hydroxyl or $C_1$-$C_6$ alkoxy, and T$_1$ is H, halo, hydroxyl, COOH, cyano, or R$_{S1}$, in which R$_S$, is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, amino, mono-$C_1$-$C_6$ alkylamino, di-$C_1$-$C_6$ alkylamino, 4 to 12-membered heterocycloalkyl, or 5- or 6-membered heteroaryl, and R$_{S1}$ is optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

R$_6$ is $C_6$-$C_{10}$ aryl or 5- or 6-membered heteroaryl, each of which is optionally substituted with one or more -Q$_2$-T$_2$, wherein Q$_2$ is a bond or $C_1$-$C_3$ alkyl linker optionally substituted with halo, cyano, hydroxyl or $C_1$-$C_6$ alkoxy, and T$_2$ is H, halo, cyano, —OR$_a$, —NR$_a$R$_b$, —(NR$_a$R$_b$R$_c$)$^+$A$^-$, —C(O)R$_a$, —C(O)OR$_a$, —C(O)NR$_a$R$_b$, —NR$_b$C(O)R$_a$, —NR$_b$C(O)OR$_a$, —S(O)$_2$R$_a$, —S(O)$_2$NR$_a$R$_b$, or R$_{S2}$, in which each of R$_a$, R$_b$, and R$_c$, independently is H or R$_{S3}$, A$^-$ is a pharmaceutically acceptable anion, each of R$_{S2}$ and R$_{S3}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or R$_a$ and R$_b$, together with the N atom to which they are attached, form a 4 to 12-membered heterocycloalkyl ring having 0 or 1 additional heteroatom, and each of R$_{S2}$, R$_{S3}$, and the 4 to 12-membered heterocycloalkyl ring formed by R$_a$ and R$_b$, is optionally substituted with one or more -Q$_3$-T$_3$, wherein Q$_3$ is a bond or $C_1$-$C_3$ alkyl linker each optionally substituted with halo, cyano, hydroxyl or $C_1$-$C_6$ alkoxy, and T$_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, OR$_d$, COOR$_d$, —S(O)$_2$R$_d$, —NR$_d$R$_e$, and —C(O)NR$_d$R$_e$, each of R$_d$ and R$_e$ independently being H or $C_1$-$C_6$ alkyl, or -Q$_3$-T$_3$ is oxo; or any two neighboring -Q$_2$-T$_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl; provided that -$Q_2$-$T_2$ is not H;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, —$OR_f$, —$C(O)R_f$, —$C(O)OR_f$, —$C(O)NR_fR_g$, —$C(O)NR_fOR_g$, —$NR_fC(O)R_g$, —$S(O)_2R_f$, or $R_{S4}$, in which each of $R_f$ and $R_g$, independently is H or $R_{S5}$, each of $R_{S4}$ and $R_{S5}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and each of $R_{S4}$ and $R_{S5}$ is optionally substituted with one or more -$Q_5$-$T_5$, wherein Q is a bond, C(O), $C(O)NR_k$, $NR_kC(O)$, $S(O)_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo; provided that $R_7$ is not H;

each of $R_8$, $R_{11}$, $R_{12}$, and $R_{13}$, independently, is H, halo, hydroxyl, COOH, cyano, $R_{S6}$, $OR_{S6}$, or $COOR_{S6}$, in which $R_{S6}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 11-membered heterocycloalkyl ring having 0 to 2 additional heteroatoms, or $R_7$ and $R_8$, together with the C atom to which they are attached, form $C_3$-$C_8$ cycloalkyl or a 4 to 11-membered heterocycloalkyl ring having 1 to 3 heteroatoms, and each of the 4 to 11-membered heterocycloalkyl rings or $C_3$-$C_8$ cycloalkyl formed by $R_7$ and $R_5$ is optionally substituted with one or more -$Q_6$-$T_6$, wherein Q6 is a bond, C(O), $C(O)NR_m$, $NR_mC(O)$, $S(O)_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo; and $R_{14}$ is absent, H, or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

One subset of the compounds of Formula (II) includes those of Formula (IIa):

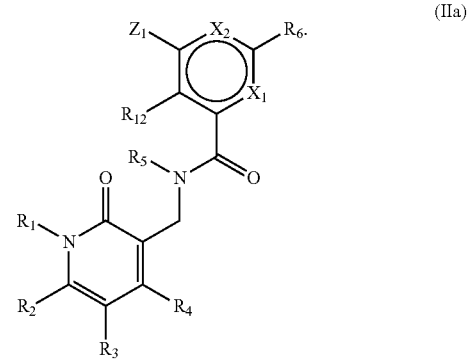

(IIa)

Another subset of the compounds of Formula (II) includes those of Formula (IIb), (IIc), or (IId):

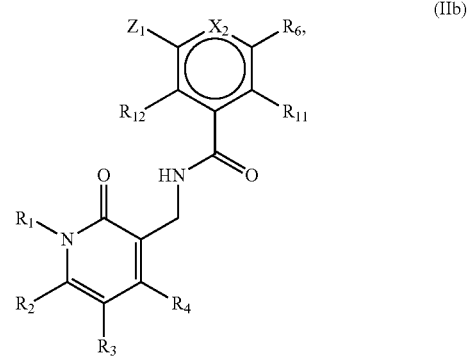

(IIb)

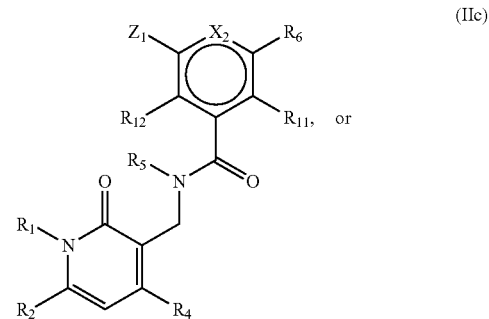

(IIc)

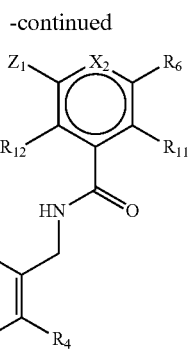
(IId)

The compounds of Formulae (II), (IIa), (IIc), and (IId) can include one or more of the following features:

For example, $X_1$ is $CR_{11}$ and $X_2$ is $CR_{13}$.
For example, $X_1$ is $CR_{11}$ and $X_2$ is N.
For example, $X_1$ is N and $X_2$ is $CR_{13}$.
For example, $X_1$ is N and $X_2$ is N.
For example, $Z_1$ is $NR_7R_8$.
For example, $Z_1$ is $CR_7R_8R_{14}$.
For example, $Z_1$ is $OR_7$.
For example, $Z_1$ is $SR_7$.
For example, $R_6$ is phenyl substituted with one or more $-Q_2-T_2$.
For example, $R_6$ is 5 to 6-membered heteroaryl containing 1-3 additional heteroatoms selected from N, O, and S and optionally substituted with one or more $-Q_2-T_2$.
For example, $R_6$ is pyridinyl, pyrazolyl, pyrimidinyl, quinolinyl, tetrazolyl, oxazolyl, isoxazolyl, thiazolyl, isothiazolyl, furyl, or thienyl, each of which is optionally substituted with one or more $-Q_2-T_2$.
For example, $Q_2$ is a bond.
For example, Q2 is an unsubstituted $C_1-C_3$ alkyl linker.
For example, $T_2$ is $C_1-C_6$ alkyl or $C_6-C_{10}$ aryl, each optionally substituted with one or more $-Q_3-T_3$.
For example, $T_2$ is an unsubstituted substituted straight chain $C_1-C_6$ or branched $C_3-C_6$ alkyl, including but not limited to, methyl, ethyl, n-propyl, i-propyl, n-butyl, s-butyl, t-butyl, n-pentyl, s-pentyl and n-hexyl.
For example, $T_2$ is phenyl.
For example, $T_2$ is halo (e.g., fluorine, chlorine, bromine, and iodine).
For example, $T_2$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, morpholinyl, 1,4-diazepanyl, 1,4-oxazepanyl, 2-oxa-5-azabicyclo[2.2.1]heptanyl, 2,5-diazabicyclo[2.2.1]heptanyl, and the like) optionally substituted with one or more $-Q_3-T_3$.
For example, $T_2$ is $-OR_a$, $-NR_aR_b$, $-(NR_aR_bR_c)^+A^-$, $-C(O)R_a$, $-C(O)OR_a$, $-C(O)NR_aR_b$, $-NR_aC(O)R_a$, $-NR_bC(O)OR_a$, $-S(O)_2R_a$, or $-S(O)_2NR_aR_b$.
For example, $T_2$ is $-NR_aR_b$ or $-C(O)NR_aR_b$, in which each of $R_a$ and $R_b$, independently is H or $C_1-C_6$ alkyl, or $R_a$ and $R_b$, together with the N atom to which they are attached, form a 4 to 7-membered heterocycloalkyl ring having 0 or 1 additional heteroatom, the $C_1-C_6$ alkyl and the 4 to 7-membered heterocycloalkyl ring being optionally substituted with one or more $-Q_3-T_3$.
For example, $Q_2$ is $C_1-C_3$ alkyl linker optionally substituted with halo or hydroxyl.

For example, $Q_2$ is a bond or methyl linker and $T_2$ is H, halo, $-OR_a$, $-NR_aR_b$, $-(NR_aR_bR_c)^+A^-$, or $-S(O)_2NR_aR_b$.
For example, each of $R_a$, $R_b$, and $R_c$, independently is H or $C_1-C_6$ alkyl optionally substituted with one or more $-Q_3-T_3$.
For example, one of $R_a$, $R_b$, and $R_c$ is H.
For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, morpholinyl, 1,4-diazepanyl, 1,4-oxazepanyl, 2-oxa-5-azabicyclo[2.2.1]heptanyl, 2,5-diazabicyclo[2.2.1]heptanyl, and the like) and the ring is optionally substituted with one or more $-Q_3-T_3$.
For example, $-Q_3-T_3$ is oxo.
For example, $T_2$ is 4 to 7-membered heterocycloalkyl or $C_3-C_8$ cycloalkyl and one or more $-Q_3-T_3$ are oxo.
For example, $Q_3$ is a bond or unsubstituted or substituted $C_1-C_3$ alkyl linker.
For example, $T_3$ is H, halo, 4 to 7-membered heterocycloalkyl, $C_1-C_3$ alkyl, $OR_d$, $COOR_d$, $-S(O)_2R_d$, or $-NR_dR_e$.
For example, one of $R_d$ and $R_e$ is H.
For example, $R_7$ is $-C(O)R_f$.
For example, $R_7$ is $-C(O)R_f$, in which $R_f$ is $C_3-C_8$ cycloalkyl.
For example, $R_7$ is $C_6-C_{10}$ aryl substituted with one or more $-Q_5-T_5$.
For example, $R_7$ is phenyl optionally substituted with one or more $-Q_5-T_5$.
For example, $R_7$ is $C_1-C_6$ alkyl optionally substituted with one or more $-Q_5-T_5$.
For example, $R_7$ is $C_3-C_8$ cycloalkyl optionally substituted with one or more $-Q_5-T_5$.
For example, $R_7$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, and morpholinyl, and the like) optionally substituted with one or more $-Q_5-T_5$.
For example, $R_7$ is 5 to 6-membered heterocycloalkyl optionally substituted with one or more $-Q_5-T_5$.
For example, $R_7$ is isopropyl.
For example, $R_7$ is pyrrolidinyl, piperidinyl, tetrahydropyran, tetrahydro-2H-thiopyranyl, cyclopentyl, or cyclohexyl, cycloheptyl, each optionally substituted with one or more $-Q_5-T_5$.
For example, $R_7$ is cyclopentyl cyclohexyl or tetrahydro-2H-thiopyranyl, each optionally substituted with one or more $-Q_5-T_5$.
For example, one or more $-Q_5-T_5$ are oxo.
For example, $R_7$ is 1-oxide-tetrahydro-2H-thiopyranyl or 1,1-dioxide-tetrahydro-2H-thiopyranyl.
For example, Q is a bond and $T_5$ is amino, mono-$C_1-C_6$ alkylamino, di-$C_1-C_6$ alkylamino.
For example, Q5 is NHC(O) and $T_5$ is $C_1-C_6$ alkyl or $C_1-C_6$ alkoxy.
For example, $T_4$ is 4 to 7-membered heterocycloalkyl or $C_3-C_8$ cycloalkyl and one or more $-Q_5-T_5$ are oxo.
For example, $T_5$ is H, halo, $C_1-C_6$ alkyl, $C_1-C_6$ alkoxyl, $C_3-C_8$ cycloalkyl, $C_6-C_{10}$ aryl, or 4 to 7-membered heterocycloalkyl.
For example, Q is a bond and $T_5$ is $C_1-C_6$ alkyl, $C_3-C_8$ cycloalkyl, or 4 to 7-membered heterocycloalkyl.

For example, $Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 7-membered heterocycloalkyl.

For example, $T_5$ is $C_1$-$C_6$ alkyl or $C_1$-$C_6$ alkoxyl, each optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.

For example, Q5 is $C_1$-$C_3$ alkyl linker and $T_5$ is H or $C_6$-$C_{10}$ aryl.

For example, Q is $C_1$-$C_3$ alkyl linker and $T_5$ is $C_3$-$C_8$ cycloalkyl, 4 to 7-membered heterocycloalkyl, or $S(O)_qR_q$.

For example, $R_{11}$ is H.

For example, each of $R_2$ and $R_4$, independently, is H or $C_1$-$C_6$ alkyl optionally substituted with amino, mono-$C_1$-$C_6$ alkylamino, di-$C_1$-$C_6$ alkylamino, or $C_6$-$C_{10}$ aryl.

For example, each of $R_2$ and $R_4$, independently is $C_1$-$C_3$ alkyl optionally substituted with $C_1$-$C_6$ alkoxyl.

For example, each of $R_2$ and $R_4$ is methyl.

For example, $R_1$ is H.

For example, $R_{12}$ is H, methyl, ethyl, ethenyl, or halo.

For example, $R_{12}$ is methyl.

For example, $R_{12}$ is ethyl.

For example, $R_{12}$ is ethenyl.

For example, $R_8$ is H, methyl, ethyl, or ethenyl.

For example, $R_8$ is methyl.

For example, $R_8$ is ethyl.

For example, $R_8$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, morpholinyl, 1,4-diazepanyl, 1,4-oxazepanyl, 2-oxa-5-azabicyclo[2.2.1]heptanyl, 2,5-diazabicyclo[2.2.1]heptanyl, and the like).

For example, $R_8$ is tetrahydropyran.

For example, $R_8$ is tetrahydropyran and $R_7$ is -$Q_4$-$T_4$, in which Q4 is a bond or $C_1$-$C_4$ alkyl linker and $T_4$ is H, $C_1$-$C_6$ alkyl, $C_3$-$C_8$ cycloalkyl or 4 to 7-membered heterocycloalkyl.

For example, $Z_1$ is $NR_7R_8$ or $CR_7R_8R_{14}$ wherein $R_7$ and $R_8$, together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, and morpholinyl, and the like) or $C_3$-$C_8$ cycloalkyl, each optionally substituted with one or more -$Q_6$-$T_6$.

For example, the ring formed by $R_7$ and $R_8$ is selected from the group consisting of azetidinyl, pyrrolidinyl, piperidinyl, morpholinyl, piperazinyl, and cyclohexenyl, each optionally substituted with one -$Q_6$-$T_6$.

For example, -$Q_6$-$T_6$ is oxo.

For example, $T_6$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.

For example, Q6 is a bond and $T_6$ is $C_1$-$C_6$ alkyl, $C_3$-$C_8$ cycloalkyl, or 4 to 7-membered heterocycloalkyl.

For example, $Q_6$ is CO, $S(O)_2$, or NHC(O); and $T_6$ is $C_1$-$C_6$ alkyl, $C_1$-$C_6$ alkoxyl, $C_3$-$C_8$ cycloalkyl, or 4 to 7-membered heterocycloalkyl.

For example, $T_6$ is $C_1$-$C_6$ alkyl or $C_1$-$C_6$ alkoxyl, each optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.

For example, $Q_6$ is $C_1$-$C_3$ alkyl linker and $T_6$ is H or $C_6$-$C_{10}$ aryl.

For example, $Q_6$ is $C_1$-$C_3$ alkyl linker and $T_6$ is $C_3$-$C_8$ cycloalkyl, 4 to 7-membered heterocycloalkyl, or $S(O)_pR_p$.

For example, each of $R_p$ and $R_q$, independently, is $C_1$-$C_6$ alkyl.

For example, $R_{13}$ is H or methyl.

For example, $R_{13}$ is H.

For example, $R_3$ is H.

For example, $A^-$ is $Br^-$.

For example, each of $R_5$, $R_9$, and $R_{10}$ is H.

Another subset of the compounds of Formula (II) includes those of Formula (IIe):

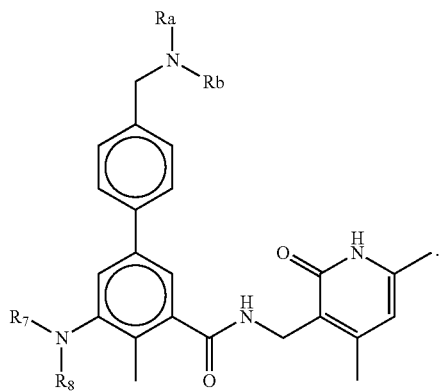

(IIe)

The compounds of Formula (IIe) can include one or more of the following features:

For example, each of $R_a$ and $R_b$, independently is H or $C_1$-$C_6$ alkyl optionally substituted with one or more -$Q_3$-$T_3$.

For example, one of $R_a$ and $R_b$ is H.

For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, morpholinyl, 1,4-diazepanyl, 1,4-oxazepanyl, 2-oxa-5-azabicyclo[2.2.1]heptanyl, 2,5-diazabicyclo[2.2.1]heptanyl, and the like) and the ring is optionally substituted with one or more -$Q_3$-$T_3$.

For example, $R_a$ and $R_b$, together with the N atom to which they are attached, form azetidinyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, or morpholinyl, and the ring is optionally substituted with one or more -$Q_3$-$T_3$.

For example, one or more -$Q_3$-$T_3$ are oxo.

For example, $Q_3$ is a bond or unsubstituted or substituted $C_1$-$C_3$ alkyl linker.

For example, $T_3$ is H, halo, 4 to 7-membered heterocycloalkyl, $C_1$-$C_3$ alkyl, $OR_d$, $COOR_d$, $-S(O)_2R_d$, or $-NR_dR_c$.

For example, one of $R_d$ and $R_e$ is H.

For example, $R_7$ is $C_3$-$C_8$ cycloalkyl or 4 to 7-membered heterocycloalkyl, each optionally substituted with one or more -$Q_5$-$T_5$.

For example, $R_7$ is piperidinyl, tetrahydropyran, tetrahydro-2H-thiopyranyl, cyclopentyl, cyclohexyl, pyrrolidinyl, or cycloheptyl, each optionally substituted with one or more -$Q_5$-$T_5$.

For example, $R_7$ is cyclopentyl cyclohexyl or tetrahydro-2H-thiopyranyl, each optionally substituted with one or more -$Q_5$-$T_5$.

For example, $Q_5$ is NHC(O) and $T_5$ is $C_1$-$C_6$ alkyl or $C_1$-$C_6$ alkoxy.

For example, one or more -$Q_5$-$T_5$ are oxo.

For example, $R_7$ is 1-oxide-tetrahydro-2H-thiopyranyl or 1,1-dioxide-tetrahydro-2H-thiopyranyl.

For example, $Q_5$ is a bond and $T_5$ is amino, mono-$C_1$-$C_6$ alkylamino, di-$C_1$-$C_6$ alkylamino.

For example, $Q_5$ is CO, S(O)$_2$, or NHC(O); and $T_5$ is $C_1$-$C_6$ alkyl, $C_1$-$C_6$ alkoxyl, $C_3$-$C_8$ cycloalkyl, or 4 to 7-membered heterocycloalkyl.

For example, $R_8$ is H, methyl, or ethyl.

The compounds suitable for use in the method of this invention also include compounds of Formula (III):

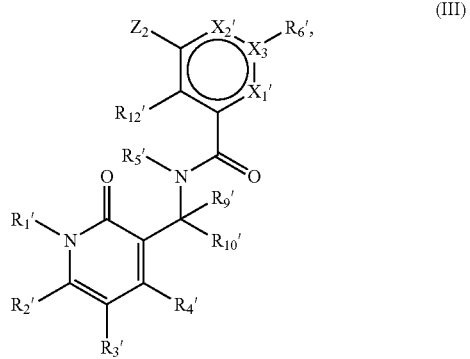

(III)

or a pharmaceutically acceptable salt or ester thereof. In Formula (III):

$X_1'$ is N or $CR_{11}'$;

$X_2'$ is N or $CR_{13}'$;

$X_3$ is N or C, and when $X_3$ is N, $R_6'$ is absent;

$Z_2$ is $NR_7'R_8'$, $OR_S'$, $S(O)_{a'}R_7'$, or $CR_7'R_8'R_{14}'$, in which a' is 0, 1, or 2;

each of $R_1'$, $R_5'$, $R_9'$, and $R_{10}'$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

each of $R_2'$, $R_3'$, and $R_4'$, independently, is -$Q_1'$-$T_1'$, in which Q1' is a bond or $C_1$-$C_3$ alkyl linker optionally substituted with halo, cyano, hydroxyl or $C_1$-$C_6$ alkoxy, and $T_1'$ is H, halo, hydroxyl, COOH, cyano, azido, or $R_{S1}'$, in which $R_{S1}'$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, amino, mono-$C_1$-$C_6$ alkylamino, di-$C_1$-$C_6$ alkylamino, 4 to 12-membered heterocycloalkyl, or 5- or 6-membered heteroaryl, and $R_{S1}'$ is optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_6'$ is H, halo, cyano, azido, $OR_a'$, —C(O)$R_a'$, —C(O)$OR_a'$, —C(O)NR$_a'$R$_b'$, —NR$_b'$C(O)R$_a'$, —S(O)$_b$R$_a'$, —S(O)$_b$NR$_a'$R$_b'$, or $R_{S2}'$, in which $R_{S2}'$ is $C_1$-$C_6$ alkyl, $C_2$-$C_6$ alkenyl, $C_2$-$C_6$ alkynyl, $C_3$-$C_8$ cycloalkyl, or 4 to 12-membered heterocycloalkyl, b' is 0, 1, or 2, each of $R_a'$ and $R_b'$, independently is H or $R_{S3}'$, and $R_{S3}'$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; or $R_a'$ and $R_b'$, together with the N atom to which they are attached, form a 4 to 12-membered heterocycloalkyl ring having 0 or 1 additional heteroatom; and each of $R_{S2}'$, $R_{S3}'$, and the 4 to 12-membered heterocycloalkyl ring formed by $R_a'$ and $R_b'$, is optionally substituted with one or more -$Q_2'$-$T_2'$, wherein $Q_2'$ is a bond or $C_1$-$C_3$ alkyl linker each optionally substituted with halo, cyano, hydroxyl or $C_1$-$C_6$ alkoxy, and $T_2'$ is H, halo, cyano, —OR$_c'$, —NR$_c'$R$_d'$, —C(O)R$_c'$, —C(O)OR$_c'$, —C(O)NR$_c'$R$_d'$, —NR$_d'$C(O)R$_c'$, —NR$_d'$C(O)OR$_c'$, —S(O)$_2$R$_c'$, —S(O)$_2$NR$_c'$R$_d'$, or $R_{S4}'$, in which each of $R_c'$ and $R_d'$, independently is H or $R_{S5}'$, each of $R_{S4}'$ and $R_{S5}'$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_c'$ and $R_d'$, together with the N atom to which they are attached, form a 4 to 12-membered heterocycloalkyl ring having 0 or 1 additional heteroatom, and each of $R_{S4}'$, $R_{S5}'$, and the 4 to 12-membered heterocycloalkyl ring formed by $R_c'$ and $R_d'$, is optionally substituted with one or more -$Q_3'$-$T_3'$, wherein Q3' is a bond or $C_1$-$C_3$ alkyl linker each optionally substituted with halo, cyano, hydroxyl or $C_1$-$C_6$ alkoxy, and $T_3'$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, OR$_e'$, COOR$_e'$, —S(O)$_2$R$_e'$, —NR$_e'$R$_f'$, and —C(O)NR$_e'$R$_f'$, each of $R_e'$ and $R_f'$ independently being H or $C_1$-$C_6$ alkyl, or -$Q_3'$-$T_3'$ is oxo; or -$Q_2'$-$T_2'$ is oxo; provided that -$Q_2'$-$T_2'$ is not H;

$R_7'$ is -$Q_4'$-$T_4'$, in which $Q_4'$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4'$ is H, halo, cyano, NR$_g'$R$_h'$, —OR$_g'$, —C(O)R$_g'$, —C(O)OR$_g'$, —C(O)NR$_g'$R$_h'$, —C(O)NR$_g'$OR$_h'$, —NR$_g'$C(O)R$_h'$, —S(O)$_2$R$_g'$, or $R_{S6}'$, in which each of $R_g'$ and $R_h'$, independently is H or $R_{S7}'$, each of $R_{S6}'$ and $R_{S7}'$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and each of $R_{S6}'$ and $R_{S7}'$ is optionally substituted with one or more -$Q_5'$-$T_5'$, wherein Q' is a bond, C(O), C(O)NR$_k'$, NR$_k'$C(O), S(O)$_2$, or $C_1$-$C_3$ alkyl linker, $R_k'$ being H or $C_1$-$C_6$ alkyl, and $T_5'$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or S(O)$_{q'}$R$_q'$ in which q' is 0, 1, or 2 and $R_q'$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5'$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5'$-$T_5'$ is oxo; provided that $R_7'$ is not H;

each of $R_8'$, $R_{11}'$, $R_{12}'$, and $R_{13}'$, independently, is H, halo, hydroxyl, COOH, cyano, $R_{S8}'$, $OR_{S8}'$, or COOR$_{S8}'$, in which $R_{S8}'$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S8}'$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7'$ and $R_8'$, together with the N atom to which they are attached, form a 4 to 12-membered heterocycloalkyl ring having 0 to 2 additional heteroatoms, or $R_7'$ and $R_8'$, together with the C atom to which they are attached, form $C_3$-$C_8$ cycloalkyl or a 4 to 12-membered heterocycloalkyl ring having 1 to 3 heteroatoms, and each of the 4 to 12-membered heterocycloalkyl rings or $C_3$-$C_8$ cycloalkyl formed by $R_7'$ and $R_8'$ is optionally substituted with one or more -$Q_6'$-$T_6'$, wherein Q6' is a bond, C(O), C(O)$NR_m'$, $NR_m'$C(O), S(O)$_2$, or $C_1$-$C_3$ alkyl linker, $R_m'$ being H or $C_1$-$C_6$ alkyl, and $T_6'$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or S(O)$_{p'}R_{p'}'$ in which p' is 0, 1, or 2 and $R_{p'}'$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6'$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6'$ is H, halo, hydroxyl, or cyano; or -$Q_6'$-$T_6'$ is oxo; and $R_{14}'$ is absent, H, or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

One subset of the compounds of Formula (III) includes those of Formula (Ma):

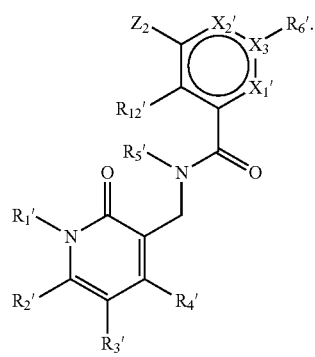
(IIIa)

Another subset of the compounds of Formula (III) includes those of Formula (IIIb), (IIIc), or (IIId):

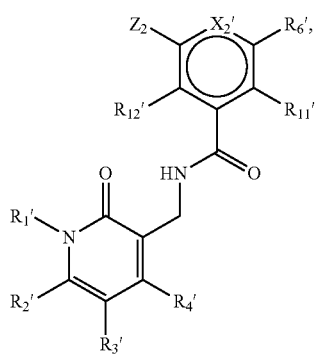
(IIIb)

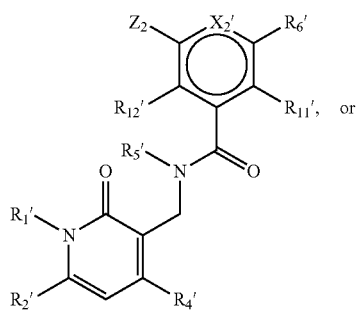
(IIIc)

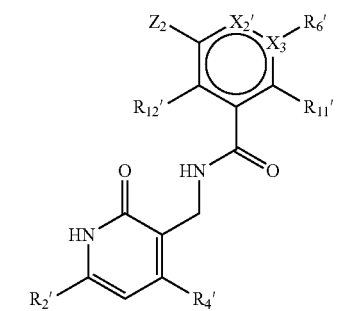
(IIId)

The compounds of Formulae (III), (IIIa), (IIIb), (IIIc), and (IIId) can include one or more of the following features:

For example, the compounds of Formula (III) are not
N-(5-(((4,6-dimethyl-2-oxo-1,2-dihydropyridin-3-yl)methyl)carbamoyl)-2-methylphenyl)furan-2-carboxamide,
N,N'-(5-(((4,6-dimethyl-2-oxo-1,2-dihydropyridin-3-yl)methyl)carbamoyl)-1,3-phenylene)diacetamide,
N-((4,6-dimethyl-2-oxo-1,2-dihydropyridin-3-yl)methyl)-3-pivalamidobenzamide,
3-(3,4-dihydro-2H-benzo[b][1,4]dioxepine-7-sulfonamido)-N-((4,6-dimethyl-2-oxo-1,2-dihydropyridin-3-yl)methyl)benzamide,
N-((4,6-dimethyl-2-oxo-1,2-dihydropyridin-3-yl)methyl)-3,5-dimethoxybenzamide,
N-((4,6-dimethyl-2-oxo-1,2-dihydropyridin-3-yl)methyl)-3,4,5-trimethoxybenzamide,
3-allyl-N-((4,6-dimethyl-2-oxo-1,2-dihydropyridin-3-yl)methyl)-4,5-dimethoxybenzamide,
4-(2-amino-2-oxoethoxy)-3-chloro-N-((4,6-dimethyl-2-oxo-1,2-dihydropyridin-3-yl)methyl)-5-methoxybenzamide,
3-chloro-N-((4,6-dimethyl-2-oxo-1,2-dihydropyridin-3-yl)methyl)-4-hydroxy-5-methoxybenzamide, or
3-bromo-N-((4,6-dimethyl-2-oxo-1,2-dihydropyridin-3-yl)methyl)-5-methoxy-4-propoxybenzamide.

For example, $X_1'$ is $CR_{11}'$ and $X_2'$ is $CR_{13}'$.
For example, $X_1'$ is $CR_{11}'$ and $X_2'$ is N.
For example, $X_1'$ is N and $X_2'$ is $CR_{13}'$.
For example, $X_1'$ is N and $X_2'$ is N.
For example, $X_3$ is C.
For example, $X_3$ is N and $R_6'$ is absent.
For example, $Z_2$ is $NR_7'R_8'$.
For example, $Z_2$ is $CR_7'R_8'R_{14}'$.
For example, $Z_2$ is $OR_7'$.
For example, $Z_2$ is S(O)$_{a'}R_7'$, in which a' is 0, 1, or 2.
For example, $R_6'$ is H.
For example, $R_6'$ is halo (e.g., fluorine, chlorine, bromine, and iodine).
For example, $R_6'$ is $C_1$-$C_3$ alkyl optionally substituted with one or more -$Q_2'$-$T_2'$.

For example, $R_6'$ is $CF_3$.

For example, $R_6'$ is $C_2$-$C_6$ alkenyl, $C_2$-$C_6$ alkynyl, or $C_3$-$C_6$ cycloalkyl each optionally substituted with one or more -$Q_2'$-$T_2'$.

For example, $R_6'$ is ethenyl.

For example, $R_6'$ is ethynyl.

For example, $R_6'$ is ethynyl substituted with one or more -$Q_2'$-$T_2'$, in which $Q_2'$ is a bond or $C_1$-$C_3$ alkyl linker and $T_2'$ is $C_1$-$C_6$ alkyl, $C_3$-$C_6$ cycloalkyl, or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) optionally substituted with one or more -$Q_3'$-$T_3'$.

For example, $R_6'$ is cyano.

For example, $R_6'$ is azido.

For example, $R_6'$ is C(O)H.

For example, $R_6'$ is $OR_a'$ or —C(O)$R_a'$.

For example, $R_a'$ is $C_3$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like), which is optionally substituted with one or more -$Q_2'$-$T_2'$.

For example, $R_6'$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) optionally substituted with one or more -$Q_2'$-$T_2'$.

For example, $R_6'$ is piperidinyl, 2,2,6,6-tetramethyl-piperidinyl, 1,2,3,6-tetrahydropyridinyl, 2,2,6,6-tetramethyl-1,2,3,6-tetrahydropyridinyl, piperazinyl, morpholinyl, tetrahydro-2H-pyranyl, 3,6-dihydro-2H-pyranyl, or pyrrolidinyl, each of which is optionally substituted with one or more -$Q_2'$-$T_2'$.

For example, $R_6'$ is 4 to 7-membered heterocycloalkyl optionally substituted with one or more -$Q_2'$-$T_2'$, and -$Q_2'$-$T_2'$ is oxo or Q2' is a bond and $T_2'$ is —$OR_c'$, —$NR_c'R_d'$, —C(O) $R_c'$, —C(O)$OR_c'$, —S(O)$_2R_c'$, $C_1$-$C_6$ alkyl, or 4 to 7-membered heterocycloalkyl, each of which is optionally substituted with one or more -$Q_3'$-$T_3'$ when $R_c'$ or $R_d'$ is not H.

For example, $R_6'$ is —C(O)$R_a'$, —C(O)$OR_a'$, —C(O) $NR_a'R_b'$, —$NR_b'$C(O)$R_a'$, —$SR_a'$, —S(O)$_2R_a'$, or —S(O)$_2NR_a'R_b'$.

For example, each of $R_a'$ and $R_b'$, independently is H, $C_1$-$C_6$ alkyl, or $C_3$-$C_8$ cycloalkyl optionally substituted with one or more -$Q_2'$-$T_2'$.

For example, one of $R_a'$ and $R_b'$ is H.

For example, $R_a'$ and $R_b'$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) and the ring is optionally substituted with one or more -$Q_2'$-$T_2'$.

For example, -$Q_2'$-$T_2'$ is oxo.

For example, Q2' is a bond.

For example, Q2' is an unsubstituted $C_1$-$C_3$ alkyl linker.

For example, $T_2'$ is $C_1$-$C_6$ alkyl or $C_6$-$C_{10}$ aryl, each optionally substituted with one or more -$Q_3'$-$T_3'$.

For example, $T_2'$ is an unsubstituted substituted straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, $T_2'$ is phenyl.

For example, $T_2'$ is halo (e.g., fluorine, chlorine, bromine, and iodine).

For example, $T_2'$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) optionally substituted with one or more -$Q_3'$-$T_3'$.

For example, $T_2'$ is —$OR_c'$, —C(O)$R_c'$, —C(O)$OR_c'$, or —S(O)$_2R_c'$.

For example, is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like), which is optionally substituted with one or more -$Q_3'$-$T_3'$.

For example, each of $R_c'$ and $R_d'$, independently is H or $C_1$-$C_6$ alkyl optionally substituted with one or more -$Q_3'$-$T_3'$.

For example, $R_c'$ is H.

For example, $R_d'$ is H.

For example, $R_c'$ and $R_d'$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3, 6-tetrahydropyridinyl, piperazinyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) and the ring is optionally substituted with one or more -$Q_3'$-$T_3'$.

For example, $Q_2'$ is a bond and $T_2'$ is —$OR_c'$, —$NR_c'R_d'$, —C(O)$R_c'$, —C(O)$OR_c'$, —S(O)$_2R_c'$, $C_1$-$C_6$ alkyl, or 4 to 7-membered heterocycloalkyl, each of which is optionally substituted with one or more -$Q_3'$-$T_3'$ when $R_c'$ or $R_d'$ is not H.

For example, -$Q_3'$-$T_3'$ is oxo.

For example, $T_2'$ is 4 to 7-membered heterocycloalkyl or $C_3$-$C_8$ cycloalkyl and one or more -$Q_3'$-$T_3'$ are oxo.

For example, Q3' is a bond or unsubstituted or substituted $C_1$-$C_3$ alkyl linker.

For example, $T_3'$ is H, halo, 4 to 7-membered heterocycloalkyl, $C_1$-$C_3$ alkyl, $OR_e'$, $COOR_e'$, —S(O)$_2R_e'$, —$NR_e'R_f'$, or —C(O)$NR_e'R_f'$.

For example, one of $R_d'$ and $R_e'$ is H.

For example, $Q_3'$ is a bond or $C_1$-$C_3$ alkyl linker and $T_3'$ is selected from the group consisting of $C_1$-$C_3$ alkyl, halo, $OR_e'$, —S(O)$_2R_e'$, —$NR_e'R_f'$, and —C(O)$NR_e'R_f'$.

For example, $Q_3'$ is a bond or $C_1$-$C_3$ alkyl linker and $T_3'$ is selected from the group consisting of $C_1$-$C_3$ alkyl, $OR_e'$, —S(O)$_2R_e'$, or —$NR_e'R_f'$.

For example, $R_e'$ is H.

For example, $R_f'$ is H.

For example, $R_7'$ is —C(O)$R_g'$.

For example, $R_7'$ is —C(O)$R_g'$, in which $R_g'$ is $C_3$-$C_8$ cycloalkyl, 4 to 7-membered heterocycloalkyl, $C_3$-$C_8$ cycloalkyl.

For example, $R_7'$ is $C_6$-$C_{10}$ aryl substituted with one or more -$Q_5'$-$T_5'$.

For example, $R_7'$ is phenyl optionally substituted with one or more -$Q_5'$-$T_5'$.

For example, $R_7'$ is $C_1$-$C_6$ alkyl optionally substituted with one or more -$Q_5'$-$T_5'$.

For example, $R_7'$ is $C_3$-$C_8$ cycloalkyl optionally substituted with one or more -$Q_5'$-$T_5'$.

For example, $R_7'$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) optionally substituted with one or more -$Q_5'$-$T_5'$.

For example, $R_7'$ is 5 to 6-membered heterocycloalkyl optionally substituted with one or more -$Q_5'$-$T_5'$.

For example, $R_7'$ is isopropyl.

For example, $R_7'$ is pyrrolidinyl, piperidinyl, tetrahydropyran, cyclopentyl, or cyclohexyl, cycloheptyl, each optionally substituted with one -$Q_5'$-$T_5'$.

For example, $R_7'$ is cyclopentyl or cyclohexyl, each optionally substituted with one -$Q'$-$T_5'$.

For example, $Q_5'$ is NHC(O) and $T_5'$ is $C_1$-$C_6$ alkyl or $C_1$-$C_6$ alkoxy.

For example, -$Q_5'$-$T_5'$ is oxo.

For example, $T_4'$ is 4 to 7-membered heterocycloalkyl, $C_3$-$C_8$ cycloalkyl, or $C_6$-$C_{10}$ aryl, and one or more -$Q_5'$-$T_5'$ are oxo.

For example, $R_7'$ is 1-oxide-tetrahydro-2H-thiopyranyl or 1,1-dioxide-tetrahydro-2H-thiopyranyl.

For example, $R_7'$ is cyclohexanonyl, e.g., cyclohexanon-4-yl.

For example, $T_5'$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.

For example, $Q5'$ is a bond and $T_5'$ is $C_1$-$C_6$ alkyl, $C_3$-$C_8$ cycloalkyl, or 4 to 7-membered heterocycloalkyl.

For example, $Q_5'$ is a bond and $T_5'$ is 5- or 6-membered heteroaryl, amino, mono-$C_1$-$C_6$ alkylamino, di-$C_1$-$C_6$ alkylamino, $T_5'$ being optionally substituted with one or more substituents selected from the group consisting of halo, hydroxyl, $C_1$-$C_6$ alkoxyl, or $C_3$-$C_8$ cycloalkyl.

For example, $Q_5'$ is CO, S(O)$_2$, or NHC(O); and $T_5'$ is $C_1$-$C_6$ alkyl, $C_1$-$C_6$ alkoxyl, $C_3$-$C_8$ cycloalkyl, or 4 to 7-membered heterocycloalkyl.

For example, $T_5'$ is $C_1$-$C_6$ alkyl or $C_1$-$C_6$ alkoxyl, each optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.

For example, $Q_5'$ is $C_1$-$C_3$ alkyl linker and $T_5'$ is H or $C_6$-$C_{10}$ aryl.

For example, $Q_5'$ is $C_1$-$C_3$ alkyl linker and $T_5'$ is $C_3$-$C_8$ cycloalkyl, 4 to 7-membered heterocycloalkyl, or S(O)$_q$'$R_q'$.

For example, $R_6'$ is halo (e.g., fluorine, chlorine, bromine, and iodine) and $Z_2$ is S(O)$_a$'$R_7'$, in which a' is 0, 1, or 2 and $R_7'$ is $C_1$-$C_6$ alkyl (e.g., methyl, ethyl, n-propyl, i-propyl, butyl, or t-butyl), $C_3$-$C_8$ cycloalkyl (e.g., cyclopentyl, cyclohexyl, or cycloheptyl) or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) and $R_7'$ is optionally substituted with one or more -$Q_5'$-$T_5'$.

For example, $R_6'$ is halo (e.g., fluorine, chlorine, bromine, and iodine) and $Z_2$ is OR$_7'$ in which $R_7'$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) and $R_7'$ is optionally substituted with one or more -$Q_5'$-$T_5'$.

For example, $R_{11}'$ is H.

For example, each of $R_2'$ and $R_4'$, independently, is H or $C_1$-$C_6$ alkyl optionally substituted with azido, halo, amino, mono-$C_1$-$C_6$ alkylamino, di-$C_1$-$C_6$ alkylamino, or $C_6$-$C_{10}$ aryl.

For example, each of $R_2'$ and $R_4'$, independently is $C_1$-$C_3$ alkyl optionally substituted with $C_1$-$C_6$ alkoxyl.

For example, each of $R_2'$ and $R_4'$ is methyl.

For example, $R_1'$ is H.

For example, $R_1'$ is $C_1$-$C_6$ alkyl optionally substituted with azido, halo, amino, mono-$C_1$-$C_6$ alkylamino, di-$C_1$-$C_6$ alkylamino, or $C_6$-$C_{10}$ aryl.

For example, $R_{12}'$ is H, methyl, ethyl, ethenyl, or halo.

For example, $R_{12}'$ is methyl.

For example, $R_{12}'$ is ethyl.

For example, $R_{12}'$ is ethenyl or propenyl.

For example, $R_{12}'$ is methoxyl.

For example, $R_8'$ is H, methyl, ethyl, or ethenyl.

For example, $R_8'$ is methyl.

For example, $R_8'$ is ethyl.

For example, $R_8'$ is propyl.

For example, $R_8'$ is ethenyl or propenyl.

For example, $R_8'$ is $C_1$-$C_6$ alkyl substituted with one or more substituents selected from the group consisting of halo (e.g., F, Cl, or Br), hydroxyl, or $C_1$-$C_6$ alkoxyl.

For example, $R_8'$ is 4 to 7-membered optionally substituted heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like).

For example, $R_8'$ is piperidinyl.

For example, $R_8'$ is 4 to 7-membered optionally substituted heterocycloalkyl and $R_7'$ is -$Q_4'$-$T_4'$, in which $Q_4'$ is a bond or $C_1$-$C_4$ alkyl linker and $T_4'$ is H, $C_1$-$C_6$ alkyl, $C_3$-$C_8$ cycloalkyl or 4 to 7-membered heterocycloalkyl.

For example, $Z_2$ is NR$_7'$R$_8'$ or CR$_7'$R$_8'$R$_{14}'$ wherein $R_7'$ and $R_8'$, together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, and the like) or C₃-C₈ cycloalkyl, each optionally substituted with one or more -Q₆'-T₆'.

For example, the ring formed by R₇' and R₈' is selected from the group consisting of azetidinyl, pyrrolidinyl, piperidinyl, morpholinyl, piperazinyl, and cyclohexenyl, each optionally substituted with one -Q₆'-T₆'.

For example, -Q₆'-T₆' is oxo.

For example, T₆' is H, halo, C₁-C₆ alkyl, C₁-C₆ alkoxyl, C₃-C₈ cycloalkyl, C₆-C₁₀ aryl, or 4 to 7-membered heterocycloalkyl.

For example, Q₆' is a bond and T₆ is C₁-C₆ alkyl, C₃-C₈ cycloalkyl, or 4 to 7-membered heterocycloalkyl.

For example, Q₆' is CO, S(O)₂, or NHC(O); and T₆' is C₁-C₆ alkyl, C₁-C₆ alkoxyl, C₃-C₈ cycloalkyl, or 4 to 7-membered heterocycloalkyl.

For example, T₆' is C₁-C₆ alkyl or C₁-C₆ alkoxyl, each optionally substituted with halo, hydroxyl, cyano, C₁-C₆ alkoxyl, amino, mono-C₁-C₆ alkylamino, di-C₁-C₆ alkylamino, or C₃-C₈ cycloalkyl.

For example, Q6' is C₁-C₃ alkyl linker and T₆' is H or C₆-C₁₀ aryl.

For example, Q6' is C₁-C₃ alkyl linker and T₆' is C₃-C₈ cycloalkyl, 4 to 7-membered heterocycloalkyl, or S(O)ₚR ₚ'.

For example, each of Rₚ' and Rq', independently, is C₁-C₆ alkyl.

For example, R₆' is —S(O)ᵦ'Rₐ' or azido, in which b' is 0, 1, or 2 and Rₐ' is C₁-C₆ alkyl or C₃-C₈ cycloalkyl; and Z₂ is NR₇'R₈', in which R₇' is C₃-C₈ cycloalkyl (e.g., cyclopentyl, cyclohexyl, or cycloheptyl) or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like), each optionally substituted with one or more -Q₅'-T₅' and R₈' is H or C₁-C₆ alkyl (e.g., methyl, ethyl, n-propyl, i-propyl, butyl, or t-butyl).

For example, R₆' is halo (e.g., fluorine, chlorine, bromine, and iodine) and Z₂ is NR₇'R₈' or CR₇'R₈'R₁₄' wherein R₇' and R₈', together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, and the like) or C₃-C₈ cycloalkyl, each optionally substituted with one or more -Q₆'-T₆'.

For example, R₁₃' is H or methyl.

For example, R₁₃' is H.

For example, R₃' is H.

For example, each of R₅', R₉', and R₁₀' is H.

Other compounds suitable for the methods of the invention are described in PCT/US2012/026953, filed on Feb. 28, 2012; U.S. Provisional Application Ser. Nos. 61/474,821, filed on Apr. 13, 2011; 61/474,825, filed on Apr. 13, 2011; 61/499,595, filed on Jun. 21, 2011; and 61/505,676, filed on Jul. 8, 2011, the contents of which are hereby incorporated by reference in their entireties.

Exemplary EZH2 inhibitor compounds of the present invention are shown in Table 1. In the table below, each occurrence of

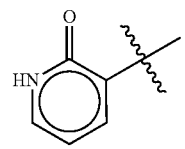

should be construed as

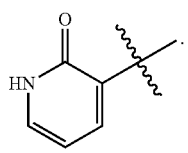

TABLE 1

| Compound Number | Structure |
|---|---|
| 1 | HO, HO''''',  adenine-ribose-S-CH₂CH₂CH(NH₂)COOH ("SAH") |
| 2 | (structure shown) |
| 3 | (structure shown) |

TABLE 1-continued
| Compound Number | Structure |
|---|---|
| 4 | 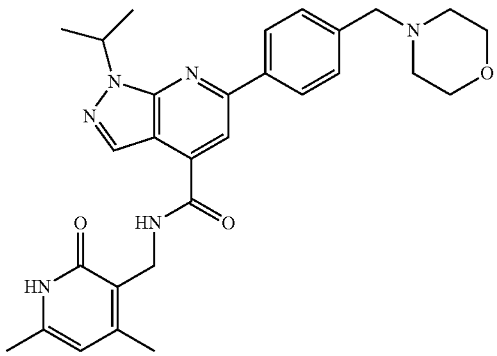 [SMILES: Cc1cc(C)c(CNC(=O)c2cc(-c3ccc(CN4CCOCC4)cc3)nc3c2cnn3C(C)C)c(=O)[nH]1] |
| 5 | 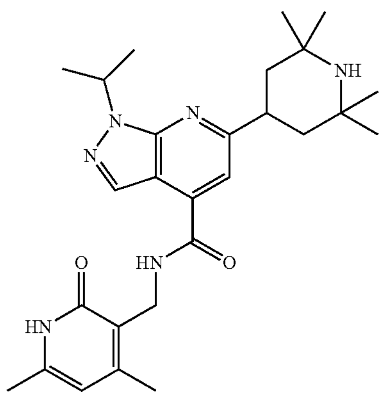 |
| 6 | 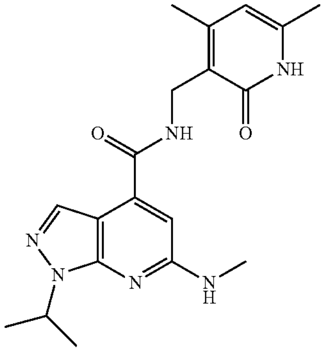 [SMILES: CNc1cc(C(=O)NCc2c(C)cc(C)[nH]c2=O)c2cnn(C(C)C)c2n1] |
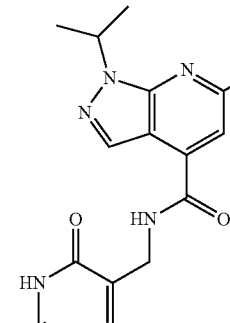
TABLE 1-continued
| Compound Number | Structure |
|---|---|
| 7 | 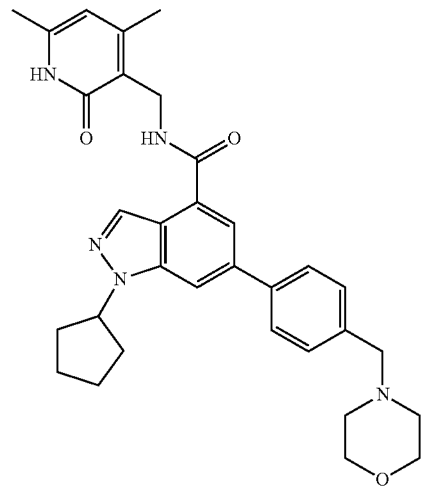 [SMILES: Cc1cc(C)c(CNC(=O)c2cc(-c3ccc(CN4CCOCC4)cc3)cc3c2cnn3C2CCCC2)c(=O)[nH]1] |
| 8 | 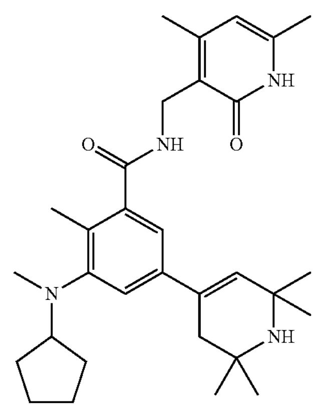 |
| 9 | 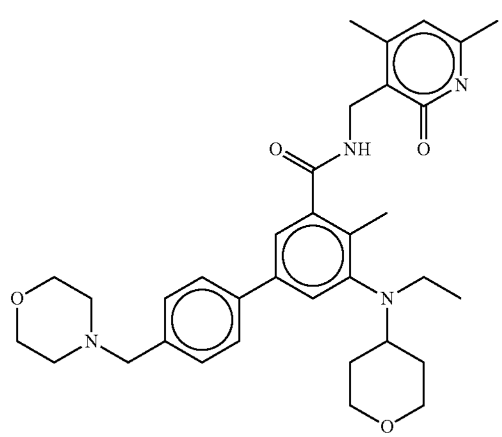 |
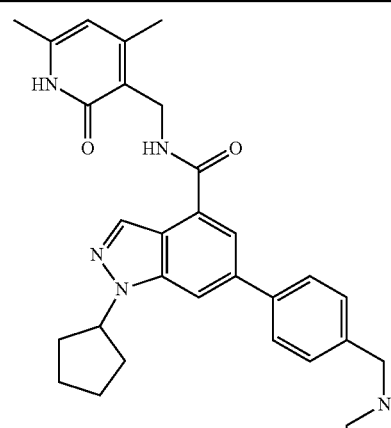

TABLE 1-continued

| Compound Number | Structure |
|---|---|
| 10 | 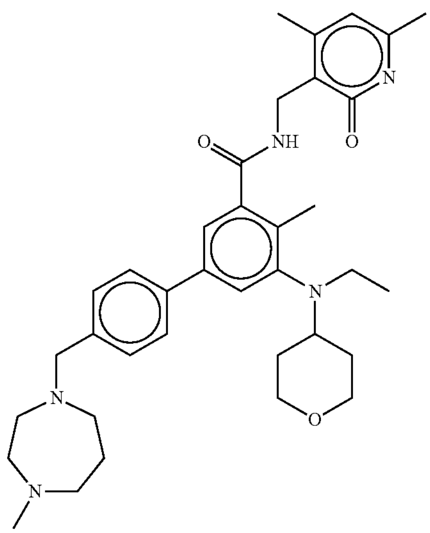 |
| 11 | 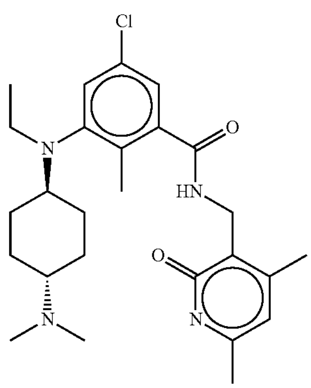 |
| 12 | 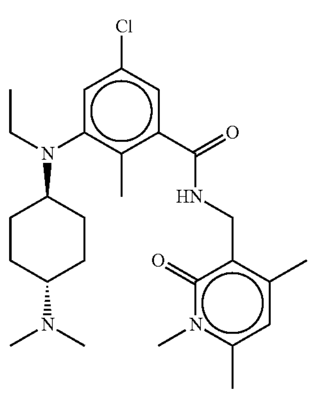 |
| 13 | |
| 14 | |
| 15 | |

TABLE 1-continued

| Compound Number | Structure |
|---|---|
| 16 | 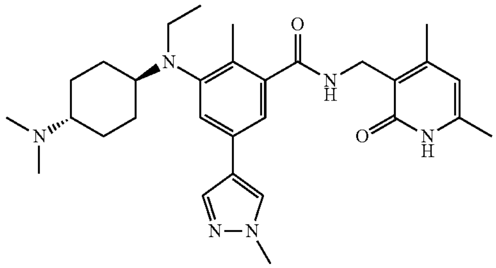 |
| 17 | 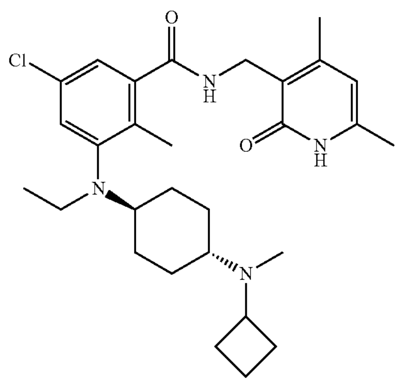 [SMILES: CCN(c1cc(Cl)cc(C(=O)NCc2c(C)cc(C)[nH]c2=O)c1C)[C@H]1CC[C@H](N(C)C2CCC2)CC1] |
| 18 | 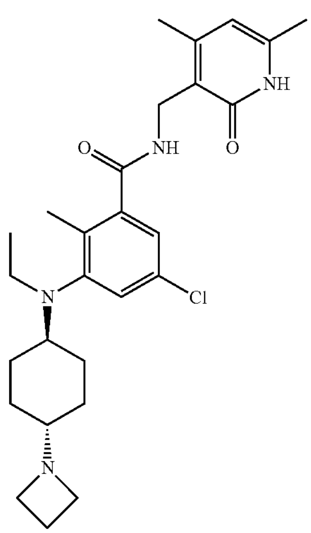 [SMILES: CCN(c1cc(Cl)cc(C(=O)NCc2c(C)cc(C)[nH]c2=O)c1C)[C@H]1CC[C@H](N2CCC2)CC1] |
| 19 | |
| 20 | |
| 21 | |

TABLE 1-continued
| Compound Number | Structure |
|---|---|
| 22 | 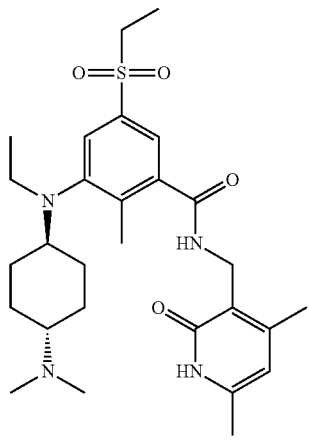 [SMILES: CCN(c1cc(S(=O)(=O)CC)cc(C(=O)NCc2c(C)cc(C)[nH]c2=O)c1C)[C@H]1CC[C@H](N(C)C)CC1] |
| 23 | 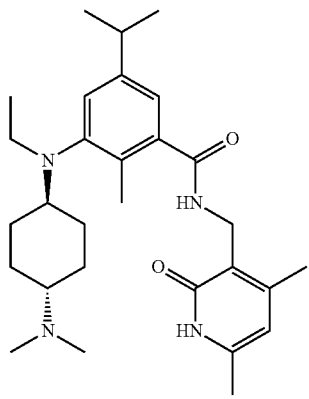 [SMILES: CCN(c1cc(C(C)C)cc(C(=O)NCc2c(C)cc(C)[nH]c2=O)c1C)[C@H]1CC[C@H](N(C)C)CC1] |
| 24 | 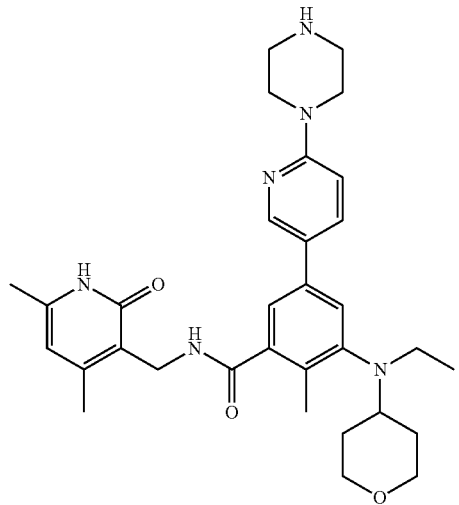 [SMILES: CCN(c1cc(-c2ccc(N3CCNCC3)nc2)cc(C(=O)NCc2c(C)cc(C)[nH]c2=O)c1C)C1CCOCC1] |
TABLE 1-continued
| Compound Number | Structure |
|---|---|
| 25 | 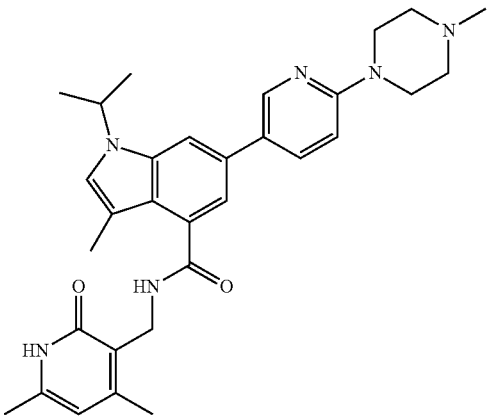 |
| 26 | 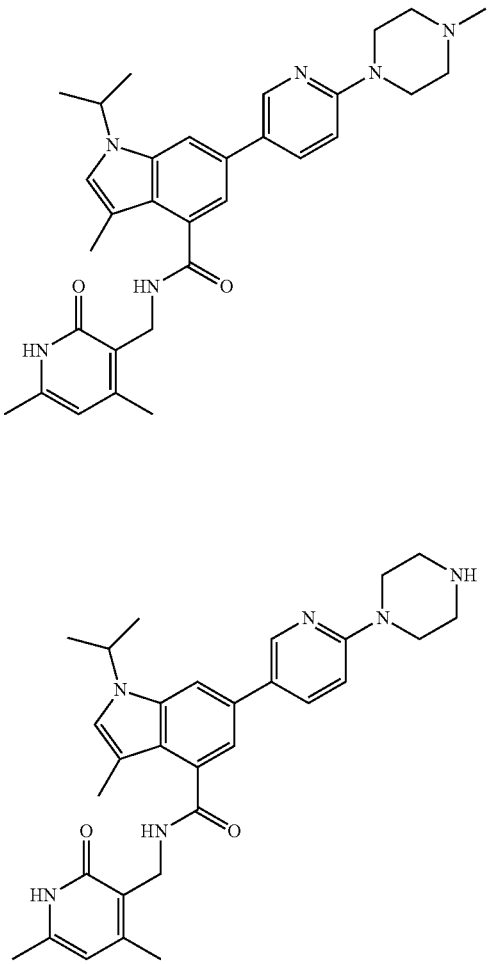 |
| 27 | 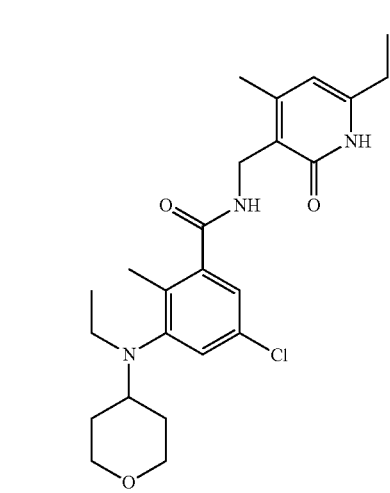 [SMILES: CCc1cc(C)c(CNC(=O)c2cc(Cl)cc(N(CC)C3CCOCC3)c2C)c(=O)[nH]1] |

TABLE 1-continued
| Compound Number | Structure |
|---|---|
| 28 | 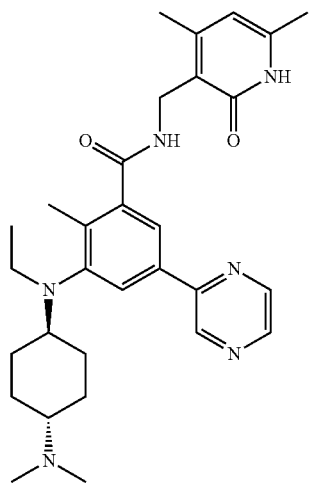 [SMILES: CCN(c1cc(-c2cnccn2)cc(C(=O)NCc2c(C)cc(C)[nH]c2=O)c1C)[C@H]1CC[C@H](N(C)C)CC1] |
| 29 | 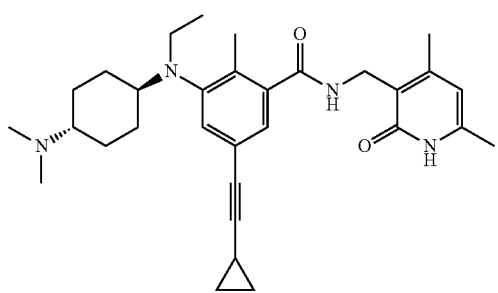 |
| 30 | 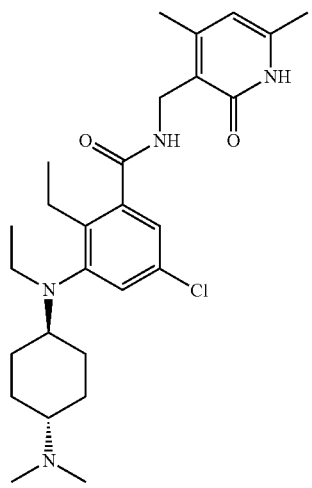 [SMILES: CCc1c(C(=O)NCc2c(C)cc(C)[nH]c2=O)cc(Cl)cc1N(CC)[C@H]1CC[C@H](N(C)C)CC1] |
| 31 | 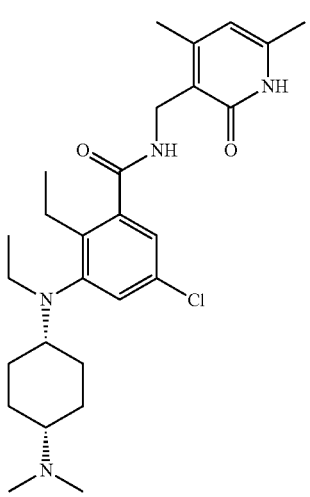 [SMILES: CCc1c(C(=O)NCc2c(C)cc(C)[nH]c2=O)cc(Cl)cc1N(CC)[C@H]1CC[C@@H](N(C)C)CC1] |
| 32 | 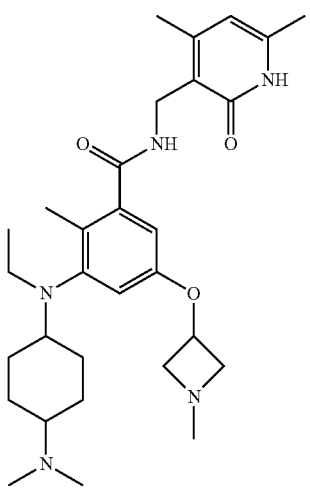 [SMILES: CCN(c1cc(OC2CN(C)C2)cc(C(=O)NCc2c(C)cc(C)[nH]c2=O)c1C)C1CCC(N(C)C)CC1] |
| 33 | 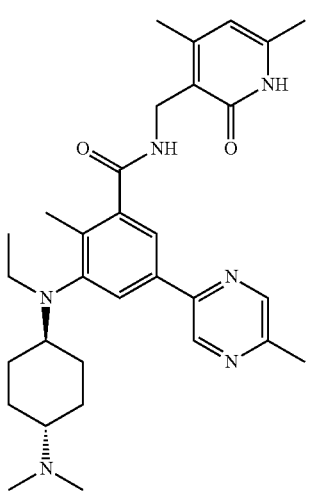 |

TABLE 1-continued

| Compound Number | Structure |
|---|---|
| 34 | 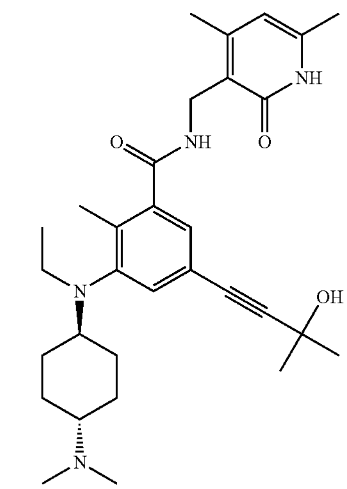 [SMILES: CCN(c1cc(C#CC(C)(C)O)cc(C(=O)NCc2c(C)cc(C)[nH]c2=O)c1C)[C@H]1CC[C@H](N(C)C)CC1] |
| 35 | 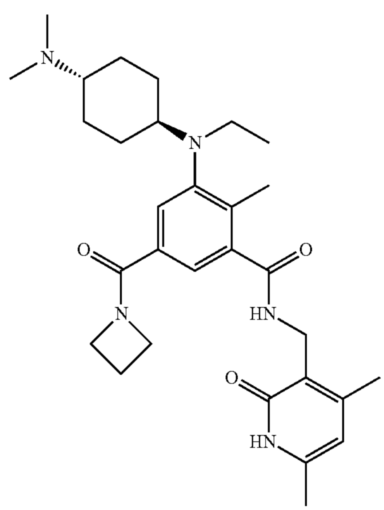 |
| 36 | 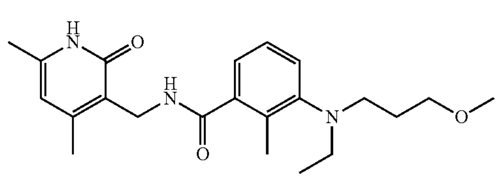 |
| 37 | |
| 38 | |
| 39 | |

TABLE 1-continued
| Compound Number | Structure |
|---|---|
| 40 | 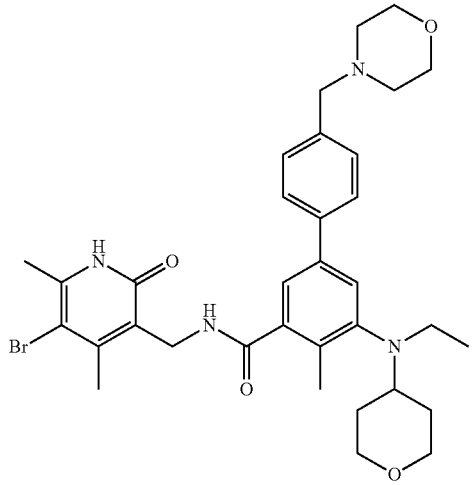 [SMILES: CCN(c1cc(-c2ccc(CN3CCOCC3)cc2)cc(C(=O)NCc2c(C)c(Br)c(C)[nH]c2=O)c1C)C1CCOCC1] |
| 41 | 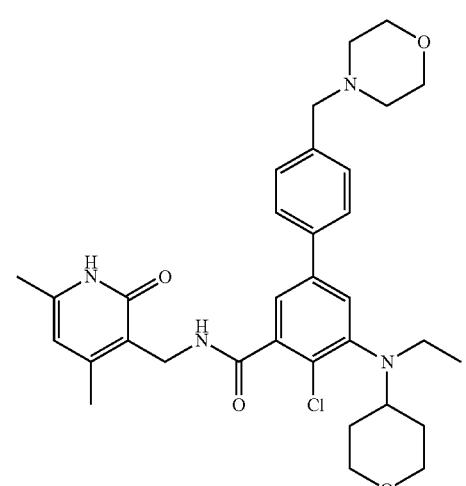 |
| 42 | 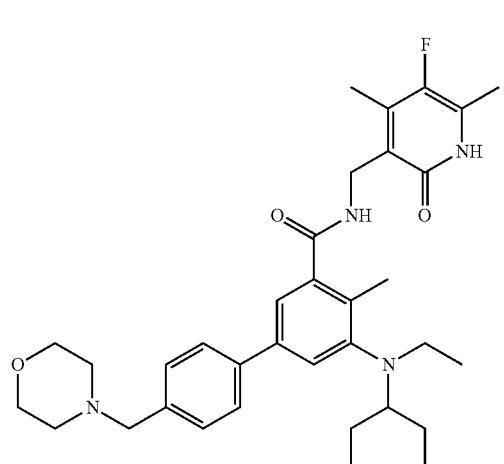 |
| 43 | 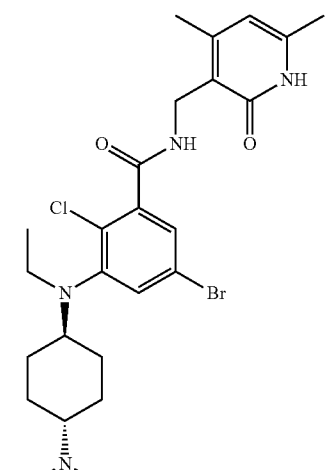 |
| 44 | 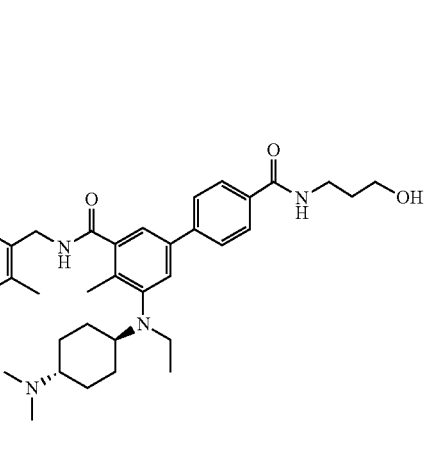 |
| 45 | 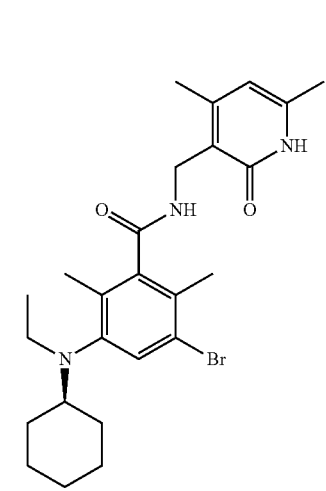 |

TABLE 1-continued

| Compound Number | Structure |
|---|---|
| 46 | 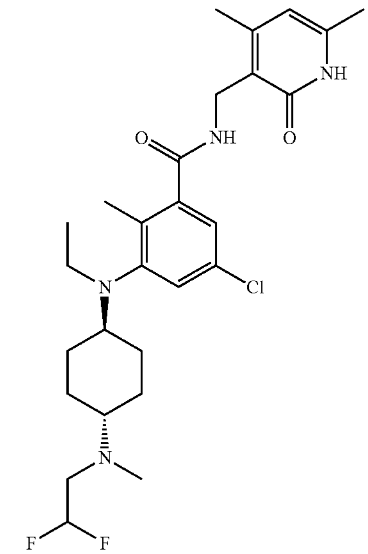 [SMILES: CCN(c1cc(Cl)cc(C(=O)NCc2c(C)cc(C)[nH]c2=O)c1C)[C@H]1CC[C@H](N(C)CC(F)F)CC1] |
| 47 | 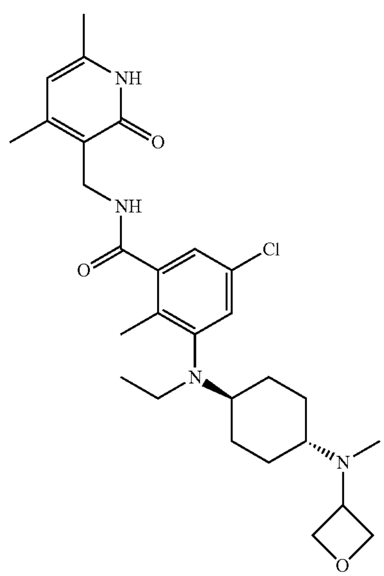 |
| 48 | 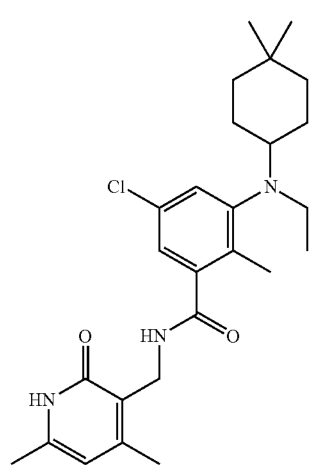 [SMILES: CCN(c1cc(Cl)cc(C(=O)NCc2c(C)cc(C)[nH]c2=O)c1C)C1CCC(C)(C)CC1] |
| 49 | 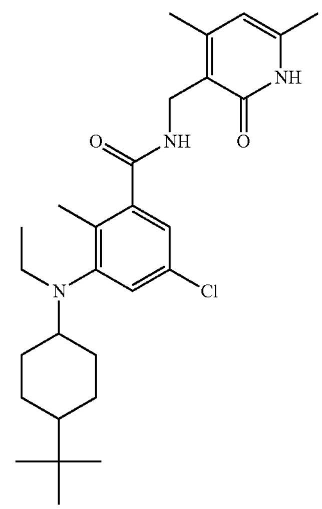 [SMILES: CCN(c1cc(Cl)cc(C(=O)NCc2c(C)cc(C)[nH]c2=O)c1C)C1CCC(C(C)(C)C)CC1] |
| 50 | 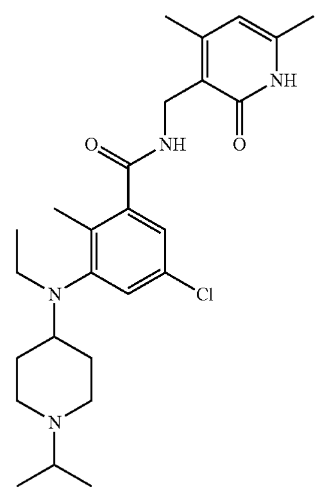 [SMILES: CCN(c1cc(Cl)cc(C(=O)NCc2c(C)cc(C)[nH]c2=O)c1C)C1CCN(C(C)C)CC1] |
| 51 | 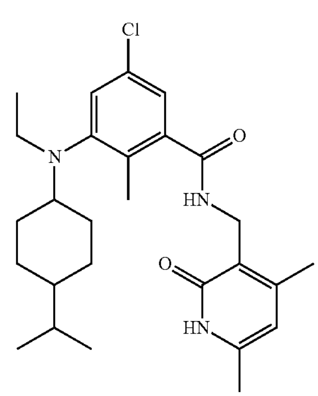 [SMILES: CCN(c1cc(Cl)cc(C(=O)NCc2c(C)cc(C)[nH]c2=O)c1C)C1CCC(C(C)C)CC1] |

TABLE 1-continued
| Compound Number | Structure |
|---|---|
| 52 | 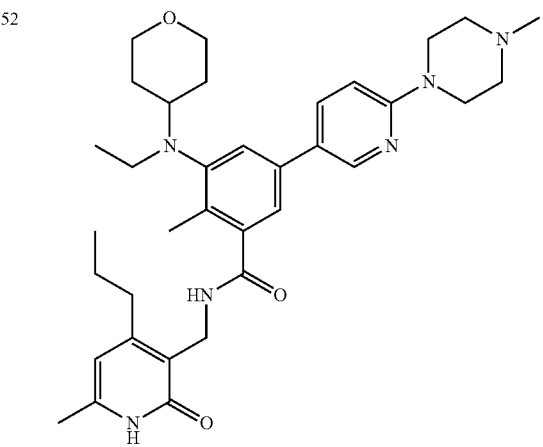 |
| 53 | 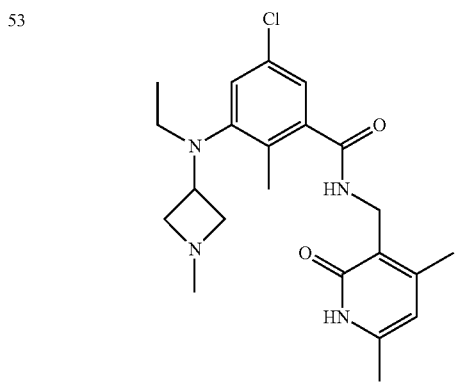 |
| 54 | 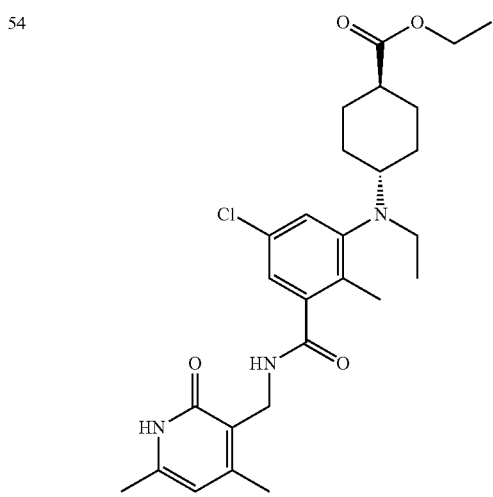 |"
| 55 | 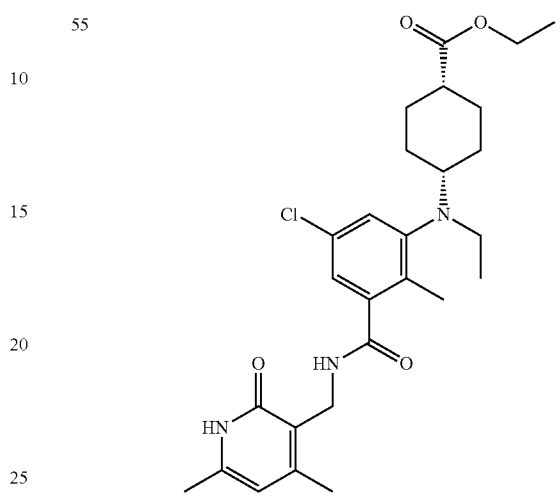 |
| 56 | 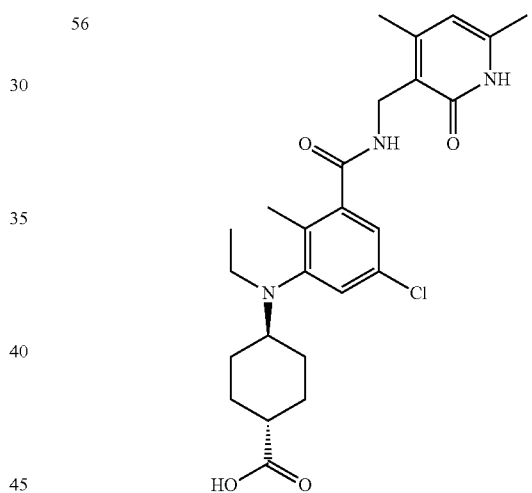 |
| 57 | 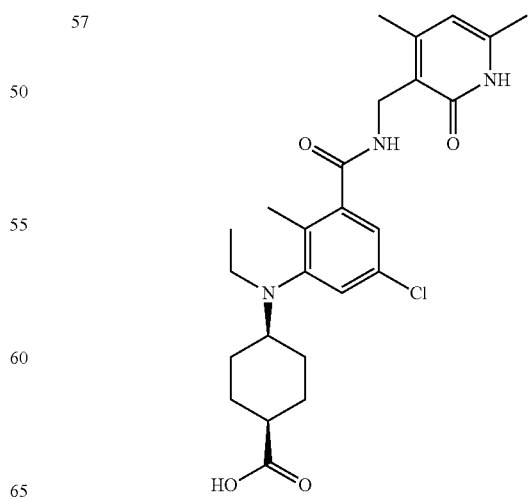 |

TABLE 1-continued

| Compound Number | Structure |
|---|---|
| 58 | 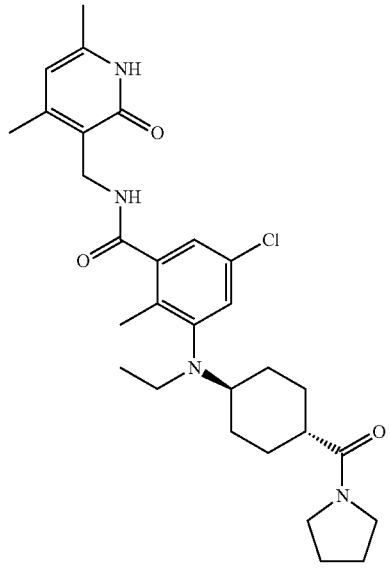 [SMILES: CCN(c1cc(Cl)cc(C(=O)NCc2c(C)cc(C)[nH]c2=O)c1C)[C@H]1CC[C@H](C(=O)N2CCCC2)CC1] |
| 59 | |
| 60 | 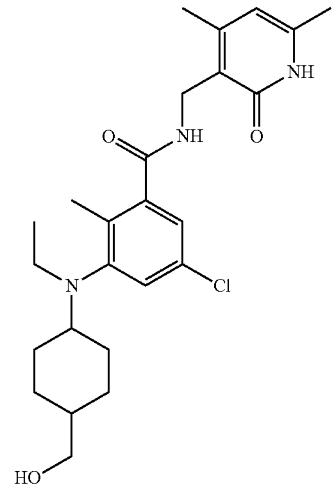 [SMILES: CCN(c1cc(Cl)cc(C(=O)NCc2c(C)cc(C)[nH]c2=O)c1C)C1CCC(CO)CC1] |
| 61 | 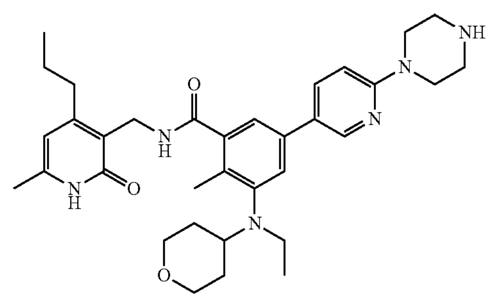 [SMILES: CCCc1cc(C)[nH]c(=O)c1CNC(=O)c1cc(-c2ccc(N3CCNCC3)nc2)cc(N(CC)C2CCOCC2)c1C] |
| 62 | 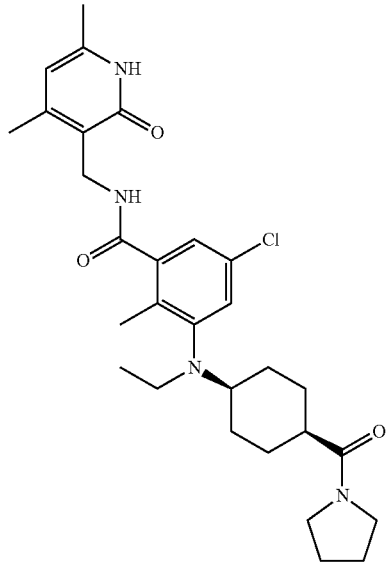 |

Unless otherwise indicated, the term "substituted" means substituted by one or more defined groups. In the case where groups may be selected from a number of alternative groups the selected groups may be the same or different.

The term "independently" means that where more than one substituent is selected from a number of possible substituents, those substituents may be the same or different.

An "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged; or spiro rings) system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1]heptanyl, and the like.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g. 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizirie.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and Spiro rings are also included.

As used herein, "heterocycle" or "heterocyclic group" includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is pxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_I$ at each occurrence is selected independently from the definition of $R_1$. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to unsubstituted or substituted —$NH_2$. "Alkylamino" includes groups of compounds wherein nitrogen of —$NH_2$ is bound to at least one alkyl group. Examples of alkylamino groups include benzylamino, methylamino, ethylamino, phenethylamino, etc. "Dialkylamino" includes groups wherein the nitrogen of —$NH_2$ is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy"; "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

The term "optionally" means that the subsequently described event(s) may or may not occur, and includes both event(s), which occur, and events that do not occur.

Herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

By the term "co-administering" and derivatives thereof as used herein is meant either simultaneous administration or any manner of separate sequential administration of one or more additional pharmaceutically active compounds, whether for treating cancer, the side effects of cancer or cancer therapy, or some other disease. Preferably, if the administration is not simultaneous, the compounds are administered in a close time proximity to each other. Furthermore, it does not matter if the compounds are administered in the same dosage form, e.g. one compound may be administered topically and another compound may be administered orally.

The compounds of Formulae (I)-(III) include the compounds themselves, as well as their salts, their solvates, their N-oxides, and their prodrugs, if applicable. In certain embodiments, compounds according to Formulae (I)-(III) may contain an acidic functional group, one acidic enough to form salts. Representative salts include pharmaceutically acceptable metal salts such as sodium, potassium, lithium, calcium, magnesium, aluminum, and zinc salts; carbonates and bicarbonates of a pharmaceutically-acceptable metal salts such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to Formulae (I)-(III) may contain a basic functional group and are therefore capable of forming pharmaceutically-acceptable acid addition salts by treatment with a suitable acid. Suitable acids include pharmaceutically-acceptable inorganic acids and pharmaceutically-acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicylate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate) and napthalene-2-sulfonate.

Compounds of the present invention that contain nitrogens can be converted to N-oxides by treatment with an oxidizing agent (e.g., 3-chloroperoxybenzoic acid (mCPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms.

Furthermore, the structures and other compounds discussed in this invention include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of keto-enol equilibria is between pyridin-2(1H)-ones and the corresponding pyridin-2-ols, as shown below.

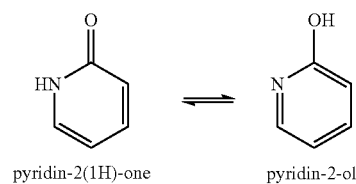 [SMILES: O=c1cccc[nH]1 ; Oc1ccccn1]

pyridin-2(1H)-one     pyridin-2-ol

It is to be understood that the compounds of the present invention may be depicted as different tautomers. It should also be understood that when compounds have tautomeric forms, all tautomeric forms, including mixtures thereof, are intended to be included in the scope of the present invention, and the naming of the compounds does not exclude any tautomer form.

The compounds of Formulae (I)-(III) may be prepared in crystalline or non-crystalline form, and, if crystalline, may optionally be solvated, e.g., as the hydrate. This invention includes within its scope stoichiometric solvates (e.g., hydrates) as well as compounds containing variable amounts of solvent (e.g., water).

Certain of the compounds described herein may contain one or more chiral atoms, or may otherwise be capable of existing as two enantiomers. The compounds claimed below include mixtures of enantiomers as well as purified enantiomers or enantiomerically enriched mixtures. Also included within the scope of the invention are the individual isomers of the compounds represented by Formulae (I)-(III), or claimed below, as well as any wholly or partially equilibrated mixtures thereof. The present invention also covers the individual isomers of the claimed compounds as mixtures with isomers thereof in which one or more chiral centers are inverted.

Where there are different isomeric forms they may be separated or resolved one from the other by conventional methods, or any given isomer may be obtained by conventional synthetic methods or by stereospecific or asymmetric syntheses.

While it is possible that, for use in therapy, a compound of Formulae (I)-(III), as well as salts, solvates, N-oxides, and the like, may be administered as a neat preparation, i.e., no additional carrier, the more usual practice is to present the active ingredient confected with a carrier or diluent. Accordingly, the invention further provides pharmaceutical compositions, which includes a compound of Formulae (I)-(III) and salts, solvates and the like, and one or more pharmaceutically acceptable carriers, diluents, or excipients. The compounds of Formulae (I)-(III) and salts, solvates, N-oxides, etc, are as described above. The carrier(s), diluent, or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the Formulae (I)-(III), or salts, solvates, N-oxides, etc, with one or more pharmaceutically acceptable carriers, diluents or excipients.

It will be appreciated by those skilled in the art that certain protected derivatives of compounds of Formulae (I)-(III), which may be made prior to a final deprotection stage, may not possess pharmacological activity as such, but may, in certain instances, be administered orally or parenterally and thereafter metabolized in the body to form compounds of the invention which are pharmacologically active. Such derivatives may therefore be described as "prodrugs". Further, certain compounds of the invention may act as prodrugs of other compounds of the invention. All protected derivatives and prodrugs of compounds of the invention are included within the scope of the invention. It will further be appreciated by those skilled in the art, that certain moieties, known to those skilled in the art as "pro-moieties" may be placed on appropriate functionalities when such functionalities are present within compounds of the invention. Preferred prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals, and ketals.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are aryl- or heteroaryl-substituted benzene compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides; tetrazoles, sulfonates and phosphonates. See, e.g., Patani and LaVoie, Chem. Rev. 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

Such compounds also include Compound 75

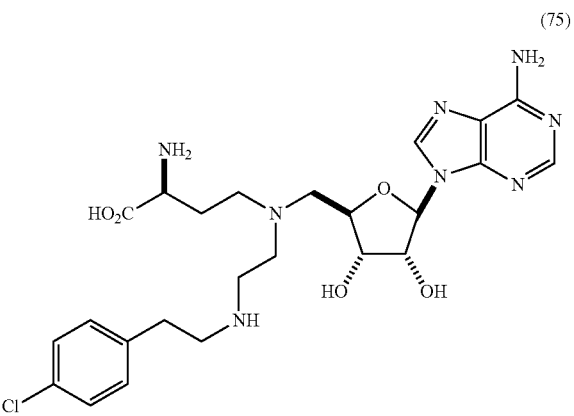

and pharmaceutically acceptable salts thereof.

The invention further includes a pharmaceutical composition comprising Compound 75

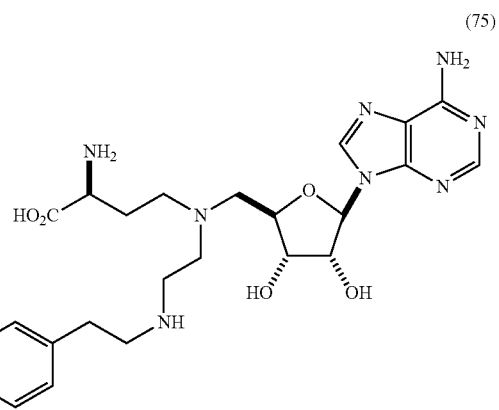

or a pharmaceutically acceptable salt thereof.

An EZH2 antagonist and optionally other therapeutics can be administered per se (neat) or in the form of a pharmaceutically acceptable salt. When used in medicine the salts should be pharmaceutically acceptable, but non-pharmaceutically acceptable salts can conveniently be used to prepare pharmaceutically acceptable salts thereof.

Compounds useful in accordance with the invention may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound useful in accordance with this invention. A "pharmaceutically acceptable counterion" is an ionic portion of a salt that is not toxic when released from the salt upon administration to a subject. Pharmaceutically compatible salts may be formed with many acids, including but not limited to hydrochloric, sulfuric, acetic, lactic, tartaric, malic, and succinic acids. Salts tend to be more soluble in water or other protic solvents than their corresponding free base forms. The present invention includes the use of such salts.

Pharmaceutically acceptable acid addition salts include those formed with mineral acids such as hydrochloric acid and hydrobromic acid, and also those formed with organic acids such as maleic acid. For example, acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di alkyl-N-(hydroxy alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Certain compounds useful in accordance with the invention and their salts may exist in more than one crystalline form (i.e., polymorph); the present invention includes the use of each of the crystal forms and mixtures thereof.

Certain compounds useful in accordance with the invention may contain one or more chiral centers, and exist in different optically active forms. When compounds useful in accordance with the invention contain one chiral center, the compounds exist in two enantiomeric forms and the present invention includes the use of both enantiomers and mixtures of enantiomers, such as racemic mixtures thereof. The enantiomers may be resolved by methods known to those skilled in the art; for example, enantiomers may be resolved by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example, via enzymatic esterification; or gas-liquid or liquid chromatography in a chiral environment, for example, on a chiral support (e.g., silica with a bound chiral ligand) or in the presence of a chiral solvent. Where the desired enantiomer is converted into another chemical entity by one of the separation procedures described above, a further step may be used to liberate the desired purified enantiomer. Alternatively, specific enantiomers may be synthesized by asymmetric synthesis using optically active reagents, substrates, catalysts or solvents, or by converting one enantiomer into the other by asymmetric transformation.

When a compound useful in accordance with the invention contains more than one chiral center, it may exist in diastereoisomeric forms. The diastereoisomeric compounds may be separated by methods known to those skilled in the art (for example, chromatography or crystallization) and the individual enantiomers may be separated as described above. The present invention includes the use of various diastereoisomers of compounds useful in accordance with the invention, and mixtures thereof. Compounds useful in accordance with the invention may exist in different tautomeric forms or as different geometric isomers, and the present invention includes the use of each tautomer and/or geometric isomer of compounds useful in accordance with the invention, and mixtures thereof. Compounds useful in accordance with the invention may exist in zwitterionic form. The present invention includes the use of each zwitterionic form of compounds useful in accordance with the invention, and mixtures thereof.

Kits

An EZH2 antagonist may, if desired, be presented in a kit (e.g., a pack or dispenser device) which may contain one or more unit dosage forms containing the EZH2 antagonist. The pack may for example comprise metal or plastic foil, such as a blister pack. The pack or dispenser device may be accompanied by instructions for administration. Compositions comprising an EZH2 antagonist of the invention formulated in a compatible pharmaceutical carrier may also be prepared, placed in an appropriate container, and labeled for treatment of an indicated condition. Instructions for use may also be provided.

Also provided herein are kits comprising a plurality of methylation detection reagents that detect the methylated H3-K27. For example, the kit includes mono-methylated H3-K27, di-methylated H3-K27 and tri-methylated H3-K27 detection reagents. The detection reagent is for example antibodies or fragments thereof, polypeptide or aptamers.

A kit may also include an EZH2 mutant detection reagent, e.g., nucleic acids that specifically identify a mutant EZH2 nucleic acid sequence by having homologous nucleic acid sequences, such as oligonucleotide sequences, complementary to a portion of the mutant EZH2 nucleic acid sequence or antibodies to proteins encoded by the mutant EZH2 nucleic acids packaged together in the form of a kit. The oligonucleotides can be fragments of the EZH2 gene. For example the oligonucleotides can be 200, 150, 100, 50, 25, 10 or less nucleotides in length. The kit may contain in separate containers an aptamer or an antibody, control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit. The assay may for example be in the form of a Western Blot analysis, Immunohistochemistry (IHC), immunofluorescence (IF), sequencing and Mass spectrometry (MS) as known in the art.

Definitions

For convenience, certain terms employed in the specification, examples, and appended claims are collected here. All definitions, as defined and used herein, supersede dictionary definitions, definitions in documents incorporated by reference, and/or ordinary meanings of the defined terms.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "precancerous condition" or "premalignant condition" refers to a disease, syndrome, or finding that, if left untreated, may lead to cancer. It is a generalized state associated with a significantly increased risk of cancer.

The term "treating" as used herein refers to alleviate of at least one symptom of the disease, disorder or condition. The term encompasses the administration and/or application of one or more compounds described herein, to a subject, for the purpose of providing management of, or remedy for a condition. "Treatment" for the purposes of this disclosure, may, but does not have to, provide a cure; rather, "treatment" may be in the form of management of the condition. When the compounds described herein are used to treat unwanted proliferating cells, including cancers, "treatment" includes partial or total destruction of the undesirable proliferating cells with minimal destructive effects on normal cells. A desired mechanism of treatment of unwanted rapidly proliferating cells, including cancer cells, at the cellular level is apoptosis.

The term "preventing" as used herein includes either preventing or slowing the onset of a clinically evident disease progression altogether or preventing or slowing the onset of a preclinically evident stage of a disease in individuals at risk. This includes prophylactic treatment of those at risk of developing a disease.

The term "subject" as used herein for purposes of treatment includes any human subject who has been diagnosed with, has symptoms of, or is at risk of developing a cancer or a precancerous condition. For methods of prevention the subject is any human subject. To illustrate, for purposes of prevention, a subject may be a human subject who is at risk of or is genetically predisposed to obtaining a disorder characterized by unwanted, rapid cell proliferation, such as cancer. The subject may be at risk due to exposure to carcinogenic agents, being genetically predisposed to disorders characterized by unwanted, rapid cell proliferation, and so on.

Except as otherwise indicated, standard methods can be used for the production of recombinant and synthetic polypeptides, fusion proteins, antibodies or antigen-binding fragments thereof, manipulation of nucleic acid sequences, production of transformed cells, and the like. Such techniques are known to those skilled in the art. See, e.g., Sambrook et al., *Molecular Cloning: A Laboratory Manual,* 3rd Ed. (Cold Spring Harbor, N.Y., 2001); F. M. Ausubel et al. *Current Protocols in Molecular Biology* (Green Publishing Associates, Inc. and John Wiley & Sons, Inc., New York).

The term "EZH2 polypeptide" encompasses functional fragments of the full-length polypeptides and functional equivalents of either of the foregoing that have substantially similar or substantially identical amino acid sequences (at least about 75%, 80%, 85%, 90%, 95% 98% or more amino acid sequence similarity or identity), where the functional fragment or functional equivalent retains one or more of the functional properties of the native polypeptide.

By "functional" it is meant that the polypeptide (or nucleic acid) has the same or substantially similar activity with respect to one or more of the biological properties of the native polypeptide (or nucleic acid), e.g., at least about 50%, 75%, 85%, 90%, 95% or 98% or more of the activity of the native polypeptide (or nucleic acid).

The term "modulate" (and grammatical equivalents) refers to an increase or decrease in activity. In particular embodiments, the term "increase" or "enhance" (and grammatical equivalents) means an elevation by at least about 25%, 50%, 75%, 2-fold, 3-fold, 5-fold, 10-fold, 15-fold, 20-fold or more. In particular embodiments, the terms "decrease" or "reduce" (and grammatical equivalents) means a diminishment by at least about 25%, 40%, 50%, 60%, 75%, 80%, 85%, 90%, 95%, 98% or more. In some embodiments, the indicated activity, substance or other parameter is not detectable. Specifically provided are antagonists of EZH2.

The term "pharmacodynamic marker" refers to a molecular marker of drug response that can be measured in patients receiving the drug. The marker should be a direct measure of modulation of the drug target and be able to show quantitative changes in response to dose. A potential pharmacodynamic marker for EZH2 antagonists could be levels of histone H3-K27 methylation in disease or surrogate tissue.

As used herein, the term "responsiveness" is interchangeable with terms "responsive", "sensitive", and "sensitivity", and it is meant that a subject showing therapeutic response when administered an EZH inhibitor, e.g., tumor cells or tumor tissues of the subject undergo apoptosis and/or necrosis, and/or display reduced growing, dividing, or proliferation.

The term "control" or "reference" refers to methylation levels (e.g., monomethylation level, dimethylation level or trimethylation level) detected in an adjacent non-tumor tissue isolated from the subject, detected in a healthy tissue from a healthy subject, or established by a pathologist with standard methods in the art.

By "sample" it means any biological sample derived from the subject, includes but is not limited to, cells, tissues samples and body fluids (including, but not limited to, mucus, blood, plasma, serum, urine, saliva, and semen).

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; and Greene, T. W., Wuts, P. G. M., *Protective Groups in Organic Synthesis*, 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds of this invention with each of the formulae described herein may be prepared according to the following procedures from commercially available starting materials or starting materials which can be prepared using literature procedures. These procedures show the preparation of representative compounds of this invention.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The invention now being generally described, it will be more readily understood by reference to the following examples, which are included merely for purposes of illustration of certain aspects and embodiments of the present invention, and are not intended to limit the invention.

Example 1

Recombinant Five-Component PRC2 Complex

Wild-type EZH2 (GenBank Accession No. NM_004456) or Tyr641 mutants were co-expressed with wild-type AEBP2 (GenBank Accession No. NM_153207), EED (GenBank Accession No. NM_003797), SUZ$_{12}$ (GenBank Accession No. NM_015355) and RbAp48 (GenBank Accession No. NM_005610) in *Spodoptera frugiperda* (Sf9) cells using a baculovirus expression system. An N-terminal FLAG tag on the EED was used to purify active PRC2 complex from cell lysates (BPS Bioscience, catalog number 51004). The purity of the final PRC2 preparations was assessed by SDS-PAGE with Coomassie blue staining.

Example 2

H3, H4 Peptide Panel

A library consisting of 44 peptides of 15 amino acids each was synthesized by $21^{st}$ Century Biochemicals (Marlboro, Mass.). This peptide panel encompassed all of the amino acids of human histones H3 and H4 with 5 residue overlaps between consecutive peptide sequences. The N-terminus of each peptide was appended with biotin, and the C-termini were represented as the amide. Purity (>95%) and identity were confirmed by liquid chromatography/mass spectral analysis.

For study of the H3-K27 methylation status dependence of enzyme activity, peptides were synthesized representing the amino acid sequence of human H3 from residues 21-44 (H3: 21-44) with lysine 27 represented as the unmodified, mono-methylated, di-methylated or tri-methylated side chain amine. These peptides were purchased from New England Peptide (Gardner, Mass.) with biotin appended to the C-terminus of each peptide.

Example 3

Evaluation of H3-K27 Methylation Status in Cells

The cell lines OCI-LY19 (ACC 528), KARPAS-422 (ACC 32), and WSU-DLCL2 (ACC 575) were obtained from DSMZ. The cell lines DB (CRL-2289) and SU-DHL6 (CRL-2959) were obtained from ATCC. OCI-LY19, WSU-DLCL2, and DB cell lines were grown in RPMI-1640 with 10% FBS, and KARPAS-422 and SU-DHL6 cell lines were grown in RPMI-1640 plus 20% FBS. Cells were grown to a density of $1.5$-$2 \times 10^6$ cells/mL and $1 \times 10^7$ cells were harvested by centrifugation at 264×g, washed in ice cold PBS and lysed by resuspension in a 10× pellet volume of RIPA lysis buffer containing 50 mM Tris-HCl, 15 0mM NaCl, 0.25% DOC, 1% NP-40, and 1 mM EDTA (Millipore#20-188), plus 0.1% SDS and protease inhibitor tablets (Roche#1836153). Lysates were sonicated by 2 rounds of 10 1-second bursts at setting 3 with a Misonix XL-2000 to ensure efficient histone extraction, and cleared by centrifugation at 4° C. using a bench top centrifuge at 14,000 rpm for 10 minutes. Protein concentration was determined by BCA assay (Pierce). Four micrograms of each lysate was fractionated on 4-20% Tris-Glycine gel (Invitrogen), transferred to PVDF, and probed with the following antibodies in ODESSEY™ blocking buffer: mouse anti-EZH2 (CST 3147; 1:2000 dilution), rabbit anti-H3-K27me3 (CST 9733; 1:10000 dilution), rabbit anti-H3-K27me2 (CST 9755; 1:5000dilution), rabbit anti-H3-K27mel(Active Motif 39377; 1:5000 dilution), and mouse anti-Total H3 (CST 3638; 1:20000 dilution). Following primary Ab incubation, membranes were probed with IRDye 800CW donkey-anti-mouse IgG (LiCOR#926-32212) or Alexa Fluor 680 goat-anti-rabbit IgG (Invitrogen#A-21076) secondary Ab and imaged using the LiCOR ODESSEY™ system.

Example 4

Enzymology

As noted above, it had previously been concluded that the disease-associated changes at Tyr641 resulted in loss of function with respect to EZH2-catalyzed H3-K27 methylation. However, a presumptive reduction in the rate of H3-K27 methylation due to'enzyme heterozygosity was difficult to rationalize as the basis for a malignant phenotype, especially in light of previous data indicating that overexpression of EZH2, loss-of-function mutations in the corresponding H3-K27 demethylase UTX, or overexpression of components of the PRC2, such as PHF19/PCL3, involved in increased H3-K27 trimethylation, all result in malignant phenotypes in specific human cancers. Morin et al. (2010) *Nat Genet* 42:181-5; Martinez-Garcia et al. (2010) *Nat Genet* 42:100-1; Bracken et al. (2003) *EMBO J* 22:5323-35; Kleer et al. (2003) *Proc Natl Acad Sci USA* 100:11606-11; Varambally et al. (2002) *Nature* 419:624-9; Simon et al. (2008) *Mutat Res* 647:21-9; van Haaften et al. (2009) *Nat Genet.* 41:521-3; Wang et al. (2004) *Gene* 343:69-78; Cao et al. (2008) *Mol Cell Biol* 28:1862-72; and Sarma et al. (2008) *Mol Cell Biol* 28:2718-31). Therefore, the enzymology of these mutations was explored in greater detail.

Recombinant PRC2 complexes were prepared with WT and Tyr641 mutant versions of human EZH2 (see Example 1 above; Cao et al. (2004) *Mol Cell* 15:57-67). Equal concentrations (nominally 8 nM, based on protein determinations) of each complex were initially tested for the ability to catalyze $^3$H-methyl transfer from labeled S-adenosyl methionine (SAM) to an unmodified peptide representing the amino acid sequence surrounding H3-K27 (H3:21-44) or to native avian erythrocyte oligonucleosomes. As previously reported (Morin et al. (2010) *Nat Genet* 42:181-5), it was found that the WT enzyme displayed robust activity for methyl transfer to this unmethylated peptidic substrate, but that none of the mutant enzymes displayed significant methyltransferase activity (FIG. 1A). In contrast to the previously reported data and that in FIG. 1A, it was found that all of the mutant EZH2 constructs were active methyltransferases against the avian nucleosome substrate (FIG. 1B). The nucleosomes isolated from the avian natural source represent an admixture of states of histone modification, including various states of H3-K27 methylation as judged by Western blotting with H3-K27 methylation-specific antibodies.

There are several potential explanations for the discordant activity of the mutant PRC2 complexes on peptide and nucleosome substrates. One possibility is that substrate recognition sites distal to the enzyme active site (i.e., exosites) are important determinants of substrate binding and turnover; these sites would engage complementary recognition elements on the nucleosome that are not available on small peptidic substrates. However, when *E. coli*-expressed, recombinant human histone H3 was tested as a substrate for the WT and mutant PRC2 complexes, the resulting pattern of activity was identical to that seen for the peptide substrate; that is, the WT enzyme demonstrated robust methyltransferase activity against the H3 substrate, the Y641F mutant showed 7% the activity of WT complex, and all other mutants displayed ≤1% the activity of WT complex. Hence, exosite engagement seems an unlikely explanation for the current results. The nucleosome presents many lysine residues beyond H3-K27 as potential sites of methylation that would not be present in the small peptidic substrate. Thus, another possibility is that mutation of Y641 alters the substrate specificity of EZH2 to result in methylation of lysine residues other than H3-K27. This possibility is unlikely given the excellent agreement between mutant activity on small peptide and recombinant H3 protein substrates.

The apparent discordance between the present results and those previously reported was resolved when the enzymatic activity of the WT and mutant PRC2 complexes were tested against a panel of peptidic substrates that represent all possible lysine (K) residues of histone H3 and histone H4 (see Example 2 above). All of the enzyme forms showed significant activity only against peptides containing the equivalent of residue H3-K27. The specific activity of the mutants, however, was greatly reduced relative to WT in the order WT>>Y641F>Y641S-Y641H>Y641N, again consistent with previous reported findings.

Example 5

Enzymology

Figure 2:
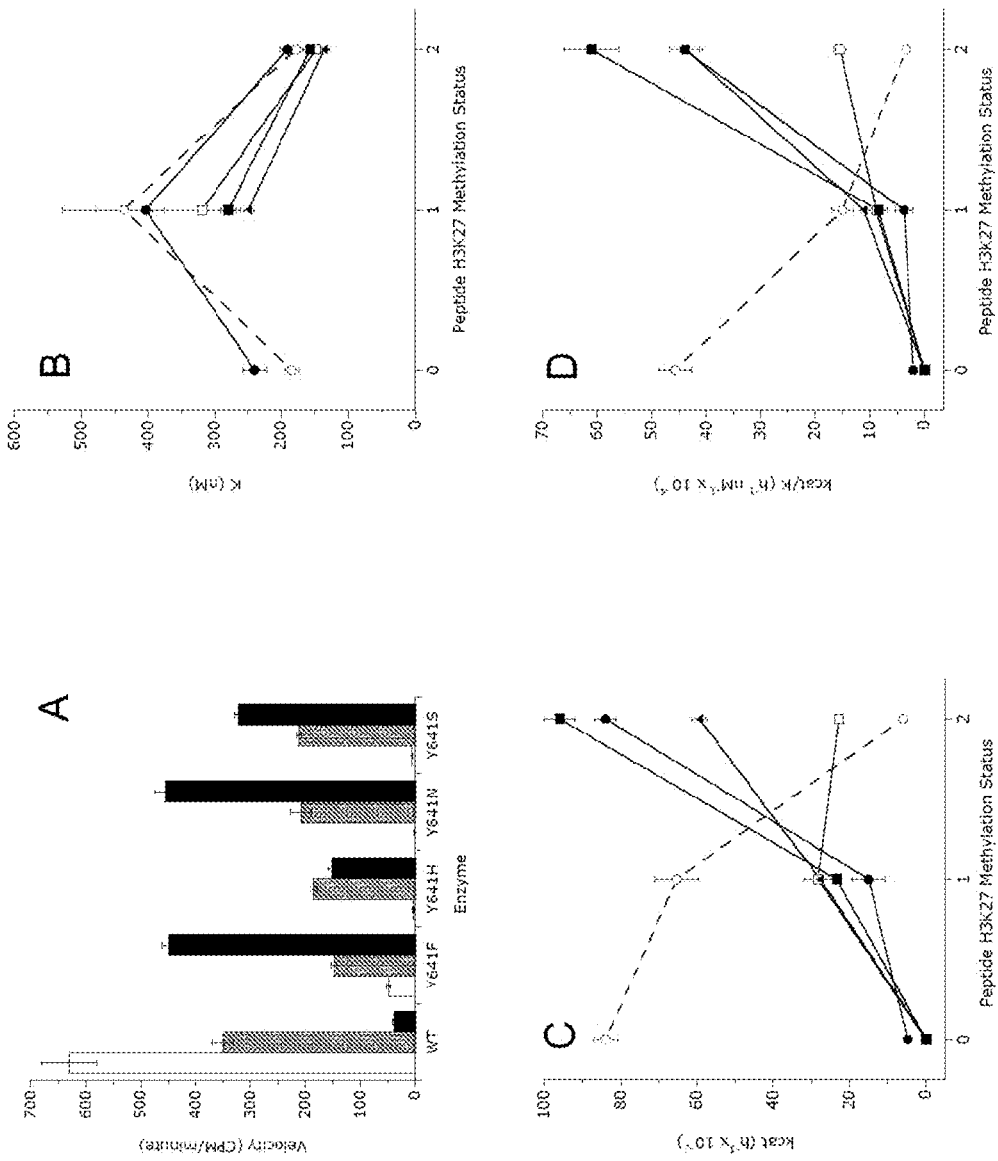
FIG. 2 is four graphs establishing that PRC2 complexes containing mutant EZH2 preferentially catalyze di- and tri-methylation of histone H3-K27. (A) Methyltransferase activity of mutant and wild-type (WT) complexes on unmethylated peptide (open bars), monomethylated peptide (hashed bars), and dimethylated peptide (closed bars). (B) Affinity for peptide substrates as judged by $K_{1/2}$ is similar across all peptide methylation states for PRC2 complexes containing wild-type (○), Y641F (●), Y641H (□), Y641N (■), and Y641S (▲) EZH2. Note that the variation in $K_{1/2}$ values across all substrates and all enzyme forms is less than 3.5-fold. For any particular methylation state of substrate the variation in $K_{1/2}$ value is less than 2-fold. (C) Enzyme turn-over number ($k_{cat}$) varies with substrate methylation status in opposing ways for WT and Y641 mutants of EZH2. The $k_{cat}$ decreases with increasing K27 methylation states for wild-type (○), but increases for Y641F (●), Y641H (□), Y641N (■), and Y641S (▲) mutants of EZH2. (D) Catalytic efficiency ($k_{cat}/K_{1/2}$) decreases with increasing K27 methylation states for wild-type (○), but increases for Y641F (●), Y641H (□), Y641N (■), and Y641S (▲) mutants of EZH2. In panels B-D, the lines drawn to connect the data points are not intended to imply any mathematical relationship; rather, they are merely intended to serve as visual aides.

To understand further the enzymatic activity of these mutants, and to reconcile the apparent discrepancy between activity against peptidic and nucleosome substrates, the ability of the enzyme forms to catalyze further methylation of various H3-K27 methylation states in the context of the H3:21-44 peptide was studied. As stated above, it was found that all of the mutant enzymes were deficient catalysts of unmodified H3-K27 peptide methylation, relative to the WT enzyme. Remarkably, however, all of the mutant enzymes were found to be superior to WT enzyme in catalyzing further methylation of the mono- and especially the di-methylated H3-K27 peptides (FIG. 2). Thus, the data suggest that the WT enzyme is most efficient in catalyzing the zero- to mono-methylation reaction. The mutant enzymes are defective in catalyzing this initial step, but are more efficient than the WT enzyme in catalyzing the subsequent steps leading from mono-methyl to di- and tri-methyl H3-K27.

The origins of the differential substrate specificities of WT and mutant EZH2 were explored through steady state enzyme kinetics. As summarized in Table 2, the mutations have minimal effects on ground-state substrate recognition, as demonstrated by the similar values of $K_m$ for nucleosome and of $K_{1/2}$ for peptide substrates. In all cases the peptidic substrates displayed sigmoidal binding behavior; hence the concentration of peptide resulting in half-maximal velocity is reported here as $K_{1/2}$ instead of the more common Michaelis constant, $K_m$. Copeland (2005) *Evaluation of Enzyme Inhibitors in Drug Discovery: A Guide to Medicinal Chemists and Pharmacologists*, Wiley. The SAM $K_m$ likewise displayed minimal variation among the enzyme forms, ranging from 208±50 to 304±64 nM. Instead, the differences in substrate utilization appear to have their origin in transition state recognition, as demonstrated by differences in $k_{cat}$ values among the enzymes for various substrates (Table 2). As a result, the catalytic efficiency, quantified as the ratio $k_{cat}/K$ (where K is either $K_m$ or $K_{1/2}$, depending on substrate identity; vide supra), varies between the WT and mutant enzymes for different states of H3-K27 methylation (Table 2).

TABLE 2

Steady state kinetic parameters for methylation reactions catalyzed by PRC2 containing wild-type or Y641 mutants of EZH2.

| Enzyme | Substrate H3-K27 Methylation Status | K (nM) | $k_{cat}$ ($h^{-1} \times 10^{-2}$) | $k_{cat}/K$ ($h^{-1} \cdot nM^{-1} \times 10^{-4}$) |
|---|---|---|---|---|
| WT | 0 | 184 ± 10 | 84.0 ± 3.0 | 45.7 ± 3.0 |
|  | 1 | 436 ± 42 | 65.4 ± 5.8 | 15.0 ± 2.0 |
|  | 2 | 178 ± 16 | 6.0 ± 0.3 | 3.4 ± 0.3 |
|  | Nucleosome | 141 ± 31 | 42.6 ± 2.6 | 30.2 ± 6.9 |
| Y641F | 0 | 240 ± 19 | 4.8 ± 0.3 | 2.0 ± 0.2 |
|  | 1 | 404 ± 124 | 15.0 ± 4.3 | 3.7 ± 1.6 |
|  | 2 | 191 ± 10 | 84.0 ± 2.8 | 44.0 ± 2.7 |
|  | Nucleosome | 176 ± 19 | 65.4 ± 2.0 | 37.2 ± 4.2 |
| Y641H | 0 | —[a] | — | — |
|  | 1 | 319 ± 57 | 28.2 ± 3.7 | 8.8 ± 2.0 |
|  | 2 | 148 ± 9 | 22.8 ± 0.9 | 15.4 ± 1.1 |
|  | Nucleosome | 140 ± 22 | 23.4 ± 1.0 | 16.7 ± 2.7 |
| Y641N | 0 | — | — | — |
|  | 1 | 280 ± 11 | 23.4 ± 0.8 | 8.4 ± 0.4 |
|  | 2 | 157 ± 11 | 96.0 ± 4.0 | 61.1 ± 5.0 |
|  | Nucleosome | 191 ± 34 | 23.4 ± 1.3 | 12.3 ± 2.3 |
| Y641S | 0 | — | — | — |
|  | 1 | 249 ± 8 | 27.6 ± 0.8 | 11.1 ± 0.5 |
|  | 2 | 136 ± 8 | 59.4 ± 2.0 | 43.7 ± 3.0 |
|  | Nucleosome | 137 ± 28 | 23.4 ± 1.4 | 17.1 ± 3.6 |

[a]Activity too low to measure.

Example 6

Enzymology

The steady state kinetic parameters listed in Table 2 made it possible to calculate the , expected levels of different H3-K27 methylation states for cells heterozygous for the various mutant EZH2 forms, relative to cells homozygous for the WT enzyme. To perform these simulations, a number of simplifying assumptions were made: (1) that steady state enzyme kinetics are relevant to PRC2-catalyzed H3-K27 methylation in the cellular context and that all measurements are made at the same time point in cell growth; (2) that the mutant and WT enzyme are expressed at equal levels in heterozygous cells and that the total EZH2 level is equal in all cells; (3) that the cellular concentration of SAM, relative to its $K_m$ is saturating and does not change among the cells; (4) that the cellular concentration of nucleosome, is similar to its $K_m$ and likewise does not change among cells; (5) that EZH1 catalyzed methylation of H3-K27 was insignificant and constant among the cells; and (6) that any H3-K27 demethylase activity was also constant among the cells.

Figure 3:
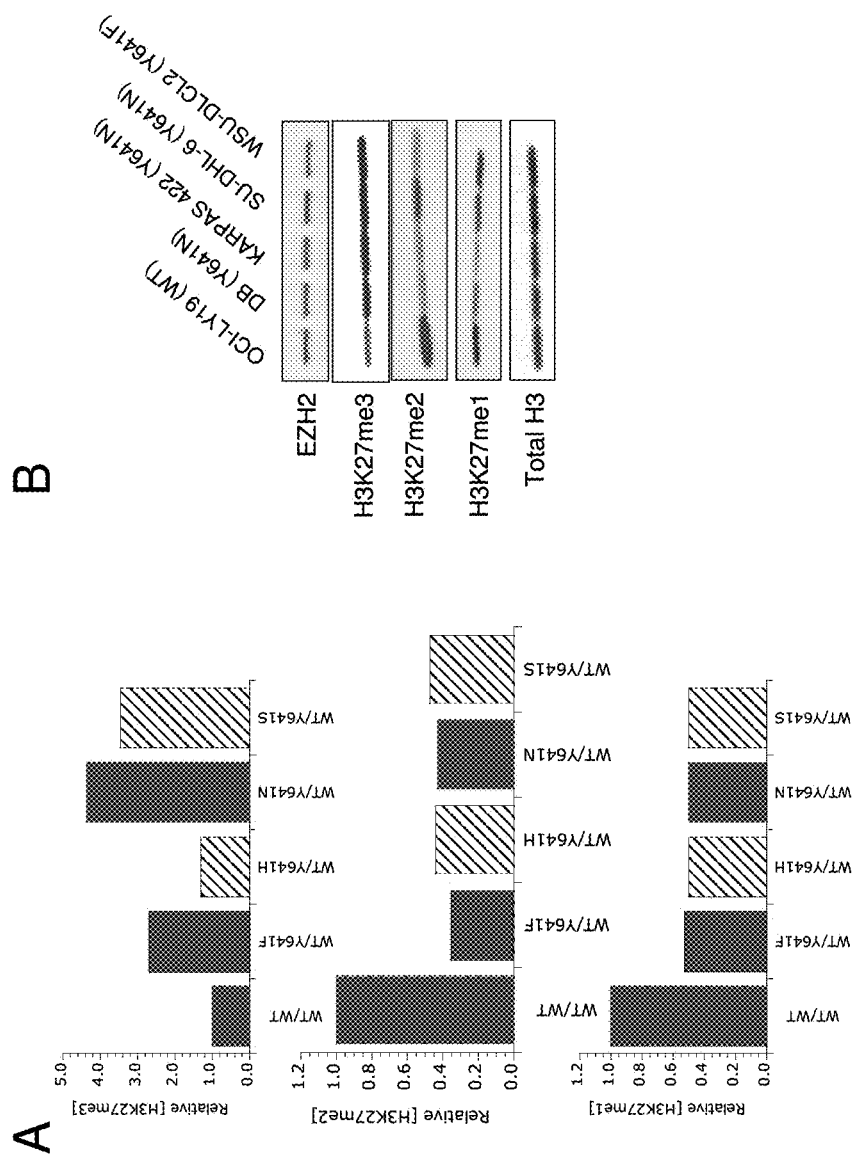
FIG. 3A is a trio of graphs depicting predicted relative levels of H3-K27me3 (top panel), H3-K27me2 (middle panel), and H3-K27me1 (bottom panel) for cells containing different EZH2 mutants. Simulations were performed using a coupled enzyme steady state velocity equation and the steady state kinetic parameters shown in Table 2. All values are relative to the homozygous WT EZH2-containing cells and assume saturating concentrations of intracellular SAM, relative to Km and intracellular nucleosome concentrations similar to Km.
FIG. 3B is a series of Western blot analyses of relative patterns of H3-K27 methylation status for lymphoma cell lines homozygous for WT EZH2, or heterozygous for the indicated EZH2 Y641 mutation. Panels from top to bottom depict the results of probing with antibodies specific for the following: total EZH2; H3-K27me3; H3-K27me2; H3-K27me1; and total histone H3 as loading control.

With these assumptions in place, the predictions illustrated in FIG. 3A were obtained for relative levels of H3-K27me3 (top panel), H3-K27me2 (middle panel) and H3-K27me1 (bottom panel). A clear pattern emerges from these simulations. The level of H3-K27me3 increases relative to WT cells for all mutant-harboring cells, ranging from a 30% increase for the Y641H mutant to >400% for the Y641N mutant. At the same time, the levels of H3-K27me2 decreases to <50% of WT for all of the mutants, and the levels of H3-K27me1 are reduced by approximately half for all mutants, relative to WT.

The relative levels of the H3-K27 methylation states in B-cell lymphoma cell lines that are known to be homozygous for WT EZH2 (OCI-LY19) or heterozygous for EZH2 Y641N (DB, KARPAS 422, and SU-DHL-6) or EZH2 Y641F (WSU-DLCL2) were then measured by Western blotting (FIG. 3B). The pattern of relative H3-K27 methylation states seen in FIG. 3b is in excellent agreement with the results of the simulations based on in vitro steady state kinetic parameters, despite the assumptions used in the simulations and the use of a non-physiological peptide surrogate as substrate.

Thus, increased H3-K27me3 was observed for all Y641 mutant-harboring cells relative to WT, decreased H3-K27me2 was observed for all Y641 mutant-harboring cells relative to WT, and decreased H3-K27me1 was observed for at least two of the four mutant cell lines. The near-comparable levels of H3-K27me1 in WT and KARPAS 422 and SU-DHL-6 cells may reflect different expression levels of WT and mutant EZH2, different contributions of EZH1, or other factors not accounted for in the simulations. Nevertheless, the concordance between the predicted and experimental patterns of H3-K27 methylation status is remarkable and supports the view that enzymatic coupling between WT and mutant EZH2 leads to increased H3-K27me3, thus resulting in the malignant phenotype of cells that are heterozygous for these mutants.

Example 7

In Vitro Assays of PRC2 Methyltransferase Activity

Flashplate Assay with Peptide Substrate.

For initial comparison of WT and Y641 mutants of EZH2, biotinylated histone H3:21-44 peptide containing unmethylated K27 (New England Peptide), monomethylated K27 (Millipore) or dimethylated K27 (Millipore) at a concentration of 800 nM was combined with a mixture of S-adenosyl-methionine-Cl (SAM) at 1,700 nM, and 300 nM tritiated SAM (Perkin Elmer). This substrate combination was then added to the PRC2 in assay buffer (20 mM BICINE, 1 mM DTT, 0.002% Tween 20, 0.005% bovine skin gelatin (BSG), pH 7.6). Reactions were allowed to proceed for the indicated time interval and then quenched by addition of excess cold SAM (600 µM final concentration). Quenched reaction mixtures were transferred to a streptavidin-coated Flashplate (Perkin Elmer, catalog number SMP410), allowed to bind for one hour, and then detected on a TopCount NXT HTS scintillation and luminescence counter (Perkin Elmer). Each time point represented the average of six individual reactions. Steady state kinetic parameters were determined under identical reaction conditions except that the concentration of peptide or SAM was varied, while at saturating conditions of the other substrate. Velocity was plotted as a function of varied substrate concentration and the data were fitted to the untransformed version of the Michaelis-Menten equation or the untransformed version of a sigmoidal kinetic equation to calculate values of K and $k_{cat}$. Standard errors of fitted parameters are listed in Table 2 and were used to construct the error bars illustrated in FIG. 2 panels B and C. Error associated with $k_{cat}/K$ (Table 2) were calculated according to standard methods of error propagation; the fractional error of $k_{cat}/K$ was determined as:

$$\mu \frac{k_{cat}}{K} = \sqrt{\left(\frac{\mu k_{cat}}{k_{cat}}\right)^2 + \left(\frac{\mu K}{K}\right)^2} \quad (1)$$

where $\mu k_{cat}$ is the standard error of $k_{cat}$ and $\mu K$ is the standard error of K.

Filterplate Assay with Oligonucleosome.

Chicken erythrocyte oligonucleosomes were purified as previously described. Fang et al. (2004) *Methods Enzymol* 377:213-26. Nucleosomes were combined with a mixture of SAM and tritiated SAM, and added to PRC2 in assay buffer (20 mM BICINE, 100 mM KCl, 1 mM DTT, 0.002% Tween 20, 0.005% BSG, pH 7.6). Reactions were run and quenched as above. Quenched reaction mixture was transferred to a glass fiber filterplate (Millipore, catalog number MSFBN6B) and washed three times with 10% trichloroacetic acid and allowed to dry. Microscint Zero (30 µL) was added and tritium incorporation was detected on a TopCount scintillation and luminescence counter. Steady state parameters were determined under identical reaction conditions except that the concentration of nucleosome or SAM was varied while at saturating conditions of the other substrate. Velocity was plotted as a function of varied substrate concentration and fitted to the untransformed version of the Michaelis-Menten equation to derive the values of $K_m$ and $k_{cat}$ as described above.

Example 8

Compound Preparation

A. Preparation of Compound 63

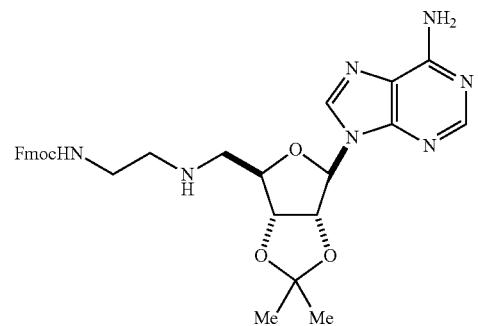

63

To a solution of 9-((3aR,4R,6R,6aR)-6-(aminomethyl)-2,2-dimethyltetrahydrofuro[3,4-d][1,3]dioxol-4-yl)-9H-purin-6-amine (Townsend, A. P. et al. (2009) *Org. Let.* 11:2976-2979) (3.05 g, 9.96 mmol) in DCE (250 mL) was added (9H-fluoren-9-yl)methyl (2-oxoethyl)carbamate (2.8 g, 9.96 mmol) and NaB(OAc)₃H (2.96 g, 13.95 mmol), the mixture stirred for 4 h at room temperature. K₂CO₃ solution was added to pH at 8-9. DCM was added, the organic layer was dried with Na₂SO4, concentrated and purified by SGC (DCM:MeOH=30:1) to give 63 (2.9 g, yield: 50.9%).

B. Preparation of Compound 65

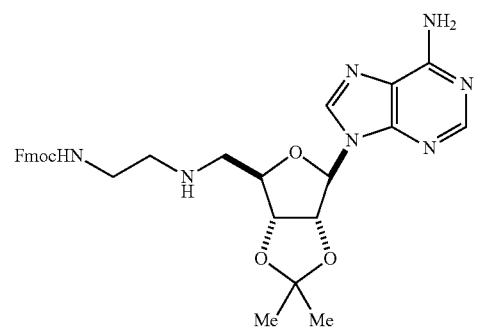

63

123
-continued

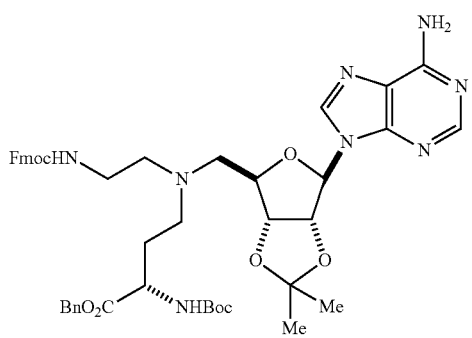
65

To a solution of 63 (2.9 g, 5.08 mmol) in DCE (250 mL), (S)-benzyl 2-((tert-butoxycarbonyl)amino)-4-oxobutanoate (1.56 g, 5.08 mmol) and NaB(OAc)₃H (1.51 g, 7.11 mmol) were added, the mixture stirred for 4 h at room temperature. K₂CO₃ solution was added to pH at 8-9. DCM was added, the organic layer was dried with Na₂SO₄, concentrated and purified with SGC (DCM: MeOH=100:1) to give 65 (2.8 g, yield: 63.9%).

C. Preparation of Compound 75

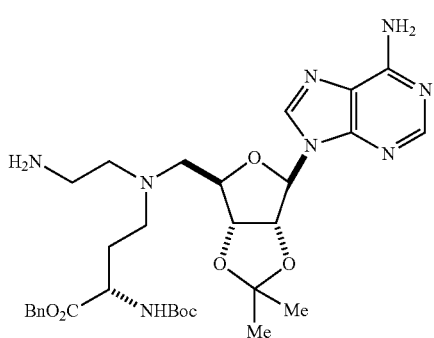
72

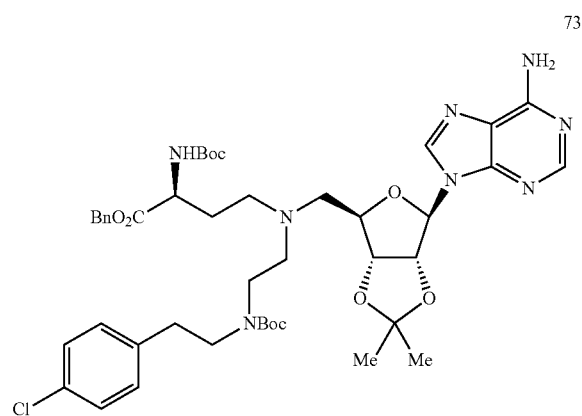
73

124
-continued

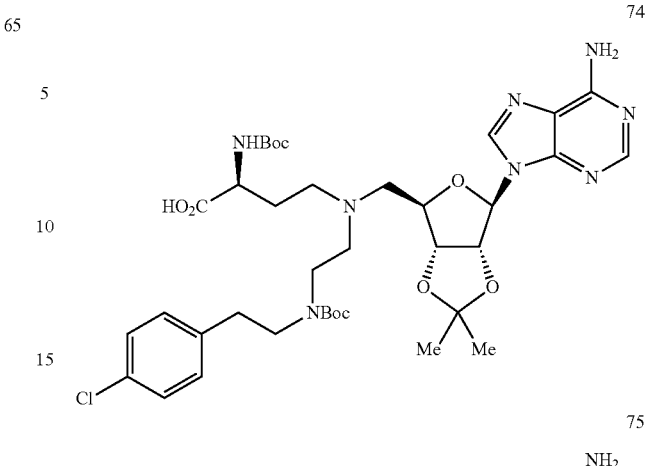
74

75

Step 1. To a solution of 65B (2.2 g, 2.55 mmol) in DCM (10 mL), Et₂NH (1.1 g, 15.3 mmol) were added, the mixture stirred for 4 h at room temperature. The mixture was concentrated to give crude 72 (2.2 g).

Step 2. To a stirred solution of 72 (167 mg, 0.26 mmol) in MeOH (4 mL), 2-(4-chlorophenyl)acetaldehyde (40 mg, 0.26 mmol) was added and stirred at room temperature for 20 min. Then Na(OAc)₃BH (83 mg, 0.39 mmol) and HOAc (0.4 mL) was added and stirred overnight. Then NaHCO₃ (aq) was added and extracted with DCM (25 mL×3), washed with brine, dried with Na₂SO₄ and concentrated. The crude product was purified by preparative TLC (DCM/MeOH=10:1) to afford 73 (30 mg, yield: 14%) as white powder. LC/MS (m/z): 779.7 [M+1]⁺.

Step 3. A mixture of 73 (30 mg, 0.038 mmol) and 10% Pd/C (15 mg) in MeOH (2 mL) was stirred at room temperature under H₂ overnight. The mixture was filtered and the filtrate was concentrated to give crude product. The crude product was purified by preparative TLC (DCM/MeOH=8:1) to afford 74 (20 mg, yield: 69%) as white powder. LC/MS (m/z): 689.7 [M+1]⁺.

Step 4. A solution of 74 (20 mg, 0.028 mmol) in 90% TFA (1 mL) was stirred at room temperature for 1 h, and concentrated as a solid to remove. TFA to give the compound 75 (TFA salt) as a colorless oil without purification. LC/MS (m/z): 549.7 [M+1]⁺.

Example 9

Inhibition of EZH2 Wild-Type and Y641 Mutants by SAH

S-Adenosyl-L-homocysteine (SAH) was serially diluted 3 fold in DMSO for 10 points and 1 µL was plated in a 384 well microtiter plate. Positive control (100% inhibition standard) was 100 µM final concentration of SAH and negative control (0% inhibition standard) contained 1 µL of DMSO. SAH was then incubated for 30 minutes with 40 µL per well of EZH2 wild-type and mutants at 8 nM in pH 7.6 assay buffer (20 mM BICINE, 100 mM KCl, 1 mM DTT, 0.002% TWEEN® 20 (generic: polvsorbate 20), 0.005% BSG). A substrate mix at 10 µL per well was added which contained S-adenosylmethionine-Cl (SAM) at 150 nM and tritiated SAM at 100 nM, and biotinylated oligonucleosome at 150 nM in pH 7.6 assay buffer. Quenched enzyme reaction was transferred to a streptavidin-coated FLASHPLATE™ (Perkin Elmer, catalog number SMP410), allowed to bind for one hour, and detected on a TOPCOUNT NXT™ HTS (Perkin Elmer).

Figure 7:
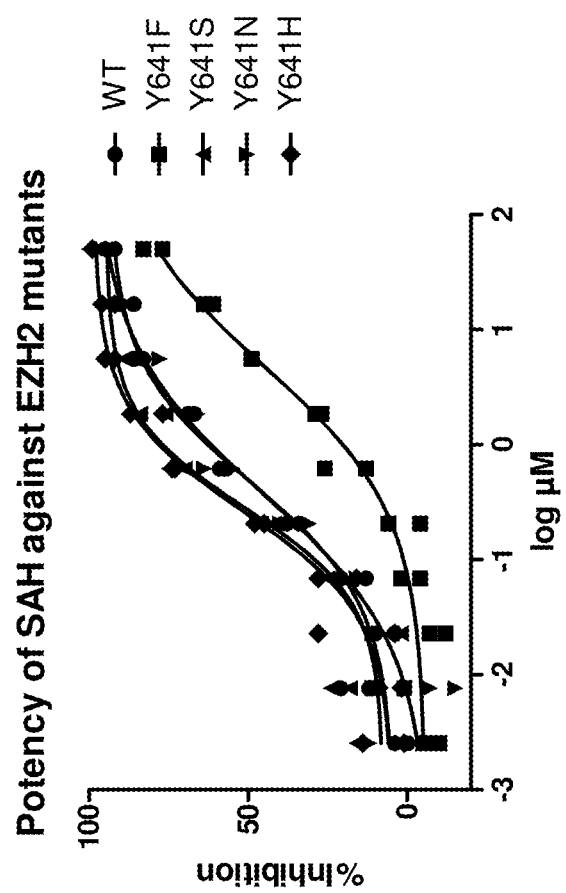
FIG. 7 is a graph depicting inhibitory potency of S-adenosyl-L-homocysteine (SAH) against EZH2 WT and Y641 mutants of EZH2. The X axis shows log concentration of SAH; the Y axis shows percent inhibition.

Results are shown in FIG. 7. IC50 values are shown in Table 3.

TABLE 3

Inhibition of WT EZH2 and Y641 mutants of EZH2 by SAH.

|  | WT | Y641H | Y641S | Y641N | Y641F |
|---|---|---|---|---|---|
| IC50, µM | 0.467 | 0.263 | 0.283 | 0.380 | 4.80 |

Example 10

Inhibition of EZH2 Wild-Type and Y641 Mutants by Compound 75

Compound 75 was serially diluted 3 fold in DMSO for 10 points and 1 µL, was plated in a 384 well microtiter plate. Positive control (100% inhibition standard) was 100 µM final concentration of SAH and negative control (0% inhibition standard) contained 1 µL, of DMSO. Compound 75 was then incubated for 30 minutes with 40 µL per well of EZH2 wild-type and mutants at 8 nM in pH 7.6 assay buffer (20 mM BICINE, 100 mM KCl, 1 mM DTT, 0.002% TWEEN® 20 (generic: polysorbate 20), 0.005% BSG). A substrate mix at 10 µL per well was added which contained S-adenosylmethionine-Cl (SAM) at 150 nM and tritiated SAM at 100 nM, and biotinylated oligonucleosome at 150 nM in pH 7.6 assay buffer. Quenched enzyme reaction was transferred to a streptavidin-coated FLASHPLATE™ (Perkin Elmer, catalog number SMP410), allowed to bind for one hour, and detected on a TOPCOUNT NXT™ HTS (Perkin Elmer).

Figure 8:
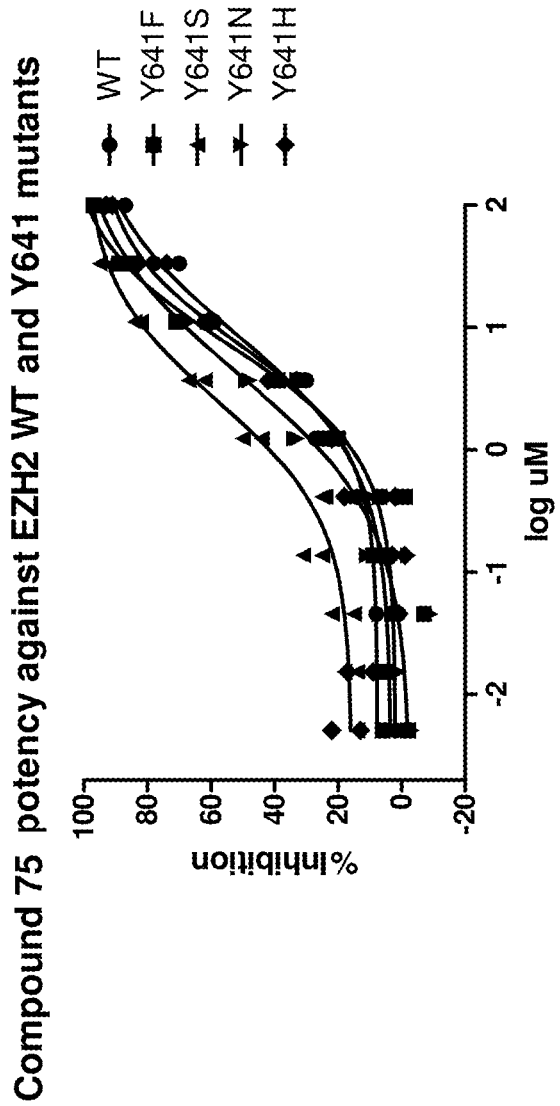
FIG. 8 is a graph depicting inhibitory potency of Compound 75 against EZH2 WT and Y641 mutants of EZH2. The X axis shows log concentration of Compound 75; the Y axis shows percent inhibition.

Results are shown in FIG. 8. IC50 values are shown in Table 4.

TABLE 4

Inhibition of WT EZH2 and Y641 mutants of EZH2 by Compound 75.

|  | WT | Y641S | Y641N | Y641F | Y641H |
|---|---|---|---|---|---|
| IC50, µM | 8.95 | 2.50 | 4.10 | 7.18 | 7.56 |

Example 11

H3-K27me2/me3 Ratios Predict Sensitivity to an EZH2 Inhibitor

Figure 9:
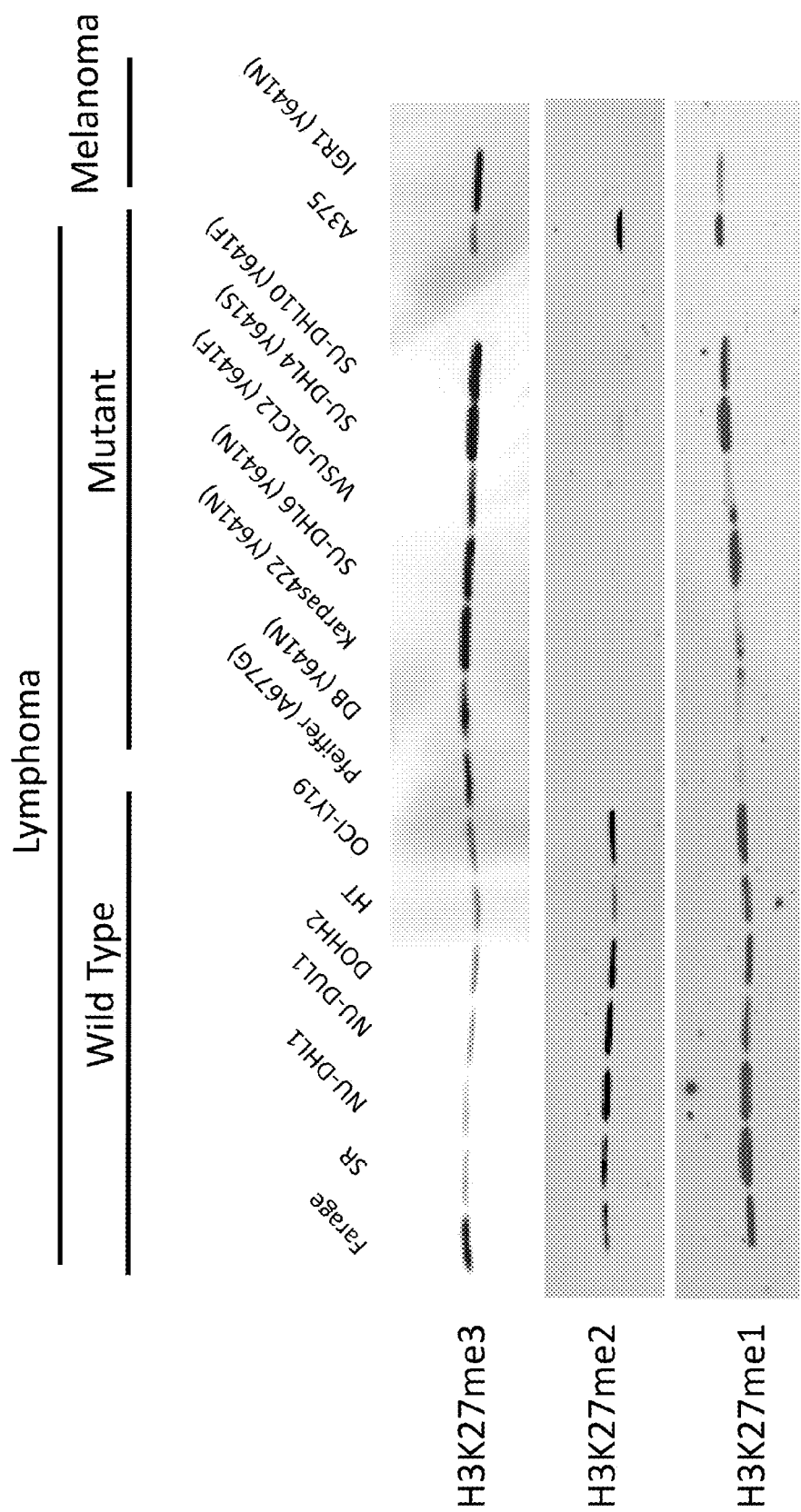
FIG. 9 depicts a Western Blot analysis of relative levels of H3-K27me1, me2 and me3 in a cell line pane, including multiple DLBCL lines expressing WT or Y641 mutatnt EZH2. Histones were extracted from the cell lines shown, fractionated by SDS-PAGE on a 4-20% gel, transferred to nitrocellulose membranes, and probed with antibodies to Histone H3, H3-K27me1, me2, or me3.

Tumor cell lines heterozygous for the EZH2 (Y641) mutation display increased levels of H3-K27me3, the methylation state of H3-K27 thought to be important in tumorigenesis. Levels of the mono (H3-K27me1), di (H3-K27me2), or trimethylated (H3-K27me3) forms of H3-K27 in a panel of cell lines that were WT for EZH2, or heterozygous for EZH2 (Y641) mutations were evaluated. Cell lines used are listed in Table 5. The majority of lines are B-cell lymphoma lines, however two melanoma lines were also included. IGR1 is a melanoma line that has recently been found to contain a Y641N mutation in EZH2, and A375 cells were included as a WT EZH2 melanoma control line. FIGS. 9A and B show the results of western blot analysis of histones isolated from this cell line panel probed with antibodies recognizing H3-K27me1, H3-K27me2, or H3-K27me3. In general, global H3-K27me3 levels are higher in Y641 mutant containing cell lines than in cell lines expressing WT EZH2 exclusively. The exception is Farage cells, where H3-K27me3 levels were similar to those in WT lines. More striking are the dramatically lower levels of H3-K27me2 in EZH2 Y641 mutant cell lines relative to wild type cell lines. Little or no H3-K27me2 signal was observed in western blot of histones extracted from Y641 mutant cell lines, whereas the signal observed with the same antibody in WT cell lines was more intense than that observed with the antibody specific for H3-K27me3. Overall, in WT cell lines the western blot signal with an HK27me2 antibody was higher than the signal observed with the H3-K27me3 antibody, whereas the opposite was true in Y641 mutant cell lines. Thus the ratio of H3-K27me3/me2 signal in Y641 lines is higher than that observed in WT lines.

The H3-K27 methylation state can also be examined by Mass spectrometry (MS), an independent method that does not rely on antibody reagents. The MS analysis demonstrated that H3-K27me3 levels are higher in Y641 mutant and Pfeiffer lines (A677G) than in the other WT lines, whereas the opposite is true for H3-K27me2 levels. In the Y641 mutant and Pfeiffer lines (A677G), H3-K27me3 levels were higher than H3-K27me2 levels, whereas the opposite was true in the other WT lines. These results are consistent with those observed by western blot analysis in FIGS. 9A and B.

Figure 10:
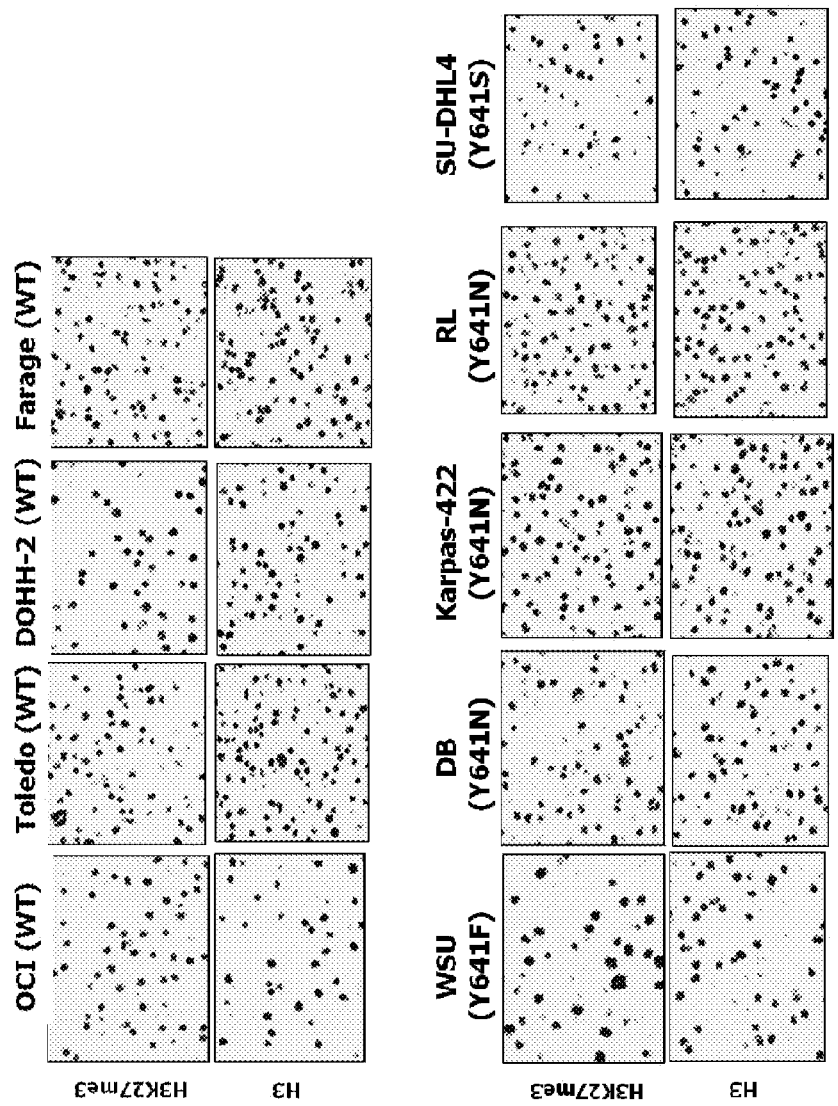
FIG. 10 depicts an immunocytochemistry analysis of H3 and H3-K27me3 levels in a panel of WT and Y641 mutant lymphoma cell lines. Cell pellets from the indicated cell lines were fixed and embedded in paraffin. Slides were prepared and levels of H3 and H3-K27me3 were evaluated by immunocytochemistry using antibodies to histone H3, or H3-K27me3.
Figure 11:
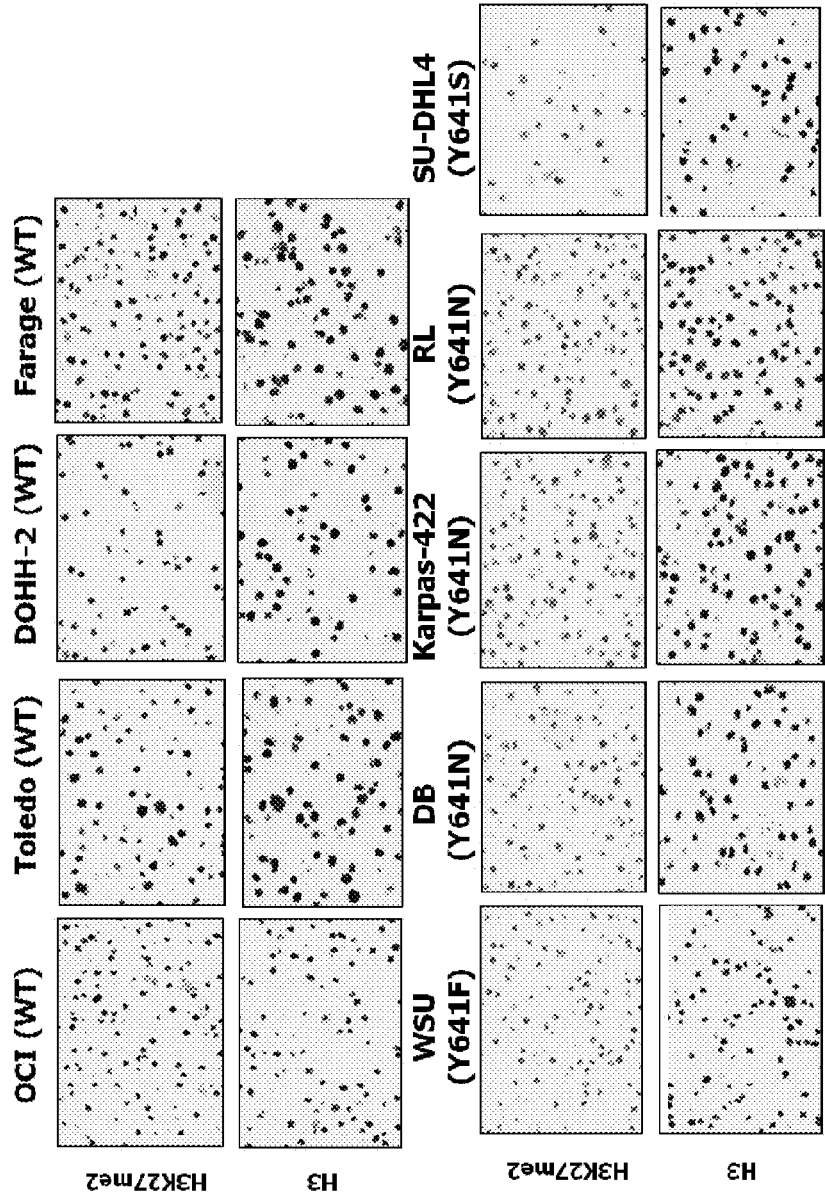
FIG. 11 depicts an immunocytochemistry analysis of H3 and H3-K27me2 levels in a panel of WT and Y641 mutant lymphoma cell lines. Cell pellets from the indicated cell lines were fixed and embedded in paraffin. Slides were prepared and levels of H3 and H3-K27me2 were evaluated by immunocytochemistry using antibodies to histone H3, or H3-K27me2.

The differences in H3-K27 methylation state was also detected by immunocytochemistry using antibodies to H3-K27me2 or H3-K27me3. This immunohistochemistry assay is used for detecting aberrant H3-K27me2/3 ratios associated with Y641 mutant EZH2 in formalin fixed paraffin embedded patient tumor tissue samples. A panel of five WT and five Y641 mutant lymphoma cell line pellets were fixed and embedded in paraffin blocks and stained with anti-H3-K27me2 or H3-K27me3 antibodies. An antibody to histone H3 was included as a positive control, since all cells should contain nuclear histone H3. FIG. 10 shows that all cell lines were positive in 100% of cells for both H3-K27me3 and H3 staining. Under these conditions, no clear difference in H3-K27me3 staining intensity was observed between WT and Y641 mutant cell lines. This may reflect the limited dynamic range of chromogenic immunocytochemistry staining compared to other methods of detection. However, as shown in FIG. 11, cell lines could be clearly segregated into those staining positive or negative for H3-K27me2. All WT cell lines stained positive for H3-K27me2, whereas all Y641 mutant cell lines and Pfeiffer cells (A677G) showed no staining with the H3-K27me2 antibody. These results are consistent with those obtained by western and MS analysis.

Figure 12:
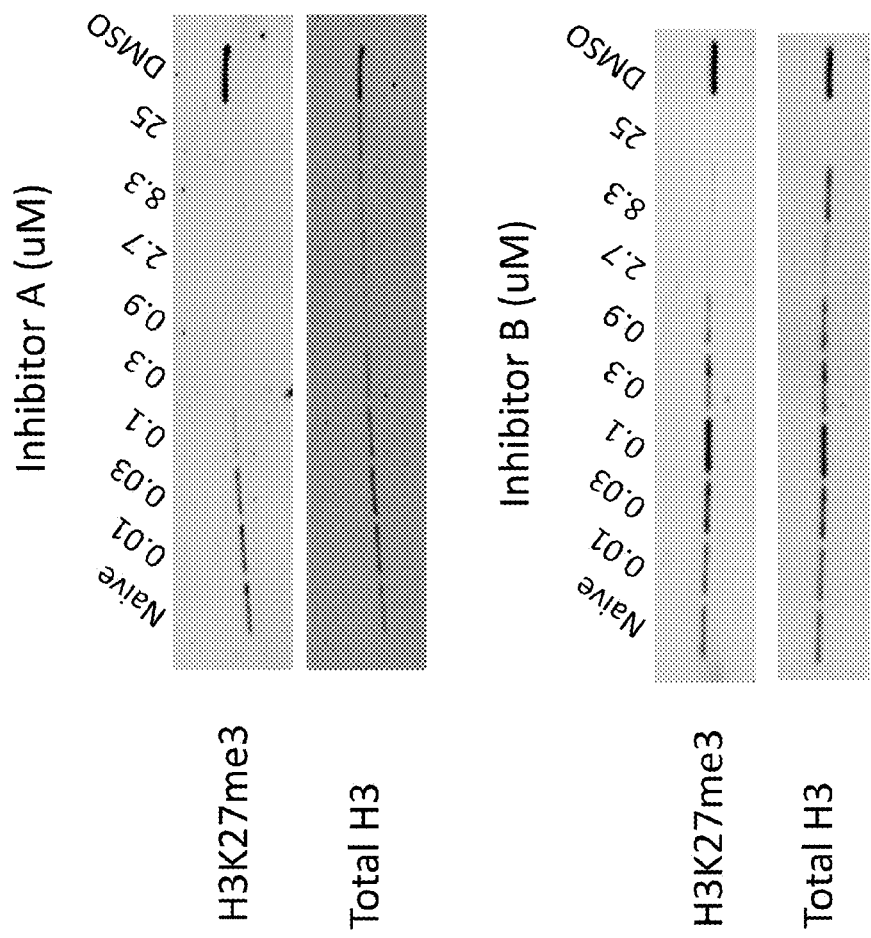
FIG. 12 is a graph depicting the inhibition of global H3-K27me3 levels by EZH2 inhibitor treatment in Y641 mutant WSU-DLCL2 cells. WSU-DLCL2 cells were treated for 4 days with the indicated concentrations of EZH2 inhibitor A or B. Following compound treatment, histones were extracted, fractionated by SDS-PAGE on a 4-20% gel, transferred to nitrocellulose membranes, and probed with antibodies to Histone H3, or H3-K27me3.

Without wishing to be bound by theory, the increased levels of H3-K27me3 associated with the gain of function EZH2 (Y641) mutations may render cells bearing EZH2 mutations more sensitive to small molecule EZH2 inhibitors. To evaluate whether the increased H3-K27me3 and/or decreased H3-K27me2 levels observed in Pfeiffer cells in the absence of an EZH2 Y641 mutation would also correlate with sensitivity to EZH2 inhibitors, two compounds that demonstrate potent inhibition of EZH2 in biochemical assays with IC50s of 85 and 16 nM respectively were tested. Treatment of WSU-DLCL2 cells with either compound led to inhibition of global H3-K27me3 levels, confirming their ability to enter cells and inhibit cellular EZH2 methyltransferase activity (FIG. 12).

The sensitivity of a panel of WT and Y641 mutant cell lines to each compound was evaluated in proliferation assays. Because the anti-proliferative activity of EZH2 inhibitors takes several days to manifest, compounds were assessed in 11-day proliferation assays. FIG. 13 shows representative growth curves for WT (OCI-LY19), or Y641 mutant (WSU-DLCL2) cell lines treated with the test compounds. Both compounds demonstrated anti-proliferative activity against WSU-DLCL2 cells, but little activity against OCI-LY19 cells. Inhibitor A was a more potent inhibitor of WSU-DLCL2 proliferation than Inhibitor B and this is consistent with Inhibitor A being a more potent inhibitor of EZH2 in biochemical assays. Proliferation assays were performed in a panel of WT and Y641 mutant lymphoma cell lines, with Inhibitor B, and day 11 IC90 values were derived. FIG. 14A shows IC90 values of lymphoma cell lines grouped by EZH2 Y641 status. Overall, Y641 mutant cell lines demonstrated increased sensitivity to EZH2 inhibitors relative to WT cell lines, although RL and SUDHL4 cells were significantly less sensitive than other mutant lines. Pfeiffer cells (A677G) demonstrate high H3-K27me3 and low H3-K27me2 levels, and so grouping cell lines according to high H3-K27me3 and low H3-K27me2 gives better discrimination of EZH2 inhibitor sensitivity as shown for Inhibitor B in FIG. 14B. Thus, high H3-K27me3 and low H3-K27me2 levels can be used to predict sensitivity to EZH2 inhibitors, independent of knowledge of mutational status.

These results demonstrates that identifying EZH2 Y641 mutations in patient tumors and/or detecting low levels of H3-K27me2 relative to H3-K27me3 through use of techniques such as western blot, MS or IHC in a patient can be used to identify which patient will respond to EZH2 inhibitor treatment.

TABLE 5

Cell lines used in this study.

| Cancer | EZH2 Status | Cell Line |
|---|---|---|
| Lymphoma: DLBCL (Diffuse Large Cell B Cell Lymphoma) and other B-cell Lymphoma | Wild Type | OCI-LY19 HT MC116 BC-1 BC-3 Toledo DOHH-2 Farage SR NU-DHL-1 NU-DUL-1 |
| | Y641 Mutation | SU-DHL-10 (Y641F) DB (Y641N) KARPAS 422 (Y641N) SU-DHL-6 (Y641N) WSU-DLCL-2 (Y641F) RL (Y641N) SU-DHL-4 (Y641S) |
| Melanoma | Wild Type | A375 |
| | Y641 Mutation | IGR-1 (Y641N) |

Example 12

Recombinant 4-Component PRC2 Complexes

Wild-type (WT) EZH2 (GenBank Accession No. NM_004456) or A677G and A687V mutants were co-expressed with wild-type EED (GenBank Accession No. NM_003797), SUZ12 (GenBank Accession No. NM_015355) and RbAp48 (GenBank Accession No. NM005610) in Spodoptera frugiperda (Sf9) cells using a baculovirus expression system. An N-terminal FLAG tag on the EED was used to purify active PRC2 complex from cell lysates. The purity of the final PRC2 preparations was assessed by SDS-PAGE with Coomassie blue staining and protein concentration was determined using a bovine serum albumin standard curve in a Bradford assay.

Example 13

In Vitro Assays of PRC2 Methyltransferase Activity

Standard Procedure for Flashplate assay with peptide substrates. Activity of the wild-type or mutant EZH2-containing PRC2 complexes was investigated using a series of four peptides representing the amino acid sequence of human H3 from residues 21-44(H3:21-44) with lysine 27 represented as the unmodified, monomethylated, dimethylated or trimethylated side chain amine, consisting of the following sequence, with the H3-K27 lysine subject to modification underlined, ATKAARKSAPATGGVKKPHRYRPGG[K-Ahx-Biot]-amide (SEQ ID NO: 20). Biotin (Biot) was appended to a C-terminal lysine (K) residue through an aminohexyl linker (AHX) attached to the lysine side chain amine (21$^{st}$ Century Biochemicals). For comparison of mutant of WT and mutant EZH2 activity, biotinylated histone H3:21-44 peptides were combined with a mixture of S-adenosylmethionine (SAM; Sigma-Aldrich) and tritiated SAM ($^3$H-SAM; American Radiolabeled Chemicals) and recombinant 4-component PRC2 in assay buffer (20 mM BICINE, 1 mM DTT, 0.002% Tween 20, 0.005% bovine skin gelatin (BSG), pH 7.6). Reactions were allowed to proceed for the indicated time interval and then quenched by addition of excess cold SAM (100 tM final concentration). Quenched reaction mixtures were transferred to a streptavidin-coated FLASHPLATE™ (Perkin Elmer, catalog number SMP410), and allowed to bind for one hour before the plates were washed in a Biotek EL-405× platewasher and read on a TOPCOUNT NXT™ HTS scintillation and luminescence counter (PerkinElmer).

Example 14

Enzymology

Figure 15:
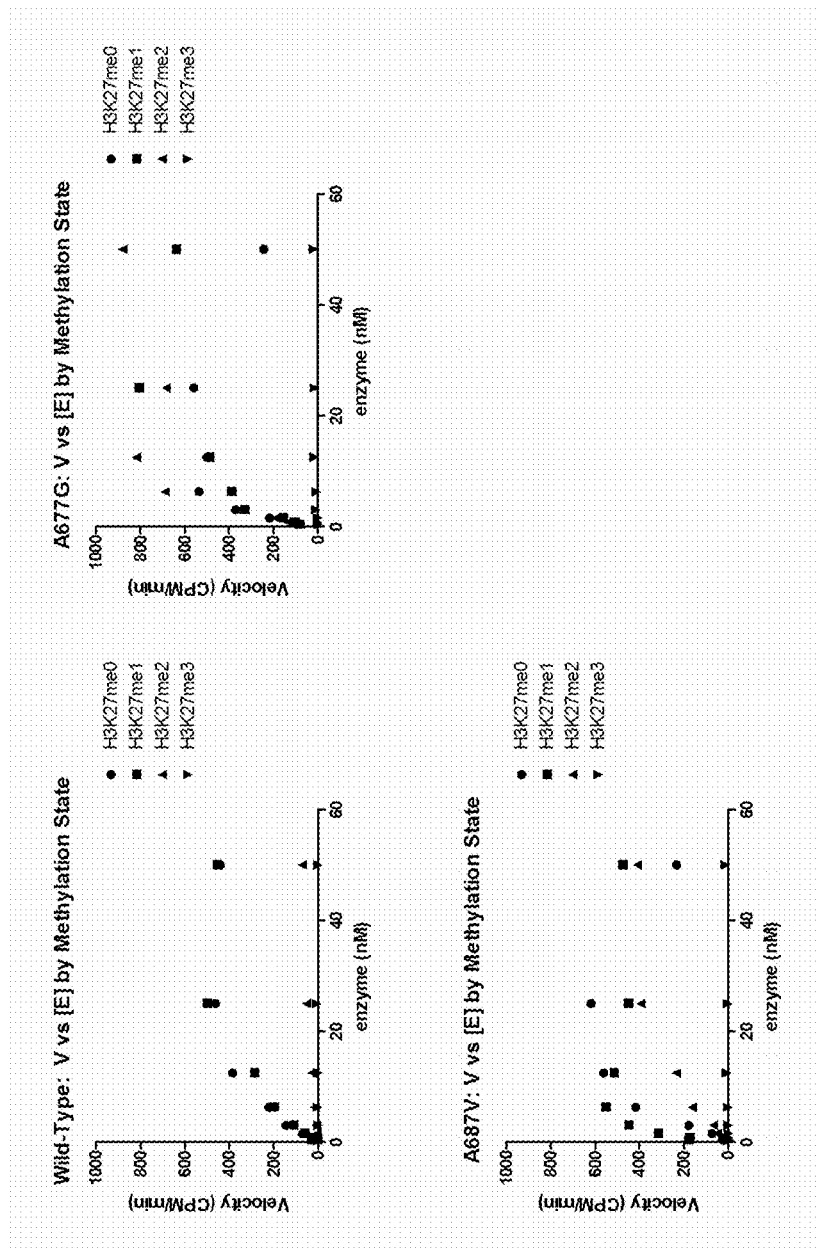
FIG. 15 is a panel of graphs showing velocity vs. enzyme concentration measured for wild-type, A677G or A687V EZH2. Biotinylated peptides representing histone H3 residues 21-44 containing un-, mono-, di- or trimethyl lysine 27 (H3K27me0 through H3K27me3) were assayed at a fixed concentration with a dilution series of the indicated EZH2 enzyme. Timepoints were sampled over the course of 90 minutes and 3H-SAM incorporation at lysine 27 of the H3 peptide was measured by capturing the peptide in a Flashplate and reading the counts per minute (CPM). Linear regression of the timecourse yielded enzyme velocity in CPM per minute (CPM/min) which was plotted as a function of enzyme concentration.

Recombinant 4-component PRC2 complexes were prepared with wild-type and either A677G or A687V mutant versions of EZH2 (see Example 12 above; Cao et al. (2004) *Mol Cell* 15:57-67). Each complex was initially tested for the ability to catalyze $^3$H-methyl transfer from labeled S-adenosyl methionine (SAM) to each of the four H3:21-44 peptides. Enzyme was serially diluted, and a mixture of peptide (200 nM) and SAM (200 nM $^3$H-SAM and 800 nM unlabeled SAM) was added. Reactions were quenched at 15 minute intervals by the addition of an excess of unlabeled SAM and reaction velocity was calculated based on the linear regression of raw counts per minute (CPM) vs. time. As shown in FIG. 15, the mutant enzymes displayed a different pattern of activity than the wild-type enzyme. The A677G and A687V mutants had robust activity on all of the unmethylated, monomethylated and dimethylated H3:21-44 peptides, whereas the wild-type enzyme only showed robust activity on the unmethylated and monomethylated peptides. The control peptide, containing fully trimethylated H3-K27 was not methylated in the assay, indicating that H3-K27 was the target lysine.

Example 15

Enzymology

To further understand the enzymatic activity of these mutants, the origins of the differential substrate specificities of wild-type and mutant EZH2 were explored through steady-state enzyme kinetics. Reactions containing a titration of the H3-K27 peptides with fixed enzyme (4 nM) and SAM (200 nM $^3$H-SAM and 800 nM unlabeled SAM) were performed. In all cases the peptidic substrates displayed sigmoidal binding behavior; hence the concentration of peptide resulting in half-maximal velocity is reported here as $K_{1/2}$ instead of the more common Michaelis-Menten constant, $K_m$ (Copeland (2005) *Evaluation of Enzyme Inhibitors in Drug Discovery: A Guide to Medicinal Chemists and Pharmacologists*, Wiley). As summarized in Table 6, the mutations have an effect on ground-state substrate recognition as demonstrated by lower $K_{1/2}$ for the unmethylated peptide substrates and higher $K_{1/2}$ values for the dimethylated peptide substrates. Additionally, the maximal velocities of the enzymes are affected by the mutations. The A677G mutation leads to 2.9-, 3.7- and 22-fold increases in $k_{cat}$ on respective un-, mono-, and dimethyl H3-K27 peptide substrates, while the A687V mutation results in a 3-fold reduction in $k_{cat}$ on the unmethyl H3-K27 peptide, but produces respective 3.5- and 2.5-fold increases in $k_{cat}$ on the mono- and dimethyl H3-K27 peptides. The SAM $K_m$ displayed minimal variation among the enzyme forms, 403±64 nM to 899±89 nM on the substrate containing the preferred methylation state at the H3-K27 residue.

TABLE 6

Summary of Steady-State Enzyme Kinetics for WT and Mutant EZH2 Enzymes

| Enzyme | Peptide Substrate H3-K27 Methylation Status | $K_{1/2}$ (nM) | $k_{cat}$ (h$^{-1}$) | $k_{cat}/K_{1/2}$ (h$^{-1}$ · nM$^{-1}$ × 10$^{-4}$) |
|---|---|---|---|---|
| *WT | 0 | 154 ± 12 | 4.80 ± 0.20 | 305 ± 26 |
| | 1 | 337 ± 26 | 3.33 ± 0.21 | 99 ± 9 |
| | 2 | 144 ± 11 | 1.08 ± 0.04 | 75 ± 6 |
| A677G | 0 | 88 ± 6 | 14.05 ± 0.54 | 1590 ± 120 |
| | 1 | 222 ± 51 | 12.25 ± 1.67 | 570 ± 150 |
| | 2 | 522 ± 117 | 23.85 ± 3.60 | 450 ± 120 |
| A687V | 0 | 43 ± 3 | 1.58 ± 0.08 | 370 ± 30 |
| | 1 | 176 ± 13 | 11.49 ± 0.50 | 650 ± 60 |
| | 2 | 352 ± 155 | 2.70 ± 0.65 | 80 ± 40 |

*Wild-type data was previously published in Wigle et al., *Febs Lett* (2011) Oct 3; 585(19): 3011-4 using 4-component EZH2.

Example 16

Inhibition of Wild-Type EZH2 and EZH2 Mutants by EZH2 Inhibitors

Test compounds were serially diluted 3-fold in DMSO in a 10 point-curve and 1 µL was spotted into a 384-well microplate in duplicate using a Platemate Plus equipped with 384-channel head (Thermo Scientific). The final top concentration of test compounds in the assay was 10 µM. Positive control (100% inhibition standard) was 1 mM final concentration of SAH and negative control (0% inhibition standard) contained 1 µL of DMSO. Test compounds were then incubated for 30 minutes with 40 µL per well of wild-type EZH2 (final concentration was 4 nM), Y641F EZH2 (final concentration was 0.1 nM) and A677G and A687V EZH2 (for each, final concentration was 2nM) and peptide in 1× assay buffer (20 mM BICINE pH =7.6, 1 mM DTT, 0.002% TWEEN® 20 (generic: polysorbate 20), 0.005% BSG). For the wild-type EZH2 and A677G EZH2 assays, biotinylated peptide H3:21-44 with unmethylated K27 was present at a final concentration of 200 nM, while in the A687V EZH2 assay, biotinylated peptide H3:21-44 with monomethylated K27 was present at a final concentration of 200 nM and in the Y641F EZH2 assay biotinylated peptide H3:21-44 with dimethylated K27 was present at a final concentration of 200 nM. To initiate the reaction containing the wild-type EZH2 enzyme, a substrate mix of 10 µL per well was added that contained unlabeled SAM (final concentration was 1800 nM) and $^3$H-SAM (final concentration was 200 nM) in 1× assay buffer. To initiate the reaction containing the Y641F EZH2 enzyme a substrate mix of 10 µL per well was added that contained unlabeled SAM (final concentration was 700 nM), and $^3$H-SAM (final concentration was 300 nM) in 1× assay buffer. To initiate the reactions containing the A677G or A687V EZH2, a substrate mix of 10 µper well was added which contained unlabeled SAM (final concentration was 400 nM) and $^3$H-SAM (final concentration was 100 nM). Reactions proceeded for 90 min, then were quenched with excess unlabeled SAM (167 µM), then were transferred to a streptavidin-coated FLASH-PLATET™ (PerkinElmer, catalog number SMP410), allowed to bind for one hour, and detected on a TOPCOUNT NXT™ HTS (PerkinElmer). The IC$_{50}$ values are obtained from 4-parameter fits of the % inhibition of enzyme activity and are tabulated in Table 7. The formulae used to derive IC$_{50}$ values are indicated below.

$$\% \ inh = 100 - \left(\frac{dpm_{cmpd} - dpm_{min}}{dpm_{max} - dpm_{min}}\right) \times 100$$

Where dpm=disintegrations per minute, cmpd=signal in assay well, and min and max are the respective minimum and maximum signal controls.

Four-Parameter 1050 Fit $$Y = Bottom + \frac{(Top - Bottom)}{\left(1 + \left(\frac{X}{IC_{50}}\right)^{HillCoefficient}\right)}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

TABLE 7

Inhibition of wild-type and mutant EZH2 by EZH2 inhibitors

| Compound Number | EZH2 Inhibitor | WT (uM) | Y641F (uM) | A677G (uM) | A687V (uM) |
|---|---|---|---|---|---|
| 1. | SAH | 6.9082 | 16.6193 | 6.2379 | 5.9034 |
| 2. | EPZ004710 | 2.9758 | 3.7887 | 0.3187 | 0.5378 |
| 3. | EPZ004744 | 1.5203 | 0.7432 | 0.1128 | 0.1354 |
| 4. | EPZ005030 | 0.2600 | 0.1846 | 0.0418 | 0.0504 |
| 5. | EPZ005100 | 0.3579 | 0.2923 | 0.0316 | 0.0599 |

TABLE 7-continued

Inhibition of wild-type and mutant EZH2 by EZH2 inhibitors

| Compound Number | EZH2 Inhibitor | WT (uM) | Y641F (uM) | A677G (uM) | A687V (uM) |
|---|---|---|---|---|---|
| 6. | EPZ005260 | 2.3755 | 1.5781 | 0.2130 | 0.3189 |
| 7. | EPZ005687 | 0.0950 | 0.0750 | 0.0113 | 0.0082 |
| 8. | EPZ006089 | 0.2300 | 0.3110 | 0.0190 | 0.0277 |
| 9. | EPZ006438 | 0.0062 | 0.0111 | 0.0022 | 0.0015 |
| 10. | EPZ006632 | 0.0025 | 0.0034 | 0.0040 | 0.0032 |
| 11. | EPZ007038 | 0.0099 | 0.0123 | 0.0060 | 0.0032 |
| 12. | EPZ007209 | 0.0065 | 0.0074 | 0.0086 | 0.0068 |
| 13. | EPZ007210 | 0.0043 | 0.0044 | 0.0038 | 0.0036 |
| 14. | EPZ007227 | 0.0143 | 0.0207 | 0.0122 | 0.0128 |
| 15. | EPZ007426 | 0.0181 | 0.0088 | 0.0034 | 0.0040 |
| 16. | EPZ007428 | 0.0014 | 0.0055 | 0.0019 | 0.0021 |
| 17. | EPZ007478 | 0.0088 | 0.0114 | 0.0042 | 0.0071 |
| 18. | EPZ007648 | 0.0025 | 0.0079 | 0.0058 | 0.0067 |
| 19. | EPZ007649 | 0.0094 | 0.0092 | 0.0096 | 0.0082 |
| 20. | EPZ007655 | 0.0125 | 0.0104 | 0.0192 | 0.0171 |
| 21. | EPZ007692 | 0.0100 | 0.0117 | 0.0116 | 0.0103 |
| 22. | EPZ007789 | 0.0108 | 0.0114 | 0.0048 | 0.0051 |
| 23. | EPZ007790 | 0.0169 | 0.0158 | 0.0073 | 0.0065 |
| 24. | EPZ008205 | 0.0129 | 0.0093 | 0.0112 | 0.0101 |
| 25. | EPZ008277 | 0.0333 | 0.0092 | 0.0023 | 0.0055 |
| 26. | EPZ008278 | 0.0384 | 0.0106 | 0.0093 | 0.0191 |
| 27. | EPZ008279 | 0.0223 | 0.0182 | 0.0022 | 0.0051 |
| 28. | EPZ008280 | 0.0067 | 0.0029 | 0.0028 | 0.0039 |
| 29. | EPZ008286 | 0.0043 | 0.0025 | 0.0015 | 0.0018 |
| 30. | EPZ008335 | 0.0065 | 0.0033 | 0.0015 | 0.0029 |
| 31. | EPZ008336 | 0.0057 | 0.0036 | 0.0013 | 0.0024 |
| 32. | EPZ008337 | 0.0087 | 0.0015 | 0.0008 | 0.0014 |
| 33. | EPZ008338 | 0.0120 | 0.0096 | 0.0031 | 0.0072 |
| 34. | EPZ008344 | 0.0124 | 0.0036 | 0.0016 | 0.0046 |
| 35. | EPZ008491 | 0.0091 | 0.0014 | 0.0029 | 0.0029 |
| 36. | EPZ008493 | 0.1320 | | 0.0127 | 0.0882 |
| 37. | EPZ008494 | 0.0079 | 0.0046 | 0.0028 | 0.0038 |
| 38. | EPZ008495 | 0.0134 | 0.0104 | 0.0063 | 0.0084 |
| 39. | EPZ008496 | 0.0154 | 0.0104 | 0.0040 | 0.0076 |
| 40. | EPZ008497 | >10.0 uM | 3.2876 | 0.9735 | 1.2184 |
| 41. | EPZ008592 | 0.0145 | 0.0051 | 0.0035 | 0.0075 |
| 42. | EPZ008623 | 0.2440 | 0.1835 | 0.0922 | 0.1067 |
| 43. | EPZ008630 | 0.0034 | 0.0029 | 0.0035 | 0.0032 |
| 44. | EPZ008681 | 0.0029 | 0.0015 | 0.0027 | 0.0047 |
| 45. | EPZ008686 | 0.0073 | 0.0055 | 0.0045 | 0.0096 |
| 46. | EPZ008989 | 0.0094 | 0.0069 | 0.0022 | 0.0028 |
| 47. | EPZ008990 | 0.0061 | 0.0067 | 0.0016 | 0.0017 |
| 48. | EPZ008991 | 0.0348 | 0.0293 | 0.0094 | 0.0193 |
| 49. | EPZ008992 | 0.3333 | 0.1678 | 0.0638 | 0.1188 |
| 50. | EPZ008994 | 0.0715 | 0.0275 | 0.0121 | 0.0205 |
| 51. | EPZ009090 | 0.0300 | 0.0111 | 0.0120 | 0.0227 |
| 52. | EPZ009097 | 0.0047 | 0.0039 | 0.0046 | 0.0036 |
| 53. | EPZ009099 | 0.0765 | 0.0255 | 0.0057 | 0.0222 |
| 54. | EPZ009152 | 0.0030 | 0.0031 | 0.0029 | 0.0033 |
| 55. | EPZ009153 | 0.0052 | 0.0032 | 0.0056 | 0.0037 |
| 56. | EPZ009154 | 0.0278 | 0.0420 | 0.0141 | 0.0438 |
| 57. | EPZ009155 | 0.0563 | 0.0524 | 0.0251 | 0.0623 |
| 58. | EPZ009156 | 0.0034 | 0.0217 | 0.0051 | 0.0132 |
| 59. | EPZ009157 | 0.0397 | 0.0443 | 0.0214 | 0.0436 |
| 60. | EPZ009158 | 0.0021 | 0.0016 | 0.0027 | 0.0027 |
| 61. | EPZ009161 | 0.0009 | | 0.0008 | 0.0011 |
| 62. | EPZ009162 | 0.0657 | 0.0351 | 0.0146 | 0.0178 |

Example 17

A677 Mutant Shows the Highest Sensitivity to the EZH2 Inhibitors

Pfeiffer cells were obtained from ATCC (CRL-2632). WSU-DLCL2 (ACC 575) and OCI-Ly19 (ACC 528) cells were obtained from DSMZ. All cells were maintained in RPMI +10% FBS. For cell proliferation analysis, exponentially growing Pfeiffer, WSU-DLC2, or OCI-Ly19 cells were plated, in triplicate, in 96-well plates at a density of $1 \times 10^4$ cells/mL, $5 \times 10^4$ cells/mL, or $2.5 \times 10^5$ cells/mL (respectively) in a final volume of 150 uL. Cells were incubated with Compound #7 at final concentrations ranging from 0.011 to 25 uM for $IC_{50}$ determination over an 11-day time course. Cells were incubated with Compound #13 at final concentrations ranging from 0.00004 to 10 uM for $IC_{50}$ determination over an 11-day time course. Every 3-4% Inhibition Calculation days, viable cell numbers were determined using the Guava VIACOUNT™ assay (Millipore#4000-0040) and analyzed on a Guava EASYCITE™ Plus instrument. After cell counts, growth media and EPZ2 inhibitor (Compound#7 or Compound#13) were replaced, and cells were split back to the original plating density. The final split-adjusted number of viable cells/mL from day 11 of the time course was used to calculate the proliferation $IC_{50}$ values, using Graphpad PrismGRAPHPAD PRISM® software.

The Pfeiffer cell line, containing the heterozygous EZH2 mutation A677G, is shown to be sensitive to EZH2 inhibition by a small molecule inhibitor Compound #7. Proliferation inhibition is seen as early as 96 hr post-inhibitor treatment. The proliferation $IC_{50}$ after 11 days for Pfeiffer cells treated with Compound #7 is 5.2 nM, compared to WSU-DLCL2 cells, which contain the Y641F heterozygous mutation, and have an $IC_{50}$ of 270 nM or OCI-Ly19 cells, which are WT for EZH2, and have an $IC_{50}$ of 3000 nM. These results show that in a cellular context, the sensitivity of WT and mutant EZH2 to inhibition by small molecule inhibitor is A677G>>>Y641F>>WT, as measured by proliferation.

The Pfeiffer cell line, containing the heterozygous EZH2 mutation A677G, is shown to be sensitive to EZH2 inhibition by a small molecule inhibitor Compound #13. Proliferation inhibition is seen as early as 96 hr post-inhibitor treatment. The proliferation $IC_{50}$ after 11 days for Pfeiffer cells treated with Compound #13 is 0.4 nM, compared to WSU-DLCL2 cells, which contain the Y641F heterozygous mutation, and have an $IC_{50}$ of 4.9 nM or OCI-Ly19 cells, which are WT for EZH2, and have an $IC_{50}$ of 430 nM. These results show that in a cellular context, the sensitivity of WT and mutant EZH2 to inhibition by small molecule inhibitor is A677G>>>Y641F>>WT, as measured by proliferation.

Equivalents

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

We claim:

1. A method for treating cancer or myelodysplastic syndromes (MDS) in a subject having a Enhancer of Zeste Homolog 2 (EZH2) mutation in the substrate pocket domain of SEQ ID NO: 6, wherein SEQ ID NO: 6 comprises a mutation at amino acid position Y641 of EZH2 of SEQ ID NO: 1, wherein the mutation at amino acid position Y641 is selected from the group consisting of a substitution of phenylalanine (F) for the wild type residue tyrosine (Y) at amino acid position 641 of SEQ ID NO: 1 (Y641 F); a substitution of histidine (H) for the wild type residue tyrosine (Y) at amino acid position 641 of SEQ ID NO: 1 (Y641 H); a substitution of asparagine (N) for the wild type residue tyrosine (Y) at amino acid position 641 of SEQ ID NO: 1 (Y641 N); and a substitution of serine (S) for the wild type residue tyrosine (Y) at amino acid position 641 of SEQ ID NO: 1 (Y641 S); comprising administering to said subject a therapeutically effective amount of an EZH2 inhibitor, wherein the EZH2 inhibitor is

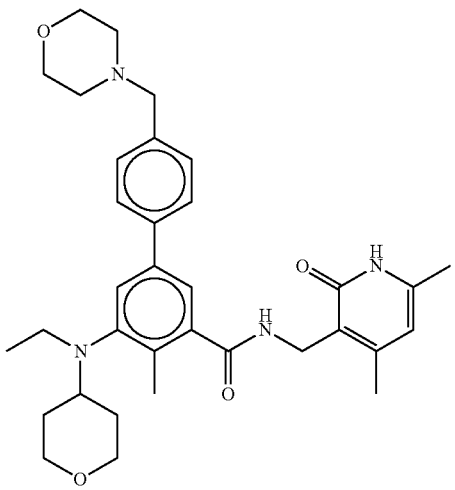

or a pharmaceutically acceptable salt thereof.

2. The method of claim 1, wherein the EZH2 mutation increases EZH2 trimethylation of Lys27 of histone H3 (H3-K27).

3. A method for treating cancer or myelodysplastic syndromes (MDS) in a subject having an increased level of trimethylated H3-K27 as a result of an EZH2 mutation in the substrate pocket domain of SEQ ID NO: 6, wherein SEQ ID NO: 6 comprises a mutation at amino acid position Y641 of EZH2 of SEQ ID NO: 1, wherein the mutation at amino acid position Y641 is selected from the group consisting of a substitution of phenylalanine (F) for the wild type residue tyrosine (Y) at amino acid position 641 of SEQ ID NO: 1 (Y641 F); a substitution of histidine (H) for the wild type residue tyrosine (Y) at amino acid position 641 of SEQ ID NO: 1 (Y641 H); a substitution of asparagine (N) for the wild type residue tyrosine (Y) at amino acid position 641 of SEQ ID NO: 1 (Y641 N); and a substitution of serine (S) for the wild type residue tyrosine (Y) at amino acid position 641 of SEQ ID NO: 1 (Y641 S); comprising administering to said subject a therapeutically effective amount of an EZH2 inhibitor, wherein the EZH2 inhibitor is

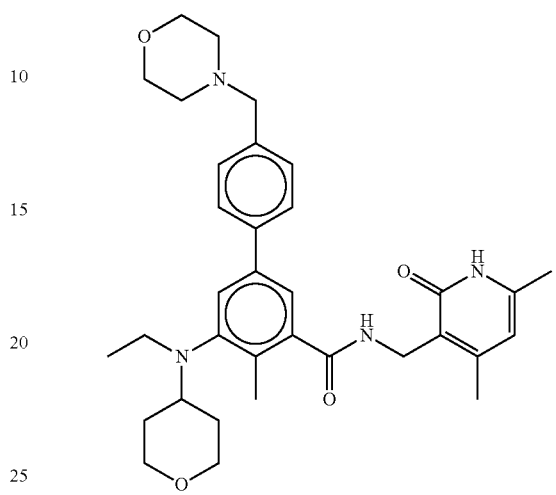

or a pharmaceutically acceptable salt thereof.

4. The method of claim 1 or 3, wherein the EZH2 inhibitor inhibits the conversion of H3K27 to trimethylated H3-K27.

5. The method of claim 1 or 3, wherein administration of the EZH2 inhibitor treats or alleviates a symptom of the cancer or MDS in the subject.

6. The method of claim 1 or 3, wherein the EZH2 mutation is a EZH2 polypeptide mutation or a nucleic acid sequence mutation encoding a mutant EZH2 polypeptide.

7. The method of claim 1 or 3, wherein the cancer is lymphoma.

8. The method of claim 7, wherein the lymphoma is selected from the group consisting of non-Hodgkin lymphoma, follicular lymphoma, and diffuse large B-cell lymphoma.

* * * * *